US012747198B2

(12) United States Patent
Karve et al.

(10) Patent No.: US 12,747,198 B2
(45) Date of Patent: Sep. 29, 2026

(54) PHENOLIC ACID LIPID BASED CATIONIC LIPIDS

(71) Applicant: Translate Bio, Inc., Lexington, MA (US)

(72) Inventors: Shrirang Karve, Cambridge, MA (US); Frank DeRosa, Cambridge, MA (US); Apiwat Wangweerawong, Cambridge, MA (US); Saswata Karmakar, Cambridge, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 893 days.

(21) Appl. No.: 17/907,739

(22) PCT Filed: Mar. 31, 2021

(86) PCT No.: PCT/US2021/025128
§ 371 (c)(1),
(2) Date: Sep. 29, 2022

(87) PCT Pub. No.: WO2021/202694
PCT Pub. Date: Oct. 7, 2021

(65) Prior Publication Data
US 2023/0150921 A1 May 18, 2023

Related U.S. Application Data

(60) Provisional application No. 63/003,698, filed on Apr. 1, 2020.

(51) Int. Cl.
*C07C 229/12* (2006.01)
*A61K 9/1272* (2025.01)
(Continued)

(52) U.S. Cl.
CPC .......... *C07C 229/12* (2013.01); *A61K 9/1272* (2013.01); *C07D 213/30* (2013.01); *C07D 295/088* (2013.01)

(58) Field of Classification Search
CPC .......................... C07C 229/12; C07D 295/088
See application file for complete search history.

(56) References Cited

U.S. PATENT DOCUMENTS 6,472,397 B1 10/2002 Ota et al.
10,022,455 B2 7/2018 Derosa et al.
2018/0028664 A1 2/2018 Besin et al.

FOREIGN PATENT DOCUMENTS

CN 106659731 A 5/2017
CN 110526885 A 12/2019
(Continued)

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016). 240 pages.
International Search Report and Written Opinion for PCT/US21/25128, dated Jul. 8, 2021. 9 pages.
(Continued)

*Primary Examiner* — Yate' K Cutliff
(74) *Attorney, Agent, or Firm* — LATHROP GPM LLP; James H. Velema, Esq.

(57) ABSTRACT

The present invention provides, in part, phenolic acid lipid compounds of Formula (I), and sub-formulas thereof, or a pharmaceutically acceptable salt thereof. The compounds provided herein can be useful for delivery and expression of mRNA and encoded protein, e.g., as a component of liposomal delivery vehicle, and accordingly can be useful for
(Continued)

treating various diseases, disorders and conditions, such as those associated with deficiency of one or more proteins.

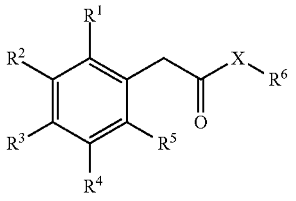

(I)

19 Claims, 1 Drawing Sheet

(51) Int. Cl.

| | |
|---|---|
| ***C07D 213/30*** | (2006.01) |
| ***C07D 295/088*** | (2006.01) |

(56) References Cited

FOREIGN PATENT DOCUMENTS

| | | | | | |
|---|---|---|---|---|---|
| JP | 2017-518371 | A | | 7/2017 | |
| JP | 2019-519601 | A | | 7/2019 | |
| WO | WO 1999/052894 | A1 | | 10/1999 | |
| WO | WO 2008/083379 | A1 | | 7/2008 | |
| WO | WO 2015/184256 | A2 | | 12/2015 | |
| WO | WO-2017201346 | A1 | * | 11/2017 | ........... C12N 9/1096 |
| WO | WO-2018089801 | A1 | * | 5/2018 | ............. A61K 9/127 |
| WO | WO-2018170306 | A1 | * | 9/2018 | ......... A61K 38/1816 |
| WO | WO 2019/207060 | A1 | | 10/2019 | |
| WO | WO 2019/226925 | A1 | | 11/2019 | |
| WO | WO 2020/056294 | A1 | | 3/2020 | |

OTHER PUBLICATIONS

International Search Report and Written Opinion for PCT International Patent Application No. PCT/US2021/025128, mailed Jul. 8, 2021.

* cited by examiner

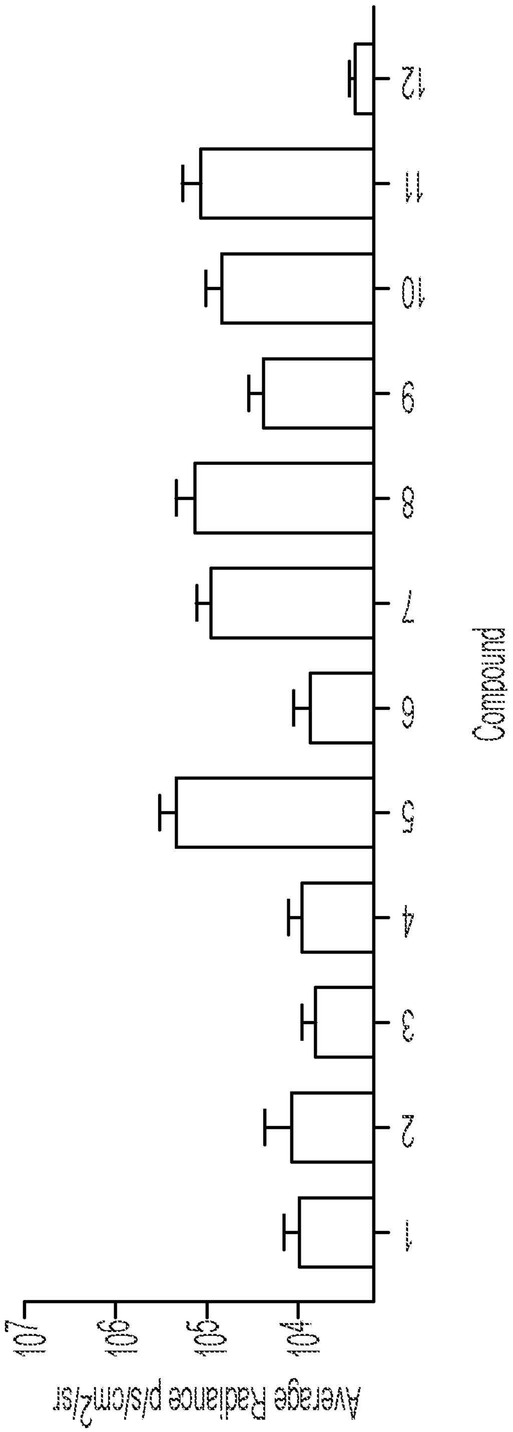
Average Radiance p/s/cm2/sr
107
106
105
104
Compound
1
2
3
4
5
6
7
8
9
10
11
12

PHENOLIC ACID LIPID BASED CATIONIC LIPIDS

CROSS-REFERENCE TO RELATED APPLICATIONS

This application is a 35 U.S.C. § 371 National Stage Application of International Application No. PCT/US2021/025128, filed on Mar. 31, 2021, which claims priority to U.S. Provisional Patent Application 63/003,698, filed Apr. 1, 2020, each of which is incorporated herein by reference in its entirety.

BACKGROUND

Delivery of nucleic acids has been explored extensively as a potential therapeutic option for certain disease states. In particular, messenger RNA (mRNA) therapy has become an increasingly important option for treatment of various diseases, including for those associated with deficiency of one or more proteins.

Efficient delivery of liposome-encapsulated nucleic acids remains an active area of research. The cationic lipid component plays an important role in facilitating effective encapsulation of the nucleic acid during the loading of liposomes. In addition, cationic lipids may play an important role in the efficient release of the nucleic acid cargo from the liposome into the cytoplasm of a target cell. Various cationic lipids suitable for in vivo use have been discovered. However, there remains a need to identify lipids that can be synthesized efficiently and cheaply without the formation of potentially toxic by-products.

Phenolic acids possess a number of advantageous characteristics which make them good starting points for the synthesis of cationic lipids for use in in vivo settings. For instance, phenolic acids show no toxicity, are available in large bulk quantities, and can easily be derivatised. Broadly speaking, phenolic acids can be divided into two groups: benzoic acids and cinnamic acids, and derivatives thereof.

Examples of benzoic acids that can be used to synthesize the cationic lipids of the present invention include:

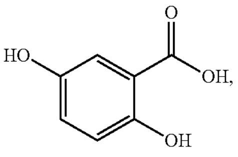,
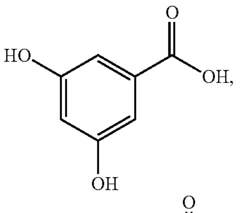,
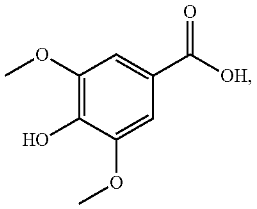,
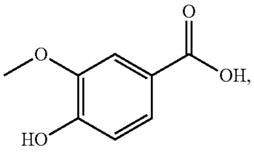,
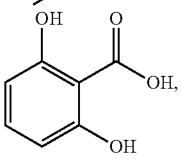,
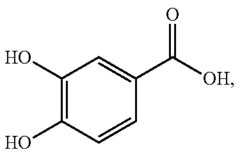,

-continued

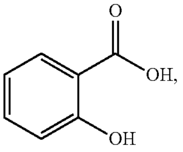,
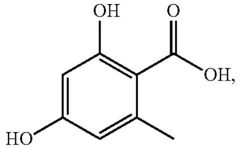, and
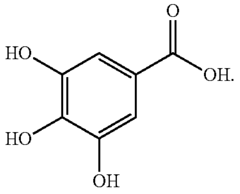.

Examples of cinnamic acids that can be used to synthesize the cationic lipids of the present invention include:

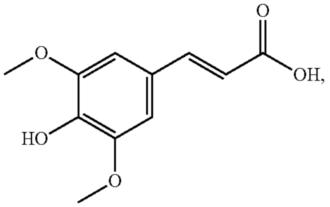,
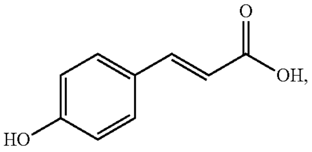,
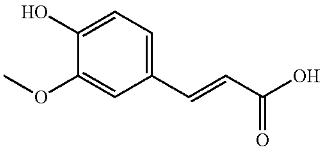 and
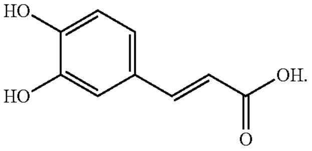.

In some embodiments, examples of cinnamic acids that can be used to synthesize the cationic lipids of the present invention include:

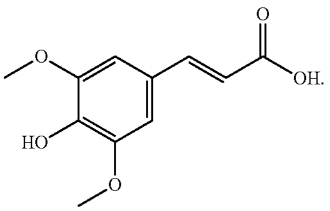 [SMILES: COc1cc(/C=C/C(=O)O)cc(OC)c1O].

In some embodiments, examples of cinnamic acids that can be used to synthesize the cationic lipids of the present invention include:

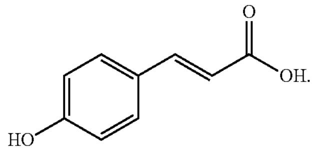 [SMILES: O=C(O)/C=C/c1ccc(O)cc1]

In some embodiments, examples of cinnamic acids that can be used to synthesize the cationic lipids of the present invention include:

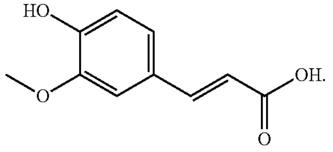

In some embodiments, examples of cinnamic acids that can be used to synthesize the cationic lipids of the present invention include:

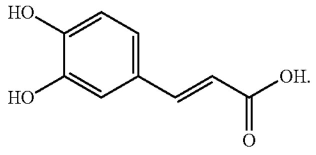 [SMILES: O=C(O)/C=C/c1ccc(O)c(O)c1]

SUMMARY

The present invention provides, among other things, a novel class of cationic lipid compounds for in vivo delivery of therapeutic agents, such as nucleic acids. It is contemplated that these compounds are capable of highly effective in vivo delivery while maintaining a favorable toxicity profile.

The cationic lipids of the present invention can be synthesized from readily available starting reagents, such as phenolic acids, benzoic acids, and cinnamic acids. The cationic lipids of the present invention also have unexpectedly high encapsulation efficiencies. The cationic lipids of the present invention also comprise cleavable groups (e.g., esters and disulphides) that are contemplated to improve biodegradability and thus contribute to their favorable toxicity profile.

In an aspect, provided herein are cationic lipids having a structure according to Formula (I),

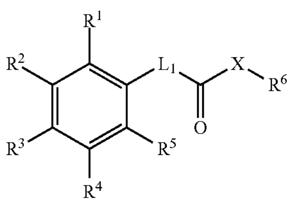

wherein $L_1$ is a bond, $(C_1$-$C_6)$alkyl or $(C_2$-$C_6)$alkenyl;

wherein X is O or S;

wherein $R^1$, $R^2$, $R^3$, $R^4$ and $R^5$ are each independently selected from H, OH, optionally substituted $(C_1$-$C_6)$alkyl, optionally substituted $(C_2$-$C_6)$alkenyl, optionally substituted $(C_2$-$C_6)$alkynyl, optionally substituted $(C_1$-$C_6)$alkoxy and —OC(O)R';

wherein at least one of $R^1$, $R^2$, $R^3$, $R^4$ or $R^5$ is —OC(O)R';

wherein R' is

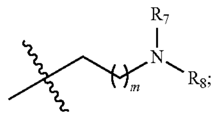

wherein $R^6$ is

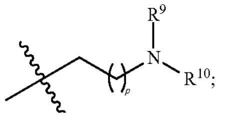

wherein m and p are each independently 0, 1, 2, 3, 4 or 5;

wherein $R^7$ is selected from H, optionally substituted $(C_1$-$C_6)$alkyl, optionally substituted $(C_2$-$C_6)$alkenyl, optionally substituted $(C_2$-$C_6)$alkynyl, optionally substituted $(C_1$-$C_6)$ acyl, $-(CH_2)_kR^A$ or $-(CH_2)_kCH(OR^{11})R^A$;

wherein $R^8$ is selected from H, optionally substituted $(C_1$-$C_6)$alkyl, optionally substituted $(C_2$-$C_6)$alkenyl, optionally substituted $(C_2$-$C_6)$alkynyl, optionally substituted $(C_1$-$C_6)$ acyl, $-(CH_2)_nR^B$ or $-(CH_2)_nCH(OR^{12})R^B$;

wherein $R^9$ is selected from H, optionally substituted $(C_1$-$C_6)$alkyl, optionally substituted $(C_2$-$C_6)$alkenyl, optionally substituted $(C_2$-$C_6)$alkynyl, optionally substituted $(C_1$-$C_6)$ acyl, $-(CH_2)_qR^C$ or $-(CH_2)_qCH(OR^{13})R^C$;

wherein $R^{10}$ is selected from H, optionally substituted $(C_1$-$C_6)$alkyl, optionally substituted $(C_2$-$C_6)$alkenyl, optionally substituted $(C_2$-$C_6)$alkynyl, optionally substituted $(C_1$-$C_6)$ acyl, $-(CH_2)_rR^D$ or $-(CH_2)_rCH(OR^{14})R^D$;

wherein k, n, q and r are each independently 1, 2, 3, 4, or 5;

or wherein (i) $R^7$ and $R^8$ or (ii) $R^9$ and $R^{10}$ together form an optionally substituted 5- or 6-membered heterocycloalkyl or heteroaryl wherein the heterocycloalkyl or heteroaryl comprises 1 to 3 heteroatoms selected from N, O and S;

wherein $R^{11}$, $R^{12}$, $R^{13}$ and $R^{14}$ are each independently selected from H, methyl, ethyl or propyl;

wherein $R^A$, $R^B$, $R^C$ and $R^D$ are each independently selected from optionally substituted $(C_6$-$C_{20})$alkyl, optionally substituted $(C_6$-$C_{20})$alkenyl, optionally substituted $(C_6$-$C_{20})$alkynyl, optionally substituted $(C_6$-$C_{20})$acyl, optionally substituted —OC(O)alkyl, optionally substituted —OC(O)alkenyl, optionally substituted $(C_1$-$C_6)$ monoalkylamino, optionally substituted $(C_1$-$C_6)$ dialkylamino, optionally substituted $(C_1$-$C_6)$ alkoxy, —OH, $-NH_2$;

wherein at least one of $R^7$, $R^8$, $R^9$, $R^{10}$ comprises a $R^A$, $R^B$, $R^C$ or $R^D$ moiety respectively wherein that $R^A$, $R^B$, $R^C$ or $R^D$ is independently selected from optionally substituted $(C_6$-$C_{20})$alkyl, optionally substituted $(C_6$-$C_{20})$alkenyl, optionally substituted $(C_6$-$C_{20})$alkynyl, optionally substituted ($C_6$-$C_{20}$)acyl, optionally substituted —OC(O)($C_6$-$C_{20}$)alkyl or optionally substituted-OC(O)($C_6$-$C_{20}$)alkenyl;

or a pharmaceutically acceptable salt thereof.

In an aspect, provided herein are cationic lipids that are pharmaceutically acceptable salts of Formula (I).

In an aspect, provided herein are compositions comprising the cationic lipid of the present invention, one or more non-cationic lipids, one or more cholesterol-based lipids and one or more PEG-modified lipid. In an aspect, the composition is a lipid nanoparticle, optionally a liposome.

In an aspect, the compositions comprising the cationic lipids of the present invention may be used in therapy.

BRIEF DESCRIPTION OF THE DRAWING

FIG. 1 illustrates in vivo protein expression following intratracheal administration of lipid nanoparticles comprising one of cationic lipid compounds 1-12. Lipid nanoparticles comprising the cationic lipids descried herein are effective in delivering FFL mRNA in vivo based on positive luciferase activity.

DETAILED DESCRIPTION OF CERTAIN EMBODIMENTS

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, the term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an I-amino acid. "Standard amino acid" refers to any of the twenty standard I-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, a bovine, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalents thereof, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Helper lipid: The term "helper lipid" as used herein refers to any neutral or zwitterionic lipid material including cholesterol. Without wishing to be held to a particular theory, helper lipids may add stability, rigidity, and/or fluidity within lipid bilayers/nanoparticles.

Improve, increase, or reduce: As used herein, the terms "improve," "increase," or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Liposome: As used herein, the term "liposome" refers to any lamellar, multilamellar, or solid nanoparticle vesicle. Typically, a liposome as used herein can be formed by mixing one or more lipids or by mixing one or more lipids and polymer(s). In some embodiments, a liposome suitable for the present invention contains a cationic lipids(s) and optionally non-cationic lipid(s), optionally cholesterol-based lipid(s), and/or optionally PEG-modified lipid(s).

messenger RNA (mRNA): As used herein, the term "messenger RNA (mRNA)" or "mRNA" refers to a polynucleotide that encodes at least one polypeptide. mRNA as used herein encompasses both modified and unmodified RNA. The term "modified mRNA" related to mRNA comprising at least one chemically modified nucleotide. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. In some embodiments, "nucleic acid" encompasses ribonucleic acids (RNA), including but not limited to any one or more of interference RNAs (RNAi), small interfering RNA (siRNA), short hairpin RNA (shRNA), antisense RNA (aRNA), messenger RNA (mRNA), modified messenger RNA (mmRNA), long non-coding RNA (lncRNA), micro-RNA (miRNA) multimeric coding nucleic acid (MCNA), polymeric coding nucleic acid (PCNA), guide RNA (gRNA) and CRISPR RNA (crRNA). In some embodiments, "nucleic acid" encompasses deoxyribonucleic acid (DNA), including but not limited to any one or more of single-stranded DNA (ssDNA), double-stranded DNA (dsDNA) and complementary DNA (cDNA). In some embodiments, "nucleic acid" encompasses both RNA and DNA. In embodiments, DNA may be in the form of antisense DNA, plasmid DNA, parts of a plasmid DNA, pre-condensed DNA, a product of a polymerase chain reaction (PCR), vectors (e.g., P1, PAC, BAC, YAC, artificial chromosomes), expression cassettes, chimeric sequences, chromosomal DNA, or derivatives of these groups. In embodiments, RNA may be in the form of messenger RNA (mRNA), ribosomal RNA (rRNA), signal recognition particle RNA (7 SL RNA or SRP RNA), transfer RNA (tRNA), transfer-messenger RNA (tmRNA), small nuclear RNA (snRNA), small nucleolar RNA (snoRNA), SmY RNA, small Cajal body-specific RNA (scaRNA), guide RNA (gRNA), ribonuclease P (RNase P), Y RNA, telomerase RNA component (TERC), spliced leader RNA (SL RNA), antisense RNA (aRNA or asRNA), cis-natural antisense transcript (cis-NAT), CRISPR RNA (crRNA), long noncoding RNA (lncRNA), micro-RNA (miRNA), piwi-interacting RNA (piRNA), small interfering RNA (siRNA), transacting siRNA (tasiRNA), repeat associated siRNA (rasiRNA), 73K RNA, retrotransposons, a viral genome, a viroid, satellite RNA, or derivatives of these groups. In some embodiments, a nucleic acid is a mRNA encoding a protein such as an enzyme.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable," as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate, and aryl sulfonate. Further pharmaceutically acceptable salts include salts formed from the quarternization of an amine using an appropriate electrophile, e.g., an alkyl halide, to form a quarternized alkylated amino salt.

Systemic distribution or delivery: As used herein, the terms "systemic distribution" or "systemic delivery," or grammatical equivalents thereof, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Chemical Definitions

Acyl: As used herein, the term "acyl" refers to $R^Z$—(C═O)—, wherein $R^Z$ is, for example, any alkyl, alkenyl, alkynyl, heteroalkyl or heteroalkylene.

Aliphatic: As used herein, the term aliphatic refers to $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ alkyls (e.g., linear or branched $C_1$-$C_{20}$ saturated alkyls), $C_2$-$C_{20}$ alkenyls (e.g., linear or branched $C_4$-$C_{20}$ dienyls, linear or branched $C_6$-$C_{20}$ trienyls, and the like), and $C_2$-$C_{20}$ alkynyls (e.g., linear or branched $C_2$-$C_{20}$ alkynyls). $C_1$-$C_{20}$ aliphatics can include $C_3$-$C_{20}$ cyclic aliphatics (e.g., $C_3$-$C_{20}$ cycloalkyls, $C_4$-$C_{20}$ cycloalkenyls, or $C_8$-$C_{20}$ cycloalkynyls). In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. An aliphatic group is unsubstituted or substituted with one or more substituent groups as described herein. For example, an aliphatic may be substituted with one or more (e.g., 1, 2, 3, 4, 5, or 6 independently selected substituents) of halogen, —COR", —$CO_2$H, —$CO_2$R", —CN, —OH, —OR", —OCOR', —$OCO_2$R", —$NH_2$, —NHR", —$N(R")_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the aliphatic is unsubstituted. In embodiments, the aliphatic does not include any heteroatoms. Alkyl: As used herein, the term "alkyl" means acyclic linear and branched hydrocarbon groups, e.g. "$C_1$-$C_{30}$ alkyl" refers to alkyl groups having 1-30 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, isohexyl, etc. The term "lower alkyl" means an alkyl group straight chain or branched alkyl having 1 to 6 carbon atoms. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —COR", —$CO_2$H, —$CO_2$R", —CN, —OH, —OR", —OCOR', —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the alkyl is substituted (e.g., with 1, 2, 3, 4, 5, or 6 substituent groups as described herein). In embodiments, an alkyl group is substituted with a-OH group and may also be referred to herein as a "hydroxyalkyl" group, where the prefix denotes the —OH group and "alkyl" is as described herein.

As used herein, "alkyl" also refers to a radical of a straight-chain or branched saturated hydrocarbon group having from 1 to 50 carbon atoms ("$C_1$-$C_{50}$ alkyl"). In some embodiments, an alkyl group has 1 to 40 carbon atoms ("$C_1$-$C_{40}$ alkyl"). In some embodiments, an alkyl group has 1 to 30 carbon atoms ("$C_1$-$C_{30}$ alkyl"). In some embodiments, an alkyl group has 1 to 20 carbon atoms ("$C_1$-$C_{20}$ alkyl"). In some embodiments, an alkyl group has 1 to 10 carbon atoms ("$C_1$-$C_{10}$ alkyl"). In some embodiments, an alkyl group has 1 to 9 carbon atoms ("$C_1$-$C_9$ alkyl"). In some embodiments, an alkyl group has 1 to 8 carbon atoms ("$C_1$-$C_8$ alkyl"). In some embodiments, an alkyl group has 1 to 7 carbon atoms ("$C_1$-$C_7$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include, without limitation, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_1$-$C_{50}$ alkyl. In certain embodiments, the alkyl group is a substituted $C_1$-$C_{50}$ alkyl.

Affixing the suffix "-ene" to a group indicates the group is a divalent moiety, e.g., arylene is the divalent moiety of aryl, and heteroarylene is the divalent moiety of heteroaryl.

Alkylene: The term "alkylene," as used herein, represents a saturated divalent straight or branched chain hydrocarbon group and is exemplified by methylene, ethylene, isopropylene and the like. Likewise, the term "alkenylene" as used herein represents an unsaturated divalent straight or branched chain hydrocarbon group having one or more unsaturated carbon-carbon double bonds that may occur in any stable point along the chain, and the term "alkynylene" herein represents an unsaturated divalent straight or branched chain hydrocarbon group having one or more unsaturated carbon-carbon triple bonds that may occur in any stable point along the chain. In certain embodiments, an alkylene, alkenylene, or alkynylene group may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. For example, an alkylene, alkenylene, or alkynylene may be substituted with one or more (e.g., 1, 2, 3, 4, 5, or 6 independently selected substituents) of halogen, —COR", —$CO_2$H, —$CO_2$R", —CN, —OH, —OR", —OCOR", —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In certain embodiments, an alkylene, alkenylene, or alkynylene is unsubstituted. In certain embodiments, an alkylene, alkenylene, or alkynylene does not include any heteroatoms.

Alkenyl: As used herein, "alkenyl" means any linear or branched hydrocarbon chains having one or more unsaturated carbon-carbon double bonds that may occur in any stable point along the chain, e.g. "$C_2$-$C_{30}$ alkenyl" refers to an alkenyl group having 2-30 carbons. For example, an alkenyl group includes prop-2-enyl, but-2-enyl, but-3-enyl, 2-methylprop-2-enyl, hex-2-enyl, hex-5-enyl, 2,3-dimethyl-but-2-enyl, and the like. In embodiments, the alkenyl comprises 1, 2, or 3 carbon-carbon double bond. In embodiments, the alkenyl comprises a single carbon-carbon double bond. In embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —COR", —$CO_2$H, —$CO_2$R", —CN, —OH, —OR", —OCOR", —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the alkenyl is unsubstituted. In embodiments, the alkenyl is substituted (e.g., with 1, 2, 3, 4, 5, or 6 substituent groups as described herein). In embodiments, an alkenyl group is substituted with a-OH group and may also be referred to herein as a "hydroxyalkenyl" group, where the prefix denotes the —OH group and "alkenyl" is as described herein.

As used herein, "alkenyl" also refers to a radical of a straight-chain or branched hydrocarbon group having from 2 to 50 carbon atoms and one or more carbon-carbon double bonds (e.g., 1, 2, 3, or 4 double bonds) ("$C_2$-$C_{50}$ alkenyl"). In some embodiments, an alkenyl group has 2 to 40 carbon atoms ("$C_2$-$C_{40}$ alkenyl"). In some embodiments, an alkenyl group has 2 to 30 carbon atoms ("$C_2$-$C_{30}$ alkenyl"). In some embodiments, an alkenyl group has 2 to 20 carbon atoms ("$C_2$-$C_{20}$ alkenyl"). In some embodiments, an alkenyl group has 2 to 10 carbon atoms ("$C_2$-$C_{10}$ alkenyl"). In some embodiments, an alkenyl group has 2 to 9 carbon atoms ("$C_2$-$C_9$ alkenyl"). In some embodiments, an alkenyl group has 2 to 8 carbon atoms ("$C_2$-$C_8$ alkenyl"). In some embodiments, an alkenyl group has 2 to 7 carbon atoms ("$C_2$-$C_7$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include, without limitation, ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_2$-$C_4$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_2$-$C_{50}$ alkenyl. In certain embodiments, the alkenyl group is a substituted $C_2$-$C_{50}$ alkenyl.

Alkynyl: As used herein, "alkynyl" means any hydrocarbon chain of either linear or branched configuration, having one or more carbon-carbon triple bonds occurring in any stable point along the chain, e.g., "$C_2$-$C_{30}$ alkynyl", refers to an alkynyl group having 2-30 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, etc. In embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —COR", —$CO_2$H, —$CO_2$R", —CN, —OH, —OR", —OCOR", —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the alkynyl is unsubstituted. In embodiments, the alkynyl is substituted (e.g., with 1, 2, 3, 4, 5, or 6 substituent groups as described herein).

As used herein, "alkynyl" also refers to a radical of a straight-chain or branched hydrocarbon group having from 2 to 50 carbon atoms and one or more carbon-carbon triple bonds (e.g., 1, 2, 3, or 4 triple bonds) and optionally one or more double bonds (e.g., 1, 2, 3, or 4 double bonds) ("$C_2$-$C_{50}$ alkynyl"). An alkynyl group that has one or more triple bonds and one or more double bonds is also referred to as an "ene-yne". In some embodiments, an alkynyl group has 2 to 40 carbon atoms ("$C_2$-$C_{40}$ alkynyl"). In some embodiments, an alkynyl group has 2 to 30 carbon atoms ("$C_2$-$C_{30}$ alkynyl"). In some embodiments, an alkynyl group has 2 to 20 carbon atoms ("$C_2$-$C_{20}$ alkynyl"). In some embodiments, an alkynyl group has 2 to 10 carbon atoms ("$C_2$-$C_{10}$ alkynyl"). In some embodiments, an alkynyl group has 2 to 9 carbon atoms ("$C_2$-$C_9$ alkynyl"). In some embodiments, an alkynyl group has 2 to 8 carbon atoms ("$C_2$-$C_8$ alkynyl"). In some embodiments, an alkynyl group has 2 to 7 carbon atoms ("$C_2$-$C_7$ alkynyl"). In some embodiments, an alkynyl group has 2 to 6 carbon atoms ("$C_2$-$C_6$ alkynyl"). In some embodiments, an alkynyl group has 2 to 5 carbon atoms ("$C_2$-$C_5$ alkynyl"). In some embodiments, an alkynyl group has 2 to 4 carbon atoms ("$C_2$-$C_4$ alkynyl"). In some embodiments, an alkynyl group has 2 to 3 carbon atoms ("$C_2$-$C_3$ alkynyl"). In some embodiments, an alkynyl group has 2 carbon atoms ("$C_2$ alkynyl"). The one or more carbon—triple bonds can be internal (such as in 2-butynyl) or terminal (such as in 1-butynyl). Examples of $C_2$-$C_4$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_2$-$C_6$ alkenyl groups include the aforementioned $C_2$-$C_4$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_2$-$C_{50}$ alkynyl. In certain embodiments, the alkynyl group is a substituted $C_2$-$C_{50}$ alkynyl.

Aryl: The term "aryl" used alone or as part of a larger moiety as in "aralkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. In embodiments, an aryl group has 6 ring carbon atoms ("$C_6$ aryl," e.g., phenyl). In some embodiments, an aryl group has 10 ring carbon atoms ("$C_{10}$ aryl," e.g., naphthyl such as 1-naphthyl and 2-naphthyl). In some embodiments, an aryl group has 14 ring carbon atoms ("$C_{14}$ aryl," e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Exemplary aryls include phenyl, naphthyl, and anthracene.

As used herein, "aryl" also refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_6$-$C_{14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_6$-$C_{14}$ aryl. In certain embodiments, the aryl group is a substituted $C_6$-$C_{14}$ aryl.

Arylene: The term "arylene" as used herein refers to an aryl group that is divalent (that is, having two points of attachment to the molecule). Exemplary arylenes include phenylene (e.g., unsubstituted phenylene or substituted phenylene).

Carbocyclyl: As used herein, "carbocyclyl" or "carbocyclic" refers to a radical of a non-aromatic cyclic hydrocarbon group having from 3 to 10 ring carbon atoms ("$C_3$-$C_{10}$ carbocyclyl") and zero heteroatoms in the non-aromatic ring system. In some embodiments, a carbocyclyl group has 3 to 8 ring carbon atoms ("$C_3$-$C_8$ carbocyclyl"). In some embodiments, a carbocyclyl group has 3 to 7 ring carbon atoms ("$C_3$-$C_7$ carbocyclyl"). In some embodiments, a carbocyclyl group has 3 to 6 ring carbon atoms ("$C_3$-$C_6$ carbocyclyl"). In some embodiments, a carbocyclyl group has 4 to 6 ring carbon atoms ("$C_4$-$C_6$ carbocyclyl"). In some embodiments, a carbocyclyl group has 5 to 6 ring carbon atoms ("$C_5$-$C_6$ carbocyclyl"). In some embodiments, a carbocyclyl group has 5 to 10 ring carbon atoms ("$C_5$-$C_{10}$ carbocyclyl"). Exemplary $C_3$-$C_6$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ carbocyclyl groups include, without limitation, the aforementioned $C_3$-$C_6$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_3$-$C_{10}$ carbocyclyl groups include, without limitation, the aforementioned $C_3$-$C_8$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_3$-$C_{10}$ carbocyclyl. In certain embodiments, the carbocyclyl group is a substituted $C_3$-$C_{10}$ carbocyclyl.

In some embodiments, "carbocyclyl" or "carbocyclic" is referred to as a "cycloalkyl", i.e., a monocyclic, saturated carbocyclyl group having from 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$, cycloalkyl"). In some embodiments, a cycloalkyl group has 4 to 6 ring carbon atoms ("$C_4$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 10 ring carbon atoms ("$C_5$-$C_{10}$ cycloalkyl"). Examples of $C_5$-$C_6$ cycloalkyl groups include cyclopentyl ($C_5$) and cyclohexyl ($C_5$). Examples of $C_3$-$C_6$ cycloalkyl groups include the aforementioned $C_5$-$C_6$ cycloalkyl groups as well as cyclopropyl ($C_3$) and cyclobutyl ($C_4$). Examples of $C_3$-$C_8$ cycloalkyl groups include the aforementioned $C_3$-$C_6$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_3$-$C_{10}$ cycloalkyl. In certain embodiments, the cycloalkyl group is a substituted $C_3$-$C_{10}$ cycloalkyl.

Halogen: As used herein, the term "halogen" means fluorine, chlorine, bromine, or iodine.

Heteroalkyl: The term "heteroalkyl" is meant a branched or unbranched alkyl, alkenyl, or alkynyl group having from 1 to 14 carbon atoms in addition to 1, 2, 3 or 4 heteroatoms independently selected from the group consisting of N, O, S, and P. Heteroalkyls include tertiary amines, secondary amines, ethers, thioethers, amides, thioamides, carbamates, thiocarbamates, hydrazones, imines, phosphodiesters, phosphoramidates, sulfonamides, and disulfides. A heteroalkyl group may optionally include monocyclic, bicyclic, or tricyclic rings, in which each ring desirably has three to six members. Examples of heteroalkyls include polyethers, such as methoxymethyl and ethoxyethyl.

Heteroalkylene: The term "heteroalkylene," as used herein, represents a divalent form of a heteroalkyl group as described herein.

Heteroaryl: The term "heteroaryl," as used herein, is fully unsaturated heteroatom-containing ring wherein at least one ring atom is a heteroatom such as, but not limited to, nitrogen and oxygen.

As used herein, "heteroaryl" also refers to a radical of a 5-14 membered monocyclic or polycyclic (e.g., bicyclic or tricyclic) 4n+2 aromatic ring system (e.g., having 6, 10, or 14 $\pi$ electrons shared in a cyclic array) having ring carbon atoms and 1 or more (e.g., 1, 2, 3, or 4 ring heteroatoms) ring heteroatoms provided in the aromatic ring system, wherein each heteroatom is independently selected from oxygen, sulfur, nitrogen, boron, silicon, and phosphorus ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-10 membered heteroaryl"). In some embodiments, a heteroaryl group is a 5-8 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-8 membered heteroaryl"). In some embodiments, a heteroaryl group is a 5-6 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-6 membered heteroaryl"). In some embodiments, the 5-6 membered heteroaryl has 1 or more (e.g., 1, 2, or 3) ring heteroatoms selected from oxygen, sulfur, nitrogen, boron, silicon, and phosphorus. In some embodiments, the 5-6 membered heteroaryl has 1 or 2 ring heteroatoms selected from oxygen, sulfur, nitrogen, boron, silicon, and phosphorus. In some embodiments, the 5-6 membered heteroaryl has 1 ring heteroatom selected from oxygen, sulfur, nitrogen, boron, silicon, and phosphorus. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, "heterocyclyl" or "heterocyclic" refers to a radical of a 3- to 14-membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")). and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-10 membered heterocyclyl"). In some embodiments, a heterocyclyl group is a 5-8 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-8 membered heterocyclyl"). In some embodiments, a heterocyclyl group is a 5-6 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-6 membered heterocyclyl"). In some embodiments, the 5-6 membered heterocyclyl has 1 or more (e.g., 1, 2, or 3) ring heteroatoms selected from oxygen, sulfur, nitrogen, boron, silicon, and phosphorus. In some embodiments, the 5-6 membered heterocyclyl has 1 or 2 ring heteroatoms selected from oxygen, sulfur, nitrogen, boron, silicon, and phosphorus. In some embodiments, the 5-6 membered heterocyclyl has 1 ring heteroatom selected from oxygen, sulfur, nitrogen, boron, silicon, and phosphorus.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation. tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Heterocycloalkyl: The term "heterocycloalkyl," as used herein, is a non-aromatic ring wherein at least one atom is a heteroatom such as, but not limited to, nitrogen, oxygen, sulfur, or phosphorus, and the remaining atoms are carbon. The heterocycloalkyl group can be substituted or unsubstituted.

As understood from the above, alkyl, alkenyl, alkynyl, acyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or 'unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2$, —$SO_3$H, —OH, —ORaa, —ON(Rbb)2, —N(Rbb)2, —N(Rbb)3+ X—, —N(ORcc)Rbb, —SeH, —SeRaa, —SH, —SRaa, —SSRcc, —C(═O)Raa, —CO2H, —CHO, —C(ORcc)2, —CO2Raa, —OC(═O)Raa, —OCO2Raa, —C(═O)N(Rbb)2, —OC(═O)N(Rbb)2, —NRbbC(═O)Raa, —NRbbCO2Raa, —NRbbC(═O)N(Rbb)2, —C(═NRbb)Raa, —C(═NRbb)ORaa, —OC(═NRbb)Raa, —OC(═NRbb)ORaa, —C(═NRbb)N(Rbb)2, —OC(═NRbb)N(Rbb)2, —NRbbC(═NRbb)N(Rbb)2, —C(═O)NRbbSO2Raa, —NRbbSO2Raa, —SO2N(Rbb)2, —SO2Raa, —$SO_2$ORaa, —OSO2Raa, —S(═O)Raa, —OS(═O)Raa, —Si(Raa)3-OSi(Raa) 3—C(═S)N(Rbb)2, —C(═O)SRaa, —C(═S)SRaa, —SC(═S)SRaa, —SC(═O)SRaa, —OC(═O)SRaa, —SC(═O)ORaa, —SC(═O)Raa, —P(═O)2Raa, —OP(═O)2Raa, —P(═O)(Raa)2, —OP(═O)(Raa)2, —OP(═O)(ORcc)2, —P(═O)2N(Rbb)2, —OP(═O)2N(Rbb)2, —P(═O)(NRbb)2, —OP(═O)(NRbb)2, —NRbbP(═O)(ORcc)2, —NRbbP(═O)(NRbb)2, —P(Rcc)2, —P(Rcc)3, —OP(Rcc)2, —OP(Rcc)3, —B(Raa)2, —B(ORcc)2, —BRaa(ORcc), C1-C50 alkyl, C2-C50 alkenyl, C2-C50 alkynyl, C3-C14 carbocyclyl, 3-14 membered heterocyclyl, C6-C14 aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group ═O, ═S, ═NN(Rbb)2, ═NNRbbC(═O)Raa, ═NNRbbC(═O)ORaa, ═NNRbbS(═O)2Raa, ═NRbb, or ═NORcc;

each instance of Raa is, independently, selected from C1-C50 alkyl, C2-C50 alkenyl, C2-C50 alkynyl, C3-C10 carbocyclyl, 3-14 membered heterocyclyl, C6-C14 aryl, and 5-14 membered heteroaryl, or two Raa groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rbb is, independently, selected from hydrogen, —OH, —ORaa, —N(Rcc)2, —CN, —C(═O)Raa, —C(═O)N(Rcc)2, —CO2Raa, —SO2Raa, —C(═NRcc)ORaa, —C(═NRcc)N(Rcc)2, —SO2N(Rcc)2, —SO2Rcc, —SO2ORcc, —SORaa, —C(═S)N(Rcc)2, —C(═O)SRcc, —C(═S)SRcc, —P(═O)2Raa, —P(═O)(Raa)2, —P(═O)2N(Rcc)2, —P(═O)(NRcc)2, C1-C50 alkyl, C2-C50 alkenyl, C2-C50 alkynyl, C3-C10 carbocyclyl, 3-14 membered heterocyclyl, C6-C14 aryl, and 5-14 membered heteroaryl, or two Rbb groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rcc is, independently, selected from hydrogen, C1-C50 alkyl, C2-C50 alkenyl, C2-C50 alkynyl, C3-C10 carbocyclyl, 3-14 membered heterocyclyl, C6-C14 aryl, and 5-14 membered heteroaryl, or two Rcc groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of Rdd is, independently, selected from halogen, —CN, —NO2, —N3, —SO2H, —SO3H, —OH, —ORee, —ON(Rff)2, —N(Rff)2, —N(Rff)3+ X—, —N(ORee)Rff, —SH, —SRee, —SSRee, —C(═O)Ree, —CO2H, —CO2Ree, —OC(═O)Ree, —$OCO_2$Ree, —C(═O)N(Rff)2, —OC(═O)N(Rff)2, —NRffC(═O)Ree, —NRffCO2Ree, —NRffC(═O)N(Rff)2, —C(═NRff)ORee, —OC(═NRff)Ree, —OC(═NRff)ORee, —C(═NRff)N(Rff)2, —OC(═NRff)N(Rff)2, —NRffC(═NRff)N(Rff)2, —NRffSO2Ree, —SO2N(Rff)2, —SO2Ree, —SO2ORee, —OSO2Ree, —S(═O)Ree, —Si(Ree)3, —OSi(Ree)3, —C(═S)N(Rff)2, —C(═O)SRee, —C(═S)SRee, —SC(═S)SRee, —P(═O)2Ree, —P(═O)(Ree)2, —OP(═O)

(Ree)2, —OP(═O) (ORee)2, C1-C50 alkyl, C2-C50 alkenyl, C2-C50 alkynyl, C3-C10 carbocyclyl, 3-10 membered heterocyclyl, C6-C10 aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups, or two geminal Rdd substituents can be joined to form ═O or ═S;

each instance of Ree is, independently, selected from C1-C50 alkyl, C2-C50 alkenyl, C2-C50 alkynyl, C3-C10 carbocyclyl, C6-C10 aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups;

each instance of Rff is, independently, selected from hydrogen, C1-C50 alkyl, C2-C50 alkenyl, C2-C50 alkynyl, C3-C10 carbocyclyl, 3-10 membered heterocyclyl, C6-C10 aryl and 5-10 membered heteroaryl, or two Rff groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rgg groups; and each instance of Rgg is, independently, halogen, —CN, —NO2, —N3, —SO2H, —SO3H, —OH, —OC1-C50 alkyl, —ON(C1-C50 alkyl)2, —N(C1-C50 alkyl)2, —N(C1-C50 alkyl)3+X—, —NH(C1-C50 alkyl)2+X—, —NH2(C1-C50 alkyl)+X—, —NH3+X—, —N(OC1-C50 alkyl)(C1-C50 alkyl), —N(OH)(C1-C50 alkyl), —NH(OH), —SH, —SC1-C50 alkyl, —SS(C1-C50 alkyl), —C(═O)(C1-C50 alkyl), —CO2H, —CO2(C1-C50 alkyl), —OC(═O)(C1-C50 alkyl), —OCO2(C1-C50 alkyl), —C(═O)$NH_2$, —C(═O)N(C1-C50 alkyl)2, —OC(═O)NH(C1-C50 alkyl), —NHC(═O)(C1-C50 alkyl), —N(C1-C50 alkyl)C(═O)(C1-C50 alkyl), —NHCO2(C1-C50 alkyl), —NHC(═O)N(C1-C50 alkyl)2, —NHC(═O)NH(C1-C50 alkyl), —NHC(═O)$NH_2$, —C(═NH)O(C1-C50 alkyl), —OC(═NH)(C1-C50 alkyl), —OC(═NH)OC1-C50 alkyl, —C(═NH)N(C1-C50 alkyl)2, —C(═NH)NH(C1-C50 alkyl), —C(═NH)$NH_2$, —OC(═NH)N(C1-C50alkyl)2, —OC(NH)NH(C1-C50 alkyl), —OC(NH)$NH_2$, —NHC(NH)N(C1-C50 alkyl)2, —NHC(═NH) $NH_2$, —NHSO2(C1-C50 alkyl), —SO2N(C1-C50 alkyl)2, —SO2NH(C1-C50 alkyl), —SO2$NH_2$, —SO2(C1-C50 alkyl), —SO2O(C1-C50 alkyl), —OSO2(C1-C6 alkyl), —SO(C1-C6 alkyl), —Si(C1-C50 alkyl)3, —OSi(C1-C6 alkyl)3, —C(═S)N(C1-C50 alkyl)2, C(═S)NH(C1-C50 alkyl), C(═S)$NH_2$, —C(═O)S(C1-C6 alkyl), —C(═S)S(C1-C6 alkyl), —SC(═S)S(C1-C6 alkyl), —P(═O)2(C1-C50 alkyl), —P(═O)(C1-C50 alkyl)2, —OP(═O)(C1-C50 alkyl)2, —OP(═O)(OC1-C50 alkyl)2, C1-C50 alkyl, C2-C50 alkenyl, C2-C50 alkynyl, C3-C10 carbocyclyl, C6-C10 aryl, 3-10 membered heterocyclyl, 5-10 membered heteroaryl; or two geminal Rgg substituents can be joined to form ═O or ═S; wherein X— is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quaternary amine in order to maintain electronic neutrality. Exemplary counterions include halide ions (e.g., F—, Cl—, Br—, I—), NO3-, ClO4-, OH−, H2PO4-, HSO4-, sulfonate ions (e.g., methansulfonate, trifluoromethanesulfonate, p-toluenesulfonate, benzenesulfonate, 10-camphor sulfonate, naphthalene-2-sulfonate, naphthalene-I-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —ORaa, —N(Rcc)2, —CN, —C(═O)Raa, —C(═O)N(Rcc)2, —CO2Raa, —SO2Raa, —C(═NRbb)Raa, —C(═NRcc)ORaa, —C(═NRcc)N(Rcc)2, —SO2N(Rcc)2, —SO2Rcc, —SO2ORcc, —SORaa, —C(═S)N(Rcc)2, —C(═O)SRcc, —C(═S)SRcc, —P(═O)2Raa, —P(═O)(Raa)2, —P(═O)2N(Rcc)2, —P(═O)(NRcc)2, C1-C50 alkyl, C2-C50 alkenyl, C2-C50 alkynyl, C3-C10 carbocyclyl, 3-14 membered heterocyclyl, C6-C14 aryl, and 5-14 membered heteroaryl, or two Rcc groups, together with the N atom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups, and wherein Raa, Rbb, Rcc and Rdd are as defined above.

In certain embodiments, the substituent present on a nitrogen atom is a nitrogen protecting group (also referred to as an amino protecting group). Nitrogen protecting groups are well known in the art and include those described in detail in Protecting Groups in Organic Synthesis, T. W. Greene and P. G. M. Wuts, 3rd edition, John Wiley & Sons, 1999, incorporated herein by reference.

For example, nitrogen protecting groups such as amide groups (e.g., —C(═O)Raa) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino) acetamide, 3-(p-hydroxyphenyl) propanamide, 3-(o-nitrophenyl) propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)ORaa) include, but are not limited to, methyl carbamate, ethyl carbamante, 9-fluorenylmethyl carbamate (Fmoc), 9-(2-sulfo) fluorenylmethyl carbamate, 9-(2,7-dibromo) fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, 0-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl) methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-I-cyclopropylmethyl carbamate, 1-methyl-1 (3,5-dimethoxyphenyl)ethyl carbamate, 1-methyl-1-(p-phenylazophenyl)ethyl carbamate, 1-methyl-I-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(═O)2Raa) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl) ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-I-cyclohexenyl)amine, N-borane derivative, N-diphenylborinic acid derivative, N-[phenyl(pentaacylchromium- or tungsten) acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-I-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl) xanthenyl, 9-(9-phenyl-10-oxo) anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio) pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy) butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary sulfur protecting groups include, but are not limited to, alkyl, benzyl, p-methoxybenzyl, 2,4,6-trimethylbenzyl, 2,4,6-trimethoxybenzyl, o-hydroxybenzyl, p-hydroxybenzyl, o-acetoxybenzyl, p-acetoxybenzyl, p-nitrobenzyl, 4-picolyl, 2-quinolinylmethyl, 2-picolyl N-oxido, 9-anthrylmethyl, 9-fluorenylmethyl, xanthenyl, ferrocenylmethyl, diphenylmethyl, bis(4-methoxyphenyl)methyl, 5-dibenzosuberyl, triphenylmethyl, diphenyl-4-pyridylmethyl, phenyl, 2,4-dinitrophenyl, t-butyl, 1-adamantyl, methoxymethyl (MOM), isobutoxymethyl, benzyloxymethyl, 2-tetrahydropyranyl, benzylthiomethyl, phenylthiomethyl, thiazolidino, acetamidomethyl, trimethylacetamidomethyl, benzamidomethyl, allyloxycarbonylaminomethyl, phenylacetamidomethyl, phthalimidomethyl, acetylmethyl, carboxymethyl, cyanomethyl, (2-nitro-1-phenyl)ethyl, 2-(2,4-dinitrophenyl)ethyl, 2-cyanoethyl, 2-(Trimethylsilyl) ethyl, 2,2-bis(carboethoxy)ethyl, (1-m-nitrophenyl-2-benzoyl) othyl, 2-phenylsulfonylethyl, 2-(4-methylphenylsulfonyl)-2-methylprop-2-yl, acetyl, benzoyl, trifluoroacetyl, N-[[(p-biphenylyl)isopropoxy]carbonyl]-N-methyl]-γ-aminothiobutyrate, 2,2,2-trichloroethoxycarbonyl, t-butoxycarbonyl, benzyloxycarbonyl, p-methoxybenzyloxycarbonyl, N-ethyl, N-methoxymethyl, sulfonate, sulfenylthiocarbonate, 3-nitro-2-pyridinesulfenyl sulfide, oxathiolone.

Compounds of the Invention

Liposomal-based vehicles are considered an attractive carrier for therapeutic agents and remain subject to continued development efforts. While liposomal-based vehicles that comprise certain lipid components have shown promising results with regard to encapsulation, stability and site localization, there remains a great need for improvement of liposomal-based delivery systems. For example, a significant drawback of liposomal delivery systems relates to the construction of liposomes that have sufficient cell culture or in vivo stability to reach desired target cells and/or intracellular compartments, and the ability of such liposomal delivery systems to efficiently release their encapsulated materials to such target cells.

In particular, there remains a need for improved lipids compounds that demonstrate improved pharmacokinetic properties and which are capable of delivering macromolecules, such as nucleic acids, to a wide variety cell types and tissues with enhanced efficiency. Importantly, there also remains a particular need for novel lipid compounds that are characterized as having reduced toxicity and are capable of efficiently delivering encapsulated nucleic acids and polynucleotides to targeted cells, tissues and organs.

Described herein a novel class of cationic lipid compounds for improved in vivo delivery of therapeutic agents, such as nucleic acids. In particular, a cationic lipid described herein may be used, optionally with other lipids, to formulate a lipid-based nanoparticle (e.g., liposome) for encapsulating therapeutic agents, such as nucleic acids (e.g., DNA, siRNA, mRNA, microRNA) for therapeutic use.

In embodiments, compounds of the invention as described herein can provide one or more desired characteristics or properties. That is, in certain embodiments, compounds of the invention as described herein can be characterized as having one or more properties that afford such compounds advantages relative to other similarly classified lipids. For example, compounds disclosed herein can allow for the control and tailoring of the properties of liposomal compositions (e.g., lipid nanoparticles) of which they are a component. In particular, compounds disclosed herein can be characterized by enhanced transfection efficiencies and their ability to provoke specific biological outcomes. Such outcomes can include, for example enhanced cellular uptake, endosomal/lysosomal disruption capabilities and/or promoting the release of encapsulated materials (e.g., polynucleotides) intracellularly. Additionally, the compounds disclosed herein have advantageous pharmacokinetic properties, biodistribution, and efficiency (e.g., due to the different disassociate rates of the polymer group used).

The present application demonstrates that not only are the cationic lipids of the present invention synthetically tractable from readily available starting materials, but they also have unexpectedly high encapsulation efficiencies.

Additionally, the cationic lipids of the present invention have cleavable groups such as ester groups and disulphides. These cleavable groups (e.g. esters and disulphides) are contemplated to improve biodegradability and thus contribute to their favorable toxicity profile.

Compounds of the Present Invention

Provided herein are compounds which are cationic lipids. For example, the cationic lipids of the present invention include compounds having a structure according to Formula (I):

(I)

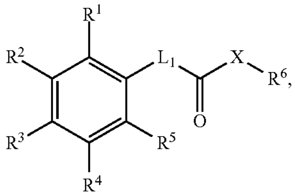

wherein $L_1$ is a bond, $(C_1\text{-}C_6)$alkyl or $(C_2\text{-}C_6)$alkenyl;

wherein X is O or S;

wherein $R^1$, $R^2$, $R^3$, $R^4$ and $R^5$ are each independently selected from H, OH, optionally substituted $(C_1\text{-}C_6)$ alkyl, optionally substituted $(C_2\text{-}C_6)$alkenyl, optionally substituted $(C_2\text{-}C_6)$alkynyl, optionally substituted $(C_1\text{-}C_6)$alkoxy and —OC(O)R';

wherein at least one of $R^1$, $R^2$, $R^3$, $R^4$ or $R^5$ is —OC(O)R';

wherein R' is

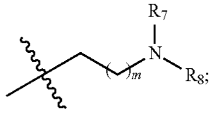

wherein $R^6$ is

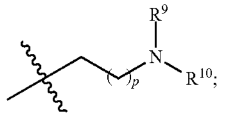

wherein m and p are each independently 0, 1, 2, 3, 4 or 5;

wherein $R^7$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$ acyl, $—(CH_2)_kR^A$ or $—(CH_2)_kCH(OR^{11})R^A$, wherein $R^8$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$ acyl, $—(CH_2)_nR^B$ or $—(CH_2)_nCH(OR^{12})R^B$;

wherein $R^9$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$ acyl, $—(CH_2)_qR^C$ or $—(CH_2)_qCH(OR^{13})R^C$;

wherein $R^{10}$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_rR^D$ or $—(CH_2)_rCH(OR^{14})R^D$;

wherein k, n, q and r are each independently 1, 2, 3, 4, or 5;

or wherein (i) $R^7$ and $R^8$ or (ii) $R^9$ and $R^{10}$ together form an optionally substituted 5- or 6-membered heterocycloalkyl or heteroaryl wherein the heterocycloalkyl or heteroaryl comprises 1 to 3 heteroatoms selected from N, O and S;

wherein $R^{11}$, $R^{12}$, $R^{13}$ and $R^{14}$ are each independently selected from H, methyl, ethyl or propyl;

wherein $R^A$, $R^B$, $R^C$ and $R^D$ are each independently selected from optionally substituted $(C_6\text{-}C_{20})$alkyl, optionally substituted $(C_6\text{-}C_{20})$alkenyl, optionally substituted $(C_6\text{-}C_{20})$alkynyl, optionally substituted $(C_6\text{-}C_{20})$acyl, optionally substituted —OC(O)alkyl, optionally substituted —OC(O)alkenyl, optionally substituted $(C_1\text{-}C_6)$ monoalkylamino, optionally substituted $(C_1\text{-}C_6)$ dialkylamino, optionally substituted $(C_1\text{-}C_6)$ alkoxy, —OH, $—NH_2$;

wherein at least one of $R^7$, $R^8$, $R^9$, $R^{10}$ comprises a $R^A$, $R^B$, $R^C$ or $R^D$ moiety respectively wherein that $R^A$, $R^B$, $R^C$ or $R^D$ is independently selected from optionally substituted $(C_6\text{-}C_{20})$alkyl, optionally substituted $(C_6\text{-}C_{20})$alkenyl, optionally substituted $(C_6\text{-}C_{20})$alkynyl, optionally substituted $(C_6\text{-}C_{20})$ acyl, optionally substituted-OC(O) $(C_6\text{-}C_{20})$alkyl or optionally substituted-OC(O) $(C_6\text{-}C_{20})$alkenyl;

or a pharmaceutically acceptable salt thereof.

In embodiments, any alkyl, alkenyl, alkynyl, acyl, alkoxy, monoalkylamino, dialkylamino, heterocycloalkyl or heteroaryl are optionally substituted with one or more substituents selected from the groups consisting of $(C_1\text{-}C_6)$alkyl, $(C_2\text{-}C_6)$alkenyl, $(C_2\text{-}C_6)$alkynyl, $(C_1\text{-}C_6)$ acyl, $(C_1\text{-}C_6)$ alkoxy, halogen, —COR, —CO2H, —CO2R, —CN, —OH, —OR, —OCOR, —OCO2R, —NH2, —NHR, —N(R)2, —SR or —SO2R, or two geminal hydrogens on a carbon atom are replaced with the group =NH, wherein each instance of R independently is C1-C10 aliphatic alkyl.

In embodiments, L1 is a bond.

In embodiments, L1 is (C1-C6)alkyl.

In embodiments, L1 is (C2-C6)alkenyl.

In embodiments, L1 is C2 alkenyl.

In embodiments, RA and RB are identical. In embodiments, RC and RD are identical. In embodiments, RA and RB are identical and RC and RD are identical.

In embodiments, RA and RB are different. In embodiments, RC and RD are different. In embodiments, RA and RB are different and RC and RD are different.

In embodiments, RA, RB, RC and RD are identical.

In embodiments, RA, RB, RC and RD are different.

In embodiments, RA, RB, RC or RD are each independently selected from optionally substituted (C6-C20)alkyl, optionally substituted (C6-C20)alkenyl, optionally substituted (C6-C20)alkynyl, optionally substituted (C6-C20) acyl, optionally substituted —OC(O)(C6-C20)alkyl or optionally substituted —OC(O)(C6-C20)alkenyl.

In embodiments, RA, RB, RC or RD are the same and selected from optionally substituted (C6-C20)alkyl, optionally substituted (C6-C20)alkenyl, optionally substituted (C6-C20)alkynyl, optionally substituted (C6-C20)acyl, optionally substituted —OC(O)(C6-C20)alkyl or optionally substituted —OC(O)(C6-C20)alkenyl.

In embodiments, RA and RB are each independently selected from optionally substituted (C6-C20)alkyl, optionally substituted (C6-C20)alkenyl, optionally substituted (C6-C20)alkynyl.

In embodiments, RA and RB are the same and selected from optionally substituted (C6-C20)alkyl, optionally substituted (C6-C20)alkenyl, optionally substituted (C6-C20) alkynyl.

In embodiments, RA and RB are each independently optionally substituted (C6-C20)alkyl.

In embodiments, RA and RB are the same and are optionally substituted (C6-C20)alkyl.

In embodiments, RA and RB are each independently optionally substituted (C6-C20)alkenyl.

In embodiments, RA and RB are the same and are optionally substituted (C6-C20)alkenyl.

In embodiments, RA and RB are each independently optionally substituted (C6-C20)alkynyl.

In embodiments, RA and RB are the same and are optionally substituted (C6-C20)alkynyl.

In embodiments, RA and RB are each independently optionally substituted (C6-C20)acyl.

In embodiments, RA and RB are the same and are optionally substituted (C6-C20)acyl.

In embodiments, RA and RB are each independently optionally substituted —OC(O)(C6-C20)alkyl.

In embodiments, RA and RB are the same and are optionally substituted —OC(O)(C6-C20)alkyl.

In embodiments, RA and RB are each independently optionally substituted —OC(O)(C6-C20)alkenyl.

In embodiments, RA and RB are the same and are optionally substituted —OC(O)(C6-C20)alkenyl.

In embodiments, R7=—$(CH_2)$kCH(OR11)RA, R8 is —(CH2)nCH(OR12)RB and RA and RB are each independently selected from:

| | |
|---|---|
| $C_8H_{17}$ | 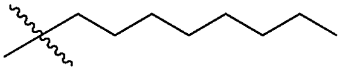 [SMILES: *CCCCCCCC] |
| $C_{10}H_{21}$ | 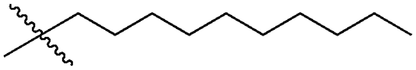 [SMILES: *CCCCCCCCCC] |
| $C_{12}H_{25}$ | 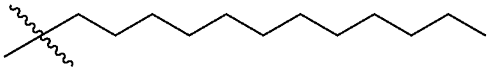 [SMILES: *CCCCCCCCCCCC] |
| $C_{14}H_{29}$ | 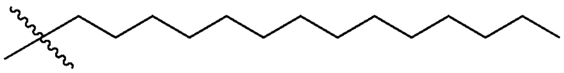 |
| $C_{16}H_{29}$ | 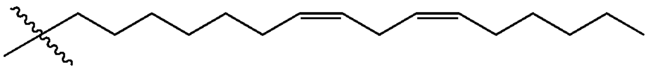 [SMILES: *CCCCCC/C=C\C/C=C\CCCCC] |
| $C_{16}H_{31}$ | 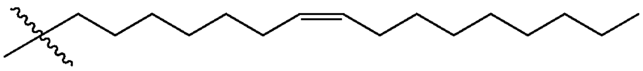 [SMILES: *CCCCCC/C=C\CCCCCCCC] |
| $C_{16}H_{33}$ | 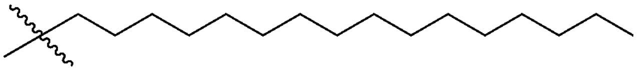 [SMILES: *CCCCCCCCCCCCCCCC] |

In embodiments, R7=—(CH2)kCH(OR11)RA, R8 is —(CH2)nCH(OR12)RB and RA and RB are the same and selected from:

| | |
|---|---|
| $C_8H_{17}$ | 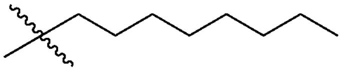 |
| $C_{10}H_{21}$ | 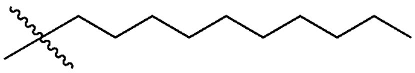 [SMILES: *CCCCCCCCCC] |
| $C_{12}H_{25}$ | 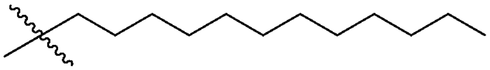 [SMILES: *CCCCCCCCCCCC] |
| $C_{14}H_{29}$ | 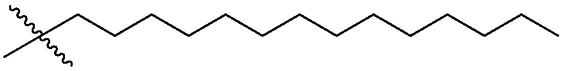 [SMILES: *CCCCCCCCCCCCCC] |
| $C_{16}H_{29}$ | 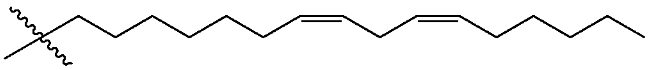 [SMILES: *CCCCCC/C=C\C/C=C\CCCCC] |
| $C_{16}H_{31}$ | 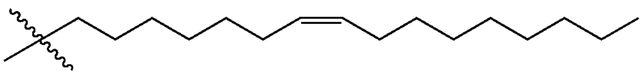 [SMILES: *CCCCCC/C=C\CCCCCCCC] |
| $C_{16}H_{33}$ | 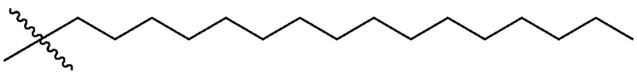 [SMILES: *CCCCCCCCCCCCCCCC] |

In embodiments, R7=—(CH2)kCH(OR11)RA, R8 is —(CH2)nCH(OR12)RB and RA and RB are both C8H17.

In embodiments, R7=—(CH2)kCH(OR11)RA, R8 is —(CH2)nCH(OR12)RB and RA and RB are both C10H21.

In embodiments, R7=—(CH2)kCH(OR11)RA, R8 is —(CH2)nCH(OR12)RB and RA and RB are both C12H25.

In embodiments, R7=—(CH2)kCH(OR11)RA, R8 is —(CH2)nCH(OR12)RB and RA and RB are both

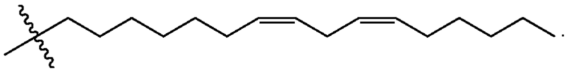 [SMILES: *CCCCCC/C=C\C/C=C\CCCCC]

In embodiments, X is O.

In embodiments, X is S.

In embodiments, only one of R1, R2, R3, R4 and R5 is —OC(O)R'. In embodiments, only one of R1, R2, R3, R4 and R5 is —OC(O)R' and none of R1, R2, R3, R4 or R5 are OH.

In embodiments, two of R1, R2, R3, R4 and R5 are —OC(O)R'. In embodiments, two of R1, R2, R3, R4 and R5 are —OC(O)R' and none of R1, R2, R3, R4 or R5 are OH.

In embodiments, three of R1, R2, R3, R4 and R5 are —OC(O)R'.

In embodiments, R1 is —OC(O)R'. In embodiments, R5 is —OC(O)R'. In embodiments, both R1 and R5 are —OC(O)R'.

In embodiments, R2 is —OC(O)R'. In embodiments, R4 is —OC(O)R'. In embodiments, both R2 and R4 are —OC(O)R'.

In embodiments, R3 is —OC(O)R'.

In embodiments, R3 is —OC(O)R' and R2 is OMe.

In embodiments, L1 is a bond, R3 is —OC(O)R' and R2 is OMe.

In embodiments, R3 is —OC(O)R' and R2 and R4 are OMe.

In embodiments, L1 is a bond, R3 is —OC(O)R' and R2 and R4 are OMe.

In embodiments, L1 is (C2-C6)alkenyl, R3 is —OC(O)R' and R2 and R4 are OMe.

In embodiments, L1 is C2 alkenyl, R3 is —OC(O)R' and R2 and R4 are OMe.

In embodiments, R7 is —(CH2)kCH(OR11)RA.

In embodiments, R7 is —(CH2)1CH(OR11)RA.

In embodiments, R7 is —(CH2)1CH(OH)RA.

In embodiments, R8 is —(CH2)nCH(OR12)RB.

In embodiments, R8 is —(CH2)1CH(OR12)RB.

In embodiments, R8 is —(CH2)1CH(OH)RB.

In embodiments, R7 is —(CH2)kCH(OR11)RA and R8 is —(CH2)nCH(OR12)RB.

In embodiments, R7 is —(CH2)1CH(OR11)RA and R8 is —(CH2)1CH(OR12)RB.

In embodiments, R7 is —(CH2)1CH(OH)RA and R8 is —(CH2)1CH(OH)RB.

In embodiments, R7 and R8 are each optionally substituted (C1-C6)alkyl, for example $(C_1\text{-}C_6)$alkyl substituted with $—CO_2R^{aa}$ wherein $R^{aa}$ is $C_1\text{-}C_{50}$ alkyl. In embodiments, $R^7$ and $R^8$ are each $(C_1\text{-}C_6)$alkyl substituted with $—CO_2R^{aa}$ wherein $R^{aa}$ $C_1\text{-}C_{40}$ alkyl. In embodiments, $R^7$ and $R^8$ are each $(C_1\text{-}C_6)$alkyl substituted with $—CO_2R^{aa}$ wherein $R^{aa}$ $C_1\text{-}C_{30}$ alkyl. In embodiments, $R^7$ and $R^8$ are each $(C_1\text{-}C_6)$alkyl substituted with $—CO_2R^{aa}$ wherein $R^{aa}$ $C_1\text{-}C_{20}$ alkyl.

In embodiments, R7 and R8 are the same and are each optionally substituted (C1-C6)alkyl, for example (C1-C6) alkyl substituted with —CO2Raa wherein Raa is C1-C50 alkyl. In embodiments, R7 and R8 are the same and are each (C1-C6)alkyl substituted with —CO2Raa wherein Raa C1-C40 alkyl. In embodiments, R7 and R8 are the same and are each (C1-C6)alkyl substituted with —CO2Raa wherein Raa C1-C30 alkyl. In embodiments, R7 and R8 are each (C1-C6)alkyl substituted with —CO2Raa wherein Raa C1-C20 alkyl.

In embodiments, R7 and R8 are each

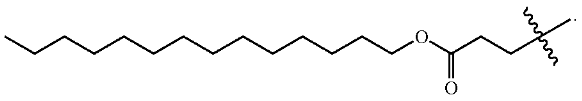 [SMILES: *CCC(=O)OCCCCCCCCCCCCCC]

In embodiments, R7 and R8 are each

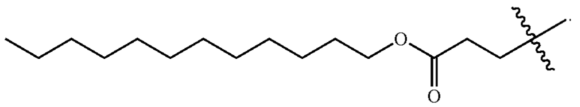 [SMILES: *CCC(=O)OCCCCCCCCCCCC]

In embodiments, R9 and R10 are each independently selected from H, optionally substituted (C1-C6)alkyl, optionally substituted (C2-C6)alkenyl, optionally substituted (C2-C6)alkynyl.

In embodiments, R9 and R10 are each independently optionally substituted (C1-C6)alkyl or optionally substituted (C2-C6)alkenyl.

In embodiments, R9 and R10 are both optionally substituted (C1-C6)alkyl or optionally substituted (C2-C6)alkenyl.

In embodiments, R9 and R10 are both optionally substituted (C1-C6)alkyl.

In embodiments, R9 and R10 are both —CH3.

In embodiments, R7 is —(CH2)kCH(OR11)RA, R8 is —(CH2)nCH(OR12)RB and R9 and R10 are both —CH3.

In embodiments, R7 is —(CH2)1CH(OR11)RA, R8 is —(CH2)1CH(OR12)RB and R9 and R10 are both —CH3.

In embodiments, R7 is —(CH2)1CH(OH)RA, R8 is —(CH2)1CH(OH)RB and R9 and R10 are both —CH3.

In embodiments, R7 is —(CH2)kCH(OR11)RA, R8 is —(CH2)nCH(OR12)RB, RA and RB are both C8H17 and R9 and R10 are both —CH3.

In embodiments, R7 is —(CH2)1CH(OH)RA, R8 is —(CH2)1CH(OH)RB, RA and RB are both C8H17 and R9 and R10 are both —CH3.

In embodiments, R7 is —(CH2)kCH(OR11)RA, R8 is —(CH2)nCH(OR12)RB, RA and RB are both C10H21 and R9 and R10 are both —CH3.

In embodiments, R7 is —(CH2)1CH(OH)RA, R8 is —(CH2)1CH(OH)RB, RA and RB are both C10H21 and R9 and R10 are both —CH3.

In embodiments, R7 is —(CH2)kCH(OR11)RA, R8 is —(CH2)nCH(OR12)RB, RA and RB are both C12H25 and R9 and R10 are both —CH3.

In embodiments, R7 is —(CH2)1CH(OH)RA, R8 is —(CH2)1CH(OH)RB, RA and RB are both C12H25 and R9 and R10 are both —CH3.

In embodiments, R7 is —(CH2)kCH(OR11)RA, R8 is —(CH2)nCH(OR12)RB, RA and RB are both C16H29 and R9 and R10 are both —CH3.

In embodiments, R7 is —(CH2)1CH(OH)RA, R8 is —(CH2)1CH(OH)RB, RA and RB are both C16H29 and R9 and R10 are both —CH3.

In embodiments, p, q and r are identical. In embodiments, one or more of p, q and r are different. In embodiments, q and r are identical and p is different. In embodiments, p and q are identical and r is different. In embodiments, p and r are identical and q is different. In embodiments, p, q and r are different.

In embodiments, k, m and n are identical. In embodiments, one or more of k, m and n are different. In embodiments, k and m are identical and n is different. In embodiments, m and n are identical and k is different. In embodiments, k and n are identical and m is different. In embodiments, k, m and n are different.

In embodiments, m is 1, 2, 3, 4 or 5. In embodiments, m is 0. In embodiments, m is 1. In embodiments, m is 2. In embodiments, m is 3. In embodiments, m is 4. In embodiments, m is 5. In embodiments m is 0, 1, 2, 3, or 4.

In embodiments, p is 1, 2, 3, 4 or 5. In embodiments, p is 0. In embodiments, p is 1. In embodiments, p is 2. In embodiments, p is 3. In embodiments, p is 4. In embodiments, p is 5. In embodiments p is 0, 1, 2, 3, or 4.

In embodiments, m is 2 and p is 2.

In embodiments, m is 3 and p is 2.

In embodiments, k and n=1 and m=2.

In embodiments, k and n=1 and m=3.

In embodiments, q and r=1 and p=2.

In embodiments, k, n, q, and r each=1, m=2 or 3, and p=2

In embodiments, R' is:

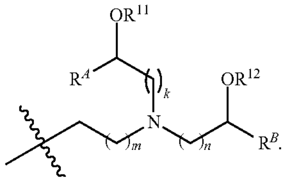

In embodiments, R' is

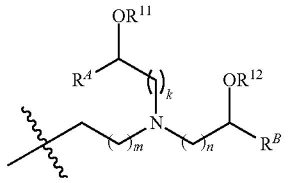

and k and n=1 and m=2 or 3.

In embodiments, R' is

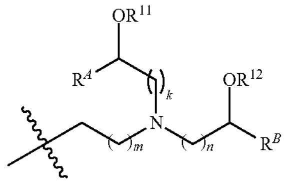

and k and n=1 and m=2.

In embodiments, R' is

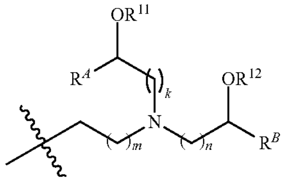

and k and n=1 and m=3.

In embodiments, R' is

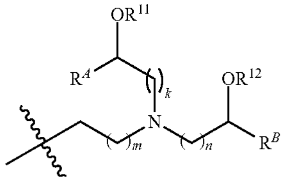

and $R^{11}$ and $R^{12}$ are H.

In embodiments, R' is

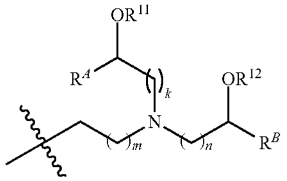

and k and n=1, m=2 or 3 and $R^{11}$ and $R^{12}$ are H.

In embodiments, R' is

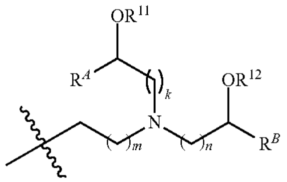

and k and n=1, m=2 and $R^{11}$ and $R^{12}$ are H.

In embodiments, R' is

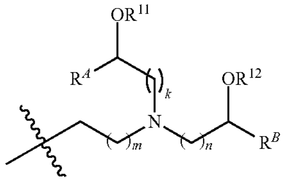

and k and n=1, m=3 and $R^{11}$ and $R^{12}$ are H.

In embodiments, R' is:
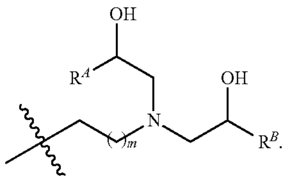
In any of the above embodiments, where R' has the structure below
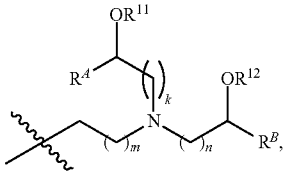
$R^A$ and $R^B$ can be as defined in any of the preceding.
In embodiments, $R^6$ is:
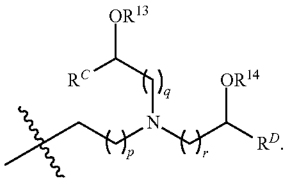
In embodiments, $R^6$ is
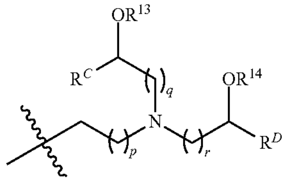
q and r=1 and p=2.
In embodiments, $R^6$ is
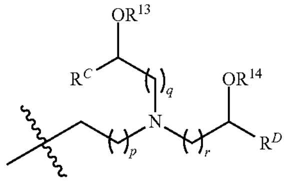
and $R^{13}$ and $R^{14}$ are H.
In embodiments, $R^6$ is
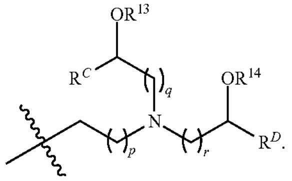
q and r=1, p=2 and $R^{13}$ and $R^{14}$ are H.
In embodiments, $R^6$ is selected from the group consisting of:
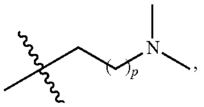
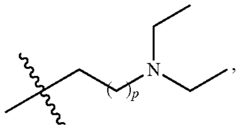
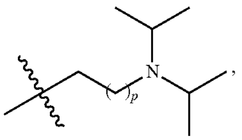
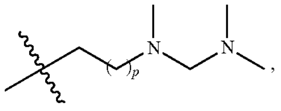
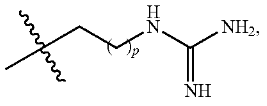
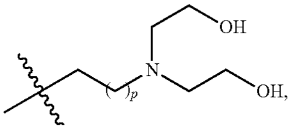
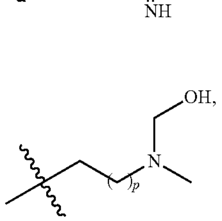
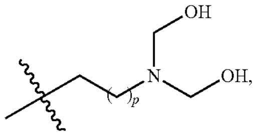
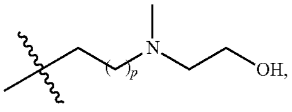
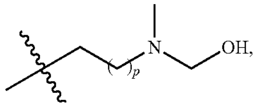
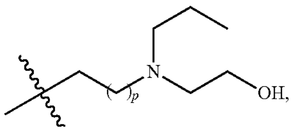
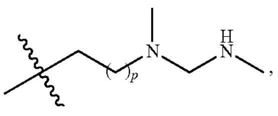
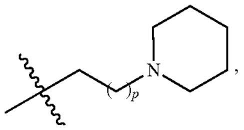
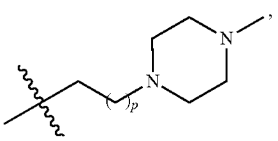
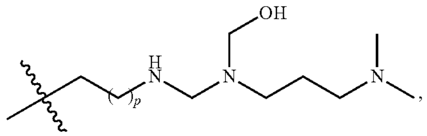

-continued
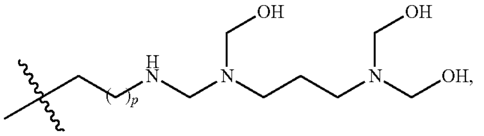
and
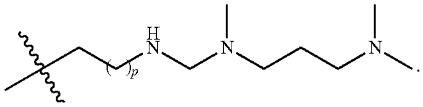
In embodiments, $R^6$ is selected from the group consisting of:
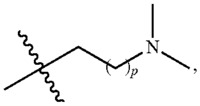
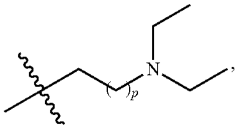
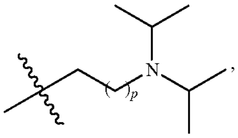
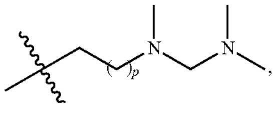
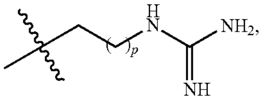
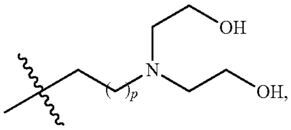
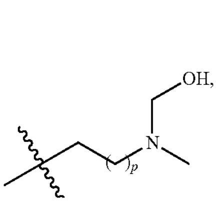
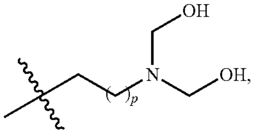
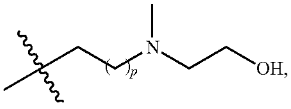
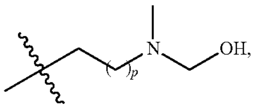
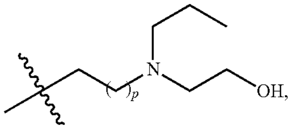
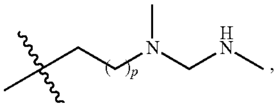
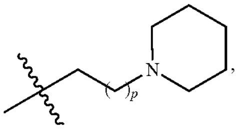
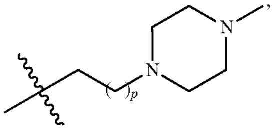
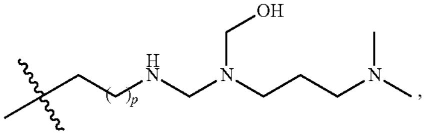
-continued
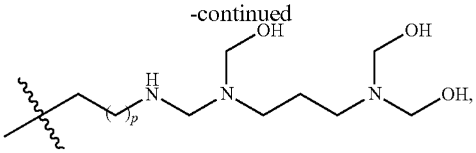
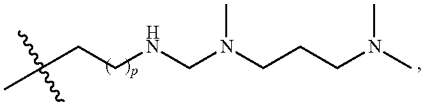
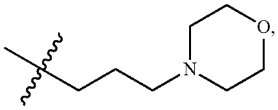
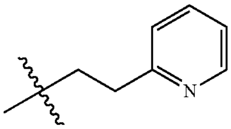
and
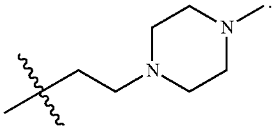
In embodiments, $R^6$ is selected from the group consisting of:
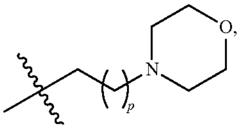
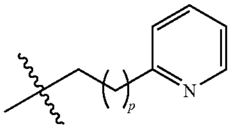
and
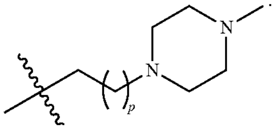
In embodiments, $R^6$ is:
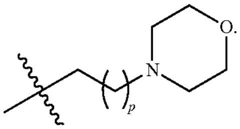
In embodiments, $R^6$ is:
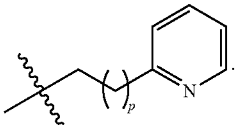
In embodiments, $R^6$ is:
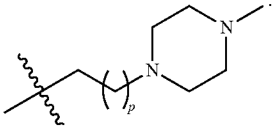

In embodiments, $R^6$ is selected from the group consisting of:

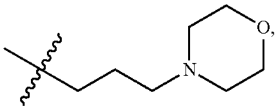

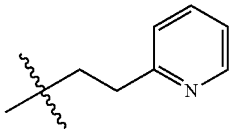

and

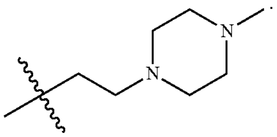

In embodiments, $R^6$ is:

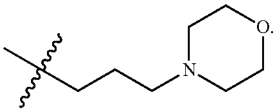 [SMILES: *CCCN1CCOCC1]

In embodiments, $R^6$ is:

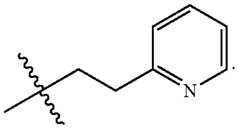 [SMILES: *CCc1ccccn1]

In embodiments, $R^6$ is:

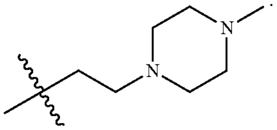 [SMILES: *CCN1CCN(C)CC1]

In embodiments, $R^6$ is:

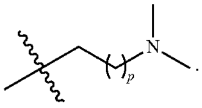

In embodiments, $R^6$ is:

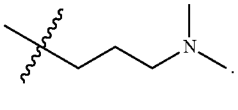

In embodiments, $R^6$ and R' are the same.

In embodiments, $R^6$ is

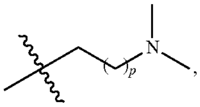

R' is

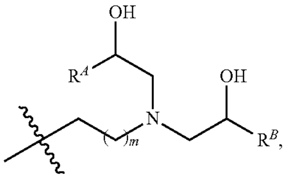

m is 2 and p is 2.

In embodiments, $R^6$ is

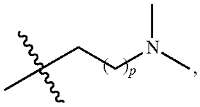

R' is

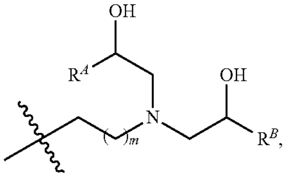

m is 3 and p is 2.

In embodiments, $L_1$ a bond, $R^3$ is —OC(O)R', $R^2$ and $R^4$ are OMe, $R^6$ is

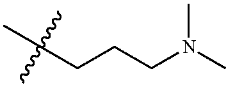

and R' is

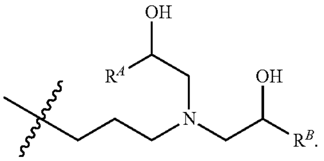

In embodiments, $L_1$ is a bond, $R^3$ is —OC(O)R', $R^2$ and $R^4$ are OMe, $R^6$ is

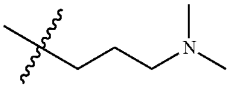

and R' is

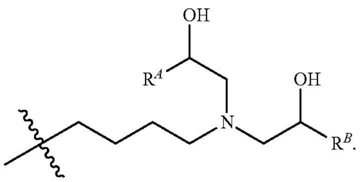

In embodiments, X═O, $L_1$ is a bond, $R^3$ is —OC(O)R', $R^2$ and $R^4$ are OMe, $R^6$ is

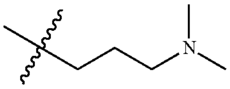

and R' is

-continued

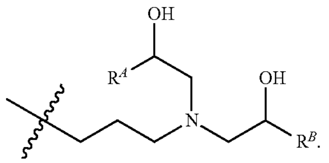

In embodiments, X═O, $L_1$ is a bond, $R^3$ is —OC(O)R', $R^2$ and $R^4$ are OMe, $R^1$ and $R^5$ are H, $R^6$ is

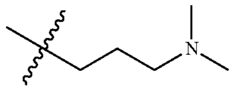 and R' is

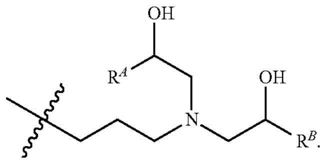

In embodiments, X═O, $L_1$ is a bond, $R^3$ is —OC(O)R', $R^2$ and $R^4$ are OMe, $R^6$ is

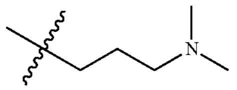 and R' is

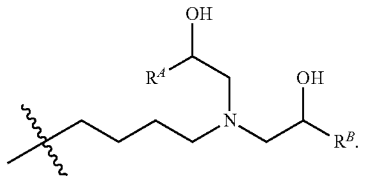

In embodiments, X═O, $L_1$ is a bond, $R^3$ is —OC(O)R', $R^2$ and $R^4$ are OMe, $R^1$ and $R^5$ are H, $R^6$ is

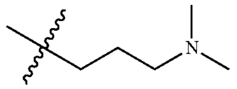 and R' is

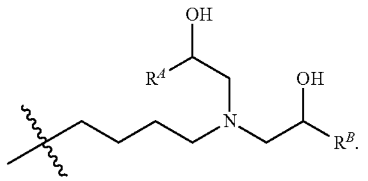

In embodiments, $L_1$ is a bond, $R^3$ is —OC(O)R', $R^2$ is OMe, $R^6$ is

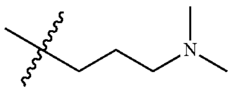 and R' is

-continued

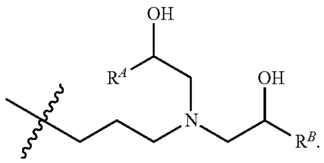

In embodiments, X═O, $L_1$ is a bond, $R^3$ is —OC(O)R', $R^2$ is OMe, $R^6$ is

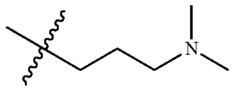 and R' is

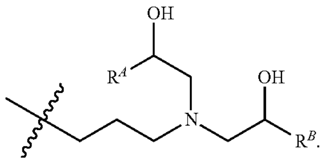

In embodiments, X═O, $L_1$ is a bond, $R^3$ is —OC(O)R', $R^2$ is OMe, $R^1$, $R^4$ and $R^5$ are H, $R^6$ is

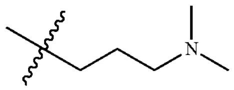 and R' is

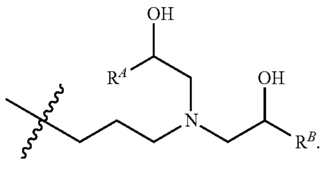

In embodiments, $L_1$ is a bond, $R^3$ is —OC(O)R', $R^2$ is OMe, $R^6$ is

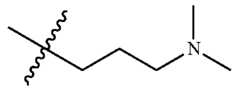 and R' is

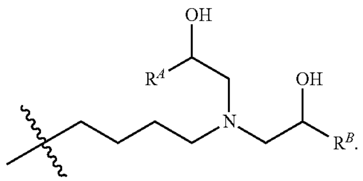

In embodiments, X═O, $L_1$ is a bond, $R^3$ is —OC(O)R', $R^2$ is OMe, $R^6$ is

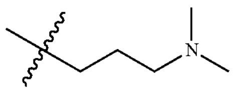 and R' is

-continued

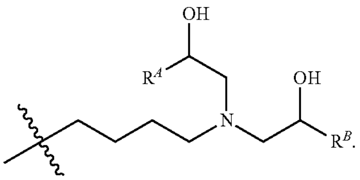

In embodiments, X═O, $L_1$ is a bond, $R^3$ is —OC(O)R', $R^2$ is OMe, $R^1$, $R^4$ and $R^5$ are H, $R^6$ is

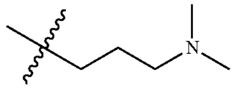
and R' is

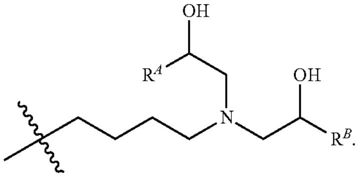

In embodiments, $L_1$ is C2 alkenyl, $R^3$ is —OC(O)R', $R^2$ and $R^4$ are OMe, $R^6$ is

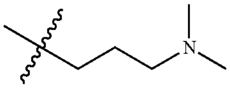
and R' is

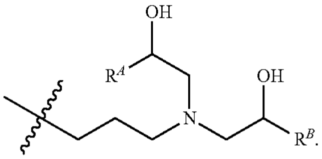

In embodiments, $L_1$ is C2 alkenyl, $R^3$ is —OC(O)R', $R^2$ and $R^4$ are OMe, $R^6$ is

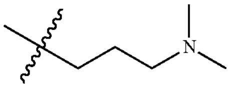
and R' is

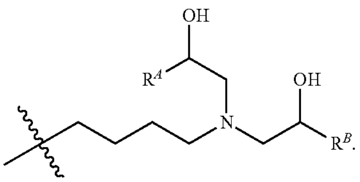

In embodiments, X═O, $L_1$ is C2 alkenyl, $R^3$ is —OC(O) R', $R^2$ and $R^4$ are OMe, $R^6$ is

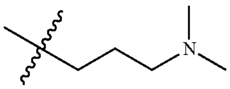
and R' is

-continued

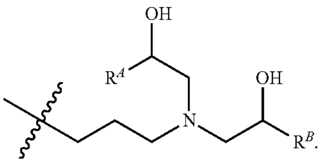

In embodiments, X═O, $L_1$ is C2 alkenyl, $R^3$ is —OC(O) R', $R^2$ and $R^4$ are OMe, $R^1$ and $R^5$ are H, $R^6$ is

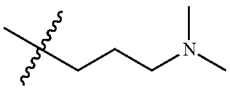
and R' is

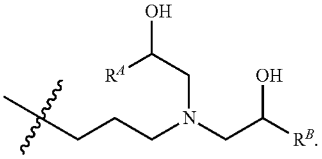

In embodiments, X═O, $L_1$ is C2 alkenyl, $R^3$ is —OC(O) R', $R^2$ and $R^4$ are OMe, $R^6$ is

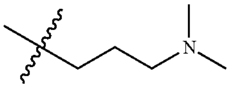
and R' is

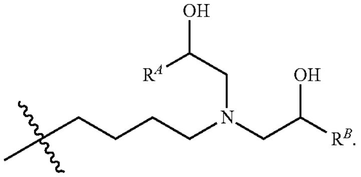

In embodiments, X═O, $L_1$ is C2 alkenyl, $R^3$ is —OC(O) R', $R^2$ and $R^4$ are OMe, $R^1$ and $R^5$ are H, $R^6$ is
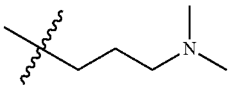
and R' is

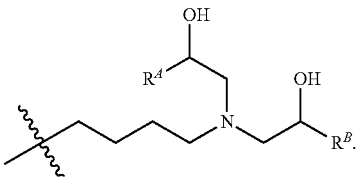

In embodiments, $R^6$ is

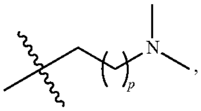
, R' is

-continued

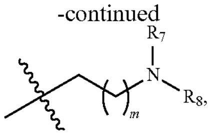

$R^7$ and $R^8$ are each $(C_1\text{-}C_6)$alkyl substituted with $—CO_2R^{aa}$ wherein $R^{aa}$ is $C_1\text{-}C_{50}$ alkyl.

In embodiments, $R^6$ is

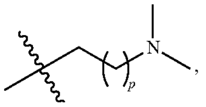

, R' is

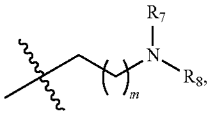

$R^7$ and $R^8$ are each $(C_1\text{-}C_6)$alkyl substituted with $—CO_2R^{aa}$ wherein $R^{aa}$ is $C_1\text{-}C_{50}$ alkyl, m is 2 and p is 2. In some embodiments $R^7$ and $R^8$ are the same. In some embodiments $L_1$ is a bond, $R^3$ is —OC(O)R', $R^2$ and $R^4$ are OMe.

In embodiments, $L_1$ is a bond, $R^3$ is —OC(O)R', $R^2$ and $R^4$ are OMe, $R^6$ is

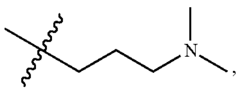

, R' is

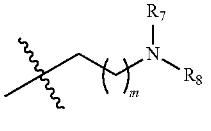

and $R^7$ and $R^8$ are each $(C_1\text{-}C_6)$alkyl substituted with $—CO_2R^{aa}$ wherein $R^{aa}$ is $C_1\text{-}C_{50}$ alkyl. In some embodiments $R^7$ and $R^8$ are the same.

In embodiments, $L_1$ is a bond, $R^3$ is —OC(O)R', $R^2$ and $R^4$ are OMe, $R^6$ is

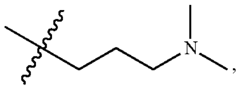

, R' is

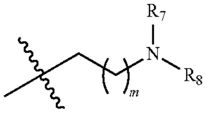

and $R^7$ and $R^8$ are each $(C_1\text{-}C_6)$alkyl substituted with $—CO_2R^{aa}$ wherein $R^{aa}$ is $C_1\text{-}C_{50}$ alkyl and m is 2. In some embodiments $R^7$ and $R^8$ are the same.

In embodiments, X═O, $L_1$ is a bond, $R^3$ is —OC(O)R', $R^2$ and $R^4$ are OMe, $R^6$ is

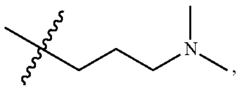

, R' is

-continued

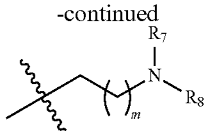

and $R^7$ and $R^8$ are each $(C_1\text{-}C_6)$alkyl substituted with $—CO_2R^{aa}$ wherein $R^{aa}$ is $C_1\text{-}C_{50}$ alkyl. In some embodiments $R^7$ and $R^8$ are the same. In some embodiments m is 2.

In embodiments, X═O, $L_1$ is a bond, $R^3$ is —OC(O)R', $R^2$ and $R^4$ are OMe, $R^1$ and $R^5$ are H, $R^6$ is

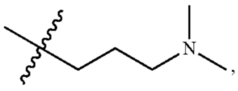

, R' is

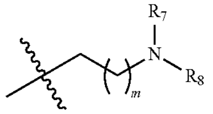

and $R^7$ and $R^8$ are each $(C_1\text{-}C_6)$alkyl substituted with $—CO_2R^{aa}$ wherein $R^{aa}$ is $C_1\text{-}C_{50}$ alkyl. In some embodiments $R^7$ and $R^8$ are the same. In some embodiments m is 2.

In embodiments, X═O, $L_1$ is a bond, $R^3$ is —OC(O)R', $R^2$ and $R^4$ are OMe, $R^6$ is

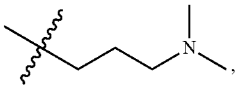

, R' is

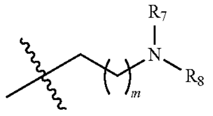

and $R^7$ and $R^8$ are each $(C_1\text{-}C_6)$alkyl substituted with $—CO_2R^{aa}$ wherein $R^{aa}$ is $C_1\text{-}C_{50}$ alkyl, and m is 2. In some embodiments $R^7$ and $R^8$ are the same.

In embodiments, X═O, $L_1$ is a bond, $R^3$ is —OC(O)R', $R^2$ and $R^4$ are OMe, $R^1$ and $R^5$ are H, $R^6$ is

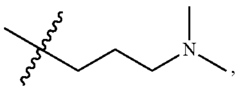

, R' is

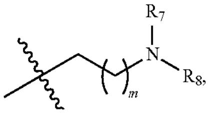

$R^7$ and $R^8$ are each $(C_1\text{-}C_6)$alkyl substituted with $—CO_2R^{aa}$ wherein $R^{aa}$ is $C_1\text{-}C_{50}$ alkyl and m is 2. In some embodiments $R^7$ and $R^8$ are the same.

In embodiments, $L_1$ is a bond, $R^3$ is —OC(O)R', $R^2$ is OMe, $R^6$ is

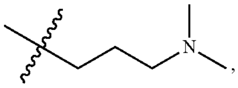

, R' is

-continued

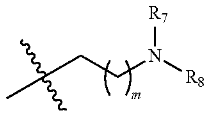

and $R^7$ and $R^8$ are each $(C_1\text{-}C_6)$ alkyl substituted with $—CO_2R^{aa}$ wherein $R^{aa}$ is $C_1\text{-}C_{50}$ alkyl. In some embodiments $R^7$ and $R^8$ are the same. In some embodiments m is 2.

In embodiments, X═O, $L_1$ is a bond, $R^3$ is —OC(O)R', $R^2$ is OMe, $R^6$ is

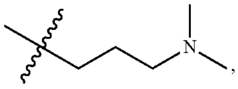, R' is 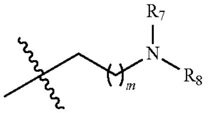

and $R^7$ and $R^8$ are each $(C_1\text{-}C_6)$alkyl substituted with $—CO_2R^{aa}$ wherein $R^{aa}$ is $C_1\text{-}C_{50}$ alkyl. In some embodiments $R^7$ and $R^8$ are the same. In some embodiments m is 2.

In embodiments, X═O, $L_1$ is a bond, $R^3$ is —OC(O)R', $R^2$ is OMe, $R^1$, $R^4$ and $R^5$ are H, $R^6$ is

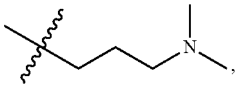, R' is 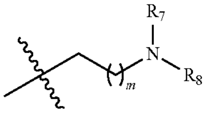

and $R^7$ and $R^8$ are each $(C_1\text{-}C_6)$alkyl substituted with $—CO_2R^{aa}$ wherein $R^{aa}$ is $C_1\text{-}C_{50}$ alkyl. In some embodiments $R^7$ and $R^8$ are the same. In some embodiments m is 2.

In embodiments, $L_1$ is a bond, $R^3$ is —OC(O)R', $R^2$ is OMe, $R^6$ is

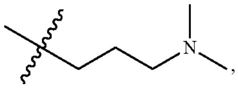, R' is 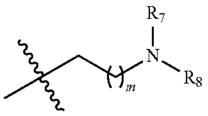

and $R^7$ and $R^8$ are each $(C_1\text{-}C_6)$alkyl substituted with $—CO_2R^{aa}$ wherein $R^{aa}$ is $C_1\text{-}C_{50}$ alkyl and m is 2. In some embodiments $R^7$ and $R^8$ are the same.

In embodiments, X═O, $L_1$ is a bond, $R^3$ is —OC(O)R', $R^2$ is OMe, $R^1$, $R^4$ and $R^5$ are H, $R^6$ is

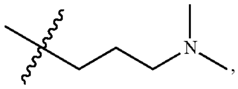, R' is 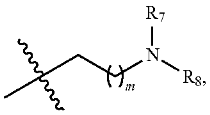

$R^7$ and $R^8$ are each $(C_1\text{-}C_6)$alkyl substituted with $—CO_2R^{aa}$ wherein $R^{aa}$ is $C_1\text{-}C_{50}$ alkyl, and m is 2. In some embodiments $R^7$ and $R^8$ are the same.

In embodiments, $L_1$ is $C_2$ alkenyl, $R^3$ is —OC(O)R', $R^2$ and $R^4$ are OMe, $R^6$ is

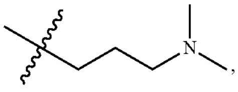, R' is 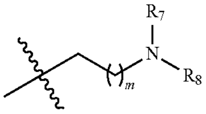

and $R^7$ and $R^8$ are each $(C_1\text{-}C_6)$alkyl substituted with $—CO_2R^{aa}$ wherein $R^{aa}$ is $C_1\text{-}C_{50}$ alkyl. In some embodiments $R^7$ and $R^8$ are the same.

In embodiments, $L_1$ is $C_2$ alkenyl, $R^3$ is —OC(O)R', $R^2$ and $R^4$ are OMe, $R^6$ is

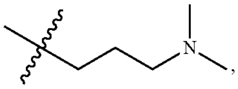, R' is 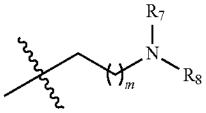

and $R^7$ and $R^8$ are each $(C_1\text{-}C_6)$alkyl substituted with $—CO_2R^{aa}$ wherein $R^{aa}$ is $C_1\text{-}C_{50}$ alkyl and m is 2. In some embodiments $R^7$ and $R^8$ are the same.

In embodiments, X═O, $L_1$ is $C_2$ alkenyl, $R^3$ is —OC(O)R', $R^2$ and $R^4$ are OMe, $R^6$ is

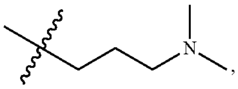, R' is 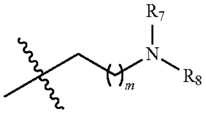

and $R^7$ and $R^8$ are each $(C_1\text{-}C_6)$alkyl substituted with $—CO_2R^{aa}$ wherein $R^{aa}$ is $C_1\text{-}C_{50}$ alkyl. In some embodiments $R^7$ and $R^8$ are the same.

In embodiments, X═O, $L_1$ is $C_2$ alkenyl, $R^3$ is —OC(O)R', $R^2$ and $R^4$ are OMe, $R^1$ and $R^5$ are H, $R^6$ is

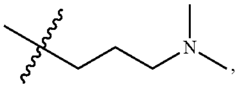, R' is 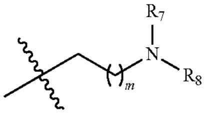

and $R^7$ and $R^8$ are each $(C_1\text{-}C_6)$ alkyl substituted with $—CO_2R^{aa}$ wherein $R^{aa}$ is $C_1\text{-}C_{50}$ alkyl. In some embodiments $R^7$ and $R^8$ are the same.

In embodiments, X═O, $L_1$ is $C_2$ alkenyl, $R^3$ is —OC(O)R', $R^2$ and $R^4$ are OMe, $R^6$ is

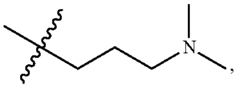 [SMILES: *CCCN(C)C], R' is 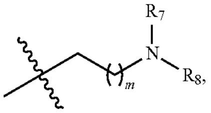

$R^7$ and $R^8$ are each $(C_1\text{-}C_6)$alkyl substituted with $—CO_2R^{aa}$ wherein $R^{aa}$ is $C_1\text{-}C_{50}$ alkyl and m is 2. In some embodiments $R^7$ and $R^8$ are the same.

In embodiments, X=O, $L_1$ is $C_2$ alkenyl, $R^3$ is —OC(O)R', $R^2$ and $R^4$ are OMe, $R^1$ and $R^5$ are H, $R^6$ is

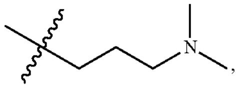

, R' is

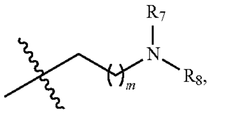

$R^7$ and $R^8$ are each $(C_1$-$C_6)$alkyl substituted with —$CO_2R^{aa}$ wherein $R^{aa}$ is $C_1$-$C_{50}$ alkyl and m is 2. In some embodiments $R^7$ and $R^8$ are the same.

In any of the above embodiments, where $R^7$ and $R^8$ are $(C_1$-$C_6)$alkyl substituted with —$CO_2R^{aa}$ wherein $R^{aa}$ is $C_1$-$C_{50}$ alkyl, $R^{aa}$ can instead be $C_1$-$C_{40}$ alkyl.

In any of the above embodiments, where $R^7$ and $R^8$ are $(C_1$-$C_6)$alkyl substituted with —$CO_2R^{aa}$ wherein $R^{aa}$ is $C_1$-$C_{50}$ alkyl, $R^{aa}$ can instead be $C_1$-$C_{30}$ alkyl.

In any of the above embodiments, where $R^7$ and $R^8$ are $(C_1$-$C_6)$alkyl substituted with —$CO_2R^{aa}$ wherein $R^{aa}$ is $C_1$-$C_{50}$ alkyl, $R^{aa}$ can instead be $C_1$-$C_{20}$ alkyl.

In any of the embodiments, where $R^7$ and $R^8$ are $(C_1$-$C_6)$ alkyl substituted with —$CO_2R^{aa}$ wherein $R^{aa}$ is $C_1$-$C_{50}$ alkyl, $R^7$ and $R^8$ can each be

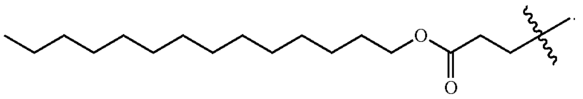 [SMILES: *CCC(=O)OCCCCCCCCCCCCCC]

In any of the embodiments, where $R^7$ and $R^8$ are each $(C_1$-$C_6)$alkyl substituted with —$CO_2R^{aa}$ wherein $R^{aa}$ is $C_1$-$C_{50}$ alkyl, $R^7$ and $R^8$ can each be

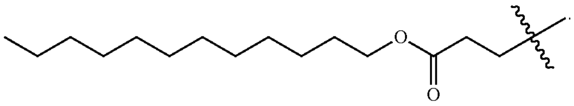 [SMILES: *CCC(=O)OCCCCCCCCCCCC]

In embodiments, the cationic lipids of the present invention include compounds having a structure according to Formula (II):

(II)

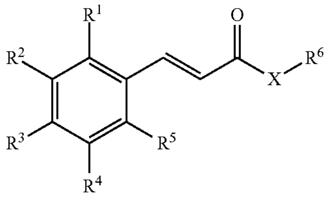

or a pharmaceutically acceptable salt thereof wherein $R^1$-$R^6$ and X are as already defined herein.

In embodiments, the cationic lipids of the present invention include compounds having a structure according to Formula (IIA):

(IIA)

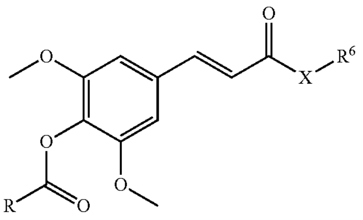

or a pharmaceutically acceptable salt thereof wherein R', $R^6$ and X are as already defined herein.

In embodiments, the cationic lipids of the present invention include compounds having a structure according to Formula (IIB), (IIC), (IID), (IIE), (IIJ), or (IIK):

(IIB)

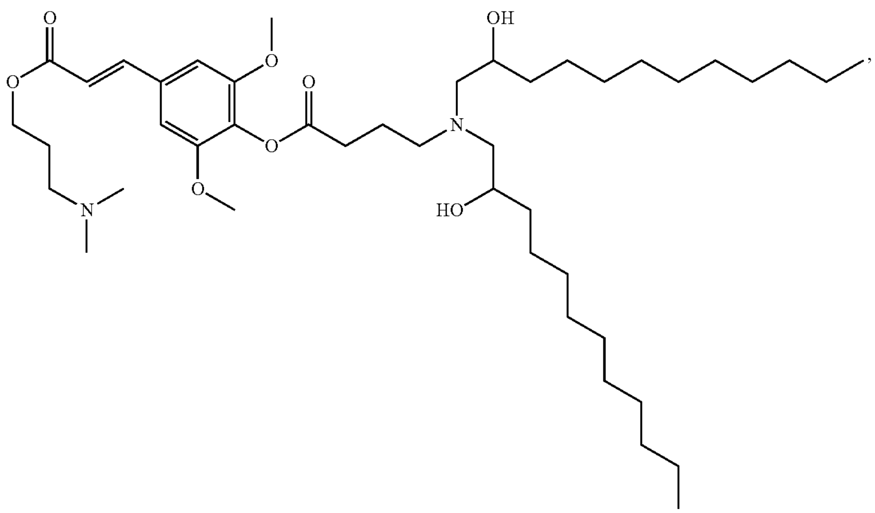

-continued
(IIC)
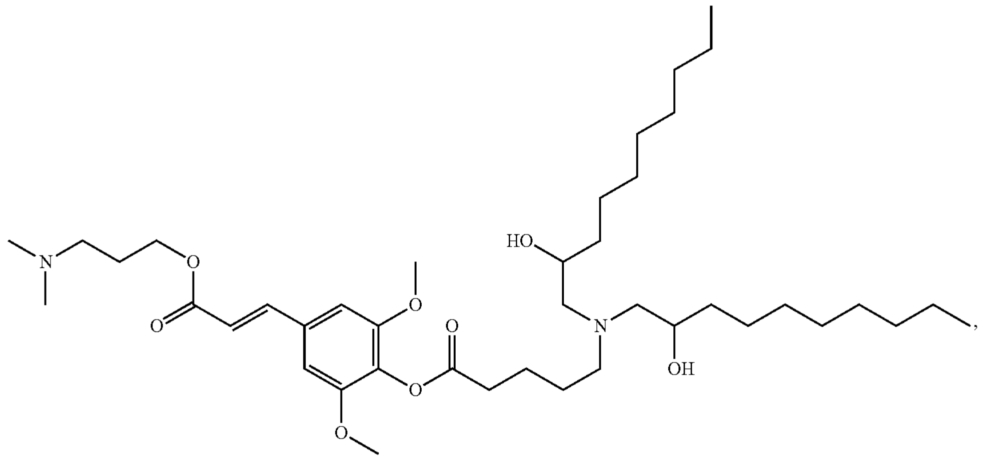
(IID)
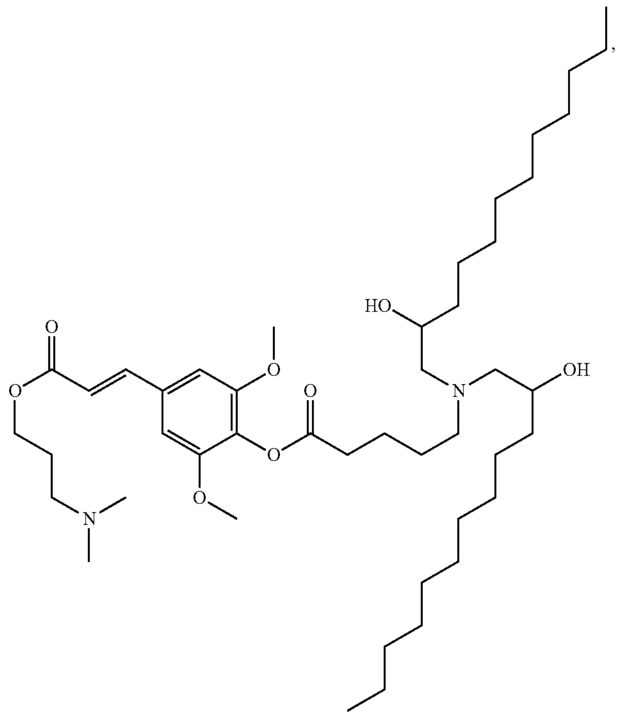

-continued
(IIE)
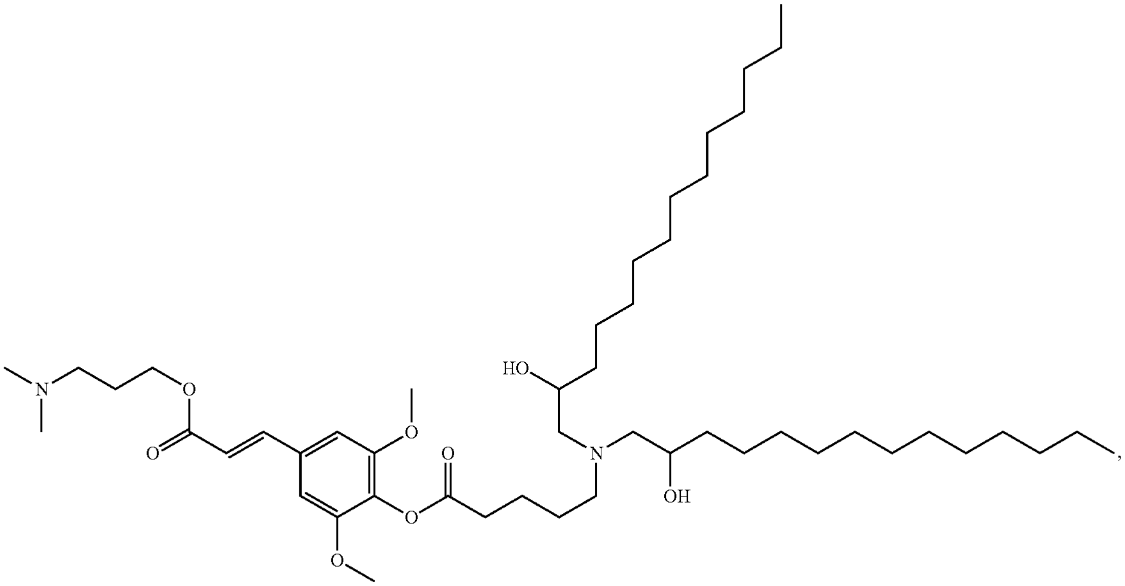
(IIJ)
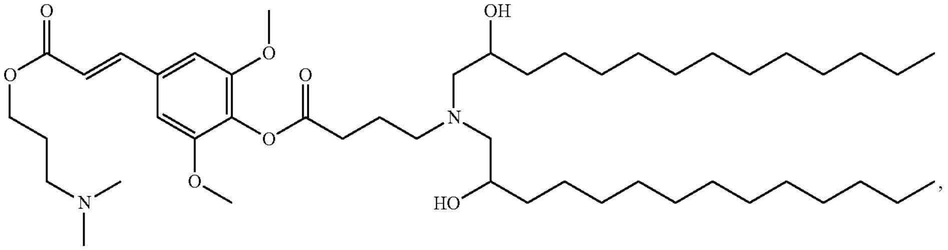
or
(IIK)
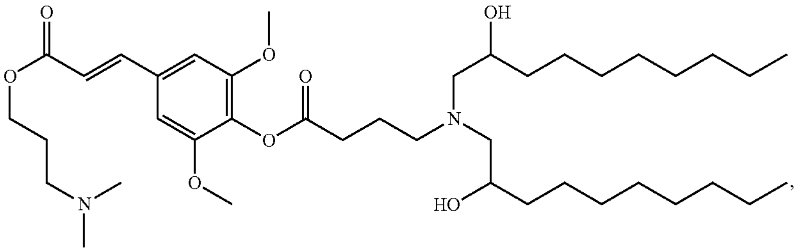
or a pharmaceutically acceptable salt thereof.

In embodiments, the cationic lipids of the present invention have the structure:
(IIB)
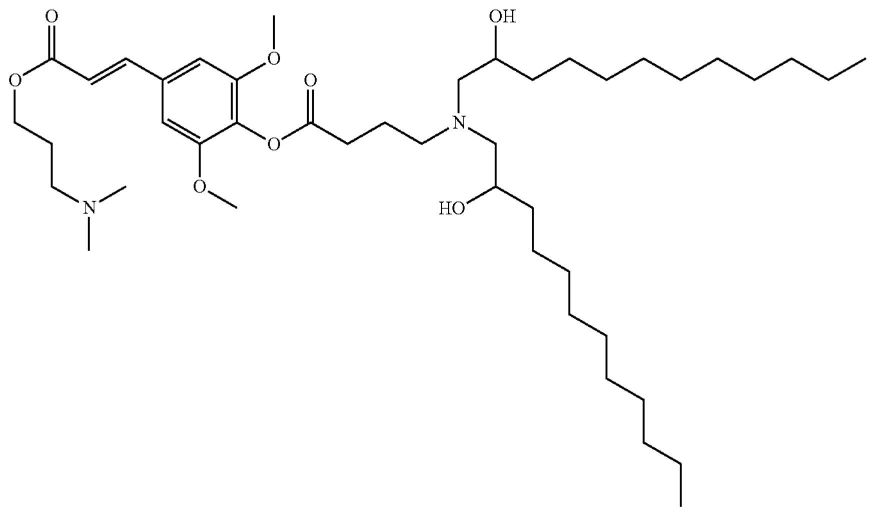
or a pharmaceutically acceptable salt thereof.
In embodiments, the cationic lipids of the present invention have the structure:
(IIC)
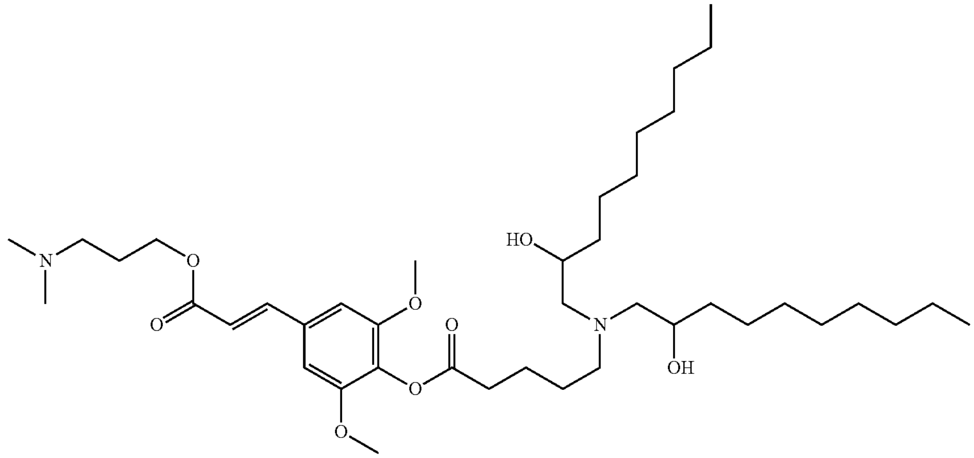
or a pharmaceutically acceptable salt thereof.

In embodiments, the cationic lipids of the present invention have the structure:
(IID)
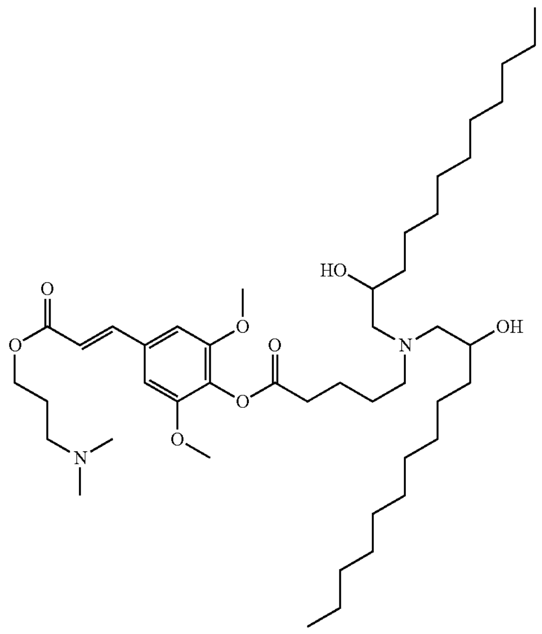
or a pharmaceutically acceptable salt thereof.
In embodiments, the cationic lipids of the present invention have the structure:
(IIE)
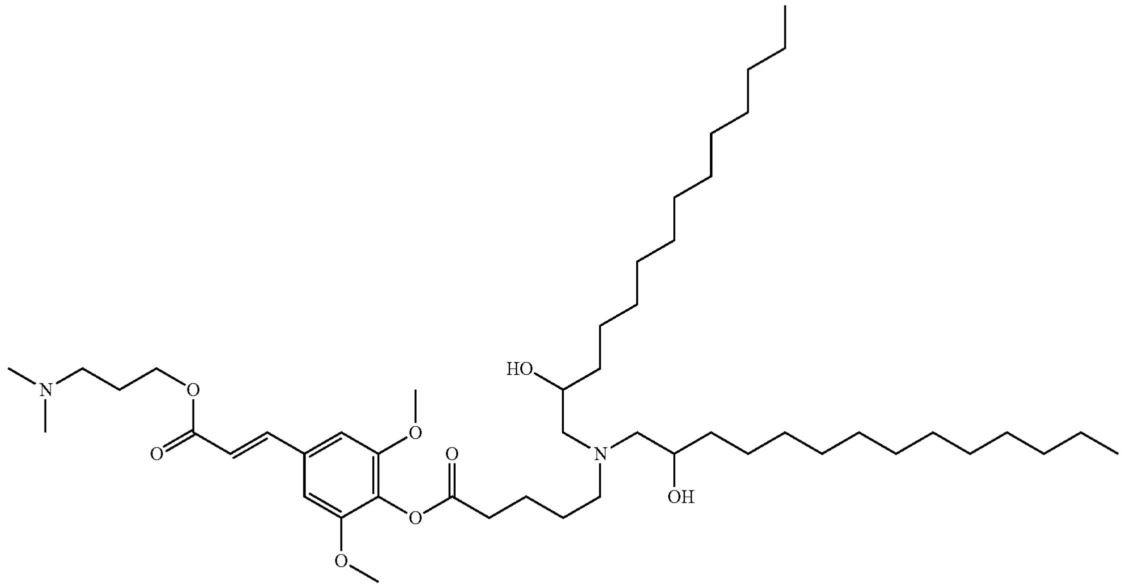
or a pharmaceutically acceptable salt thereof.

In embodiments, the cationic lipids of the present invention include compounds having a structure according to Formula (IIF):

(IIF)

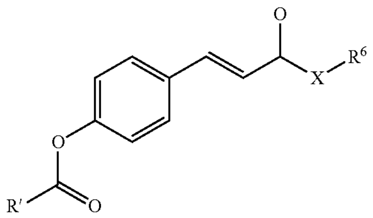

or a pharmaceutically acceptable salt thereof wherein R', $R^6$ and X are as already defined herein.

In embodiments, the cationic lipids of the present invention include compounds having a structure according to Formula (IIG):

(IIG)

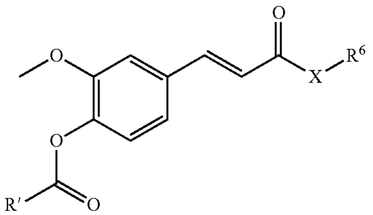

or a pharmaceutically acceptable salt thereof wherein R', $R^6$ and X are as already defined herein.

In embodiments, the cationic lipids of the present invention include compounds having a structure according to Formula (IIH):

(IIH)

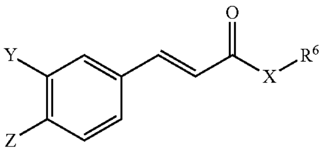

wherein one of Y and Z is OH and the other is —OC(O)R', or wherein both Y and Z are each independently —OC(O)R', and wherein R', $R^6$ and X are as already defined herein.

In embodiments, the cationic lipids of the present invention include compounds having a structure according to Formula (III):

(III)

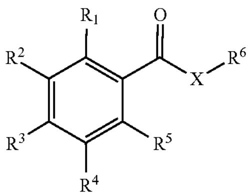

or a pharmaceutically acceptable salt thereof wherein $R^1$-$R^6$ and X are as already defined herein.

In embodiments, the cationic lipids of the present invention include compounds having a structure according to Formula (IIIA):

(IIIA)

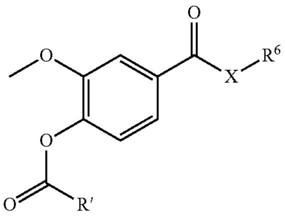

or a pharmaceutically acceptable salt thereof wherein R', $R^6$ and X are as already defined herein.

In embodiments, the cationic lipids of the present invention include compounds having a structure according to Formula (IIIB):

(IIIB)

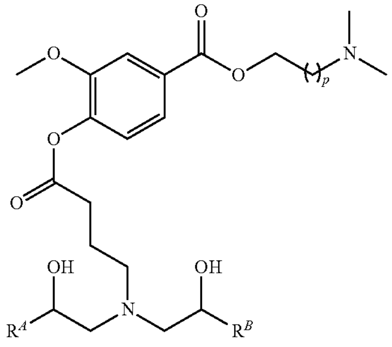

or a pharmaceutically acceptable salt thereof wherein $R^A$, $R^B$ and p are as already defined herein.

In embodiments, the cationic lipids of the present invention have the structure:

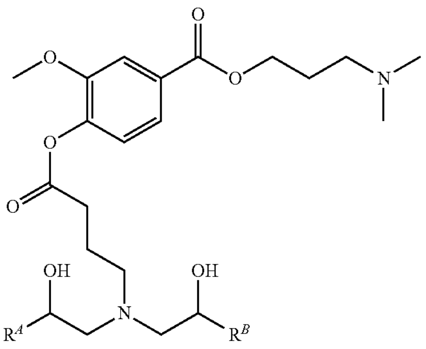

or a pharmaceutically acceptable salt thereof wherein $R^A$ and $R^B$ are as already defined herein.

In embodiments, the cationic lipids of the present invention have the structure:

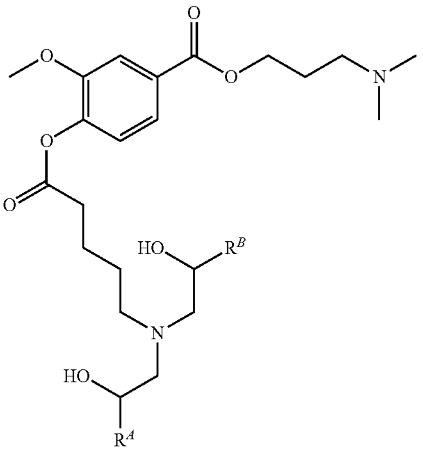

or a pharmaceutically acceptable salt thereof wherein $R^A$ and $R^B$ are as already defined herein.

In embodiments, the cationic lipids of the present invention have the structure:

(IIIC)

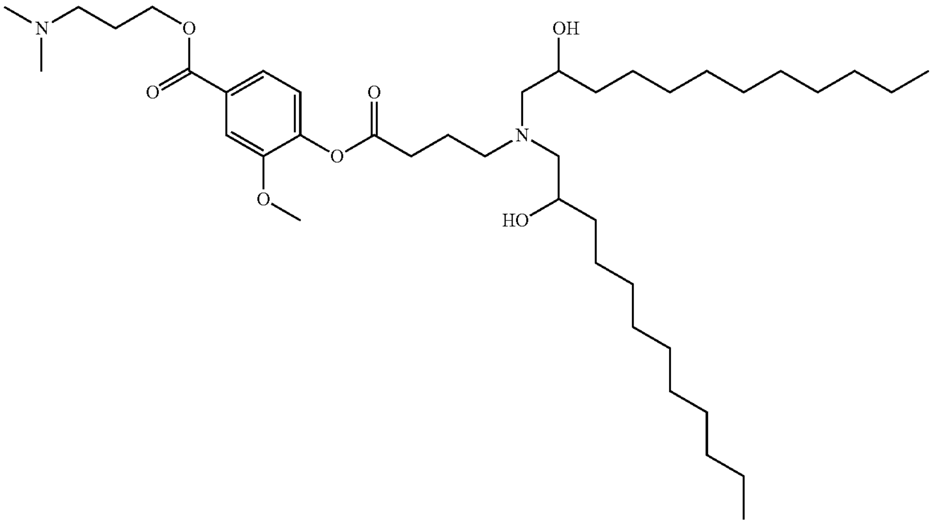

or a pharmaceutically acceptable salt thereof.

In embodiments, the cationic lipids of the present invention have the structure:

(IIIM)

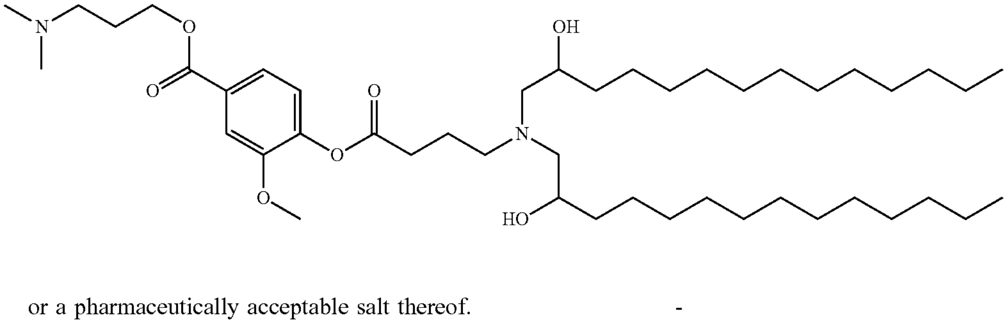

or a pharmaceutically acceptable salt thereof.

In embodiments, the cationic lipids of the present invention include compounds having a structure according to Formula (IIID):

(IIID)

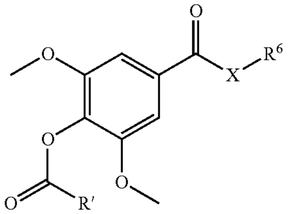

or a pharmaceutically acceptable salt thereof wherein R', $R^6$ and X are as already defined herein.

In embodiments, the cationic lipids of the present invention include compounds having a structure according to Formula (IIIE), (IIIF), (IIIG), (IIIH), (IIII), (IIIJ) or (IIIK):

(IIIE)

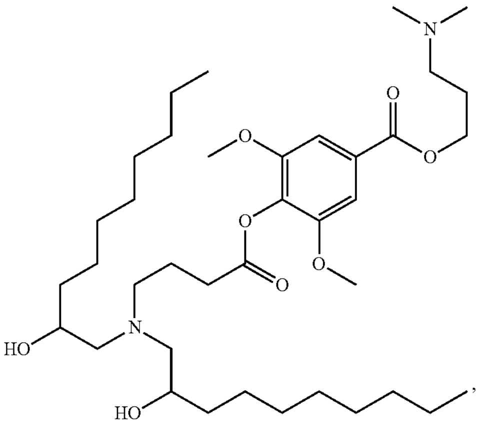

, (IIIF)

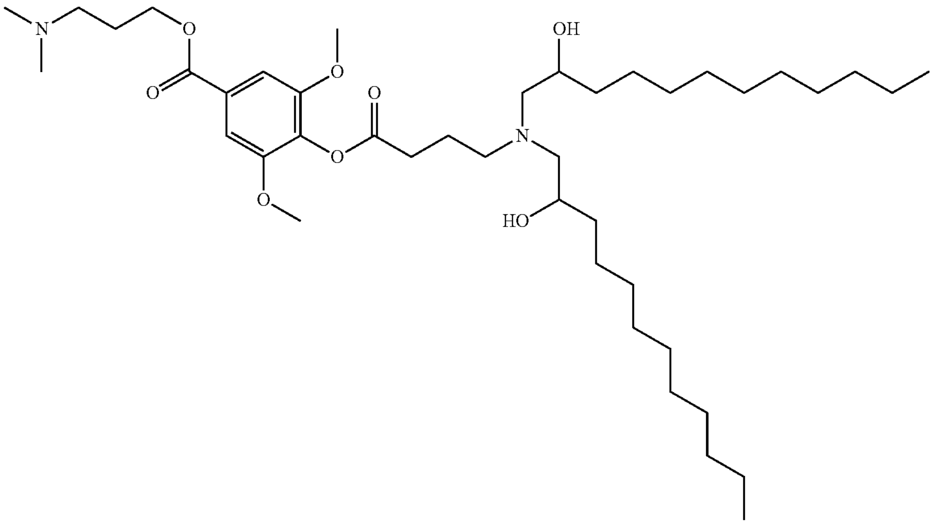

,

-continued
(IIIG)
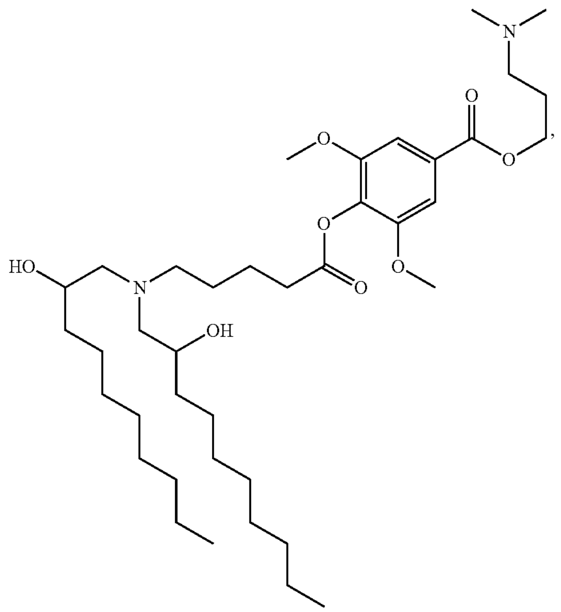
(IIIH)
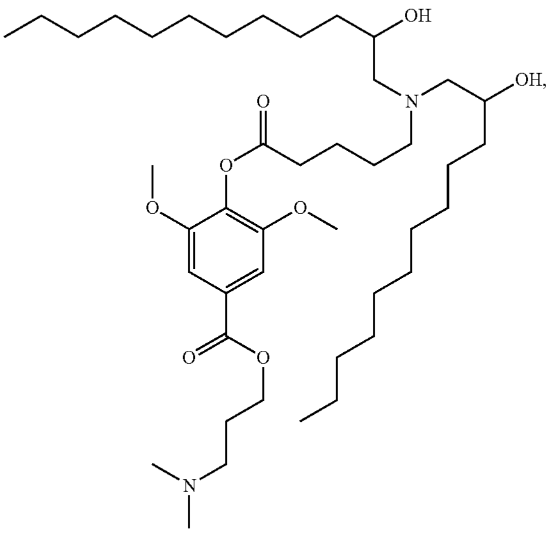
(IIII)
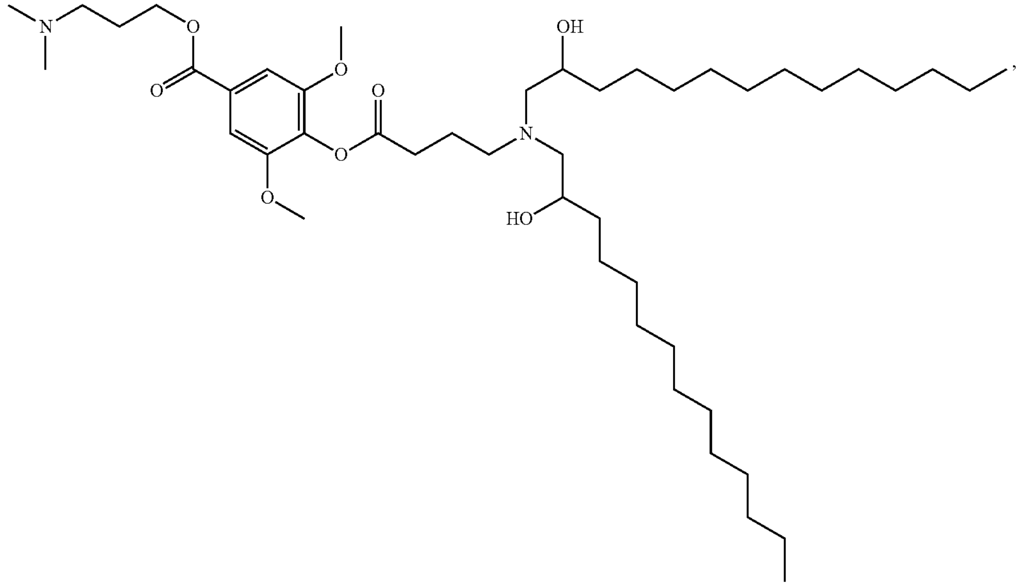

-continued
(IIIJ)
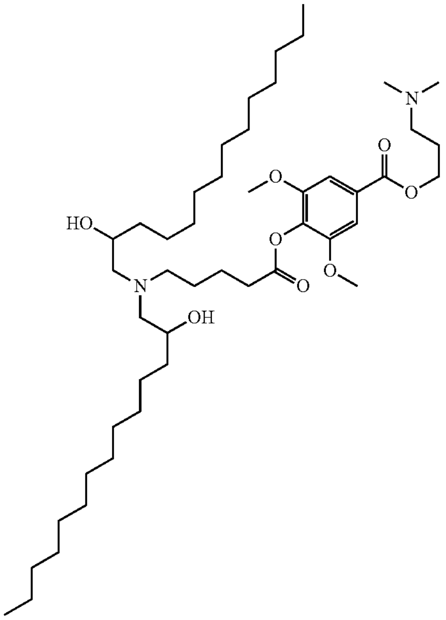
or
(IIIK)
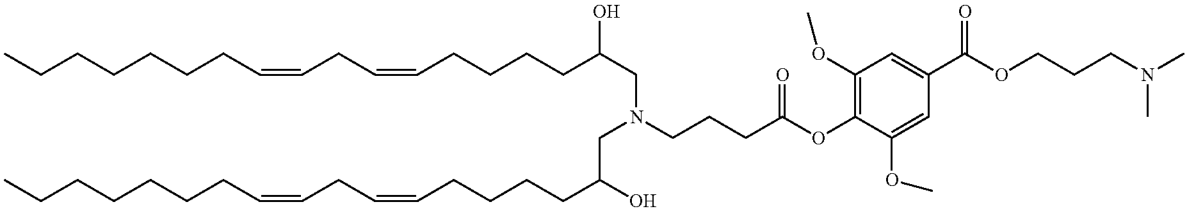
or a pharmaceutically acceptable salt thereof.
In embodiments, the cationic lipids of the present invention have the structure:
(IIIE)
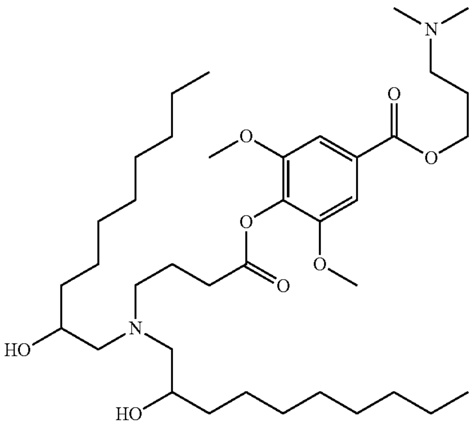

In embodiments, the cationic lipids of the present invention have the structure:
(IIIF)
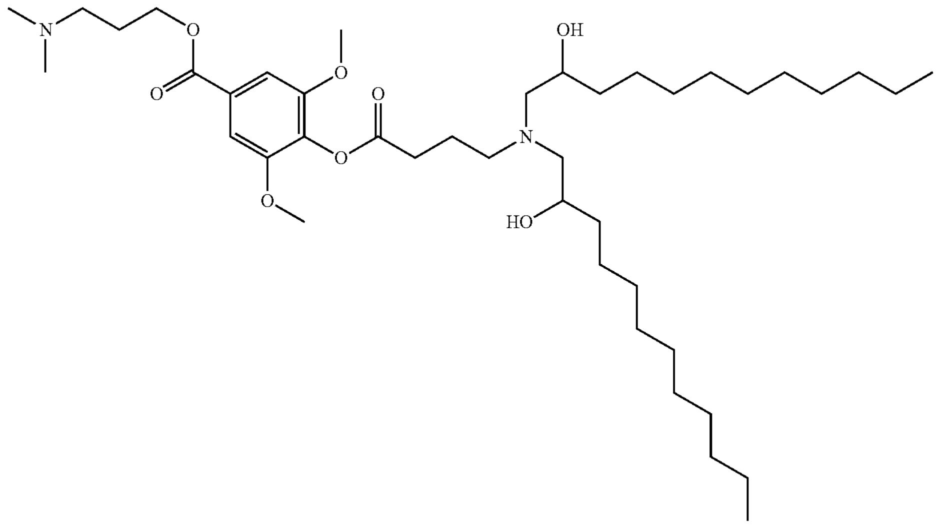
In embodiments, the cationic lipids of the present invention have the structure:
(IIIG)
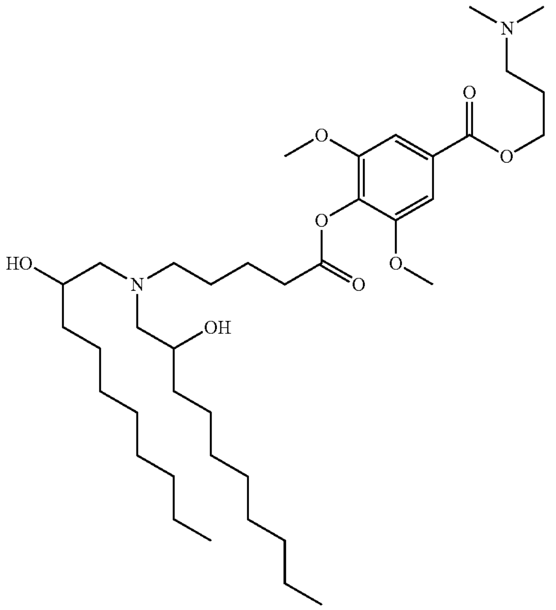
In embodiments, the cationic lipids of the present invention have the structure:
(IIIH)
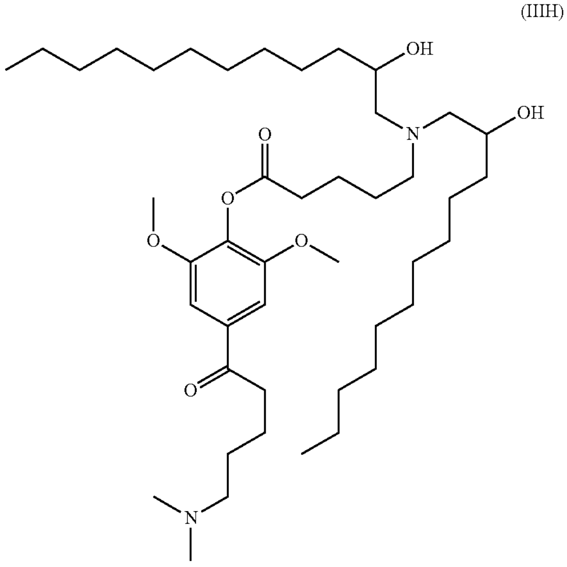 [SMILES: CCCCCCCCCCC(O)CN(CCCCC(=O)Oc1c(OC)cc(C(=O)CCCCN(C)C)cc1OC)CC(O)CCCCCCCCCC]

In embodiments, the cationic lipids of the present invention have the structure:
(IIII)
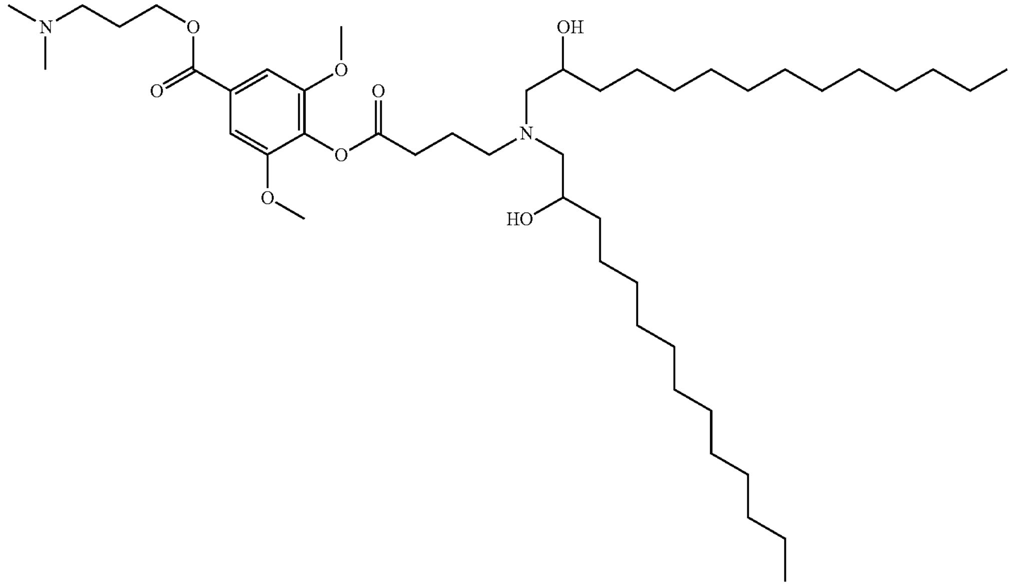
In embodiments, the cationic lipids of the present invention have the structure:
(IIIJ)
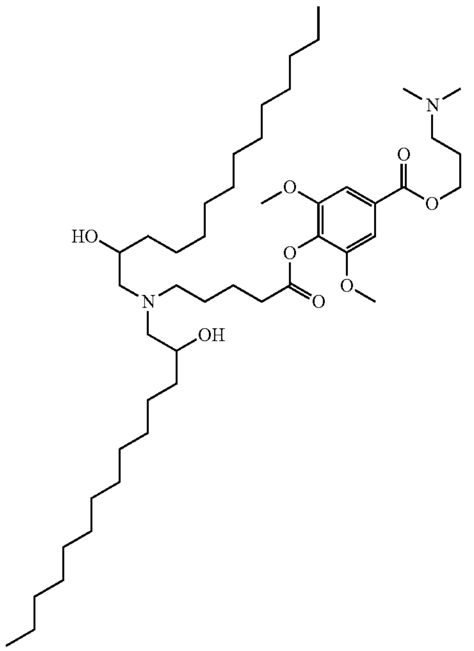

In embodiments, the cationic lipids of the present invention have the structure:

(IIIK)

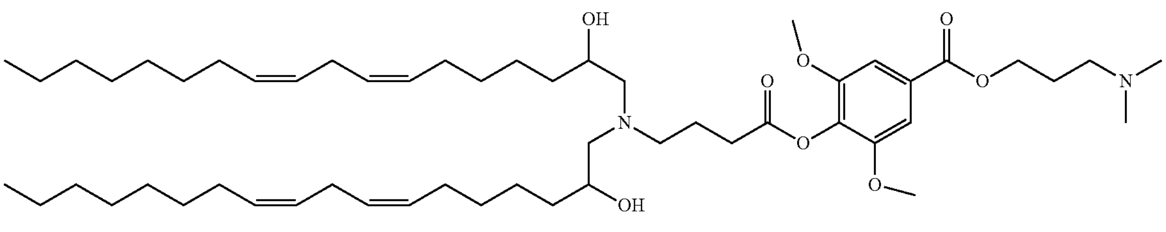

In embodiments, the cationic lipids of the present invention include compounds having a structure according to Formula (IIIL):

(IIIL)

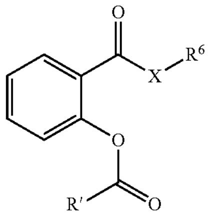

or a pharmaceutically acceptable salt thereof wherein R', $R^6$ and X are as already defined herein.

In embodiments, the cationic lipids of the present invention include compounds having a structure according to Formula (IV):

(IV)

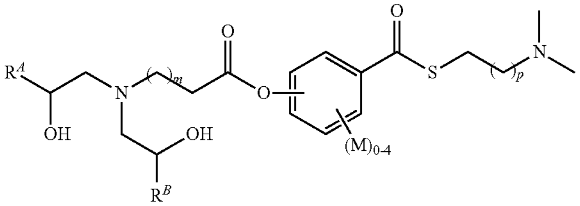

wherein M is selected from H, OH, OMe or Me, or a pharmaceutically acceptable salt thereof wherein $R^A$, $R^B$, m and p are as already defined herein.

In embodiments, the cationic lipids of the present invention include compounds having a structure according to Formula (VI), (VII), (VIII), (IX) or (X):

(VI)

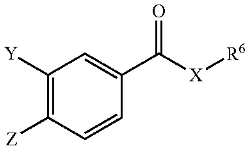

-continued (VII)

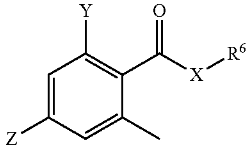

(VIII)

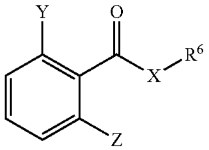

(IX)

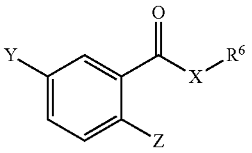

(X)

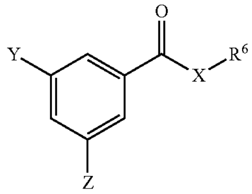

or a pharmaceutically acceptable salt thereof, wherein one of Y and Z is OH and the other is —OC(O)R', or wherein both Y and Z are each independently —OC(O)R', and wherein R', $R^6$ and X are as already defined herein or a pharmaceutically acceptable salt thereof.

In embodiments, one of Y and Z is OH and the other is —OC(O)R'.

In embodiments, Y is OH and Z is —OC(O)R'.

In embodiments, Y is —OC(O)R' and Z is OH.

In embodiments, both Y and Z are —OC(O)R'.

In embodiments, a composition comprising the cationic lipid of any one of the preceding embodiments, one or more non-cationic lipids, one or more cholesterol-based lipids and one or more PEG-modified lipid is provided. In embodiments, this composition is a lipid nanoparticle. In embodiments, the one or more cationic lipid(s) constitute(s) about 30 mol %-60 mol % of the lipid nanoparticle. In embodiments, the one or more non-cationic lipid(s) constitute(s) 10 mol %-50 mol % of the lipid nanoparticle. In embodiments, the one or more PEG-modified lipid(s) constitute(s) 1 mol %-10 mol % of the lipid nanoparticle. In embodiments, the cholesterol-based lipid constitutes 10 mol %-50 mol % of the lipid nanoparticle. In embodiments, the lipid nanoparticle encapsulates a nucleic acid, optionally an mRNA encoding a peptide or protein. In embodiments, the lipid nanoparticles have an encapsulation percentage for mRNA of at least 70%. In embodiments, the lipid nanoparticles have an encapsulation percentage for mRNA of at least 75%. In embodiments, the lipid nanoparticles have an encapsulation percentage for mRNA of at least 80%. In embodiments, the lipid nanoparticles have an encapsulation percentage for mRNA of at least 85%. In embodiments, the lipid nanoparticles have an encapsulation percentage for mRNA of at least 90%. In embodiments, the lipid nanoparticles have an encapsulation percentage for mRNA of at least 95%.

In embodiments, the composition of any one of the preceeding embodiments is for use in therapy.

In embodiments, the composition of any one of the preceeding embodiments is for use in a method of treating or preventing a disease amenable to treatment or prevention by the peptide or protein encoded by the mRNA, optionally wherein the disease is (a) a protein deficiency, optionally wherein the protein deficiency affects the liver, lung, brain or muscle, (b) an autoimmune disease, (c) an infectious disease, or (d) cancer.

In embodiments, the composition is administered intravenously, intrathecally or intramuscularly, or by pulmonary delivery, optionally through nebulization.

Exemplary Compounds

Exemplary compounds include those described in Tables 1-8

TABLE 1

| No. | Structure |
|---|---|
| 1 | 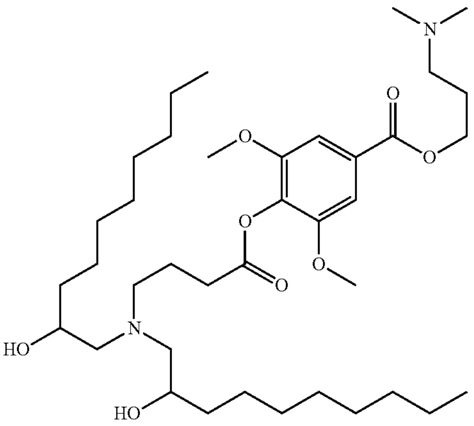 [SMILES: CCCCCCCCC(O)CN(CCCC(=O)Oc1c(OC)cc(C(=O)OCCCN(C)C)cc1OC)CC(O)CCCCCCCC] |
| 2 | 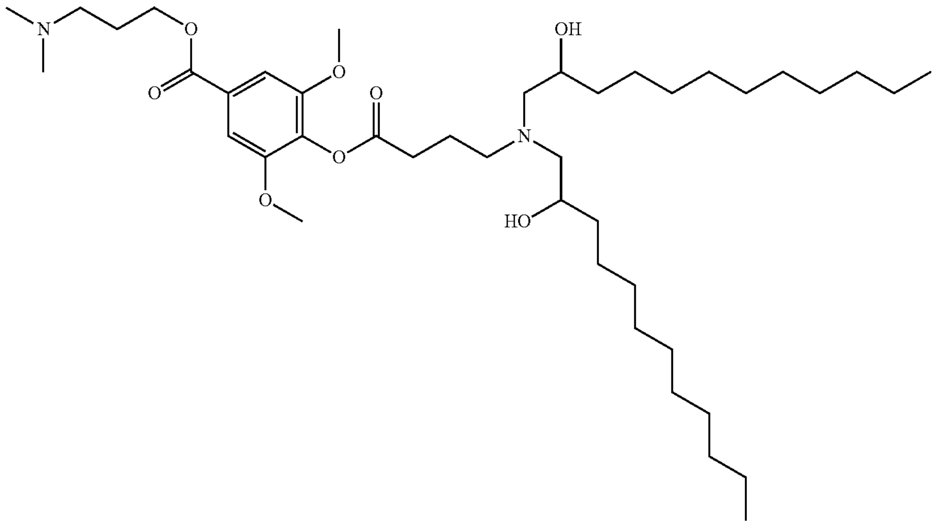 [SMILES: CCCCCCCCCCC(O)CN(CCCC(=O)Oc1c(OC)cc(C(=O)OCCCN(C)C)cc1OC)CC(O)CCCCCCCCCC] |

TABLE 1-continued
| No. | Structure |
| --- | --- |
| 3 | 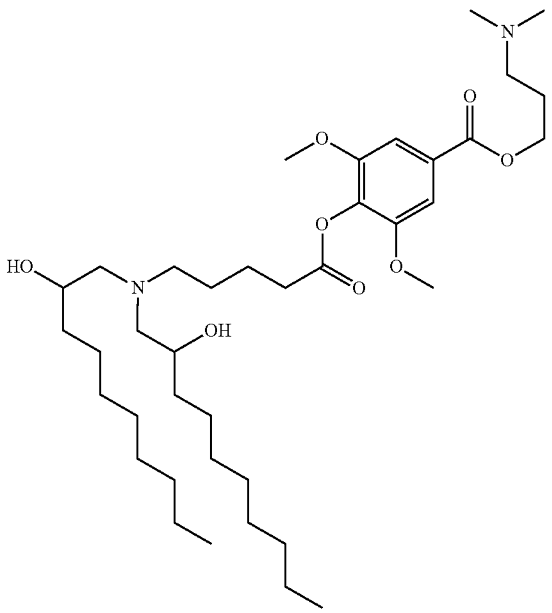 [SMILES: CCCCCCCCC(O)CN(CCCCC(=O)Oc1c(OC)cc(C(=O)OCCCN(C)C)cc1OC)CC(O)CCCCCCCC] |
| 4 | 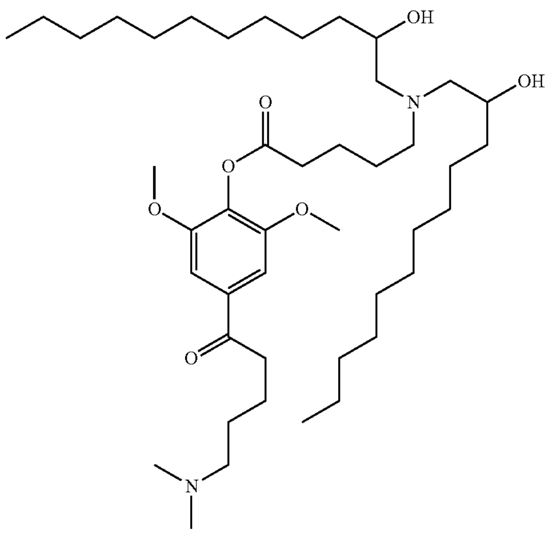 [SMILES: CCCCCCCCCCC(O)CN(CCCCC(=O)Oc1c(OC)cc(C(=O)CCCCN(C)C)cc1OC)CC(O)CCCCCCCCCC] |

TABLE 1-continued
| No. | Structure |
| --- | --- |
| 5 | 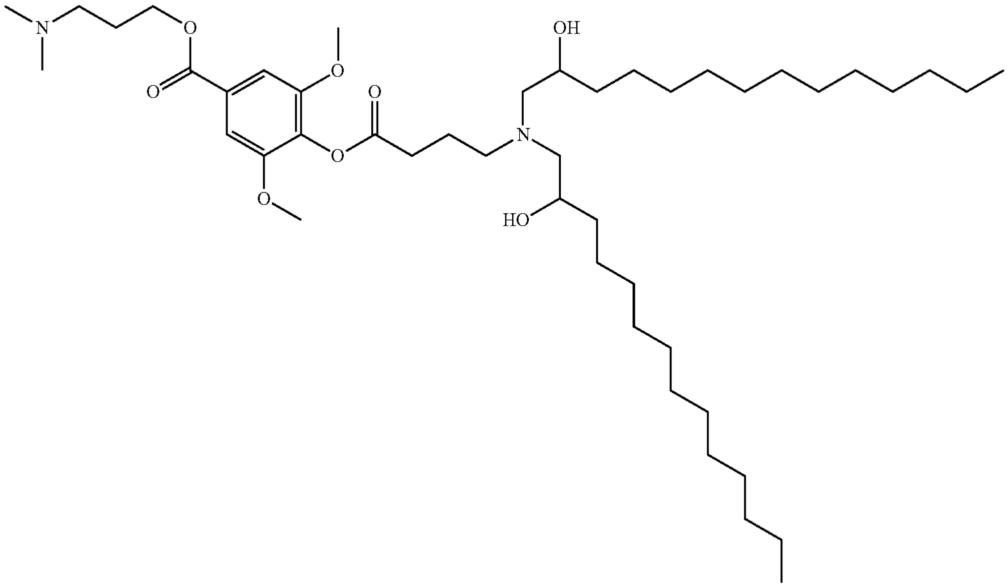 [SMILES: CCCCCCCCCCCCC(O)CN(CCCC(=O)Oc1c(OC)cc(C(=O)OCCCN(C)C)cc1OC)CC(O)CCCCCCCCCCCC] |
| 6 | 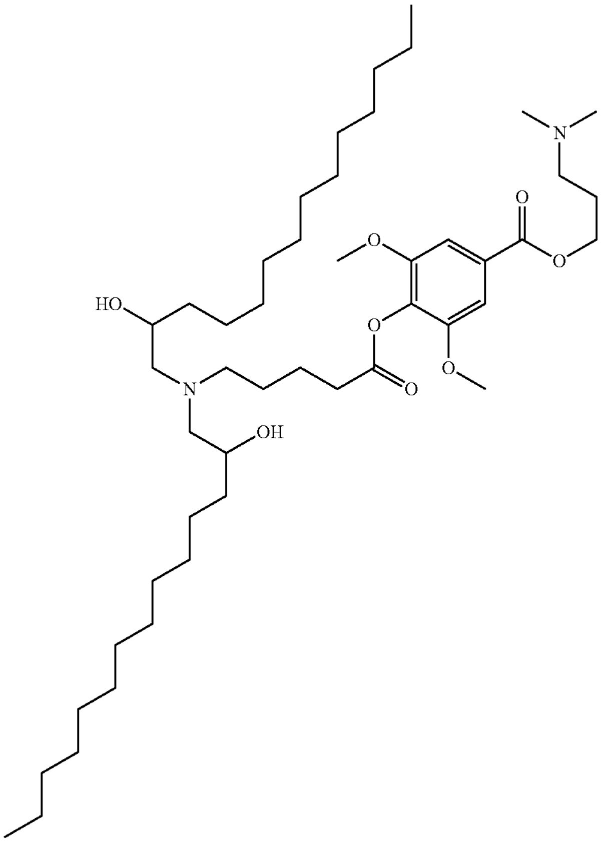 [SMILES: CCCCCCCCCCCCC(O)CN(CCCCC(=O)Oc1c(OC)cc(C(=O)OCCCN(C)C)cc1OC)CC(O)CCCCCCCCCCCC] |

TABLE 1-continued
| No. | Structure |
|---|---|
| 7 | 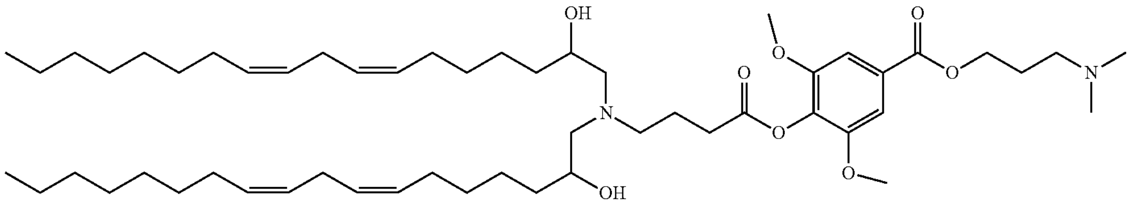 [SMILES: CCCCCCC/C=C\C/C=C\CCCCC(O)CN(CCCC(=O)Oc1c(OC)cc(C(=O)OCCCN(C)C)cc1OC)CC(O)CCCC/C=C\C/C=C\CCCCCCC] |
| 8 | 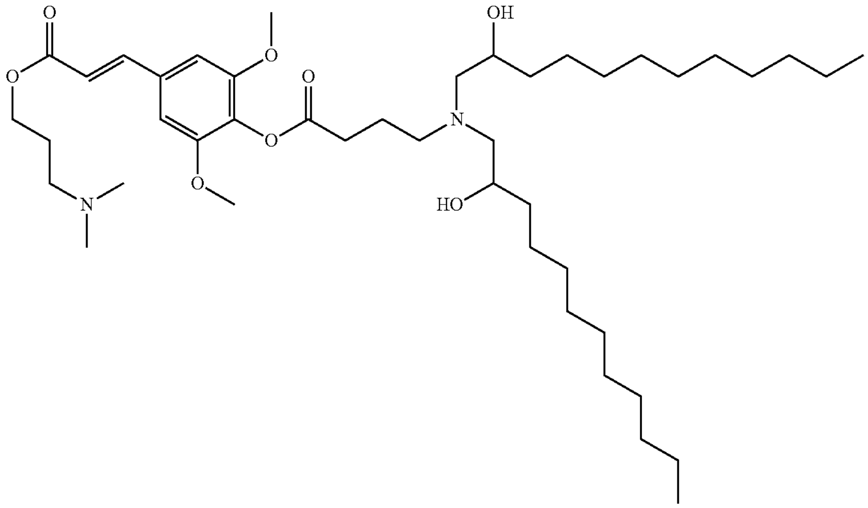 [SMILES: CCCCCCCCCCC(O)CN(CCCC(=O)Oc1c(OC)cc(/C=C/C(=O)OCCCN(C)C)cc1OC)CC(O)CCCCCCCCCC] |
| 9 | 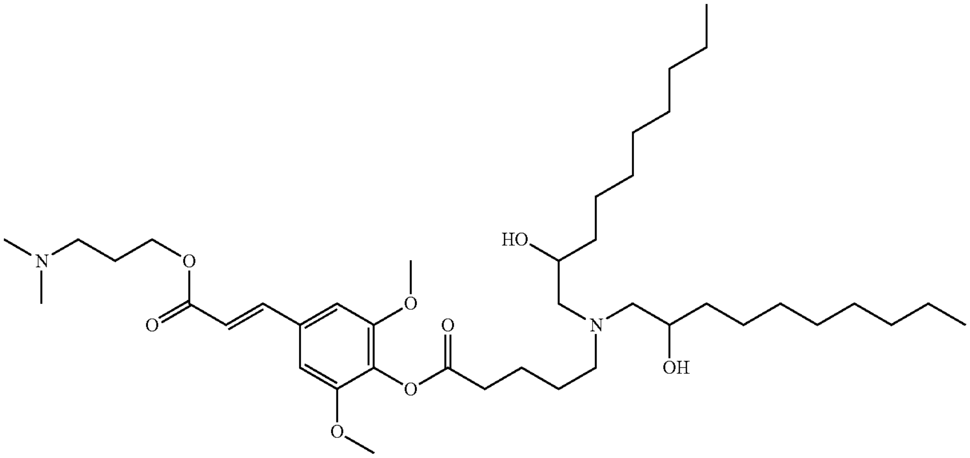 [SMILES: CCCCCCCCC(O)CN(CCCCC(=O)Oc1c(OC)cc(/C=C/C(=O)OCCCN(C)C)cc1OC)CC(O)CCCCCCCC] |

TABLE 1-continued
| No. | Structure |
| --- | --- |
| 10 | 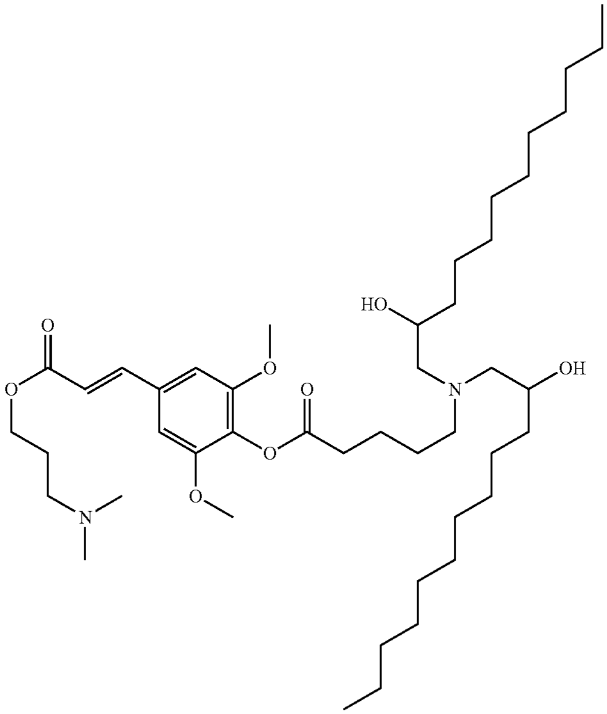 [SMILES: CCCCCCCCCCC(O)CN(CCCCC(=O)Oc1c(OC)cc(/C=C/C(=O)OCCCN(C)C)cc1OC)CC(O)CCCCCCCCCC] |
| 11 | 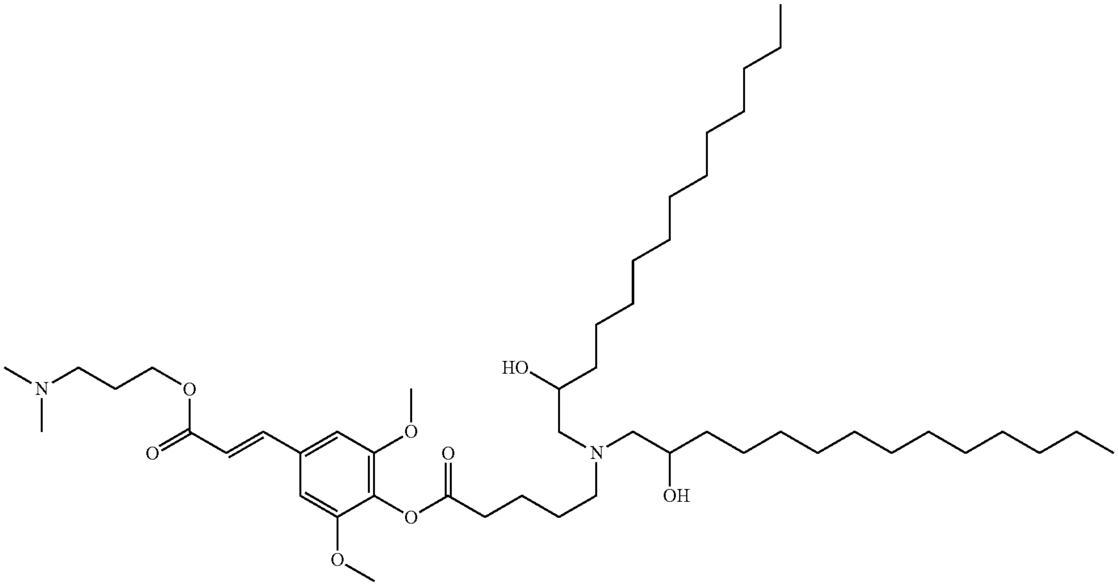 [SMILES: CCCCCCCCCCCCC(O)CN(CCCCC(=O)Oc1c(OC)cc(/C=C/C(=O)OCCCN(C)C)cc1OC)CC(O)CCCCCCCCCCCC] |

TABLE 1-continued
| No. | Structure |
|---|---|
| 12 | 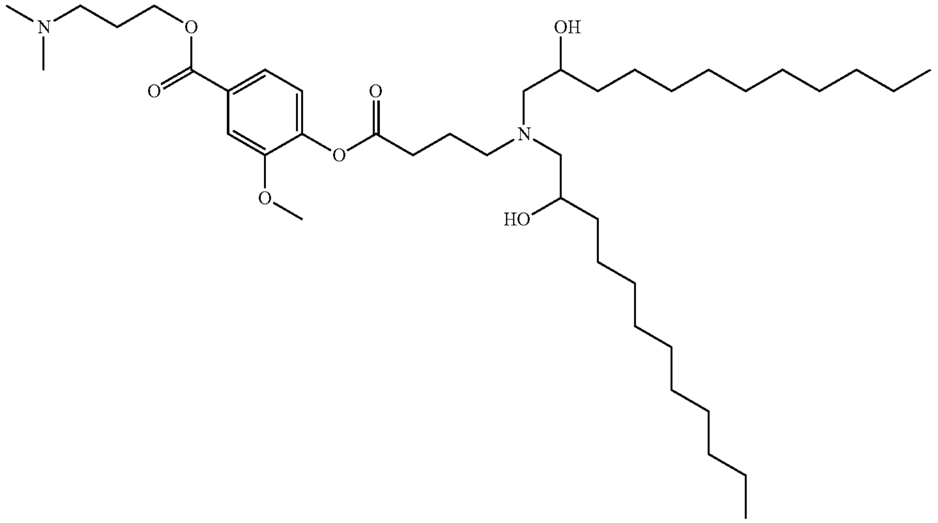 [SMILES: CCCCCCCCCCC(O)CN(CCCC(=O)Oc1ccc(C(=O)OCCCN(C)C)cc1OC)CC(O)CCCCCCCCCC] |
TABLE 2
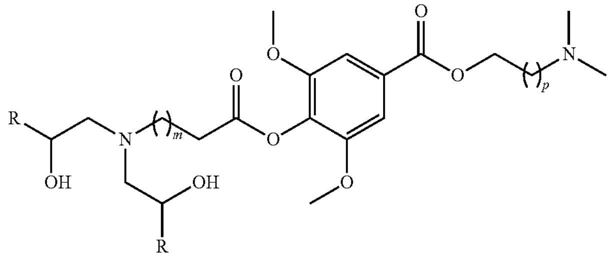
Syringic acid core
| No. | m | d | R |
|---|---|---|---|
| 13 | 1 | 1 | C8H17 |
| 1 | 2 | 2 | C8H17 |
| 14 | 3 | 3 | C8H17 |
| 15 | 4 | 4 | C8H17 |
| 16 | 1 | 2 | C8H17 |
| 17 | 1 | 3 | C8H17 |
| 18 | 1 | 4 | C8H17 |
| 19 | 2 | 1 | C8H17 |
| 20 | 2 | 3 | C8H17 |
| 21 | 2 | 4 | C8H17 |
| 22 | 3 | 1 | C8H17 |
| 3 | 3 | 2 | C8H17 |
| 23 | 3 | 4 | C8H17 |
| 24 | 4 | 1 | C8H17 |
| 25 | 4 | 2 | C8H17 |
| 26 | 4 | 3 | C8H17 |
| 27 | 1 | 1 | C10H21 |
| 2 | 2 | 2 | C10H21 |
| 28 | 2 | 3 | C10H21 |
| 29 | 3 | 3 | C10H21 |
| 30 | 4 | 4 | C10H21 |
| 31 | 1 | 2 | C10H21 |
| 32 | 1 | 3 | C10H21 |
| 33 | 1 | 4 | C10H21 |
| 34 | 2 | 1 | C10H21 |
| 36 | 2 | 4 | C10H21 |
| 37 | 3 | 1 | C10H21 |
| 4 | 3 | 2 | C10H21 |
| 38 | 3 | 4 | C10H21 |
| 39 | 4 | 1 | C10H21 |
| 40 | 4 | 2 | C10H21 |

TABLE 2-continued
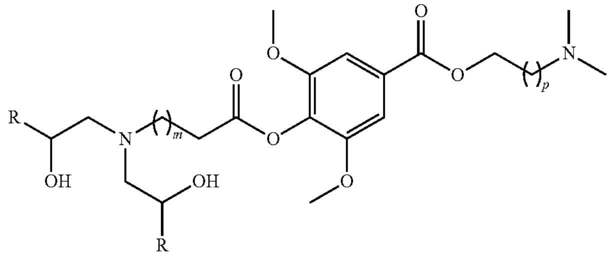
Syringic acid core
| No. | m | d | R |
|---|---|---|---|
| 41 | 4 | 3 | C10H21 |
| 42 | 1 | 1 | C12H25 |
| 5 | 2 | 2 | C12H25 |
| 43 | 3 | 3 | C12H25 |
| 44 | 4 | 4 | C12H25 |
| 45 | 1 | 2 | C12H25 |
| 46 | 1 | 3 | C12H25 |
| 47 | 1 | 4 | C12H25 |
| 48 | 2 | 1 | C12H25 |
| 49 | 2 | 3 | C12H25 |
| 50 | 2 | 4 | C12H25 |
| 51 | 3 | 1 | C12H25 |
| 6 | 3 | 2 | C12H25 |
| 52 | 3 | 4 | C12H25 |
| 53 | 4 | 1 | C12H25 |
| 54 | 4 | 2 | C12H25 |
| 55 | 4 | 3 | C12H25 |
| 56 | 1 | 1 | C14H29 |
| 57 | 2 | 2 | C14H29 |
| 58 | 3 | 3 | C14H29 |
| 59 | 4 | 4 | C14H29 |
| 60 | 1 | 2 | C14H29 |
| 61 | 1 | 3 | C14H29 |
| 62 | 1 | 4 | C14H29 |
| 63 | 2 | 1 | C14H29 |
| 64 | 2 | 3 | C14H29 |
| 65 | 2 | 4 | C14H29 |
| 66 | 3 | 1 | C14H29 |
| 67 | 3 | 2 | C14H29 |
| 68 | 3 | 4 | C14H29 |
| 69 | 4 | 1 | C14H29 |
| 70 | 4 | 2 | C14H29 |
| 71 | 4 | 3 | C14H29 |
| 72 | 1 | 1 | C16H33 |
| 73 | 2 | 2 | C16H33 |
| 74 | 3 | 3 | C16H33 |
| 75 | 4 | 4 | C16H33 |
| 76 | 1 | 2 | C16H33 |
| 77 | 1 | 3 | C16H33 |
| 78 | 1 | 4 | C16H33 |
| 79 | 2 | 1 | C16H33 |
| 80 | 2 | 3 | C16H33 |
| 81 | 2 | 4 | C16H33 |
| 82 | 3 | 1 | C16H33 |
| 83 | 3 | 2 | C16H33 |
| 84 | 3 | 4 | C16H33 |
| 85 | 4 | 1 | C16H33 |
| 86 | 4 | 2 | C16H33 |
| 87 | 4 | 3 | C16H33 |
| 88 | 1 | 1 | C16H31 |
| 89 | 2 | 2 | C16H31 |
| 90 | 3 | 3 | C16H31 |
| 91 | 4 | 4 | C16H31 |
| 92 | 1 | 2 | C16H31 |
| 93 | 1 | 3 | C16H31 |
| 94 | 1 | 4 | C16H31 |
| 95 | 2 | 1 | C16H31 |
| 96 | 2 | 3 | C16H31 |
| 97 | 2 | 4 | C16H31 |
| 98 | 3 | 1 | C16H31 |
| 99 | 3 | 2 | C16H31 |
| 100 | 3 | 4 | C16H31 |
| 101 | 4 | 1 | C16H31 |

TABLE 2-continued
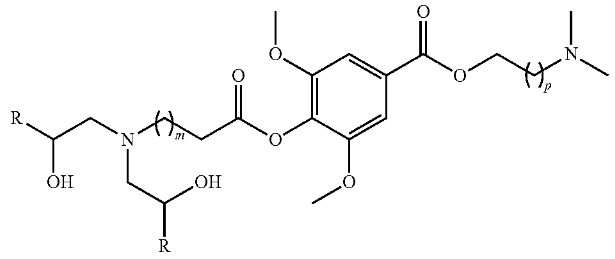
Syringic acid core
| No. | m | d | R |
|---|---|---|---|
| 102 | 4 | 2 | C16H31 |
| 103 | 4 | 3 | C16H31 |
| 104 | 1 | 1 | C16H29 |
| 7 | 2 | 2 | C16H29 |
| 105 | 3 | 3 | C16H29 |
| 106 | 4 | 4 | C16H29 |
| 107 | 1 | 2 | C16H29 |
| 108 | 1 | 3 | C16H29 |
| 109 | 1 | 4 | C16H29 |
| 110 | 2 | 1 | C16H29 |
| 111 | 2 | 3 | C16H29 |
| 112 | 2 | 4 | C16H29 |
| 113 | 3 | 1 | C16H29 |
| 114 | 3 | 2 | C16H29 |
| 115 | 3 | 4 | C16H29 |
| 116 | 4 | 1 | C16H29 |
| 117 | 4 | 2 | C16H29 |
| 118 | 4 | 3 | C16H29 |
TABLE 3
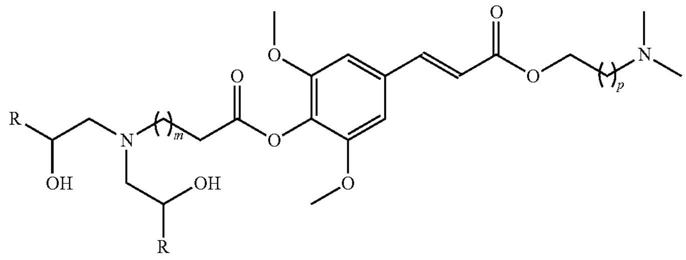
Sinapinic acid core
| No. | m | p | R |
|---|---|---|---|
| 119 | 1 | 1 | C8H17 |
| 120 | 2 | 2 | C8H17 |
| 121 | 3 | 3 | C8H17 |
| 122 | 4 | 4 | C8H17 |
| 123 | 1 | 2 | C8H17 |
| 124 | 1 | 3 | C8H17 |
| 125 | 1 | 4 | C8H17 |
| 126 | 2 | 1 | C8H17 |
| 127 | 2 | 3 | C8H17 |
| 128 | 2 | 4 | C8H17 |
| 129 | 3 | 1 | C8H17 |
| 9 | 3 | 2 | C8H17 |
| 130 | 3 | 4 | C8H17 |
| 131 | 4 | 1 | C8H17 |
| 132 | 4 | 2 | C8H17 |
| 133 | 4 | 3 | C8H17 |
| 134 | 1 | 1 | C10H21 |
| 8 | 2 | 2 | C10H21 |
| 135 | 2 | 3 | C10H21 |
| 136 | 3 | 3 | C10H21 |
| 137 | 4 | 4 | C10H21 |
| 138 | 1 | 2 | C10H21 |
| 139 | 1 | 3 | C10H21 |

TABLE 3-continued
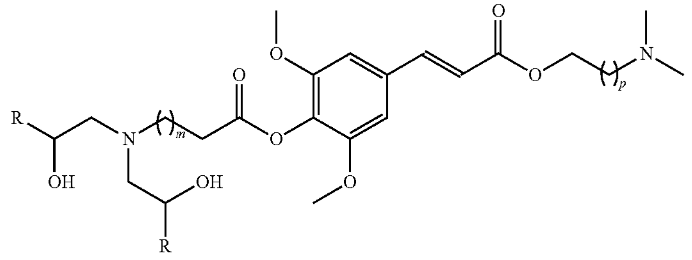
Sinapinic acid core
| No. | m | p | R |
|---|---|---|---|
| 140 | 1 | 4 | C10H21 |
| 141 | 2 | 1 | C10H21 |
| 142 | 2 | 4 | C10H21 |
| 143 | 3 | 1 | C10H21 |
| 10 | 3 | 2 | C10H21 |
| 144 | 3 | 4 | C10H21 |
| 145 | 4 | 1 | C10H21 |
| 146 | 4 | 2 | C10H21 |
| 147 | 4 | 3 | C10H21 |
| 148 | 1 | 1 | C12H25 |
| 149 | 2 | 2 | C12H25 |
| 150 | 3 | 3 | C12H25 |
| 151 | 4 | 4 | C12H25 |
| 152 | 1 | 2 | C12H25 |
| 153 | 1 | 3 | C12H25 |
| 154 | 1 | 4 | C12H25 |
| 155 | 2 | 1 | C12H25 |
| 156 | 2 | 3 | C12H25 |
| 157 | 2 | 4 | C12H25 |
| 158 | 3 | 1 | C12H25 |
| 11 | 3 | 2 | C12H25 |
| 159 | 3 | 4 | C12H25 |
| 160 | 4 | 1 | C12H25 |
| 161 | 4 | 2 | C12H25 |
| 162 | 4 | 3 | C12H25 |
| 163 | 1 | 1 | C14H29 |
| 164 | 2 | 2 | C14H29 |
| 165 | 3 | 3 | C14H29 |
| 166 | 4 | 4 | C14H29 |
| 167 | 1 | 2 | C14H29 |
| 168 | 1 | 3 | C14H29 |
| 169 | 1 | 4 | C14H29 |
| 170 | 2 | 1 | C14H29 |
| 171 | 2 | 3 | C14H29 |
| 172 | 2 | 4 | C14H29 |
| 173 | 3 | 1 | C14H29 |
| 174 | 3 | 2 | C14H29 |
| 175 | 3 | 4 | C14H29 |
| 176 | 4 | 1 | C14H29 |
| 177 | 4 | 2 | C14H29 |
| 178 | 4 | 3 | C14H29 |
| 179 | 1 | 1 | C16H33 |
| 180 | 2 | 2 | C16H33 |
| 181 | 3 | 3 | C16H33 |
| 182 | 4 | 4 | C16H33 |
| 183 | 1 | 2 | C16H33 |
| 184 | 1 | 3 | C16H33 |
| 185 | 1 | 4 | C16H33 |
| 186 | 2 | 1 | C16H33 |
| 187 | 2 | 3 | C16H33 |
| 188 | 2 | 4 | C16H33 |
| 189 | 3 | 1 | C16H33 |
| 190 | 3 | 2 | C16H33 |
| 191 | 3 | 4 | C16H33 |
| 192 | 4 | 1 | C16H33 |
| 193 | 4 | 2 | C16H33 |
| 194 | 4 | 3 | C16H33 |
| 195 | 1 | 1 | C16H31 |
| 196 | 2 | 2 | C16H31 |
| 197 | 3 | 3 | C16H31 |
| 198 | 4 | 4 | C16H31 |
| 199 | 1 | 2 | C16H31 |
| 200 | 1 | 3 | C16H31 |

TABLE 3-continued
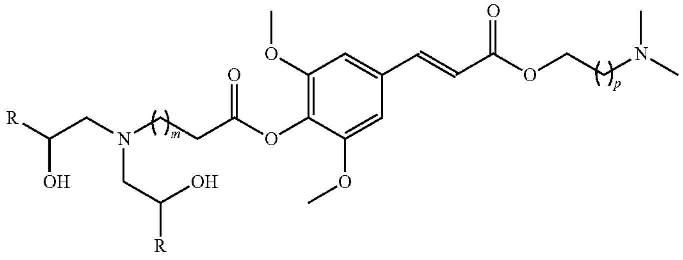
Sinapinic acid core
| No. | m | p | R |
|---|---|---|---|
| 201 | 1 | 4 | C16H31 |
| 202 | 2 | 1 | C16H31 |
| 203 | 2 | 3 | C16H31 |
| 204 | 2 | 4 | C16H31 |
| 205 | 3 | 1 | C16H31 |
| 206 | 3 | 2 | C16H31 |
| 207 | 3 | 4 | C16H31 |
| 208 | 4 | 1 | C16H31 |
| 209 | 4 | 2 | C16H31 |
| 210 | 4 | 3 | C16H31 |
| 211 | 1 | 1 | C16H29 |
| 212 | 2 | 2 | C16H29 |
| 213 | 3 | 3 | C16H29 |
| 214 | 4 | 4 | C16H29 |
| 215 | 1 | 2 | C16H29 |
| 216 | 1 | 3 | C16H29 |
| 217 | 1 | 4 | C16H29 |
| 218 | 2 | 1 | C16H29 |
| 219 | 2 | 3 | C16H29 |
| 220 | 2 | 4 | C16H29 |
| 221 | 3 | 1 | C16H29 |
| 222 | 3 | 2 | C16H29 |
| 223 | 3 | 4 | C16H29 |
| 224 | 4 | 1 | C16H29 |
| 225 | 4 | 2 | C16H29 |
| 226 | 4 | 3 | C16H29 |
TABLE 4
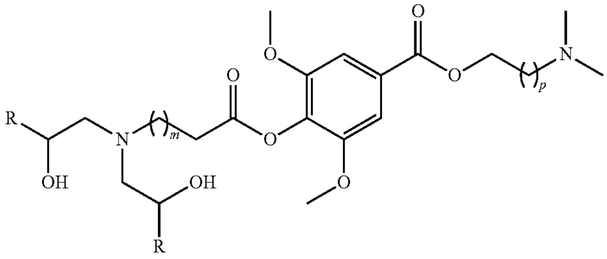
Vanillic acid core
| No. | m | p | R |
|---|---|---|---|
| 227 | 1 | 1 | C8H17 |
| 228 | 2 | 2 | C8H17 |
| 229 | 3 | 3 | C8H17 |
| 230 | 4 | 4 | C8H17 |
| 231 | 1 | 2 | C8H17 |
| 232 | 1 | 3 | C8H17 |
| 233 | 1 | 4 | C8H17 |
| 234 | 2 | 1 | C8H17 |
| 235 | 2 | 3 | C8H17 |
| 236 | 2 | 4 | C8H17 |
| 237 | 3 | 1 | C8H17 |
| 238 | 3 | 2 | C8H17 |
| 239 | 3 | 4 | C8H17 |
| 240 | 4 | 1 | C8H17 |

TABLE 4-continued
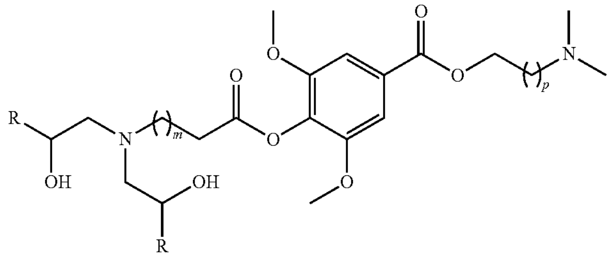
Vanillic acid core
| No. | m | p | R |
|---|---|---|---|
| 241 | 4 | 2 | C8H17 |
| 242 | 4 | 3 | C8H17 |
| 243 | 1 | 1 | C10H21 |
| 12 | 2 | 2 | C10H21 |
| 244 | 2 | 3 | C10H21 |
| 245 | 3 | 3 | C10H21 |
| 246 | 4 | 4 | C10H21 |
| 247 | 1 | 2 | C10H21 |
| 248 | 1 | 3 | C10H21 |
| 249 | 1 | 4 | C10H21 |
| 250 | 2 | 1 | C10H21 |
| 251 | 2 | 4 | C10H21 |
| 252 | 3 | 1 | C10H21 |
| 253 | 3 | 2 | C10H21 |
| 254 | 3 | 4 | C10H21 |
| 255 | 4 | 1 | C10H21 |
| 256 | 4 | 2 | C10H21 |
| 257 | 4 | 3 | C10H21 |
| 258 | 1 | 1 | C12H25 |
| 259 | 2 | 2 | C12H25 |
| 260 | 3 | 3 | C12H25 |
| 261 | 4 | 4 | C12H25 |
| 262 | 1 | 2 | C12H25 |
| 263 | 1 | 3 | C12H25 |
| 264 | 1 | 4 | C12H25 |
| 265 | 2 | 1 | C12H25 |
| 266 | 2 | 3 | C12H25 |
| 267 | 2 | 4 | C12H25 |
| 268 | 3 | 1 | C12H25 |
| 269 | 3 | 2 | C12H25 |
| 270 | 3 | 4 | C12H25 |
| 271 | 4 | 1 | C12H25 |
| 272 | 4 | 2 | C12H25 |
| 273 | 4 | 3 | C12H25 |
| 274 | 1 | 1 | C14H29 |
| 275 | 2 | 2 | C14H29 |
| 276 | 3 | 3 | C14H29 |
| 277 | 4 | 4 | C14H29 |
| 278 | 1 | 2 | C14H29 |
| 279 | 1 | 3 | C14H29 |
| 280 | 1 | 4 | C14H29 |
| 281 | 2 | 1 | C14H29 |
| 282 | 2 | 3 | C14H29 |
| 283 | 2 | 4 | C14H29 |
| 284 | 3 | 1 | C14H29 |
| 285 | 3 | 2 | C14H29 |
| 286 | 3 | 4 | C14H29 |
| 287 | 4 | 1 | C14H29 |
| 288 | 4 | 2 | C14H29 |
| 289 | 4 | 3 | C14H29 |
| 290 | 1 | 1 | C16H33 |
| 291 | 2 | 2 | C16H33 |
| 292 | 3 | 3 | C16H33 |
| 293 | 4 | 4 | C16H33 |
| 294 | 1 | 2 | C16H33 |
| 295 | 1 | 3 | C16H33 |
| 296 | 1 | 4 | C16H33 |
| 297 | 2 | 1 | C16H33 |
| 298 | 2 | 3 | C16H33 |
| 299 | 2 | 4 | C16H33 |
| 300 | 3 | 1 | C16H33 |
| 301 | 3 | 2 | C16H33 |
| 302 | 3 | 4 | C16H33 |

TABLE 4-continued
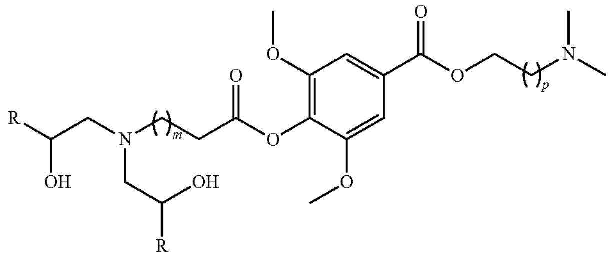
Vanillic acid core
| No. | m | p | R |
|---|---|---|---|
| 303 | 4 | 1 | C16H33 |
| 304 | 4 | 2 | C16H33 |
| 305 | 4 | 3 | C16H33 |
| 306 | 1 | 1 | C16H31 |
| 307 | 2 | 2 | C16H31 |
| 308 | 3 | 3 | C16H31 |
| 309 | 4 | 4 | C16H31 |
| 310 | 1 | 2 | C16H31 |
| 311 | 1 | 3 | C16H31 |
| 312 | 1 | 4 | C16H31 |
| 313 | 2 | 1 | C16H31 |
| 314 | 2 | 3 | C16H31 |
| 315 | 2 | 4 | C16H31 |
| 316 | 3 | 1 | C16H31 |
| 317 | 3 | 2 | C16H31 |
| 318 | 3 | 4 | C16H31 |
| 319 | 4 | 1 | C16H31 |
| 320 | 4 | 2 | C16H31 |
| 321 | 4 | 3 | C16H31 |
| 322 | 1 | 1 | C16H29 |
| 323 | 2 | 2 | C16H29 |
| 324 | 3 | 3 | C16H29 |
| 325 | 4 | 4 | C16H29 |
| 326 | 1 | 2 | C16H29 |
| 327 | 1 | 3 | C16H29 |
| 328 | 1 | 4 | C16H29 |
| 329 | 2 | 1 | C16H29 |
| 330 | 2 | 3 | C16H29 |
| 331 | 2 | 4 | C16H29 |
| 332 | 3 | 1 | C16H29 |
| 333 | 3 | 2 | C16H29 |
| 334 | 3 | 4 | C16H29 |
| 335 | 4 | 1 | C16H29 |
| 336 | 4 | 2 | C16H29 |
| 337 | 4 | 3 | C16H29 |
TABLE 5
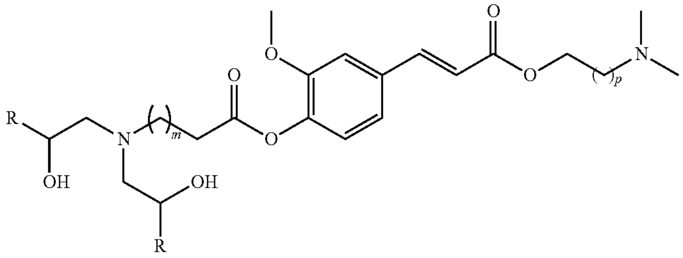
Ferulic Acid core
| No. | m | p | R |
|---|---|---|---|
| 338 | 1 | 1 | C8H17 |
| 339 | 2 | 2 | C8H17 |
| 340 | 3 | 3 | C8H17 |
| 341 | 4 | 4 | C8H17 |
| 342 | 1 | 2 | C8H17 |
| 343 | 1 | 3 | C8H17 |

TABLE 5-continued
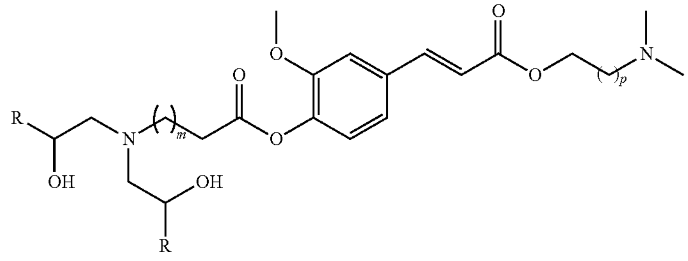
Ferulic Acid core
| No. | m | p | R |
|---|---|---|---|
| 344 | 1 | 4 | C8H17 |
| 345 | 2 | 1 | C8H17 |
| 346 | 2 | 3 | C8H17 |
| 347 | 2 | 4 | C8H17 |
| 348 | 3 | 1 | C8H17 |
| 349 | 3 | 2 | C8H17 |
| 350 | 3 | 4 | C8H17 |
| 351 | 4 | 1 | C8H17 |
| 352 | 4 | 2 | C8H17 |
| 353 | 4 | 3 | C8H17 |
| 354 | 1 | 1 | C10H21 |
| 355 | 2 | 2 | C10H21 |
| 356 | 2 | 3 | C10H21 |
| 357 | 3 | 3 | C10H21 |
| 358 | 4 | 4 | C10H21 |
| 359 | 1 | 2 | C10H21 |
| 360 | 1 | 3 | C10H21 |
| 361 | 1 | 4 | C10H21 |
| 362 | 2 | 1 | C10H21 |
| 363 | 2 | 4 | C10H21 |
| 364 | 3 | 1 | C10H21 |
| 365 | 3 | 2 | C10H21 |
| 366 | 3 | 4 | C10H21 |
| 367 | 4 | 1 | C10H21 |
| 368 | 4 | 2 | C10H21 |
| 369 | 4 | 3 | C10H21 |
| 370 | 1 | 1 | C12H25 |
| 371 | 2 | 2 | C12H25 |
| 372 | 3 | 3 | C12H25 |
| 373 | 4 | 4 | C12H25 |
| 374 | 1 | 2 | C12H25 |
| 375 | 1 | 3 | C12H25 |
| 376 | 1 | 4 | C12H25 |
| 377 | 2 | 1 | C12H25 |
| 378 | 2 | 3 | C12H25 |
| 379 | 2 | 4 | C12H25 |
| 380 | 3 | 1 | C12H25 |
| 381 | 3 | 2 | C12H25 |
| 382 | 3 | 4 | C12H25 |
| 383 | 4 | 1 | C12H25 |
| 384 | 4 | 2 | C12H25 |
| 385 | 4 | 3 | C12H25 |
| 386 | 1 | 1 | C14H29 |
| 387 | 2 | 2 | C14H29 |
| 388 | 3 | 3 | C14H29 |
| 389 | 4 | 4 | C14H29 |
| 390 | 1 | 2 | C14H29 |
| 391 | 1 | 3 | C14H29 |
| 392 | 1 | 4 | C14H29 |
| 393 | 2 | 1 | C14H29 |
| 394 | 2 | 3 | C14H29 |
| 395 | 2 | 4 | C14H29 |
| 396 | 3 | 1 | C14H29 |
| 397 | 3 | 2 | C14H29 |
| 398 | 3 | 4 | C14H29 |
| 399 | 4 | 1 | C14H29 |
| 400 | 4 | 2 | C14H29 |
| 401 | 4 | 3 | C14H29 |
| 402 | 1 | 1 | C16H33 |
| 403 | 2 | 2 | C16H33 |
| 404 | 3 | 3 | C16H33 |
| 405 | 4 | 4 | C16H33 |
| 406 | 1 | 2 | C16H33 |

TABLE 5-continued
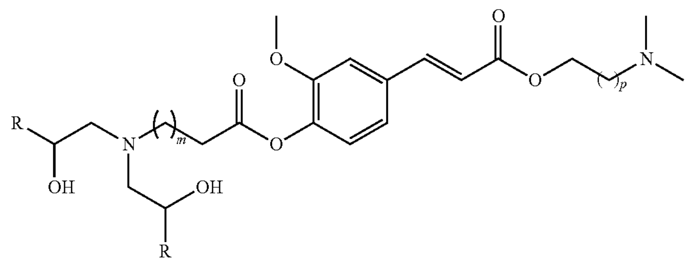
Ferulic Acid core
| No. | m | p | R |
|---|---|---|---|
| 407 | 1 | 3 | C16H33 |
| 408 | 1 | 4 | C16H33 |
| 409 | 2 | 1 | C16H33 |
| 410 | 2 | 3 | C16H33 |
| 411 | 2 | 4 | C16H33 |
| 412 | 3 | 1 | C16H33 |
| 413 | 3 | 2 | C16H33 |
| 414 | 3 | 4 | C16H33 |
| 415 | 4 | 1 | C16H33 |
| 416 | 4 | 2 | C16H33 |
| 417 | 4 | 3 | C16H33 |
| 418 | 1 | 1 | C16H31 |
| 419 | 2 | 2 | C16H31 |
| 420 | 3 | 3 | C16H31 |
| 421 | 4 | 4 | C16H31 |
| 422 | 1 | 2 | C16H31 |
| 423 | 1 | 3 | C16H31 |
| 424 | 1 | 4 | C16H31 |
| 425 | 2 | 1 | C16H31 |
| 426 | 2 | 3 | C16H31 |
| 427 | 2 | 4 | C16H31 |
| 428 | 3 | 1 | C16H31 |
| 429 | 3 | 2 | C16H31 |
| 430 | 3 | 4 | C16H31 |
| 431 | 4 | 1 | C16H31 |
| 432 | 4 | 2 | C16H31 |
| 433 | 4 | 3 | C16H31 |
| 434 | 1 | 1 | C16H29 |
| 435 | 2 | 2 | C16H29 |
| 436 | 3 | 3 | C16H29 |
| 437 | 4 | 4 | C16H29 |
| 438 | 1 | 2 | C16H29 |
| 439 | 1 | 3 | C16H29 |
| 440 | 1 | 4 | C16H29 |
| 441 | 2 | 1 | C16H29 |
| 442 | 2 | 3 | C16H29 |
| 443 | 2 | 4 | C16H29 |
| 444 | 3 | 1 | C16H29 |
| 445 | 3 | 2 | C16H29 |
| 446 | 3 | 4 | C16H29 |
| 447 | 4 | 1 | C16H29 |
| 448 | 4 | 2 | C16H29 |
| 449 | 4 | 3 | C16H29 |

TABLE 6
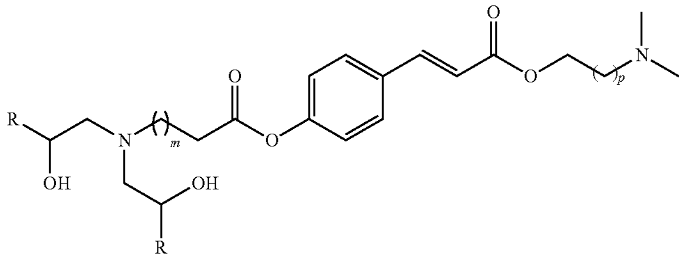
p-Coumaric Acid core
| No. | m | p | R |
|---|---|---|---|
| 450 | 1 | 1 | C8H17 |
| 451 | 2 | 2 | C8H17 |
| 452 | 3 | 3 | C8H17 |
| 453 | 4 | 4 | C8H17 |
| 454 | 1 | 2 | C8H17 |
| 455 | 1 | 3 | C8H17 |
| 456 | 1 | 4 | C8H17 |
| 457 | 2 | 1 | C8H17 |
| 458 | 2 | 3 | C8H17 |
| 459 | 2 | 4 | C8H17 |
| 460 | 3 | 1 | C8H17 |
| 461 | 3 | 2 | C8H17 |
| 462 | 3 | 4 | C8H17 |
| 463 | 4 | 1 | C8H17 |
| 464 | 4 | 2 | C8H17 |
| 465 | 4 | 3 | C8H17 |
| 466 | 1 | 1 | C10H21 |
| 467 | 2 | 2 | C10H21 |
| 468 | 2 | 3 | C10H21 |
| 469 | 3 | 3 | C10H21 |
| 470 | 4 | 4 | C10H21 |
| 471 | 1 | 2 | C10H21 |
| 472 | 1 | 3 | C10H21 |
| 473 | 1 | 4 | C10H21 |
| 474 | 2 | 1 | C10H21 |
| 475 | 2 | 4 | C10H21 |
| 476 | 3 | 1 | C10H21 |
| 477 | 3 | 2 | C10H21 |
| 478 | 3 | 4 | C10H21 |
| 479 | 4 | 1 | C10H21 |
| 480 | 4 | 2 | C10H21 |
| 481 | 4 | 3 | C10H21 |
| 482 | 1 | 1 | C12H25 |
| 483 | 2 | 2 | C12H25 |
| 484 | 3 | 3 | C12H25 |
| 485 | 4 | 4 | C12H25 |
| 486 | 1 | 2 | C12H25 |
| 487 | 1 | 3 | C12H25 |
| 488 | 1 | 4 | C12H25 |
| 489 | 2 | 1 | C12H25 |
| 490 | 2 | 3 | C12H25 |
| 491 | 2 | 4 | C12H25 |
| 492 | 3 | 1 | C12H25 |
| 493 | 3 | 2 | C12H25 |
| 494 | 3 | 4 | C12H25 |
| 495 | 4 | 1 | C12H25 |
| 496 | 4 | 2 | C12H25 |
| 497 | 4 | 3 | C12H25 |
| 498 | 1 | 1 | C14H29 |
| 499 | 2 | 2 | C14H29 |
| 500 | 3 | 3 | C14H29 |
| 501 | 4 | 4 | C14H29 |
| 502 | 1 | 2 | C14H29 |
| 503 | 1 | 3 | C14H29 |
| 504 | 1 | 4 | C14H29 |
| 505 | 2 | 1 | C14H29 |
| 506 | 2 | 3 | C14H29 |
| 507 | 2 | 4 | C14H29 |
| 508 | 3 | 1 | C14H29 |
| 509 | 3 | 2 | C14H29 |
| 510 | 3 | 4 | C14H29 |
| 511 | 4 | 1 | C14H29 |
| 512 | 4 | 2 | C14H29 |

TABLE 6-continued
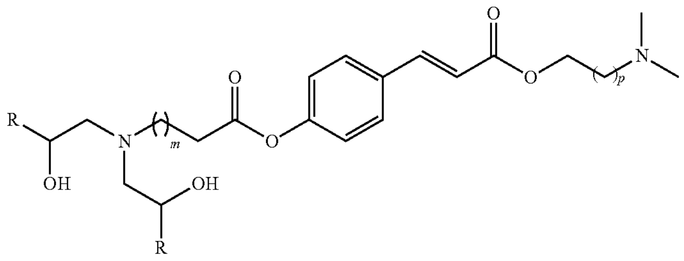
p-Coumaric Acid core
| No. | m | p | R |
|---|---|---|---|
| 513 | 4 | 3 | C14H29 |
| 514 | 1 | 1 | C16H33 |
| 515 | 2 | 2 | C16H33 |
| 516 | 3 | 3 | C16H33 |
| 517 | 4 | 4 | C16H33 |
| 518 | 1 | 2 | C16H33 |
| 519 | 1 | 3 | C16H33 |
| 520 | 1 | 4 | C16H33 |
| 521 | 2 | 1 | C16H33 |
| 522 | 2 | 3 | C16H33 |
| 523 | 2 | 4 | C16H33 |
| 524 | 3 | 1 | C16H33 |
| 525 | 3 | 2 | C16H33 |
| 526 | 3 | 4 | C16H33 |
| 527 | 4 | 1 | C16H33 |
| 528 | 4 | 2 | C16H33 |
| 529 | 4 | 3 | C16H33 |
| 530 | 1 | 1 | C16H31 |
| 531 | 2 | 2 | C16H31 |
| 532 | 3 | 3 | C16H31 |
| 533 | 4 | 4 | C16H31 |
| 534 | 1 | 2 | C16H31 |
| 535 | 1 | 3 | C16H31 |
| 536 | 1 | 4 | C16H31 |
| 537 | 2 | 1 | C16H31 |
| 538 | 2 | 3 | C16H31 |
| 539 | 2 | 4 | C16H31 |
| 540 | 3 | 1 | C16H31 |
| 541 | 3 | 2 | C16H31 |
| 542 | 3 | 4 | C16H31 |
| 543 | 4 | 1 | C16H31 |
| 544 | 4 | 2 | C16H31 |
| 545 | 4 | 3 | C16H31 |
| 546 | 1 | 1 | C16H29 |
| 547 | 2 | 2 | C16H29 |
| 548 | 3 | 3 | C16H29 |
| 549 | 4 | 4 | C16H29 |
| 550 | 1 | 2 | C16H29 |
| 551 | 1 | 3 | C16H29 |
| 552 | 1 | 4 | C16H29 |
| 553 | 2 | 1 | C16H29 |
| 554 | 2 | 3 | C16H29 |
| 555 | 2 | 4 | C16H29 |
| 556 | 3 | 1 | C16H29 |
| 557 | 3 | 2 | C16H29 |
| 558 | 3 | 4 | C16H29 |
| 559 | 4 | 1 | C16H29 |
| 560 | 4 | 2 | C16H29 |
| 561 | 4 | 3 | C16H29 |

TABLE 7

| No. | Structure |
| --- | --- |
| 562 | 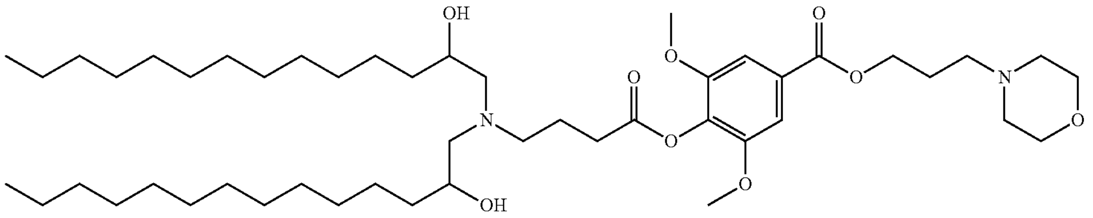 [SMILES: CCCCCCCCCCCCC(O)CN(CCCC(=O)Oc1c(OC)cc(C(=O)OCCCN2CCOCC2)cc1OC)CC(O)CCCCCCCCCCCC] |
| 563 | 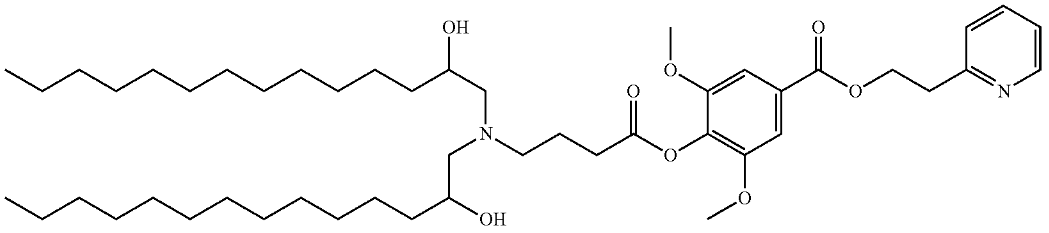 [SMILES: CCCCCCCCCCCCC(O)CN(CCCC(=O)Oc1c(OC)cc(C(=O)OCCc2ccccn2)cc1OC)CC(O)CCCCCCCCCCCC] |
| 564 | 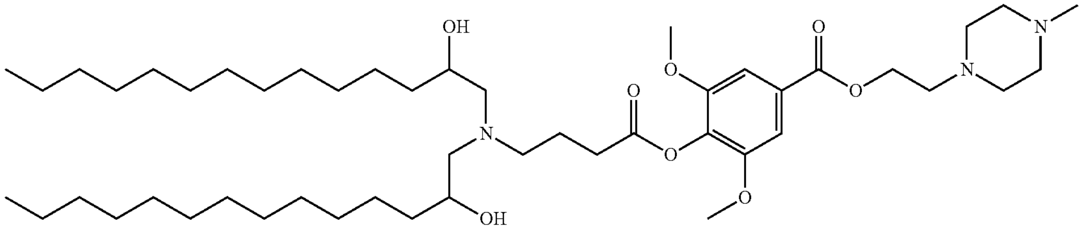 [SMILES: CCCCCCCCCCCCC(O)CN(CCCC(=O)Oc1c(OC)cc(C(=O)OCCN2CCN(C)CC2)cc1OC)CC(O)CCCCCCCCCCCC] |

TABLE 8

| No. | Structure |
| --- | --- |
| 565 | 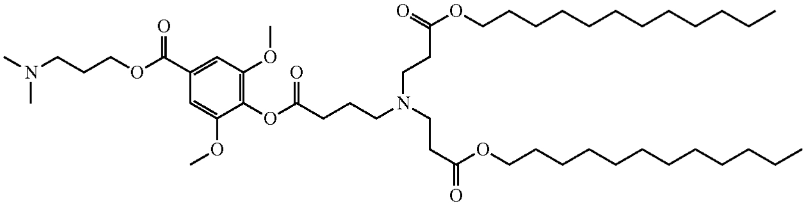 [SMILES: CCCCCCCCCCCCOC(=O)CCN(CCCC(=O)Oc1c(OC)cc(C(=O)OCCCN(C)C)cc1OC)CCC(=O)OCCCCCCCCCCCC] |
| 566 | 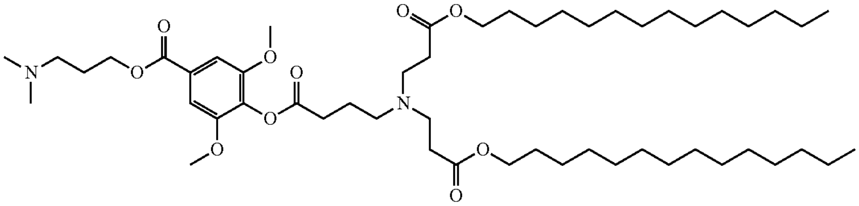 [SMILES: CCCCCCCCCCCCCCOC(=O)CCN(CCCC(=O)Oc1c(OC)cc(C(=O)OCCCN(C)C)cc1OC)CCC(=O)OCCCCCCCCCCCCCC] |

Any of the compounds identified in Tables 1 to 8 above may be provided in the form of a pharmaceutically acceptable salt and such salts are intended to be encompassed by the present invention.

Unless otherwise specified, R=$C_{16}H_{29}$ has the structure:

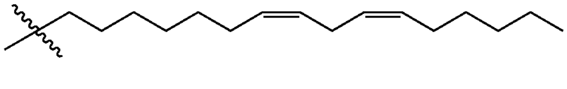 [SMILES: *CCCCCC/C=C\C/C=C\CCCCC]

Unless otherwise specified, R=$C_{16}H_{31}$ has the structure:

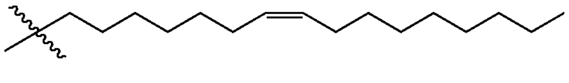 [SMILES: *CCCCCC/C=C\CCCCCCCC]

The compounds of the invention as described herein can be prepared according to methods known in the art, including the exemplary syntheses of the Examples provided herein.

Nucleic Acids

The compounds of the invention as described herein can be used to prepare compositions useful for the delivery of nucleic acids.

Synthesis of Nucleic Acids

Nucleic acids according to the present invention may be synthesized according to any known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, mutated T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7, mutated T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Modified mRNA comprise nucleotide modifications in the RNA. A modified mRNA according to the invention can thus include nucleotide modification that are, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queuosine, beta-D-mannosyl-queuosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

Pharmaceutical Formulations of Cationic Lipids and Nucleic Acids

In certain embodiments, the compounds of the invention as described herein, as well as pharmaceutical and liposomal compositions comprising such lipids, can be used in formulations to facilitate the delivery of encapsulated materials (e.g., one or more polynucleotides such as mRNA) to, and subsequent transfection of one or more target cells. For example, in certain embodiments cationic lipids described herein (and compositions such as liposomal compositions comprising such lipids) are characterized as resulting in one or more of receptor-mediated endocytosis, clathrin-mediated and caveolae-mediated endocytosis, phagocytosis and macropinocytosis, fusogenicity, endosomal or lysosomal disruption and/or releasable properties that afford such compounds advantages relative other similarly classified lipids.

According to the present invention, a nucleic acid, e.g., mRNA encoding a protein (e.g., a full length, fragment or portion of a protein) as described herein may be delivered via a delivery vehicle comprising a compound of the invention as described herein.

As used herein, the terms "delivery vehicle," "transfer vehicle," "nanoparticle," or grammatical equivalents thereof, are used interchangeably.

For example, the present invention provides a composition (e.g., a pharmaceutical composition) comprising a compound described herein and one or more polynucleotides. A composition (e.g., a pharmaceutical composition) may further comprise one or more cationic lipids, one or more non-cationic lipids, one or more cholesterol-based lipids and/or one or more PEG-modified lipids.

In certain embodiments a composition exhibits an enhanced (e.g., increased) ability to transfect one or more target cells. Accordingly, also provided herein are methods of transfecting one or more target cells. Such methods generally comprise the step of contacting the one or more target cells with the cationic lipids and/or pharmaceutical compositions disclosed herein (e.g., a liposomal formulation comprising a compound described herein encapsulating one or more polynucleotides) such that the one or more target cells are transfected with the materials encapsulated therein (e.g., one or more polynucleotides). As used herein, the terms "transfect" or "transfection" refer to the intracellular introduction of one or more encapsulated materials (e.g., nucleic acids and/or polynucleotides) into a cell, or preferably into a target cell. The introduced polynucleotide may be stably or transiently maintained in the target cell. The term "transfection efficiency" refers to the relative amount of such encapsulated material (e.g., polynucleotides) up-taken by, introduced into, and/or expressed by the target cell which is subject to transfection. In practice, transfection efficiency may be estimated by the amount of a reporter polynucleotide product produced by the target cells following transfection. In certain embodiments, the compounds and pharmaceutical compositions described herein demonstrate high transfection efficiencies thereby improving the likelihood that appropriate dosages of the encapsulated materials (e.g., one or more polynucleotides) will be delivered to the site of pathology and subsequently expressed, while at the same time minimizing potential systemic adverse effects or toxicity associated with the compound or their encapsulated contents.

Following transfection of one or more target cells by, for example, the polynucleotides encapsulated in the one or more lipid nanoparticles comprising the pharmaceutical or liposomal compositions disclosed herein, the production of the product (e.g., a polypeptide or protein) encoded by such polynucleotide may be preferably stimulated and the capability of such target cells to express the polynucleotide and produce, for example, a polypeptide or protein of interest is enhanced. For example, transfection of a target cell by one or more compounds or pharmaceutical compositions encapsulating mRNA will enhance (i.e., increase) the production of the protein or enzyme encoded by such mRNA.

Further, delivery vehicles described herein (e.g., liposomal delivery vehicles) may be prepared to preferentially distribute to other target tissues, cells or organs, such as the heart, lungs, kidneys, spleen. In embodiments, the lipid nanoparticles of the present invention may be prepared to achieve enhanced delivery to the target cells and tissues. For example, polynucleotides (e.g., mRNA) encapsulated in one or more of the compounds or pharmaceutical and liposomal compositions described herein can be delivered to and/or transfect targeted cells or tissues. In some embodiments, the encapsulated polynucleotides (e.g., mRNA) are capable of being expressed and functional polypeptide products produced (and in some instances excreted) by the target cell, thereby conferring a beneficial property to, for example the target cells or tissues. Such encapsulated polynucleotides (e.g., mRNA) may encode, for example, a hormone, enzyme, receptor, polypeptide, peptide or other protein of interest.

Liposomal Delivery Vehicles

In some embodiments, a composition is a suitable delivery vehicle. In embodiments, a composition is a liposomal delivery vehicle, e.g., a lipid nanoparticle.

The terms "liposomal delivery vehicle" and "liposomal composition" are used interchangeably.

Enriching liposomal compositions with one or more of the cationic lipids disclosed herein may be used as a means of improving (e.g., reducing) the toxicity or otherwise conferring one or more desired properties to such enriched liposomal composition (e.g., improved delivery of the encapsulated polynucleotides to one or more target cells and/or reduced in vivo toxicity of a liposomal composition). Accordingly, also contemplated are pharmaceutical compositions, and in particular liposomal compositions, that comprise one or more of the cationic lipids disclosed herein.

Thus, in certain embodiments, the compounds of the invention as described herein may be used as a component of a liposomal composition to facilitate or enhance the delivery and release of encapsulated materials (e.g., one or more therapeutic agents) to one or more target cells (e.g., by permeating or fusing with the lipid membranes of such target cells).

As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16:307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue.

In certain embodiments, such compositions (e.g., liposomal compositions) are loaded with or otherwise encapsulate materials, such as for example, one or more biologically-active polynucleotides (e.g., mRNA).

In embodiments, a composition (e.g., a pharmaceutical composition) comprises an mRNA encoding a protein, encapsulated within a liposome. In embodiments, a liposome comprises one or more cationic lipids, one or more non-cationic lipids, one or more cholesterol-based lipids and one or more PEG-modified lipids, and wherein at least one cationic lipid is a compound of the invention as described herein. In embodiments, a composition comprises an mRNA encoding for a protein (e.g., any protein described herein). In embodiments, a composition comprises an mRNA encoding for cystic fibrosis transmembrane conductance regulator (CFTR) protein. In embodiments, a composition comprises an mRNA encoding for ornithine transcarbamylase (OTC) protein.

In embodiments, a composition (e.g., a pharmaceutical composition) comprises a nucleic acid encapsulated within a liposome, wherein the liposome comprises a compound described herein.

In embodiments, a nucleic acid is an mRNA encoding a peptide or protein. In embodiments, an mRNA encodes a peptide or protein for use in the delivery to or treatment of the lung of a subject or a lung cell (e.g., an mRNA encodes cystic fibrosis transmembrane conductance regulator (CFTR) protein). In embodiments, an mRNA encodes a peptide or protein for use in the delivery to or treatment of the liver of a subject or a liver cell (e.g., an mRNA encodes ornithine transcarbamylase (OTC) protein). Still other exemplary mRNAs are described herein.

In embodiments, a liposomal delivery vehicle (e.g., a lipid nanoparticle) can have a net positive charge.

In embodiments, a liposomal delivery vehicle (e.g., a lipid nanoparticle) can have a net negative charge.

In embodiments, a liposomal delivery vehicle (e.g., a lipid nanoparticle) can have a net neutral charge.

In embodiments, a lipid nanoparticle that encapsulates a nucleic acid (e.g., mRNA encoding a peptide or protein) comprises one or more compounds of the invention as described herein.

For example, the amount of a compound of the invention as described herein in a composition can be described as a percentage ("wt %") of the combined dry weight of all lipids of a composition (e.g., the combined dry weight of all lipids present in a liposomal composition).

In embodiments of the pharmaceutical compositions described herein, a compound of the invention as described herein is present in an amount that is about 0.5 wt % to about 30 wt % (e.g., about 0.5 wt % to about 20 wt %) of the combined dry weight of all lipids present in a composition (e.g., a liposomal composition).

In embodiments, a compound of the invention as described herein is present in an amount that is about 1 wt % to about 30 wt %, about 1 wt % to about 20 wt %, about 1 wt % to about 15 wt %, about 1 wt % to about 10 wt %, or about 5 wt % to about 25 wt % of the combined dry weight of all lipids present in a composition (e.g., a liposomal composition). In embodiments, a compound of the invention as described herein is present in an amount that is about 0.5 wt % to about 5 wt %, about 1 wt % to about 10 wt %, about 5 wt % to about 20 wt %, or about 10 wt % to about 20 wt % of the combined dry weight of all lipids present in a composition such as a liposomal delivery vehicle.

In embodiments, the amount of a compound of the invention as described herein is present in an amount that is at least about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 96 wt %, about 97 wt %, about 98 wt %, or about 99 wt % of the combined dry weight of total lipids in a composition (e.g., a liposomal composition).

In embodiments, the amount of a compound of the invention as described herein is present in an amount that is no more than about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 96 wt %, about 97 wt %, about 98 wt %, or about 99 wt % of the combined dry weight of total lipids in a composition (e.g., a liposomal composition).

In embodiments, a composition (e.g., a liposomal delivery vehicle such as a lipid nanoparticle) comprises about 0.1 wt % to about 20 wt % (e.g., about 0.1 wt % to about 15 wt %) of a compound described herein. In embodiments, a delivery vehicle (e.g., a liposomal delivery vehicle such as a lipid nanoparticle) comprises about 0.5 wt %, about 1 wt %, about 3 wt %, about 5 wt %, or about 10 wt % of a compound described herein. In embodiments, a delivery vehicle (e.g., a liposomal delivery vehicle such as a lipid nanoparticle) comprises up to about 0.5 wt %, about 1 wt %, about 3 wt %, about 5 wt %, about 10 wt %, about 15 wt %, or about 20 wt % of a compound described herein. In embodiments, the percentage results in an improved beneficial effect (e.g., improved delivery to targeted tissues such as the liver or the lung).

The amount of a compound of the invention as described herein in a composition also can be described as a percentage ("mol %") of the combined molar amounts of total lipids of a composition (e.g., the combined molar amounts of all lipids present in a liposomal delivery vehicle).

In embodiments of pharmaceutical compositions described herein, a compound of the invention as described herein is present in an amount that is about 0.5 mol % to about 50 mol % (e.g., about 0.5 mol % to about 20 mol %) of the combined molar amounts of all lipids present in a composition such as a liposomal delivery vehicle.

In embodiments, a compound of the invention as described herein is present in an amount that is about 0.5 mol % to about 5 mol %, about 1 mol % to about 10 mol %, about 5 mol % to about 20 mol %, about 10 mol % to about 20 mol %, about 15 mol % to about 30 mol %, about 20 mol % to about 35 mol %, about 25 mol % to about 40 mol %, about 30 mol % to about 45 mol %, about 35 mol % to about 50 mol %, about 40 mol % to about 55 mol %, or about 45 mol % to about 60 mol % of the combined molar amounts of all lipids present in a composition such as a liposomal delivery vehicle. In embodiments, a compound of the invention as described herein is present in an amount that is about 1 mol % to about 60 mol %, 1 mol % to about 50 mol %, 1 mol % to about 40 mol %, 1 mol % to about 30 mol %, about 1 mol % to about 20 mol %, about 1 mol % to about 15 mol %, about 1 mol % to about 10 mol %, about 5 mol % to about 55 mol %, about 5 mol % to about 45 mol %, about 5 mol % to about 35 mol % or about 5 mol % to about 25 mol % of the combined molar amounts of all lipids present in a composition such as a liposomal delivery vehicle In certain embodiments, a compound of the invention as described herein can comprise from about 0.1 mol % to about 50 mol %, or from 0.5 mol % to about 50 mol %, or from about 1 mol % to about 25 mol %, or from about 1 mol % to about 10 mol % of the total amount of lipids in a composition (e.g., a liposomal delivery vehicle).

In certain embodiments, a compound of the invention as described herein can comprise greater than about 0.1 mol %, or greater than about 0.5 mol %, or greater than about 1 mol %, greater than about 5 mol %, greater than about 10 mol %, greater than about 20 mol %, greater than about 30 mol %, or greater than about 40 mol % of the total amount of lipids in the lipid nanoparticle.

In certain embodiments, a compound as described can comprise less than about 60 mol %, or less than about 55 mol %, or less than about 50 mol %, or less than about 45 mol %, or less than about 40 mol %, or less than about 35 mol %, less than about 30 mol %, or less than about 25 mol %, or less than about 10 mol %, or less than about 5 mol %, or less than about 1 mol % of the total amount of lipids in a composition (e.g., a liposomal delivery vehicle).

In embodiments, the amount of a compound of the invention as described herein is present in an amount that is at least about 5 mol %, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, about 96 mol %, about 97 mol %, about 98 mol %, or about 99 mol % of the combined molar amounts of total lipids in a composition (e.g., a liposomal composition).

In embodiments, the amount of a compound of the invention as described herein is present in an amount that is no more than about 5 mol %, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, about 96 mol %, about 97 mol %, about 98 mol %, or about 99 mol % of the combined molar amounts of total lipids in a composition (e.g., a liposomal composition).

In embodiments, the percentage results in an improved beneficial effect (e.g., improved delivery to targeted tissues such as the liver or the lung).

In a typical embodiment, a composition of the invention (e.g., a liposomal composition) comprises one or more cationic lipids, one or more non-cationic lipids, one or more cholesterol-based lipids, and one or more PEG-modified lipids, wherein at least one cationic lipid is a compound of the invention as described herein. For example, a composition suitable for practicing the invention has four lipid components comprising a compound of the invention as described herein as the cationic lipid component, a non-cationic lipid, a cholesterol-based lipid and a PEG-modified lipid. The non-cationic lipid may be DOPE or DEPE. The cholesterol-based lipid may be cholesterol. The PEG-modified lipid may be DMG-PEG2K.

In embodiments, the composition of the present invention comprises the cationic lipid of the present invention, DMG-PEG2000, Cholesterol and DOPE and the molar ratio of cationic lipid: DMG-PEG2000: Cholesterol: DOPE is 40:5:25:30.

In further embodiments, pharmaceutical (e.g., liposomal) compositions comprise one or more of a PEG-modified lipid, a non-cationic lipid and a cholesterol lipid. In other embodiments, such pharmaceutical (e.g., liposomal) compositions comprise: one or more PEG-modified lipids; one or more non-cationic lipids; and one or more cholesterol lipids. In yet further embodiments, such pharmaceutical (e.g., liposomal) compositions comprise: one or more PEG-modified lipids and one or more cholesterol lipids.

In embodiments, a composition (e.g., lipid nanoparticle) that encapsulates a nucleic acid (e.g., mRNA encoding a peptide or protein) comprises one or more compounds of the invention as described herein and one or more lipids selected from the group consisting of a cationic lipid, a non-cationic lipid, and a PEGylated lipid.

In embodiments, a composition (e.g., lipid nanoparticle) that encapsulates a nucleic acid (e.g., mRNA encoding a peptide or protein) comprises one or more compound of the invention as described herein; one or more lipids selected from the group consisting of a cationic lipid, a non-cationic lipid, and a PEGylated lipid; and further comprises a cholesterol-based lipid. Typically, such a composition has four lipid components comprising a compound of the invention as described herein as the cationic lipid component, a non-cationic lipid (e.g., DOPE), a cholesterol-based lipid (e.g., cholesterol) and a PEG-modified lipid (e.g., DMG-PEG2K).

In embodiments, a lipid nanoparticle that encapsulates a nucleic acid (e.g., mRNA encoding a peptide or protein) comprises one or more compounds of the invention as described herein, as well as one or more lipids selected from the group consisting of a cationic lipid, a non-cationic lipid, a PEGylated lipid, and a cholesterol-based lipid.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly.

In some embodiments, the ratio of cationic lipid(s) to non-cationic lipid(s) to cholesterol-based lipid(s) to PEG-modified lipid(s) may be between about 30-60:20-40:20-30:1-10, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5.

Cationic Lipids

In addition to any of the compounds of the invention as described herein, a composition may comprise one or more additional cationic lipids.

In some embodiments, liposomes may comprise one or more additional cationic lipids. As used herein, the phrase "cationic lipid" refers to any of a number of lipid species that have a net positive charge at a selected pH, such as physiological pH. Several cationic lipids have been described in the literature, many of which are commercially available.

Suitable additional cationic lipids for use in the compositions include the cationic lipids as described in the literature.

Helper Lipids

Compositions (e.g., liposomal compositions) may also comprise one or more helper lipids. Such helper lipids include non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), 1,2-Dierucoyl-sn-glycero-3-phosphoethanolamine (DEPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-I-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, I-stearoyl-2-oleoyl-phosphatidyethanolamine (SOPE), or a mixture thereof. A non-cationic or helper lipid suitable for practicing the invention is dioleoylphosphatidylethanolamine (DOPE). Alternatively, 1,2-Dierucoyl-sn-glycero-3-phosphoethanolamine (DEPE) can be used as a non-cationic or helper lipid.

In some embodiments, a non-cationic lipid is a neutral lipid, i.e., a lipid that does not carry a net charge in the conditions under which the composition is formulated and/or administered.

In some embodiments, a non-cationic lipid may be present in a molar ratio (mol %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a molar ratio (mol %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 mol %, greater than about 10 mol %, greater than about 20 mol %, greater than about 30 mol %, or greater than about 40 mol %. In some embodiments, the percentage total non-cationic lipids in a liposome may be greater than about 5 mol %, greater than about 10 mol %, greater than about 20 mol %, greater than about 30 mol %, or greater than about 40 mol %. In some embodiments, the percentage of non-cationic lipid in a liposome is no more than about 5 mol %, no more than about 10 mol %, no more than about 20 mol %, no more than about 30 mol %, or no more than about 40 mol %. In some embodiments, the percentage total non-cationic lipids in a liposome may be no more than about 5 mol %, no more than about 10 mol %, no more than about 20 mol %, no more than about 30 mol %, or no more than about 40 mol %.

In some embodiments, a non-cationic lipid may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 wt %, greater than about 10 wt %, greater than about 20 wt %, greater than about 30 wt %, or greater than about 40 wt %. In some embodiments, the percentage total non-cationic lipids in a liposome may be greater than about 5 wt %, greater than about 10 wt %, greater than about 20 wt %, greater than about 30 wt %, or greater than about 40 wt %. In some embodiments, the percentage of non-cationic lipid in a liposome is no more than about 5 wt %, no more than about 10 wt %, no more than about 20 wt %, no more than about 30 wt %, or no more than about 40 wt %. In some embodiments, the percentage total non-cationic lipids in a liposome may be no more than about 5 wt %, no more than about 10 wt %, no more than about 20 wt %, no more than about 30 wt %, or no more than about 40 wt %.

Cholesterol-Based Lipids

In some embodiments, a composition (e.g., a liposomal composition) comprises one or more cholesterol-based lipids. For example, a suitable cholesterol-based lipid for practicing the invention is cholesterol. Other suitable cholesterol-based lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or imidazole cholesterol ester (ICE), which has the following structure, ("ICE")

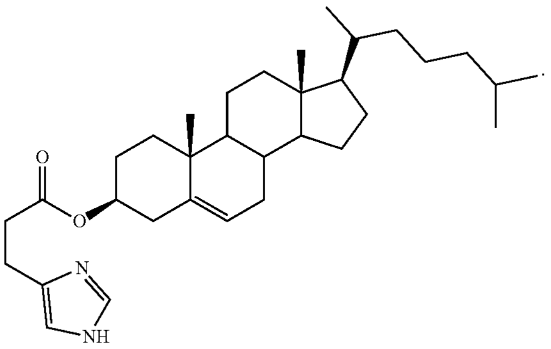

In some embodiments, a cholesterol-based lipid may be present in a molar ratio (mol %) of about 1% to about 30%, or about 5% to about 20% of the total lipids present in a liposome. In some embodiments, the percentage of cholesterol-based lipid in the lipid nanoparticle may be greater than about 5 mol %, greater than about 10 mol %, greater than about 20 mol %, greater than about 30 mol %, or greater than about 40 mol %. In some embodiments, the percentage of cholesterol-based lipid in the lipid nanoparticle may be no more than about 5 mol %, no more than about 10 mol %, no more than about 20 mol %, no more than about 30 mol %, or no more than about 40 mol %.

In some embodiments, a cholesterol-based lipid may be present in a weight ratio (wt %) of about 1% to about 30%, or about 5% to about 20% of the total lipids present in a liposome. In some embodiments, the percentage of cholesterol-based lipid in the lipid nanoparticle may be greater than about 5 wt %, greater than about 10 wt %, greater than about 20 wt %, greater than about 30 wt %, or greater than about 40 wt %. In some embodiments, the percentage of cholesterol-based lipid in the lipid nanoparticle may be no more than about 5 wt %, no more than about 10 wt %, no more than about 20 wt %, no more than about 30 wt %, or no more than about 40 wt %.

PEGylated Lipids

In some embodiments, a composition (e.g., a liposomal composition) comprises one or more further PEGylated lipids. A suitable PEG-modified or PEGylated lipid for practicing the invention is 1,2-dimyristoyl-rac-glycero-3-methoxypolyethylene glycol-2000 (DMG-PEG2K).

For example, the use of polyethylene glycol (PEG)-modified phospholipids and derivatized lipids such as derivatized ceramides (PEG-CER), including N-octanoyl-sphingosine-1-[succinyl(methoxy polyethylene glycol)-2000] (C8 PEG-2000 ceramide) is also contemplated by the present invention in combination with one or more of compounds of the invention as described herein and, in some embodiments, other lipids together which comprise the liposome. In some embodiments, particularly useful exchangeable lipids are PEG-ceramides having shorter acyl chains (e.g., $C_{14}$ Or $C_{18}$).

Contemplated further PEG-modified lipids (also referred to herein as a PEGylated lipid, which term is interchangeable with PEG-modified lipid) include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

Further PEG-modified phospholipid and derivatized lipids of the present invention may be present in a molar ratio (mol %) from about 0% to about 10%, about 0.5% to about 10%, about 1% to about 10%, about 2% to about 10%, or about 3% to about 5% of the total lipid present in the composition (e.g., a liposomal composition).

Pharmaceutical Formulations and Therapeutic Uses

Compounds of the invention as described herein may be used in the preparation of compositions (e.g., to construct liposomal compositions) that facilitate or enhance the delivery and release of encapsulated materials (e.g., one or more therapeutic polynucleotides) to one or more target cells (e.g., by permeating or fusing with the lipid membranes of such target cells).

For example, when a liposomal composition (e.g., a lipid nanoparticle) comprises or is otherwise enriched with one or more of the compounds disclosed herein, the phase transition in the lipid bilayer of the one or more target cells may facilitate the delivery of the encapsulated materials (e.g., one or more therapeutic polynucleotides encapsulated in a lipid nanoparticle) into the one or more target cells.

Similarly, in certain embodiments compounds of the invention as described herein may be used to prepare liposomal vehicles that are characterized by their reduced toxicity in vivo. In certain embodiments, the reduced toxicity is a function of the high transfection efficiencies associated with the compositions disclosed herein, such that a reduced quantity of such composition may administered to the subject to achieve a desired therapeutic response or outcome.

Thus, pharmaceutical formulations comprising a compound described and nucleic acids provided by the present invention may be used for various therapeutic purposes. To facilitate delivery of nucleic acids in vivo, a compound described herein and nucleic acids can be formulated in combination with one or more additional pharmaceutical carriers, targeting ligands or stabilizing reagents. In some embodiments, a compound described herein can be formulated via pre-mixed lipid solution. In other embodiments, a composition comprising a compound described herein can be formulated using post-insertion techniques into the lipid membrane of the nanoparticles. Techniques for formulation and administration of drugs may be found in "Remington's Pharmaceutical Sciences," Mack Publishing Co., Easton, Pa., latest edition.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the nucleic acids to a muscle cell. In some embodiments the administration results in delivery of the nucleic acids to a hepatocyte (i.e., liver cell).

A common route for administering a liposomal composition of the invention may be intravenous delivery, in particular when treating metabolic disorders, especially those affecting the liver (e.g., ornithine transcarbamylase (OTC) deficiency). Alternatively, depending on the disease or disorder to be treated, the liposomal composition may be administered via pulmonary delivery (e.g., for the treatment of cystic fibrosis). For vaccination, a liposomal composition of the invention is typically administered intramuscularly. Diseases or disorders affecting the eye may be treated by administering a liposomal composition of the invention intravitreally.

Alternatively or additionally, pharmaceutical formulations of the invention may be administered in a local rather than systemic manner, for example, via injection of the pharmaceutical formulation directly into a targeted tissue, preferably in a sustained release formulation. Local delivery can be affected in various ways, depending on the tissue to be targeted. Exemplary tissues in which delivered mRNA may be delivered and/or expressed include, but are not limited to the liver, kidney, heart, spleen, serum, brain, skeletal muscle, lymph nodes, skin, and/or cerebrospinal fluid. In embodiments, the tissue to be targeted in the liver. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection.

Compositions described herein can comprise mRNA encoding peptides including those described herein (e.g., a polypeptide such as a protein).

In embodiments, a mRNA encodes a polypeptide.

In embodiments, a mRNA encodes a protein.

Exemplary peptides encoded by mRNA (e.g., exemplary proteins encoded by mRNA) are described herein.

The present invention provides methods for delivering a composition having full-length mRNA molecules encoding a peptide or protein of interest for use in the treatment of a subject, e.g., a human subject or a cell of a human subject or a cell that is treated and delivered to a human subject.

Accordingly, in certain embodiments the present invention provides a method for producing a therapeutic composition comprising full-length mRNA that encodes a peptide or protein for use in the delivery to or treatment of the lung of a subject or a lung cell. In certain embodiments the present invention provides a method for producing a therapeutic composition having full-length mRNA that encodes for cystic fibrosis transmembrane conductance regulator (CFTR) protein. In certain embodiments the present invention provides a method for producing a therapeutic composition having full-length mRNA that encodes for ATP-binding cassette sub-family A member 3 protein. In certain embodiments the present invention provides a method for producing a therapeutic composition having full-length mRNA that encodes for dynein axonemal intermediate chain 1 protein. In certain embodiments the present invention provides a method for producing a therapeutic composition having full-length mRNA that encodes for dynein axonemal heavy chain 5 (DNAH5) protein. In certain embodiments the present invention provides a method for producing a therapeutic composition having full-length mRNA that encodes for alpha-1-antitrypsin protein. In certain embodiments the present invention provides a method for producing a therapeutic composition having full-length mRNA that encodes for forkhead box P3 (FOXP3) protein. In certain embodiments the present invention provides a method for producing a therapeutic composition having full-length mRNA that encodes one or more surfactant protein, e.g., one or more of surfactant A protein, surfactant B protein, surfactant C protein, and surfactant D protein.

In certain embodiments the present invention provides a method for producing a therapeutic composition having full-length mRNA that encodes a peptide or protein for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition having full-length mRNA that encodes for a protein associated with a urea cycle disorder. In certain embodiments the present invention provides a method for producing a therapeutic composition having full-length mRNA that encodes for ornithine transcarbamylase (OTC) protein. In certain embodiments the present invention provides a method for producing a therapeutic composition having full-length mRNA that encodes for argininosuccinate synthetase 1 protein. In certain embodiments the present invention provides a method for producing a therapeutic composition having full-length mRNA that encodes for carbamoyl phosphate synthetase I protein. In certain embodiments the present invention provides a method for producing a therapeutic composition having full-length mRNA that encodes for arginosuccinate lyase protein. In certain embodiments the present invention provides a method for producing a therapeutic composition having full-length mRNA that encodes for arginase protein.

In certain embodiments the present invention provides a method for producing a therapeutic composition having full-length mRNA that encodes for a protein associated with a lysosomal storage disorder. In certain embodiments the present invention provides a method for producing a therapeutic composition having full-length mRNA that encodes for alpha galactosidase protein. In certain embodiments the present invention provides a method for producing a therapeutic composition having full-length mRNA that encodes for glucocerebrosidase protein. In certain embodiments the present invention provides a method for producing a therapeutic composition having full-length mRNA that encodes for iduronate-2-sulfatase protein. In certain embodiments the present invention provides a method for producing a therapeutic composition having full-length mRNA that encodes for iduronidase protein. In certain embodiments the present invention provides a method for producing a therapeutic composition having full-length mRNA that encodes for N-acetyl-alpha-D-glucosaminidase protein. In certain embodiments the present invention provides a method for producing a therapeutic composition having full-length mRNA that encodes for heparan N-sulfatase protein. In certain embodiments the present invention provides a method for producing a therapeutic composition having full-length mRNA that encodes for galactosamine-6 sulfatase protein. In certain embodiments the present invention provides a method for producing a therapeutic composition having full-length mRNA that encodes for beta-galactosidase protein. In certain embodiments the present invention provides a method for producing a therapeutic composition having full-length mRNA that encodes for lysosomal lipase protein. In certain embodiments the present invention provides a method for producing a therapeutic composition having full-length mRNA that encodes for arylsulfatase B (N-acetylgalactosamine-4-sulfatase) protein. In certain embodiments the present invention provides a method for producing a therapeutic composition having full-length mRNA that encodes for transcription factor EB (TFEB).

In certain embodiments the present invention provides a method for producing a therapeutic composition having full-length mRNA that encodes for a protein associated with a glycogen storage disorder. In certain embodiments the present invention provides a method for producing a therapeutic composition having full-length mRNA that encodes for acid alpha-glucosidase protein. In certain embodiments the present invention provides a method for producing a therapeutic composition having full-length mRNA that encodes for glucose-6-phosphatase (G6PC) protein. In certain embodiments the present invention provides a method for producing a therapeutic composition having full-length mRNA that encodes for liver glycogen phosphorylase protein. In certain embodiments the present invention provides a method for producing a therapeutic composition having full-length mRNA that encodes for muscle phosphoglycerate mutase protein. In certain embodiments the present invention provides a method for producing a therapeutic composition having full-length mRNA that encodes for glycogen debranching enzyme.

In certain embodiments the present invention provides a method for producing a therapeutic composition having full-length mRNA that encodes for a protein associated with amino acid metabolism. In certain embodiments the present invention provides a method for producing a therapeutic composition having full-length mRNA that encodes for phenylalanine hydroxylase enzyme. In certain embodiments the present invention provides a method for producing a therapeutic composition having full-length mRNA that encodes for glutaryl-CoA dehydrogenase enzyme. In certain embodiments the present invention provides a method for producing a therapeutic composition having full-length mRNA that encodes for propionyl-CoA caboxylase enzyme. In certain embodiments the present invention provides a method for producing a therapeutic composition having full-length mRNA that encodes for oxalase alanine-glyoxylate aminotransferase enzyme.

In certain embodiments the present invention provides a method for producing a therapeutic composition having full-length mRNA that encodes for a protein associated with a lipid metabolism or fibrotic disorder. In certain embodiments the present invention provides a method for producing a therapeutic composition having full-length mRNA that encodes for a mTOR inhibitor. In certain embodiments the present invention provides a method for producing a therapeutic composition having full-length mRNA that encodes for ATPase phospholipid transporting 8B1 (ATP8B1) protein. In certain embodiments the present invention provides a method for producing a therapeutic composition having full-length mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition having full-length mRNA that encodes for PPAR-gamma protein or an active variant.

In certain embodiments the present invention provides a method for producing a therapeutic composition having full-length mRNA that encodes for a protein associated with methylmalonic acidemia. For example, in certain embodiments the present invention provides a method for producing a therapeutic composition having full-length mRNA that encodes for methylmalonyl CoA mutase protein. In certain embodiments the present invention provides a method for producing a therapeutic composition having full-length mRNA that encodes for methylmalonyl CoA epimerase protein.

In certain embodiments the present invention provides a method for producing a therapeutic composition having full-length mRNA for which delivery to or treatment of the liver can provide therapeutic benefit. In certain embodiments the present invention provides a method for producing a therapeutic composition having full-length mRNA that encodes for ATP7B protein, also known as Wilson disease protein. In certain embodiments the present invention provides a method for producing a therapeutic composition having full-length mRNA that encodes for porphobilinogen deaminase enzyme. In certain embodiments the present invention provides a method for producing a therapeutic composition having full-length mRNA that encodes for one or clotting enzymes, such as Factor VIII, Factor IX, Factor VII, and Factor X. In certain embodiments the present invention provides a method for producing a therapeutic composition having full-length mRNA that encodes for human hemochromatosis (HFE) protein.

In certain embodiments the present invention provides a method for producing a therapeutic composition having full-length mRNA that encodes a peptide or protein for use in the delivery to or treatment of the cardiovasculature of a subject or a cardiovascular cell. In certain embodiments the present invention provides a method for producing a therapeutic composition having full-length mRNA that encodes for vascular endothelial growth factor A protein. In certain embodiments the present invention provides a method for producing a therapeutic composition having full-length mRNA that encodes for relaxin protein. In certain embodiments the present invention provides a method for producing a therapeutic composition having full-length mRNA that encodes for bone morphogenetic protein-9 protein. In certain embodiments the present invention provides a method for producing a therapeutic composition having full-length mRNA that encodes for bone morphogenetic protein-2 receptor protein.

In certain embodiments the present invention provides a method for producing a therapeutic composition having full-length mRNA that encodes a peptide or protein for use in the delivery to or treatment of the muscle of a subject or a muscle cell. In certain embodiments the present invention provides a method for producing a therapeutic composition having full-length mRNA that encodes for dystrophin protein. In certain embodiments the present invention provides a method for producing a therapeutic composition having full-length mRNA that encodes for frataxin protein. In certain embodiments the present invention provides a method for producing a therapeutic composition having full-length mRNA that encodes a peptide or protein for use in the delivery to or treatment of the cardiac muscle of a subject or a cardiac muscle cell. In certain embodiments the present invention provides a method for producing a therapeutic composition having full-length mRNA that encodes for a protein that modulates one or both of a potassium channel and a sodium channel in muscle tissue or in a muscle cell. In certain embodiments the present invention provides a method for producing a therapeutic composition having full-length mRNA that encodes for a protein that modulates a Kv7.1 channel in muscle tissue or in a muscle cell. In certain embodiments the present invention provides a method for producing a therapeutic composition having full-length mRNA that encodes for a protein that modulates a Nav1.5 channel in muscle tissue or in a muscle cell.

In certain embodiments the present invention provides a method for producing a therapeutic composition having full-length mRNA that encodes a peptide or protein for use in the delivery to or treatment of the nervous system of a subject or a nervous system cell. For example, in certain embodiments the present invention provides a method for producing a therapeutic composition having full-length mRNA that encodes for survival motor neuron 1 protein. For example, in certain embodiments the present invention provides a method for producing a therapeutic composition having full-length mRNA that encodes for survival motor neuron 2 protein. In certain embodiments the present invention provides a method for producing a therapeutic composition having full-length mRNA that encodes for frataxin protein. In certain embodiments the present invention provides a method for producing a therapeutic composition having full-length mRNA that encodes for ATP binding cassette subfamily D member 1 (ABCD1) protein. In certain embodiments the present invention provides a method for producing a therapeutic composition having full-length mRNA that encodes for CLN3 protein.

In certain embodiments the present invention provides a method for producing a therapeutic composition having full-length mRNA that encodes a peptide or protein for use in the delivery to or treatment of the blood or bone marrow of a subject or a blood or bone marrow cell. In certain embodiments the present invention provides a method for producing a therapeutic composition having full-length mRNA that encodes for beta globin protein. In certain embodiments the present invention provides a method for producing a therapeutic composition having full-length mRNA that encodes for Bruton's tyrosine kinase protein. In certain embodiments the present invention provides a method for producing a therapeutic composition having full-length mRNA that encodes for one or clotting enzymes, such as Factor VIII, Factor IX, Factor VII, and Factor X.

In certain embodiments the present invention provides a method for producing a therapeutic composition having full-length mRNA that encodes a peptide or protein for use in the delivery to or treatment of the kidney of a subject or a kidney cell. In certain embodiments the present invention provides a method for producing a therapeutic composition having full-length mRNA that encodes for collagen type IV alpha 5 chain (COL4A5) protein.

In certain embodiments the present invention provides a method for producing a therapeutic composition having full-length mRNA that encodes a peptide or protein for use in the delivery to or treatment of the eye of a subject or an eye cell. In certain embodiments the present invention provides a method for producing a therapeutic composition having full-length mRNA that encodes for ATP-binding cassette sub-family A member 4 (ABCA4) protein. In certain embodiments the present invention provides a method for producing a therapeutic composition having full-length mRNA that encodes for retinoschisin protein. In certain embodiments the present invention provides a method for producing a therapeutic composition having full-length mRNA that encodes for retinal pigment epithelium-specific 65 kDa (RPE65) protein. In certain embodiments the present invention provides a method for producing a therapeutic composition having full-length mRNA that encodes for centrosomal protein of 290 kDa (CEP290).

In certain embodiments the present invention provides a method for producing a therapeutic composition having full-length mRNA that encodes a peptide or protein for use in the delivery of or treatment with a vaccine for a subject or a cell of a subject. For example, in certain embodiments the present invention provides a method for producing a therapeutic composition having full-length mRNA that encodes for an antigen from an infectious agent, such as a virus. In certain embodiments the present invention provides a method for producing a therapeutic composition having full-length mRNA that encodes for an antigen from influenza virus. In certain embodiments the present invention provides a method for producing a therapeutic composition having full-length mRNA that encodes for an antigen from respiratory syncytial virus. In certain embodiments the present invention provides a method for producing a therapeutic composition having full-length mRNA that encodes for an antigen from rabies virus. In certain embodiments the present invention provides a method for producing a therapeutic composition having full-length mRNA that encodes for an antigen from cytomegalovirus. In certain embodiments the present invention provides a method for producing a therapeutic composition having full-length mRNA that encodes for an antigen from rotavirus. In certain embodiments the present invention provides a method for producing a therapeutic composition having full-length mRNA that encodes for an antigen from a hepatitis virus, such as hepatitis A virus, hepatitis B virus, or hepatis C virus. In certain embodiments the present invention provides a method for producing a therapeutic composition having full-length mRNA that encodes for an antigen from human papillomavirus. In certain embodiments the present invention provides a method for producing a therapeutic composition having full-length mRNA that encodes for an antigen from a herpes simplex virus, such as herpes simplex virus 1 or herpes simplex virus 2. In certain embodiments the present invention provides a method for producing a therapeutic composition having full-length mRNA that encodes for an antigen from a human immunodeficiency virus, such as human immunodeficiency virus type 1 or human immunodeficiency virus type 2. In certain embodiments the present invention provides a method for producing a therapeutic composition having full-length mRNA that encodes for an antigen from a human metapneumovirus. In certain embodiments the present invention provides a method for producing a therapeutic composition having full-length mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition having full-length mRNA that encodes for an antigen from malaria virus. In certain embodiments the present invention provides a method for producing a therapeutic composition having full-length mRNA that encodes for an antigen from zika virus. In certain embodiments the present invention provides a method for producing a therapeutic composition having full-length mRNA that encodes for an antigen from chikungunya virus.

In certain embodiments the present invention provides a method for producing a therapeutic composition having full-length mRNA that encodes for an antigen associated with a cancer of a subject or identified from a cancer cell of a subject. In certain embodiments the present invention provides a method for producing a therapeutic composition having full-length mRNA that encodes for an antigen determined from a subject's own cancer cell, i.e., to provide a personalized cancer vaccine. In certain embodiments the present invention provides a method for producing a therapeutic composition having full-length mRNA that encodes for an antigen expressed from a mutant KRAS gene.

In certain embodiments the present invention provides a method for producing a therapeutic composition having full-length mRNA that encodes for an antibody. In certain embodiments, the antibody can be a bi-specific antibody. In certain embodiments, the antibody can be part of a fusion protein. In certain embodiments the present invention provides a method for producing a therapeutic composition having full-length mRNA that encodes for an antibody to OX40. In certain embodiments the present invention provides a method for producing a therapeutic composition having full-length mRNA that encodes for an antibody to VEGF. In certain embodiments the present invention provides a method for producing a therapeutic composition having full-length mRNA that encodes for an antibody to tissue necrosis factor alpha. In certain embodiments the present invention provides a method for producing a therapeutic composition having full-length mRNA that encodes for an antibody to CD3. In certain embodiments the present invention provides a method for producing a therapeutic composition having full-length mRNA that encodes for an antibody to CD19.

In certain embodiments the present invention provides a method for producing a therapeutic composition having full-length mRNA that encodes for an immunomodulator. In certain embodiments the present invention provides a method for producing a therapeutic composition having full-length mRNA that encodes for Interleukin 12. In certain embodiments the present invention provides a method for producing a therapeutic composition having full-length mRNA that encodes for Interleukin 23. In certain embodiments the present invention provides a method for producing a therapeutic composition having full-length mRNA that encodes for Interleukin 36 gamma. In certain embodiments the present invention provides a method for producing a therapeutic composition having full-length mRNA that encodes for a constitutively active variant of one or more stimulator of interferon genes (STING) proteins.

In certain embodiments the present invention provides a method for producing a therapeutic composition having full-length mRNA that encodes for an endonuclease. In certain embodiments the present invention provides a method for producing a therapeutic composition having full-length mRNA that encodes for an RNA-guided DNA endonuclease protein, such as Cas 9 protein. In certain embodiments the present invention provides a method for producing a therapeutic composition having full-length mRNA that encodes for a meganuclease protein. In certain embodiments the present invention provides a method for producing a therapeutic composition having full-length mRNA that encodes for a transcription activator-like effector nuclease protein. In certain embodiments the present invention provides a method for producing a therapeutic composition having full-length mRNA that encodes for a zinc finger nuclease protein.

Delivery Methods

The route of delivery used in the methods of the invention allows for non-invasive, self-administration of the compounds of the invention. In some embodiments, the methods involve intratracheal or pulmonary administration by aerosolization, nebulization, or instillation of a compositions comprising mRNA encoding a therapeutic protein in a suitable transfection or lipid carrier vehicles as described above. In some embodiments, the protein is encapsulated with a liposome. In some embodiments, the liposome comprises a lipid, which is a compound of the invention. As used herein below, administration of a compound of the invention includes administration of a composition comprising a compound of the invention.

Although the local cells and tissues of the lung represent a potential target capable of functioning as a biological depot or reservoir for production and secretion of the protein encoded by the mRNA, applicants have discovered that administration of the compounds of the invention to the lung via aerosolization, nebulization, or instillation results in the distribution of even non-secreted proteins outside the lung cells. Without wishing to be bound by any particular theory, it is contemplated that nanoparticle compositions of the invention pass, through the lung airway-blood barrier, resulting in translation of the intact nanoparticle to non-lung cells and tissues, such as, e.g., the heart, the liver, the spleen, where it results in the production of the encoded protein in these non-lung tissues. Thus, the utility of the compounds of the invention and methods of the invention extend beyond production of therapeutic protein in lung cells and tissues of the lung and can be used to delivery to non-lung target cells and/or tissues. They are useful in the management and treatment of a large number of diseases, and in particular peripheral diseases which result from both secreted and non-secreted protein and/or enzyme deficiencies (e.g., one or more lysosomal storage disorders). In certain embodiments, the compounds of the invention, used in the methods of the invention result in the distribution of the mRNA encapsulated nanoparticles and production of the encoded protein in the liver, spleen, heart, and/or other non-lung cells. For example, administration of the compounds of the invention, by aerosolization, nebulization, or instillation to the lung will result in the composition itself and its protein product (e.g., functional beta galactosidase protein) will be detectable in both the local cells and tissues of the lung, as well as in peripheral target cells, tissues and organs as a result of translocation of the mRNA and delivery vehicle to non-lung cells.

In certain embodiments, the compounds of the invention may be employed in the methods of the invention to specifically target peripheral cells or tissues. Following the pulmonary delivery, it is contemplated the compounds of the invention cross the lung airway-blood barrier and distribute into cells other than the local lung cells. Accordingly, the compounds disclosed herein may be administered to a subject by way of the pulmonary route of administration, using a variety of approach known by those skilled in the art (e.g., by inhalation), and distribute to both the local target cells and tissues of the lung, as well as in peripheral non-lung cells and tissues (e.g., cells of the liver, spleen, kidneys, heart, skeletal muscle, lymph nodes, brain, cerebrospinal fluid, and plasma). As a result, both the local cells of the lung and the peripheral non-lung cells can serve as biological reservoirs or depots capable of producing and/or secreting a translation product encoded by one or more polynucleotides. Accordingly, the present invention is not limited to the treatment of lung diseases or conditions, but rather can be used as a non-invasive means of facilitating the delivery of polynucleotides, or the production of enzymes and proteins encoded thereby, in peripheral organs, tissues and cells (e.g., hepatocytes) which would otherwise be achieved only by systemic administration. Exemplary peripheral non-lung cells include, but are not limited to, hepatocytes, epithelial cells, hematopoietic cells, epithelial cells, endothelial cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following administration of the composition to the subject, the protein product encoded by the mRNA (e.g., a functional protein or enzyme) is detectable in the peripheral target tissues for at least about one to seven days or longer following administration of the compound to the subject. The amount of protein product necessary to achieve a therapeutic effect will vary depending on the condition being treated, the protein encoded, and the condition of the patient. For example, the protein product may be detectable in the peripheral target tissues at a concentration (e.g., a therapeutic concentration) of at least 0.025-1.5 μg/ml (e.g., at least 0.050 μg/ml, at least 0.075 μg/ml, at least 0.1 μg/ml, at least 0.2 μg/ml, at least 0.3 μg/ml, at least 0.4 μg/ml, at least 0.5 μg/ml, at least 0.6 μg/ml, at least 0.7 μg/ml, at least 0.8 g/ml, at least 0.9 μg/ml, at least 1.0 μg/ml, at least 1.1 μg/ml, at least 1.2 μg/ml, at least 1.3 μg/ml, at least 1.4 μg/ml, or at least 1.5 μg/ml), for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 days or longer following administration of the compound to the subject.

It has been demonstrated that nucleic acids can be delivered to the lungs by intratracheal administration of a liquid suspension of the compound and inhalation of an aerosol mist produced by a liquid nebulizer or the use of a dry powder apparatus such as that described in U.S. Pat. No. 5,780,014, incorporated herein by reference.

In certain embodiments, the compounds of the invention may be formulated such that they may be aerosolized or otherwise delivered as a particulate liquid or solid prior to or upon administration to the subject. Such compounds may be administered with the assistance of one or more suitable devices for administering such solid or liquid particulate compositions (such as, e.g., an aerosolized aqueous solution or suspension) to generate particles that are easily respirable or inhalable by the subject. In some embodiments, such devices (e.g., a metered dose inhaler, jet-nebulizer, ultrasonic nebulizer, dry-powder-inhalers, propellant-based inhaler or an insufflator) facilitate the administration of a predetermined mass, volume or dose of the compositions (e.g., about 0.5 mg/kg of mRNA per dose) to the subject. For example, in certain embodiments, the compounds of the invention are administered to a subject using a metered dose inhaler containing a suspension or solution comprising the compound and a suitable propellant. In certain embodiments, the compounds of the invention may be formulated as a particulate powder (e.g., respirable dry particles) intended for inhalation. In certain embodiments, compositions of the invention formulated as respirable particles are appropriately sized such that they may be respirable by the subject or delivered using a suitable device (e.g., a mean D50 or D90 particle size less than about 500 μm, 400 μm, 300 μm, 250 μm, 200 μm, 150 μm, 100 μm, 75 μm, 50 μm, 25 μm, 20 μm, 15 μm, 12.5 μm, 10 μm, 5 μm, 2.5 μm or smaller). In yet other embodiments, the compounds of the invention are formulated to include one or more pulmonary surfactants (e.g., lamellar bodies). In some embodiments, the compounds of the invention are administered to a subject such that a concentration of at least 0.05 mg/kg, at least 0.1 mg/kg, at least 0.5 mg/kg, at least 1.0 mg/kg, at least 2.0 mg/kg, at least 3.0 mg/kg, at least 4.0 mg/kg, at least 5.0 mg/kg, at least 6.0 mg/kg, at least 7.0 mg/kg, at least 8.0 mg/kg, at least 9.0 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, at least 50 mg/kg, at least 55 mg/kg, at least 60 mg/kg, at least 65 mg/kg, at least 70 mg/kg, at least 75 mg/kg, at least 80 mg/kg, at least 85 mg/kg, at least 90 mg/kg, at least 95 mg/kg, or at least 100 mg/kg body weight is administered in a single dose. In some embodiments, the compounds of the invention are administered to a subject such that a total amount of at least 0.1 mg, at least 0.5 mg, at least 1.0 mg, at least 2.0 mg, at least 3.0 mg, at least 4.0 mg, at least 5.0 mg, at least 6.0 mg, at least 7.0 mg, at least 8.0 mg, at least 9.0 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg or at least 100 mg mRNA is administered in one or more doses.

EXAMPLES

While certain compounds, compositions and methods of the present invention have been described with specificity in accordance with certain embodiments, the following examples serve only to illustrate the compounds of the invention and are not intended to limit the same.

Synthetic Scheme for Vanillic Acid Lipids
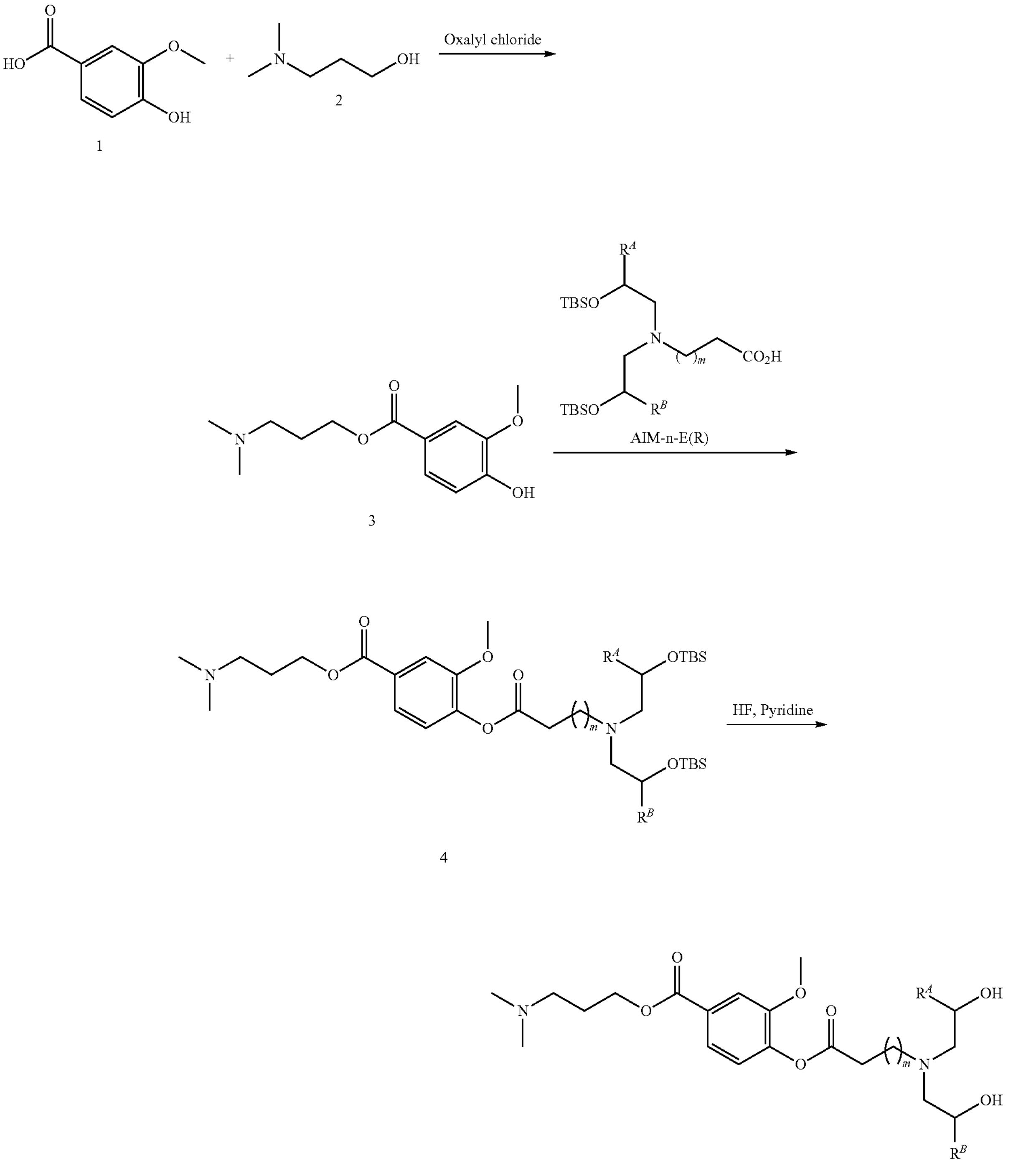
1
2
3
4
VA-n-E(R)-DMAPr
Synthesis of 3-(Dimethylamino)propyl 4-hydroxy-3-methoxybenzoate (3)
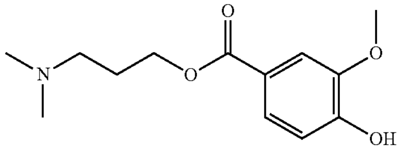

To a suspension of vanillic acid 1 (1.0 g, 5.9 mmol) in 25 ml dichloromethane at 0° C. was added oxalyl chloride (2.0 mL, 23.8 mmol) followed by dimethylformamide (1 drop), and the resulting mixture was stirred for 2 h at this temperature. The reaction mixture was evaporated to dryness, and the residue was dissolved in 20 mL dichloromethane. After cooling to 0° C., 3-(dimethylamino)propan-1-ol 2 (0.7 mL, 5.9 mmol) was added slowly, and the reaction mixture was stirred at room temperature overnight. The precipitate was filtered to give 3-(dimethylamino)propyl 4-hydroxy-3-methoxybenzoate 3 as white solid (1.18 g, 79%).

Synthesis of 3-(Dimethylamino)propyl 4-((4-(bis(2-((tert-butyldimerhtylsilyl)oxy)dodecyl)amino)butanoyl)oxy)-3-methoxybenzoate (4)

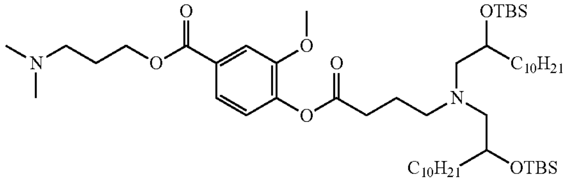

To a solution of 4-(bis(2-((tert-butyldimethylsilyl)oxy) dodecyl)amino)butanoic acid AIM-3-E12 (1.0 g, 1.43 mmol) in 20 mL dichloromethane at 0° C. was added oxalyl chloride (0.15 mL, 1.72 mmol) followed by dimethylformamide (1 drop), and the mixture was stirred at 0° C. for 2 h. The reaction mixture was evaporated to dryness, and the residue was dissolved in 20 ml dichloromethane. After cooling to 0° C., 3-(dimethylamino) propyl 4-hydroxy-3-methoxybenzoate 3 (0.18 g, 0.7 mmol) was added followed by pyridine (0.4 mL, 4.9 mmol), and the reaction mixture was stirred at room temperature overnight. Ice was added to quench the reaction, and the organic layer was washed with brine, dried with anhydrous sodium sulfate. After filtration and concentration, the crude was purified by flash chromatography to get 3-(dimethylamino)propyl 4-((4-(bis(2-((tert-butyldimethylsilyl)oxy)dodecyl)amino)butanoyl)oxy)-3-methoxybenzoate 4 as pale yellow oil (330 mg, 50%).

Synthesis of 3-(Dimethylamino)propyl 4-((4-(bis(2-((hydroxydodecyl)amino)butanoyl) oxy)-3-methoxybenzoate

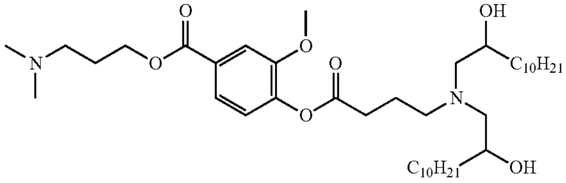

(VA-3-E12-DMAPr)

To a solution of 3-(dimethylamino) propyl 4-((4-(bis(2-((tert-butyldimethylsilyl)oxy) dodecyl)amino)butanoyl) oxy)-3-methoxybenzoate 4 (330 mg, 0.35 mmol) in 10 mL tetrahydrofuran at 0° C. was added hydrofluoric acid in pyridine (70%, 2.5 mL) dropwise, and the reaction mixture was stirred at room temperature overnight. Saturated sodium bicarbonate solution was added to pH=7-8, and the mixture was extracted with ethyl acetate. The organic layer was washed with brine, dried with anhydrous sodium sulfate. After filtration and concentration, the crude product was purified by reverse phase column chromatography (C18: 5-95% MeCN/water/0.1% TFA) to get 3-(dimethylamino) propyl 4-((4-(bis(2-hydroxydodecyl)amino)butanoyl)oxy)-3-methoxybenzoate as TFA salt (120 mg, 48%). This compound was stored in 2-butanol to prevent decomposition.

All of other lipids were prepared followed the representative procedure in similar yields.

Synthetic Scheme for Syringic Acid Lipids

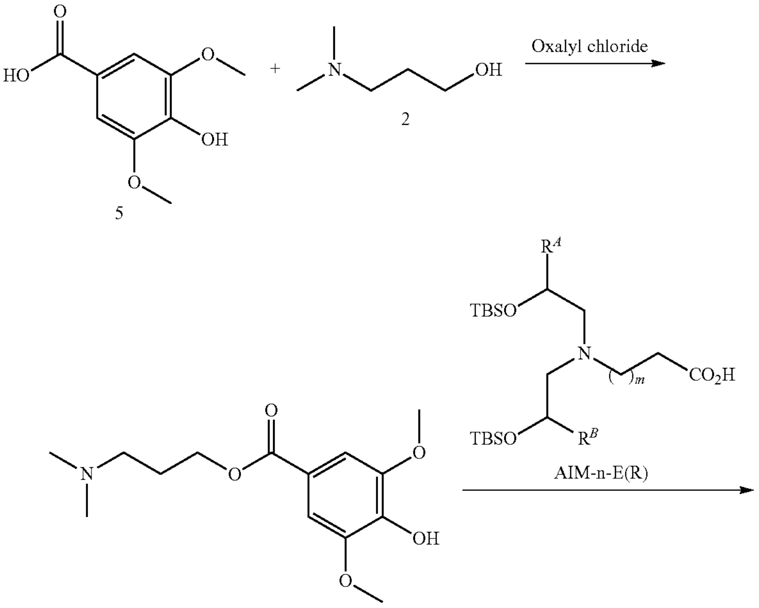

5

2

6

-continued

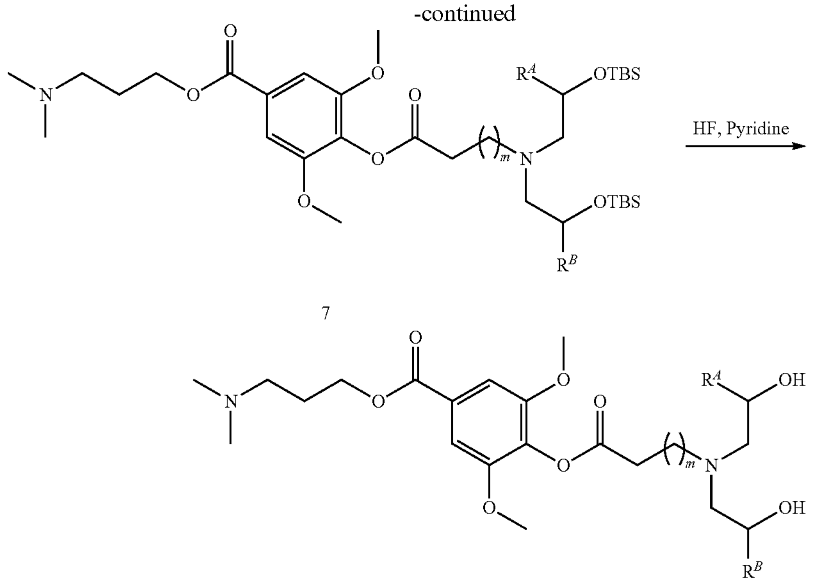

7

SA-n-E(R)-DMAPr

Synthesis of 3-(Dimethylamino)propyl 4-hydroxy-3,5-dimethoxybenzoate (6)

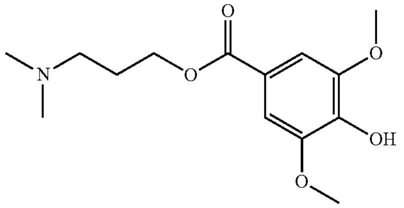

To a suspension of syringic acid 5 (7.5 g, 0.04 moles) in 100 mL dichloromethane at 0° C. was added oxalyl chloride (12.8 mL, 0.15 mole) followed by dimethylformamide (5 drops), and the resulting mixture was stirred for 2 h at this temperature. The reaction mixture was evaporated to dryness, and the residue was dissolved in 100 ml dichloromethane. After cooling to 0° C., 3-(dimethylamino)propan-1-ol 2 (4.5 mL, 40 mmol) was added slowly, and the reaction mixture was stirred at room temperature overnight. The precipitate was filtered to give 3-(dimethylamino)propyl 4-hydroxy-3,5-dimethoxybenzoate 6 as white solid (6.2 g, 58%).

Synthesis of 3-(Dimethylamino)propyl 4-((4-(bis(2-((tert-butyldimerhtylsilyl)oxy)dodecyl)amino)butanoyl)oxy)-3,5-methoxybenzoate (7)

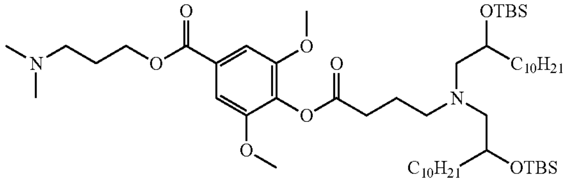

To a solution of 4-(bis(2-((tert-butyldimethylsilyl)oxy) dodecyl)amino)butanoic acid AIM-3-E12 (0.99 g, 1.41 mmol) in 20 mL dichloromethane at 0° C. was added oxalyl chloride (0.15 mL, 1.72 mmol) followed by dimethylformamide (1 drop), and the mixture was stirred at 0° C. for 2 h. The reaction mixture was evaporated to dryness, and the residue was dissolved in 20 ml dichloromethane. After cooling to 0° C., 3-(dimethylamino)propyl 4-hydroxy-3,5-dimethoxybenzoate 6 (0.2 g, 0.7 mmol) was added followed by pyridine (0.35 mL, 4.34 mmol), and the reaction mixture was stirred at room temperature overnight. Ice was added to quench the reaction, and the organic layer was washed with brine, dried with anhydrous sodium sulfate. After filtration and concentration, the crude was purified by flash chromatography to get 3-(dimethylamino)propyl 4-((4-(bis(2-((tert-butyldimethylsilyl)oxy) dodecyl)amino)butanoyl)oxy)-3,5-dimethoxybenzoate 7 as pale yellow oil (380 mg, 50%).

Synthesis of 3-(Dimethylamino)propyl 4-((4-(bis(2-((hydroxydodecyl)amino)butanoyl) oxy)-3,5-dimemethoxybenzoate

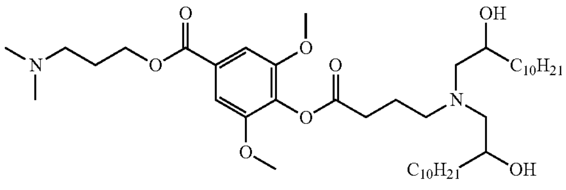

(SA-3-E12-DMAPr)

To a solution of 3-(dimethylamino) propyl 4-((4-(bis(2-((tert-butyldimethylsilyl)oxy) dodecyl)amino)butanoyl) oxy)-3,5-dimethoxybenzoate 7 (380 mg, 0.39 mmol) in 10 mL tetrahydrofuran at 0° C. was added hydrofluoric acid in pyridine (70%, 2.5 mL) dropwise, and the reaction mixture was stirred at room temperature overnight. Saturated sodium bicarbonate solution was added to pH=7-8, and the mixture was extracted with ethyl acetate. The organic layer was washed with brine, dried with anhydrous sodium sulfate. After filtration and concentration, the crude product was purified by reverse phase column chromatography (C18: 5-95% MeCN/water/0.1% TFA) to get 3-(dimethylamino) propyl 4-((4-(bis(2-hydroxydodecyl)amino)butanoyl)oxy)-3,5-dimethoxybenzoate as TFA salt (94 mg, 32%).

All of other lipids were prepared followed the representative procedure in similar yields.

Synthetic Scheme for Sinapinic Acid Lipids

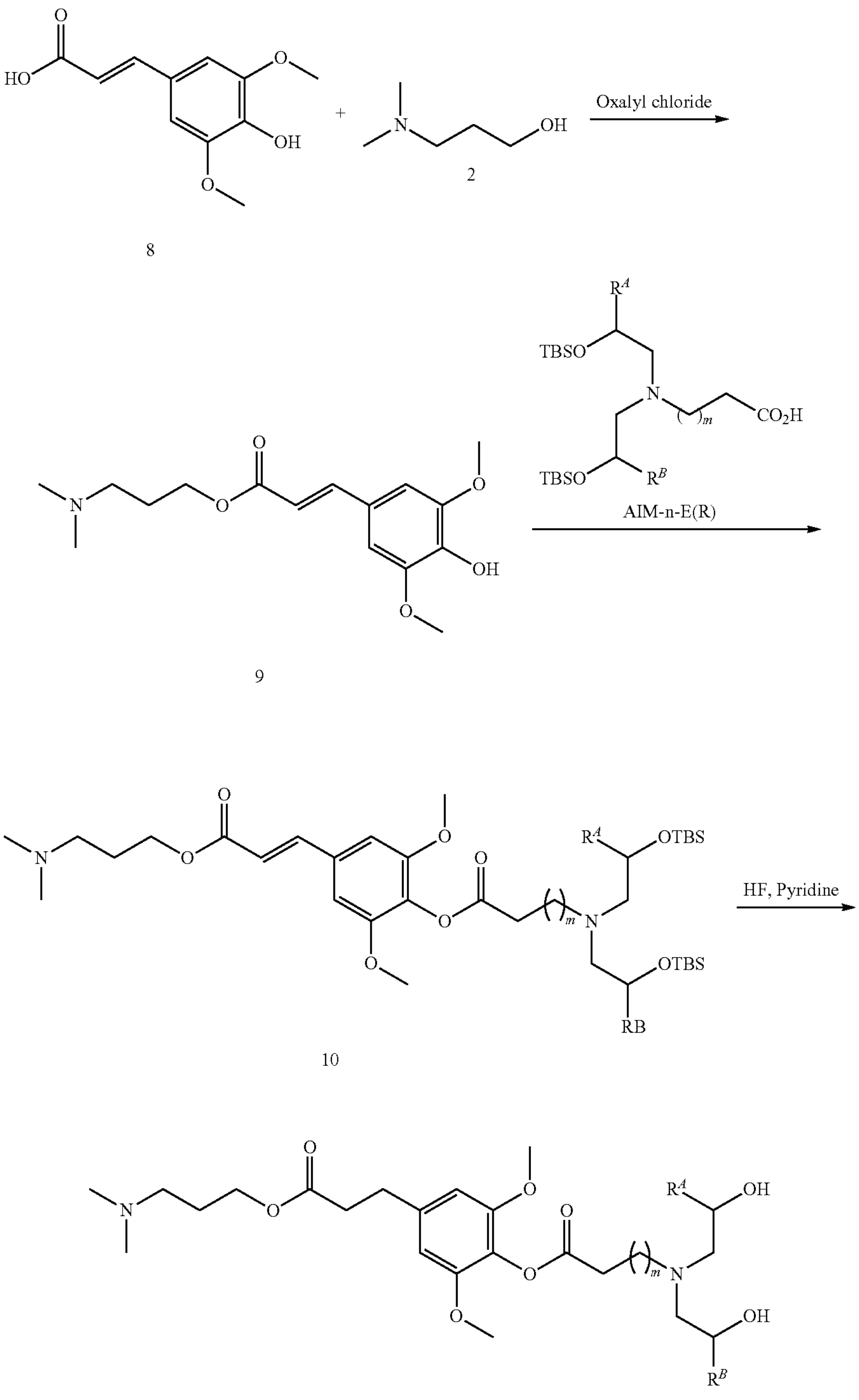

8

2

9

10

SI-n-E(R)-DMAPr

-continued

Synthesis of 3-(Dimethylamino)propyl (E)-3-(4-hydroxy-3,5-dimethoxyphenyl)acrylate (9)

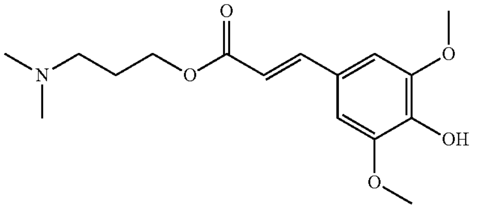

To a suspension of sinapinic acid 8 (5 g, 22 mmol) in 100 ml dichloromethane at 0° C. was added oxalyl chloride (7.5 mL, 90 mmol) followed by dimethylformamide (5 drops), and the resulting mixture was stirred for 2 h at this temperature. The reaction mixture was evaporated to dryness, and the residue was dissolved in 100 ml dichloromethane. After cooling to 0° C., 3-(dimethylamino)propan-1-ol 2 (2.64 mL, 22 mmol) was added slowly, and the reaction mixture was stirred at room temperature overnight. The precipitate was filtered to give 3-(dimethylamino)propyl (E)-3-(4-hydroxy-3,5-dimethoxyphenyl) acrylate 9 as pale yellow solid (2.66 g, 39%).

Synthesis of (E)-4-(3-(3-(Dimethylamino)propoxy)-3-oxoprop-1-en-1-yl)-2,6-dimethoxy phenyl 4-(bis(2-((tert-butyldimethylsilyl)oxy) dodecyl)amino)butanoate (10)

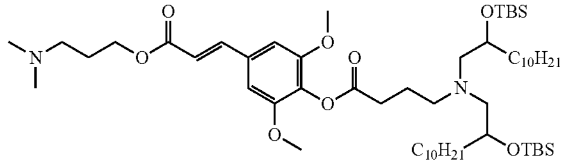

To a solution of 4-(bis(2-((tert-butyldimethylsilyl)oxy) dodecyl)amino)butanoic acid AIM-3-E12 (1.8 g, 2.59 mmol) in 20 mL dichloromethane at 0° C. was added oxalyl chloride (0.3 mL, 3.09 mmol) followed by dimethylformamide (1 drop), and the mixture was stirred at 0° C. for 2 h. The reaction mixture was evaporated to dryness, and the residue was dissolved in 20 ml dichloromethane. After cooling to 0° C., 3-(dimethylamino)propyl (E)-3-(4-hydroxy-3,5-dimethoxyphenyl) acrylate 9 (0.4 g, 1.29 mmol) was added followed by pyridine (0.62 mL, 7.7 mmol), and the reaction mixture was stirred at room temperature overnight. Ice was added to quench the reaction, and the organic layer was washed with brine, dried with anhydrous sodium sulfate. After filtration and concentration, the crude was purified by flash chromatography to get (E)-4-(3-(3-(dimethylamino)propoxy)-3-oxoprop-1-en-1-yl)-2,6-dimeth oxyphenyl 4-(bis(2-((tert-butyldimethylsilyl)oxy)dodecyl) amino)butanoate 10 as pale yellow oil (540 mg, 42%).

Synthesis of (E)-4-(3-(3-(Dimethylamino)propoxy)-3-oxoprop-1-en-1-yl)-2,6-dimethoxy phenyl 4-(bis(2-hydroxydodecyl)amino)butanoate

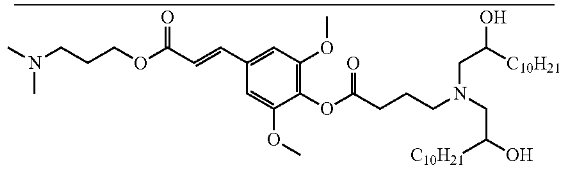

(SI-3-E12-DMAPr)

To a solution of (E)-4-(3-(3-(dimethylamino)propoxy)-3-oxoprop-1-en-1-yl)-2,6-dimethoxy phenyl 4-(bis(2-((tert-butyldimethylsilyl)oxy)dodecyl)amino)butanoate 10 (540 mg, 0.55 mmol) in 10 mL tetrahydrofuran at 0° C. was added hydrofluoric acid in pyridine (70%, 2.5 mL) dropwise, and the reaction mixture was stirred at room temperature overnight. Saturated sodium bicarbonate solution was added to pH=7-8, and the mixture was extracted with ethyl acetate. The organic layer was washed with brine, dried with anhydrous sodium sulfate. After filtration and concentration, the crude product was purified by reverse phase column chromatography (C18: 5-95% MeCN/water/0.1% TFA) to get (E)-4-(3-(3-(dimethylamino)propoxy)-3-oxoprop-1-en-1-yl)-2,6-dimethoxy phenyl 4-(bis(2-hydroxydodecyl)amino) butanoate as TFA salt (330 mg, 80%).

All of other lipids were prepared followed the representative procedure in similar yields.

Synthetic Scheme A for Phenolic Acid Lipids
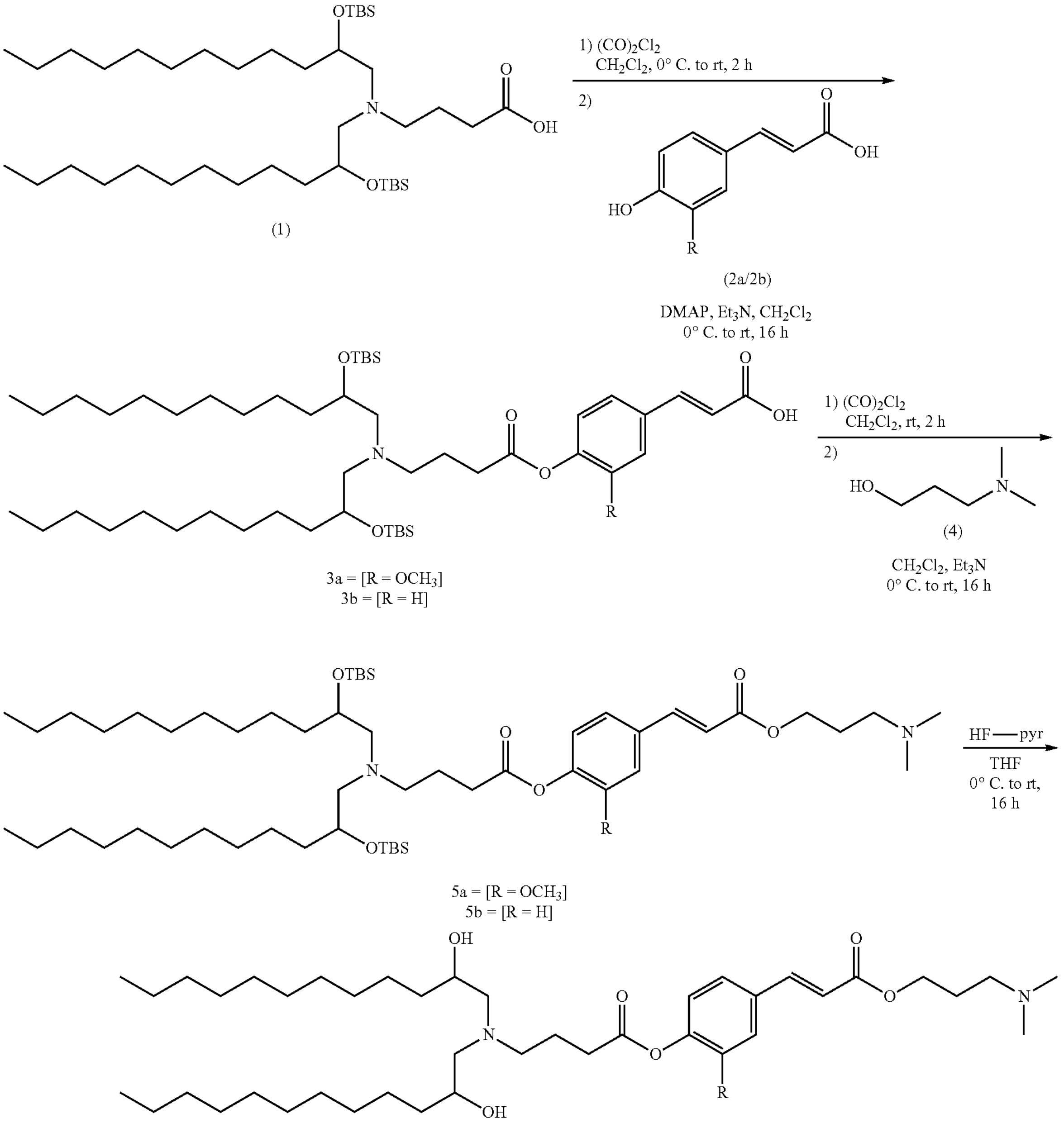
(1)
(2a/2b)
(4)
3a = [R = $OCH_3$]
3b = [R = H]
5a = [R = $OCH_3$]
5b = [R = H]
TBL-0731 (6a) = [R = $OCH_3$]
TBL-0750 (6b) = [R = H]
Synthesis of intermediate (3a) in Synthetic Scheme A
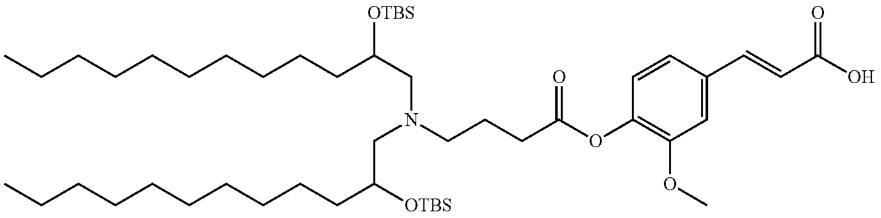

To the solution of (1) (2.00 g, 2.86 mmol) in anhydrous $CH_2Cl_2$ (10 mL) at 0° C. was added oxalyl chloride (0.98 mL, 4.0 equiv) dropwise before the reaction mixture is slowly warmed up to room temperature and stirred for 2 h. Excess solvent and oxalyl chloride were removed under reduced pressure before remaining residue is redissolved in anhydrous $CH_2Cl_2$ (30 mL). To the stirring acid chloride solution at 0° C. was added (2a) (555 mg, 1.0 equiv), DMAP (349 mg, 1.0 equiv), and followed by triethylamine (3.18 mL, 8.0 equiv). Reaction mixture was slowly warmed up to room temperature and then stirred at the same temperature for 16 h. After 16 h, the reaction mixture was diluted with $CH_2Cl_2$ and washed with saturated $NaHCO_3$(aq) solution. The separated organic layer was washed with brine, dried over $Na_2SO_4$, and concentrated under reduced pressure to deliver crude material. Crude material was first purified using 50% EtOAc in hexanes before repurified using 15% EtOAc in $CH_2Cl_2$ to obtain (3a) (623 mg, 25%) as viscous oil. MS(ESI+) Calculated $C_{50}H_{93}NO_7Si_2$, $[M+H]^+$=876.65, Observed=876.6.

Synthesis of intermediate (3b) in Synthetic Scheme A

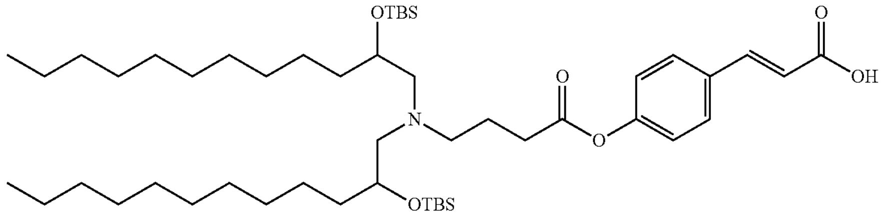

The procedure for (3a) was followed using (2b) to provide (3b) (557 mg, 23%) as viscous oil. MS(ESI+) Calculated $C_{49}H_{91}NO_6Si_2$, $[M+H]^+$=846.64, Observed=846.6.

Synthesis of intermediate (5a) in Synthetic Scheme A

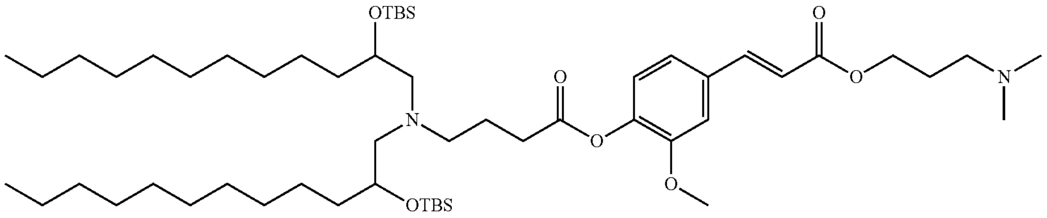

To the solution (3a) (308 mg, 0.351 mmol) in anhydrous $CH_2Cl_2$ (3 mL) was added oxalyl chloride (0.15 mL, 5.0 equiv) at room temperature and stirred at the same temperature for 2 h. Excess solvent and oxalyl chloride were removed under reduced pressure before remaining residue is redissolved in anhydrous $CH_2Cl_2$ (3 mL). To the stirring acid chloride solution at 0° C. was added 3-dimethylaminopropanol (4) (109 mg, 3 equiv) followed by triethylamine (0.10 mL, 2.0 equiv). Reaction mixture was slowly warmed up to room temperature and then stirred at the same temperature for 16 h. After completion of reaction as monitored by MS, the reaction mixture was concentrated to dryness under reduced pressure and purified using 0-10% MeOH in $CH_2Cl_2$ to obtain (5a) (204 mg, 60%) as viscous oil. MS(ESI+) Calculated $C_{55}H_{104}N_2O_7Si_2$, $[M+H]^+$=961.74, Observed=961.7.

Synthesis of intermediate (5b) in Synthetic Scheme A

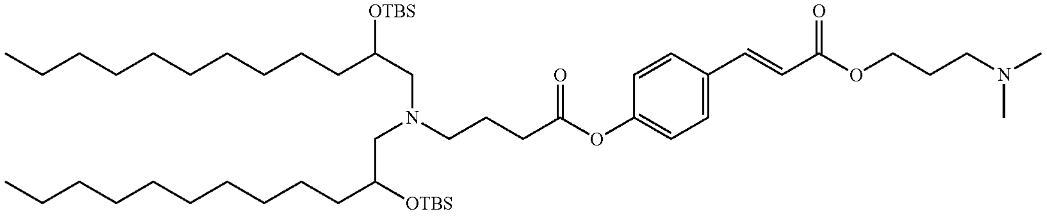

The procedure for (5a) was followed using (3b) to provide (5b) (248 mg, 90%) as viscous oil. MS(ESI+) Calculated $C_{54}H_{102}N_2O_6Si_2$, $[M+H]^+$=931.73, Observed=931.7.

Synthesis of TBL-0731 compound 355 (6a) in Synthetic Scheme A

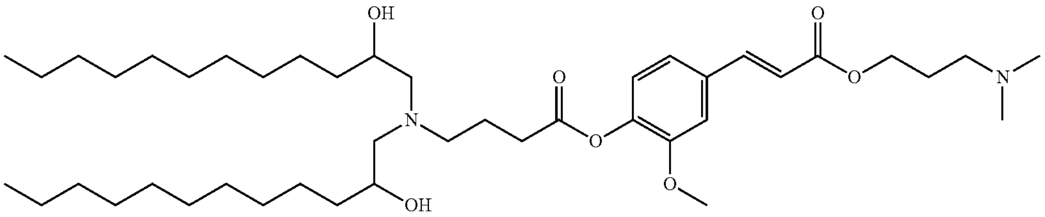

To the stirring solution of (5a) (204 mg, 0.212 mmol) in anhydrous THF (3 mL) at 0° C. was added 70% hydrogen fluoride in pyridine (1.09 mL, 197 equiv) dropwise before slowly warmed up to room temperature. The reaction mixture was stirred at room temperature for 16 h. After completion of reaction as monitored by MS, the reaction mixture was cooled to 0° C. and quenched with batch-wise addition of solid $NaHCO_3$. After gas formation has minimized, the resulting mixture was diluted with EtOAc and neutralized with saturated $NaHCO_3$(aq) solution. The separated organic layer was washed with brine, dried over $Na_2SO_4$, and concentrated under reduced pressure to deliver crude material. Crude material was purified using 0-20% MeOH in $CH_2Cl_2$ to obtain TBL-0731 (6a) (132 mg, 85%) as viscous oil. MS(ESI+) Calculated $C_{43}H_{76}N_2O_7$, $[M+H]^+$=733.57, Observed=733.5. $^1H$ NMR (500 MHZ, $CDCl_3$) δ 7.64 (d, J=15.9 Hz, 1H), 7.14-7.08 (m, 2H), 7.05 (d, J=8.1, 3.5 Hz, 1H), 6.37 (d, J=16.0 Hz, 1H), 4.27 (t, J=6.4 Hz, 2H), 3.86 (s, 3H), 3.72-3.63 (m, 2H), 2.78-2.70 (m, 2H), 2.67-2.47 (m, 6H), 2.46-2.40 (m, 2H), 2.36 (s, 6H), 2.02-1.90 (m, 4H), 1.49-1.35 (m, 4H), 1.34-1.15 (m, 32H), 0.87 (t, J=6.9 Hz, 6H).

Synthesis of TBL-0750 compound 467 (6b) in Synthetic Scheme A

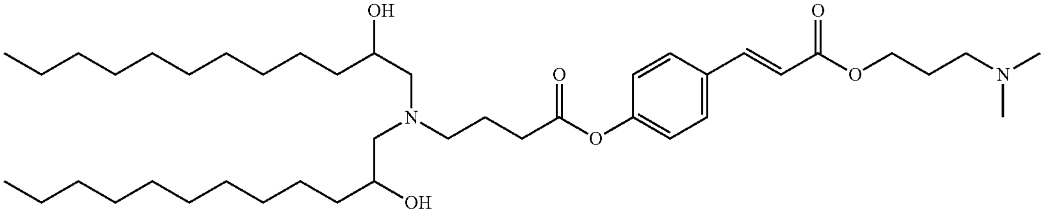

The procedure for (6a) was followed using (5b) to provide TBL-0750 (6b) (153 mg, 82%) as viscous oil. MS(ESI+) Calculated $C_{42}H_{74}N_2O_6$, $[M+H]^+$=703.55, Observed=703.6. $^1H$ NMR (400 MHz, $CDCl_3$) δ 7.66 (d, J=16.0 Hz, 1H), 7.53 (d, J=8.7, 1.3 Hz, 2H), 7.12 (d, J=8.6, 1.5 Hz, 2H), 6.38 (d, J=16.0, 0.9 Hz, 1H), 4.26 (t, J=6.4 Hz, 2H), 3.70-3.63 (m, 2H), 2.73-2.64 (m, 2H), 2.64-2.46 (m, 6H), 2.45-2.40 (m, 2H), 2.34 (s, 6H), 1.99-1.88 (m, 4H), 1.43-1.34 (m, 4H), 1.31-1.21 (m, 32H), 0.87 (t, J=6.8 Hz, 6H).

Synthetic Scheme B for Phenolic Acid Lipids

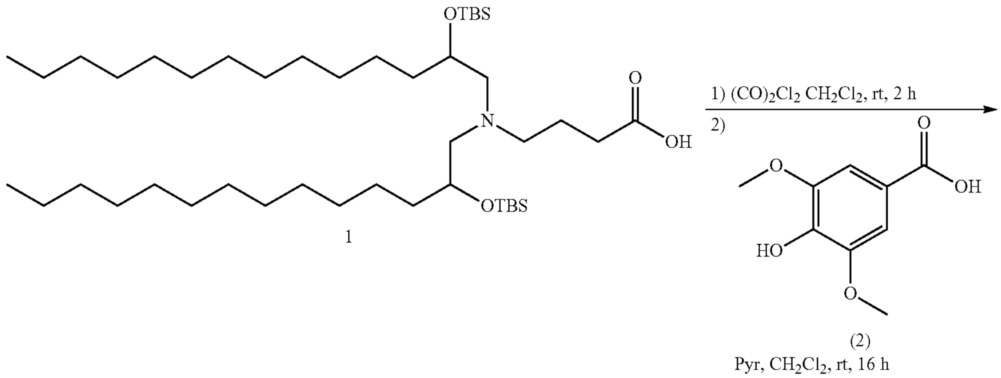

1

(2)

-continued

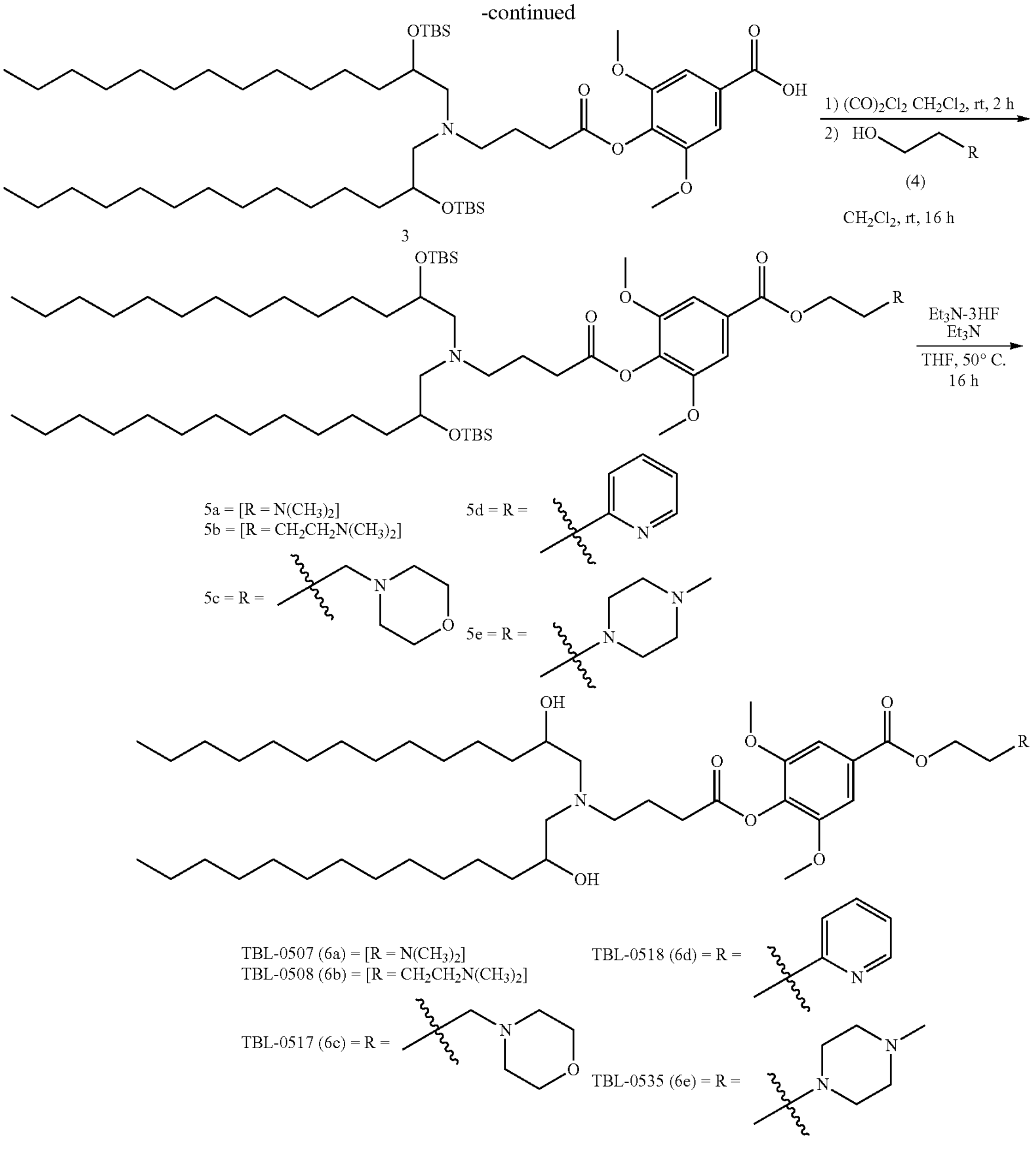

Synthesis of intermediate (3) in Synthetic Scheme B:

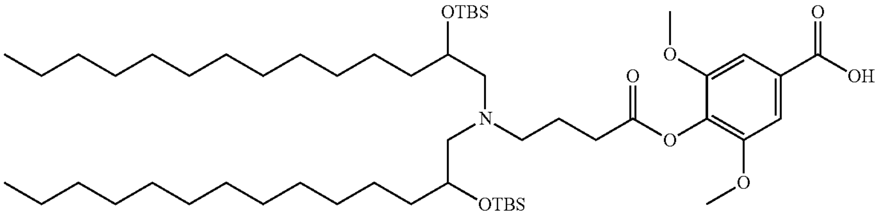

To the solution of acid intermediate (1) (4.58 g) in $CH_2Cl_2$ (30 mL, anhydrous) was added oxalyl chloride (1.04 mL, 2 equiv) and stirred at room temperature for 2 hours. All volatiles were removed under reduced pressure and the remaining residue was re-dissolved in $CH_2Cl_2$ (30 mL, anhydrous). To this solution was then added syringic acid (2) (1.32 g, 1.1 equiv) followed by pyridine (2.93 mL, 6 equiv), and the resulting mixture was stirred at room temperature overnight. After stirring overnight, solvents were removed under reduced pressure and the remaining residue was solubilized with minimal $CH_2Cl_2$ before filtered through a short silica gel plug with 100% EtOAc as eluent. The clear filtrate was concentrated to dryness to provide the crude material, which was purified using 10-100% EtOAc in hexanes gradient over 10 CV on the MPLC to provide the acid product (3) (3.70 g, 78%). MS(ESI+) Calculated $C_{53}H_{101}NO_8Si_2$, $[M+H]^+$=936.7, Observed=936.7.

Synthesis of intermediate (5a) in Synthetic Scheme B

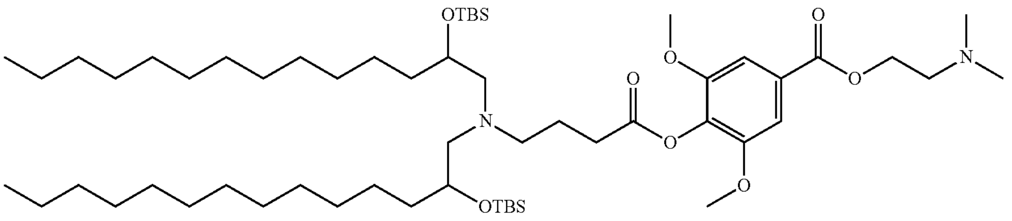

To the solution of benzoic acid (3) (400 mg) in $CH_2Cl_2$ (4 mL, anhydrous) was added oxalyl chloride (0.18 mL, 5 equiv) and stirred at room temperature for 2 hours. All the volatiles were removed under reduced pressure, and the remaining residue was re-dissolved in $CH_2Cl_2$ (3 mL, anhydrous). The resulting solution was cooled with ice bath and then added a solution of 2-aminoethanol (4a) (76 mg) in $CH_2Cl_2$ (1 mL). The reaction mixture was warmed up to room temperature and stirred at the same temperature for 16 hours. After complete consumption of starting material as monitored by LC-MS, the reaction mixture was concentrated to dryness and the crude material was purified using 0-20% MeOH in $CH_2Cl_2$ gradient over 12 CV on the MPLC to provide the product (5a) as viscous oil (225 mg, 52%). MS(ESI+) Calculated $C_{57}H_{110}N_2O_8Si_2$, $[M+H]^+$=1007.8, Observed=1007.6.

Synthesis of intermediate (5b) in Synthetic Scheme B

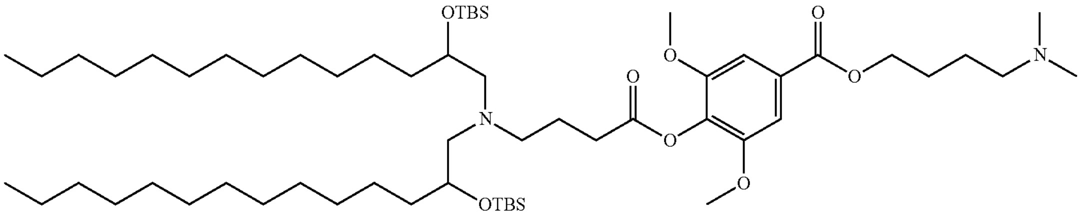

The procedure for synthesis of (5a) was followed using 4-aminobutanol (4b) to provide the product (5b) as viscous oil (360 mg, 81%). MS(ESI+) Calculated $C_{59}H_{114}N_2O_8Si_2$, $[M+H]^+$=1035.8, Observed=1035.6.

Synthesis of intermediate (5c) in Synthetic Scheme B

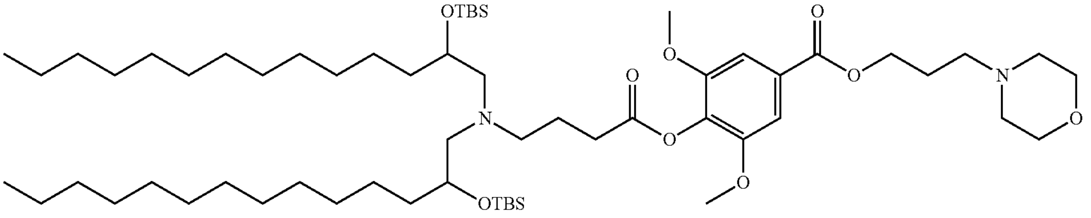

The procedure for synthesis of (5a) was followed using intermediate (3) (500 mg) and 3-morpholinopropanol (4c) to provide product (5c) (350 mg, 62%). MS(ESI+) Calculated $C_{60}H_{114}N_2O_9Si_2$, $[M+H]^+$=1063.8, Observed=1063.6.

Synthesis of intermediate (5d) in Synthetic Scheme B

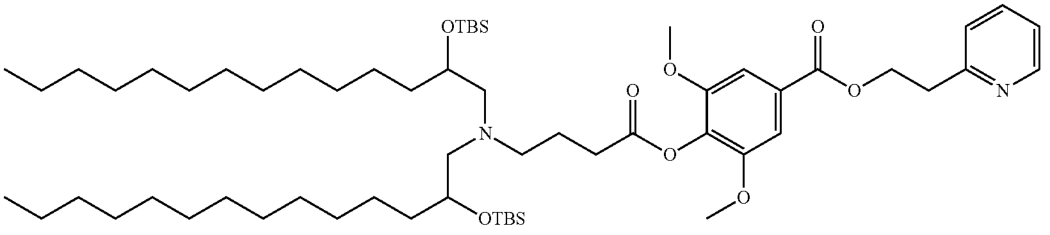

The procedure for synthesis of (5a) was followed using intermediate (3) (500 mg) and 2-pyridinylethanol (4d) to provide product (5d) (237 mg, 43%). MS(ESI+) Calculated $C_{60}H_{108}N_2O_8Si_2$, [M+H]+=1041.8, Observed=1041.6.

Synthesis of intermediate (5e) in Synthetic Scheme B

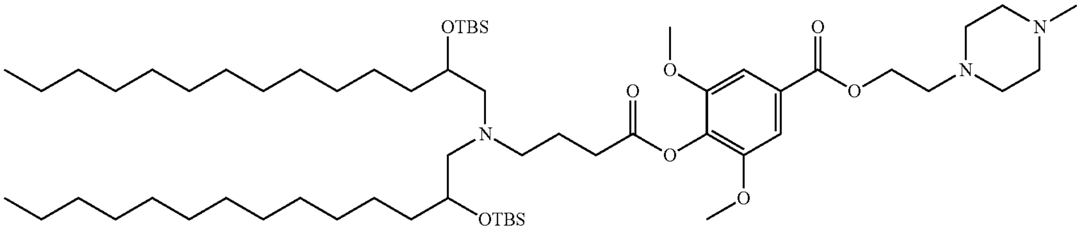

The procedure for synthesis of 5a was followed using intermediate (3) (843 mg) and 4-methylpiperazinylethanol (4e) to provide product (5e) (346 mg, 36%). MS(ESI+) Calculated $C_{60}H_{115}N_3O_8Si_2$, $[M+H]^+$=1062.8, Observed=1062.7.

Synthesis of TBL-0507 compound 48 (6a) in Synthetic Scheme B

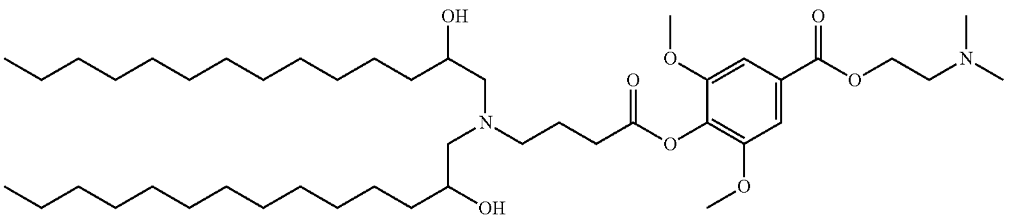

To a stirred solution of TBS-protected intermediate (5a) (225 mg) in THF (3 mL, anhydrous) inside a plastic polymer scintillation vial (non-glass) was added triethylamine (0.16 mL, 5 equiv) followed by triethylamine-3HF (0.36 mL, 10 equiv) dropwise. The reaction mixture was stirred at 50° C. overnight. The reaction was monitored by suspending two drops of reaction mixture between layers of EtOAc and $NaHCO_{3(aq)}$ and analyze the organic layer (TLC or LC-MS). Once starting material is consumed, excess HF and volatiles were removed by blowing down with $N_2$ gas inside the fume hood, and the remaining material was diluted with EtOAc and neutralized with saturated $NaHCO_3$ aqueous solution (check with pH paper). The separated organic layer was washed with brine, dried with $Na_2SO_4$, and concentrated under reduced pressure to provide the crude material. Crude material was purified using 0-40% MeOH in $CH_2Cl_2$ gradient over 10 CV on the MPLC to provide TBL-0507 (6a) (90 mg, 52%). MS(ESI+) Calculated $C_{45}H_{82}N_2O_8$, $[M+H]^+$=779.6, Observed=779.5.

Synthesis of TBL-0508 compound 49 (6b) in Synthetic Scheme B

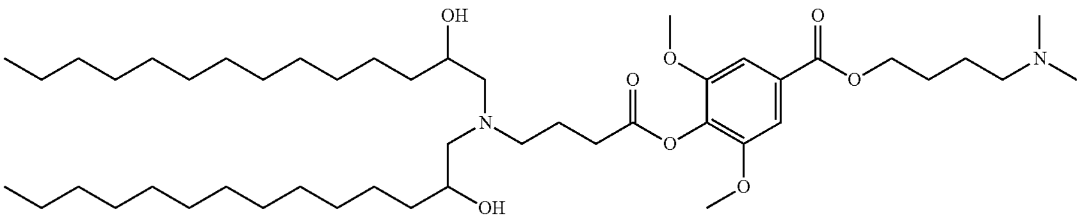

The procedure for (6a) was followed using the TBS-protected intermediate (5b) (360 mg) to provide TBL-0508 (6b) (71 mg, 25%). MS(ESI+) Calculated $C_{47}H_{36}N_2O_8$, $[M+H]^+$=807.6, Observed=807.5.

Synthesis of TBL-0517 compound 562 (6c) in Synthetic Scheme B

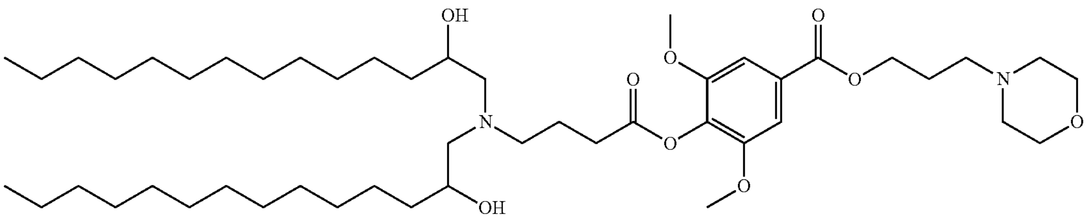

The procedure for (6a) was followed using the TBS-protected intermediate (5c) (350 mg) and purified with 0-10% MeOH in $CH_2Cl_2$ gradient to provide TBL-0517 (6c) (164 mg, 60%). MS(ESI+) Calculated $C_{48}H_{86}N_2O_9$, $[M+H]^+$=835.6, Observed=835.5.

Synthesis of TBL-0518 compound 563 (6d) in Synthetic Scheme B

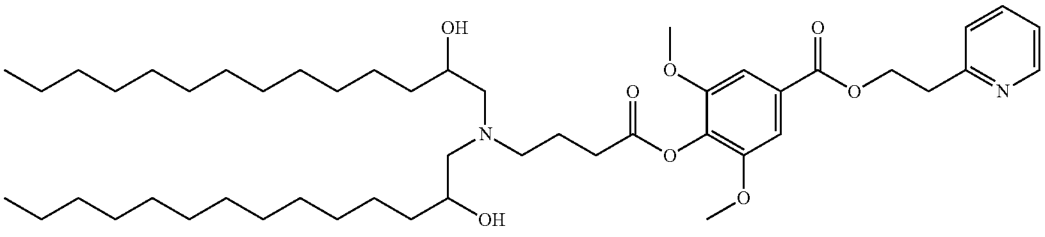

The procedure for (6a) was followed using the TBS-protected intermediate (5d) (237 mg) and purified with 0-10% MeOH in $CH_2Cl_2$ gradient to provide TBL-0518 (6d) (111 mg, 60%). MS(ESI+) Calculated $C_{48}H_{80}N_2O_8$, $[M+H]^+$=813.6, Observed=813.5.

Synthesis of TBL-0535 compound 564 (6e) in Synthetic Scheme B

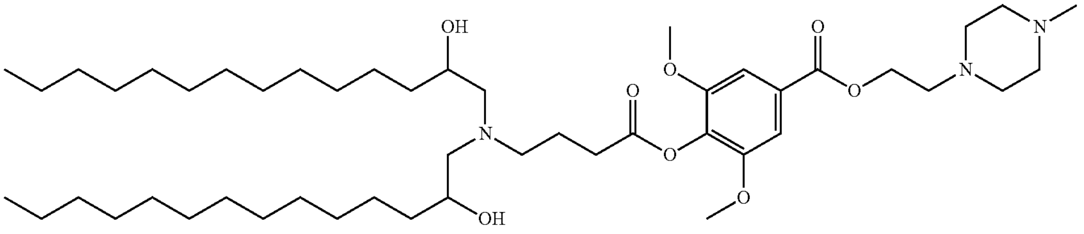

The procedure for (6a) was followed using the TBS-protected intermediate (5e) (346 mg) and purified with 0-20% MeOH in $CH_2Cl_2$ gradient to provide TBL-0535 (6e) (88 mg, 32%). MS(ESI+) Calculated $C_{48}H_{87}N_3O_8$, $[M+H]^+$=834.6, Observed=834.6.
Synthetic Scheme C for Phenolic Acid Lipids
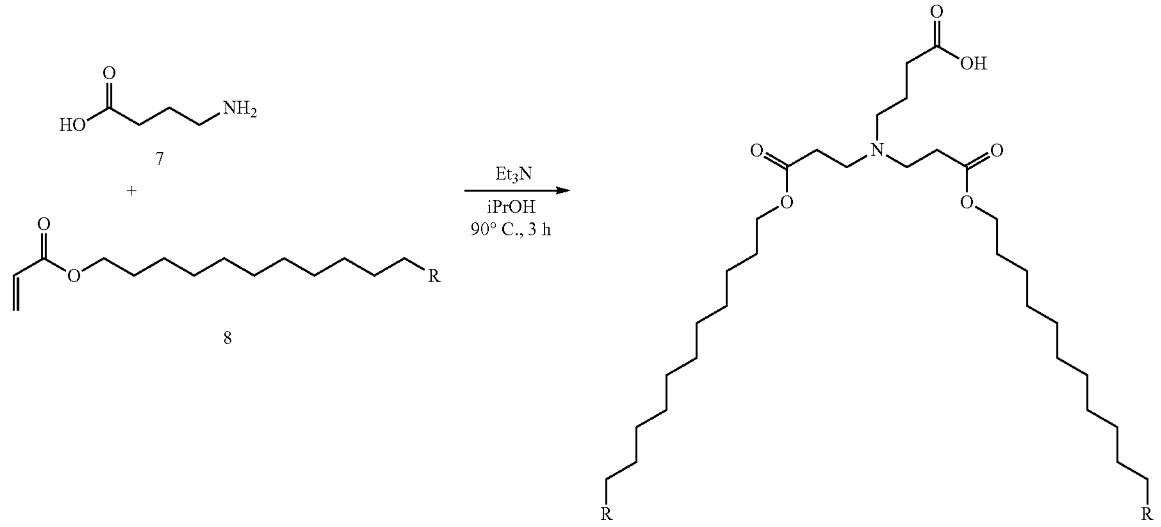
9a = [R = $CH_3$]
9b = [R = $CH_2CH_2CH_3$]
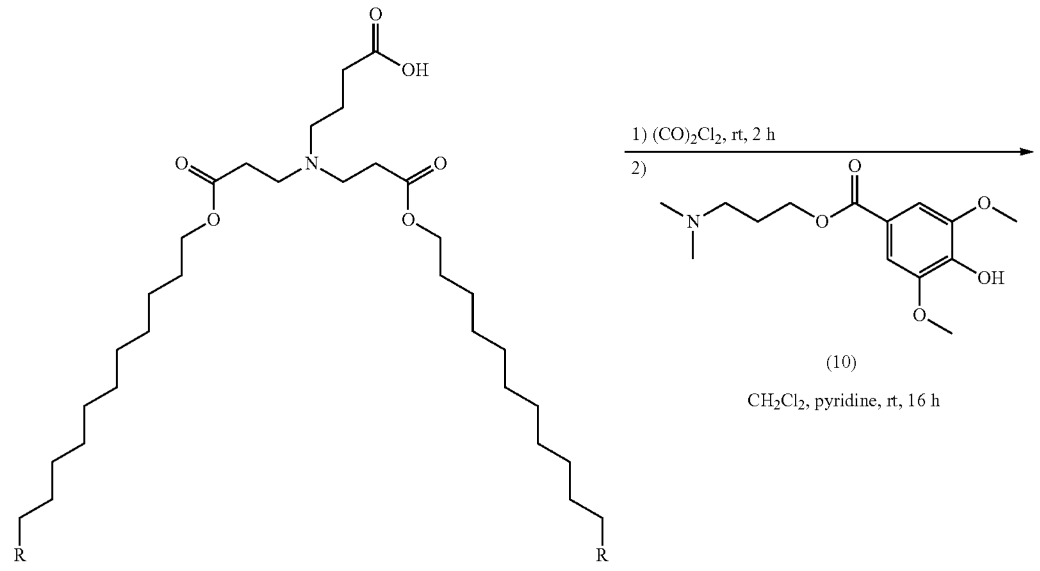
(9)

-continued

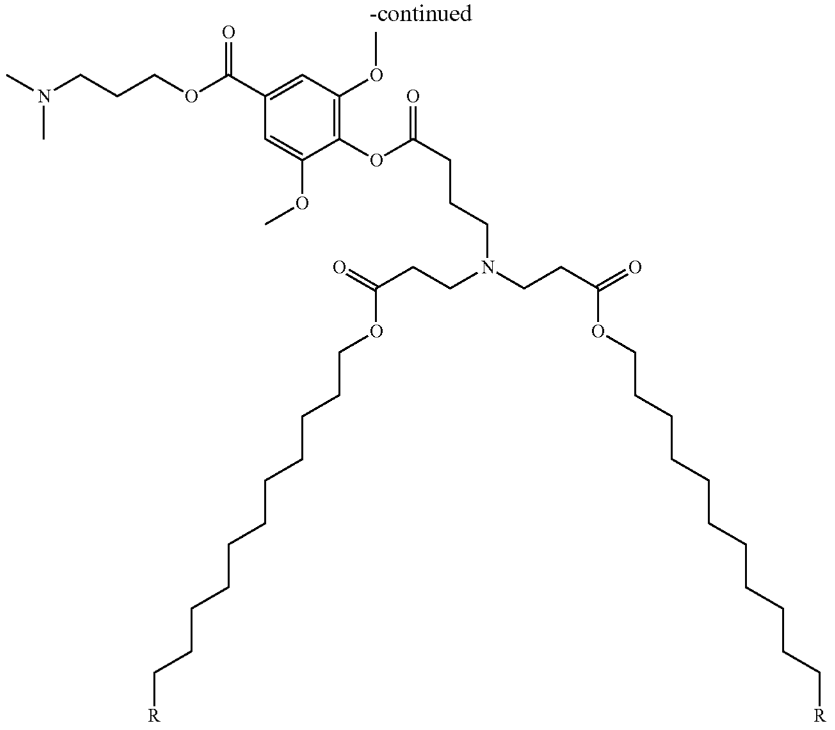

TBL-0484 (11a) = [R = $CH_3$]
TBL-0485 (11b) = [R = $CH_2CH_2CH_3$]

Synthesis of intermediate (9a) in Synthetic Scheme C

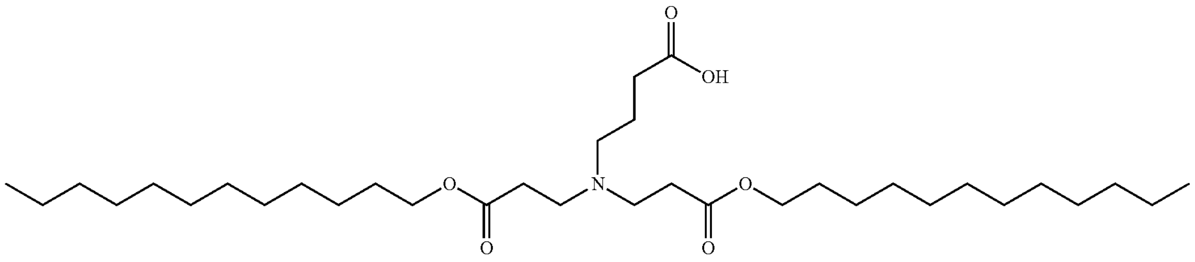

To the flask containing amino acid (7) (500 mg) and dodecyl acrylate (8a) (2.91 g, 2.5 equiv) was added isopropanol (5 mL) and triethylamine (1.35 mL, 2 equiv). The resulting mixture was heated at 90° C. for 3 h. After completion of reaction as monitored by MS, the reaction mixture was cooled down to room temperature and concentrated down under reduced pressure. The remaining material was purified using 0-12% MeOH in $CH_2Cl_2$ on MPLC to provide product (9a) (987 mg, 35%). MS(ESI+) Calculated $C_{34}H_{65}NO_6$, $[M+H]^+$=584.5, Observed=584.5.

Synthesis of intermediate (9b) in Synthetic Scheme C

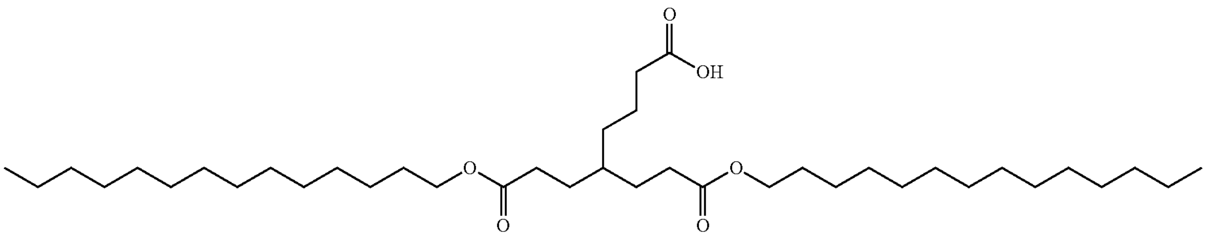

The procedure for (9a) was followed using amino acid (7) (1.00 g), tetradecyl acrylate (8b) (6.51 g, 2.5 equiv), isopropanol (10 mL), and triethylamine (2.70 mL, 2 equiv) to provide product (9b) (1.80 g, 29%). MS(ESI+) Calculated $C_{38}H_{73}NO_6$, $[M+H]^+$=640.5, Observed=640.5.

Synthesis of TBL-0484 compound 565 (11a) in Sythetic Scheme C

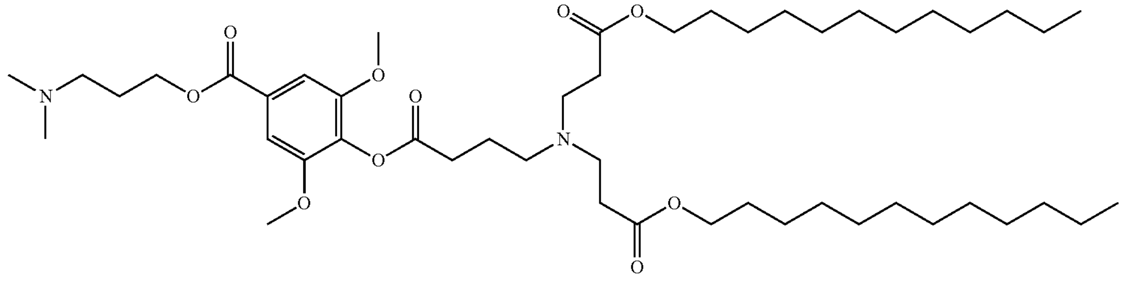

To the solution of intermediate (9a) (300 mg) in anhydrous $CH_2Cl_2$ (3 mL) at room temperature was added oxalyl chloride (1.0 mL, 23 equiv) dropwise and stirred at the same temperature for 2 h. Excess solvent and oxalyl chloride were removed under reduced pressure before remaining residue was redissolved in anhydrous $CH_2Cl_2$ (3 mL). To the stirring acid chloride solution at room temperature was added phenolic acid (10) (146 mg, 1.0 equiv) and pyridine (0.21 mL, 5 equiv) before stirred at the same temperature for 16 h. After completion of reaction as monitored by MS, the reaction mixture was concentrated down under reduced pressure. The remaining crude material was purified using 0-10% MeOH in $CH_2Cl_2$ on MPLC to provide TBL-0484 (11a) (90 mg, 21%). MS(ESI+) Calculated $C_{48}H_{84}N_2O_{10}$, $[M+H]^+$=849.6, Observed=849.5.

Synthesis of TBL-0485 compound 566 (11b) in Synthetic Scheme C

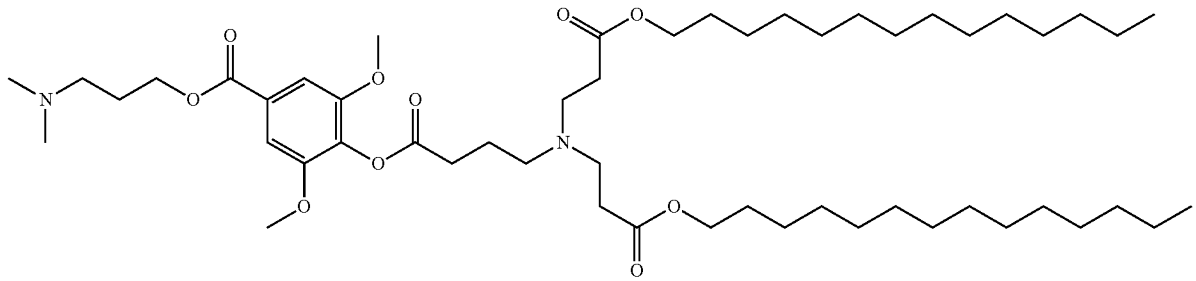

The procedure for (11a) was followed using intermediate (9b) (300 mg) to provide TBL-0485 (11b) (80 mg, 19%). MS(ESI+) Calculated $C_{52}H_{92}N_2O_{10}$, $[M+H]^+$=905.7, Observed=905.6.

Example 1: Lipid Nanoparticle Formulation

Cationic lipids described herein can be used in the preparation of lipid nanoparticles according to methods known in the art. For example, suitable methods include methods described in International Publication No. WO 2018/089801, which is hereby incorporated by reference in its entirety.

One exemplary process for lipid nanoparticle formulation is Process A of WO 2018/089801 (see, e.g., Example 1 and FIG. 1 of WO 2018/089801). Process A ("A") relates to a conventional method of encapsulating mRNA by mixing mRNA with a mixture of lipids, without first pre-forming the lipids into lipid nanoparticles. In an exemplary process, an ethanol lipid solution and an aqueous buffered solution of mRNA were prepared separately. A solution of mixture of lipids (cationic lipid, helper lipids, zwitterionic lipids, PEG lipids etc.) was prepared by dissolving lipids in ethanol. The mRNA solution was prepared by dissolving the mRNA in citrate buffer. The mixtures were then both heated to 65° C. prior to mixing. Then, these two solutions were mixed using a pump system. In some instances, the two solutions were mixed using a gear pump system. In certain embodiments, the two solutions were mixing using a 'T' junction (or "Y" junction). The mixture was then purified by diafiltration with a TFF process. The resultant formulation concentrated and stored at 2-8° C. until further use.

A second exemplary process for lipid nanoparticle formulation is Process B of WO 2018/089801 (see, e.g., Example 2 and FIG. 2 of WO 2018/089801). Process B ("B") refers to a process of encapsulating messenger RNA (mRNA) by mixing pre-formed lipid nanoparticles with mRNA. A range of different conditions, such as varying temperatures (i.e., heating or not heating the mixture), buffers, and concentrations, may be employed in Process B. In an exemplary process, lipids dissolved in ethanol and citrate buffer were mixed using a pump system. The instantaneous mixing of the two streams resulted in the formation of empty lipid nanoparticles, which was a self-assembly process. The resultant formulation mixture was empty lipid nanoparticles in citrate buffer containing alcohol. The formulation was then subjected to a TFF purification process wherein buffer exchange occurred. The resulting suspension of pre-formed empty lipid nanoparticles was then mixed with mRNA using a pump system. For certain cationic lipids, heating the solution post-mixing resulted in a higher percentage of lipid nanoparticles containing mRNA and a higher total yield of mRNA.

The lipid nanoparticle formulations of Table 5 were prepared by either Process A or B. Each formulation comprised mRNA encoding firefly luciferase protein (FFL mRNA) and lipids (Cationic Lipid: DMG-PEG2000; Cholesterol: DOPE) in the mol % ratios set forth in Table 5.

TABLE 5

Exemplary lipid nanoparticle formulations for intratracheal administration

| Cationic Lipid Compound | Process | Composition (mol %) (Cationic Lipid:DMG-PEG2000; Cholesterol:DOPE) | N/P | Size (nm) | PDI | Encapsulation % |
|---|---|---|---|---|---|---|
| 1 | A | 40:5:25:30 | 4 | 47.6 | 0.235 | 94 |
| 2 | A | 40:5:25:30 | 4 | 48.9 | 0.251 | 94 |
| 3 | A | 40:5:25:30 | 4 | 40.3 | 0.207 | 89 |
| 4 | A | 40:5:25:30 | 4 | 41.4 | 0.198 | 91 |
| 5 | A | 40:5:25:30 | 4 | 48.4 | 0.249 | 97 |
| 6 | A | 40:5:25:30 | 4 | 47.0 | 0.208 | 73 |
| 7 | A | 40:5:25:30 | 4 | 64.2 | 0.429 | 95 |
| 8 | A | 40:5:25:30 | 4 | 43.3 | 0.193 | 95 |
| 9 | A | 40:5:25:30 | 4 | 42.3 | 0.213 | 79 |
| 10 | A | 40:5:25:30 | 4 | 43.3 | 0.213 | 94 |
| 11 | A | 40:5:25:30 | 4 | 44.0 | 0.214 | 98 |
| 12 | A | 40:5:25:30 | 4 | 65.1 | 0.173 | 96 |

Delivery of FFL mRNA by Intrathracheal Administration

Lipid nanoparticle formulations comprising FFL mRNA in Table 5 were administered to male CD1 mice (6-8 weeks old) by a single intratracheal aerosol administration via a Microsprayer® (50 ul/animal) while under anesthesia. At approximately 24 hours post-dose, the animals were dosed with luciferin at 150 mg/kg (60 mg/ml) by intraperitoneal injection at 2.5 ml/kg. After 5-15 minutes, all animals were imaged using an IVIS imaging system to measure luciferase production in the lung. FIG. 1 shows that lipid nanoparticles comprising the cationic lipids descried herein are effective in delivering FFL mRNA in vivo based on positive luciferase activity.

NUMBERED EMBODIMENTS

1. A cationic lipid having a structure according to Formula (I):

(I)

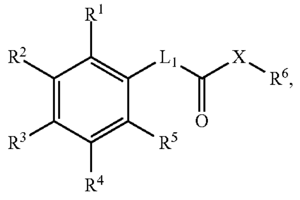

wherein $L_1$ is a bond, $(C_1\text{-}C_6)$alkyl or $(C_2\text{-}C_6)$alkenyl;
wherein X is O or S;
wherein $R^1$, $R^2$, $R^3$, $R^4$ and $R^5$ are each independently selected from H, OH, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$alkoxy and —OC(O)R';
wherein at least one of $R^1$, $R^2$, $R^3$, $R^4$ or $R^5$ is —OC(O)R';
wherein R' is

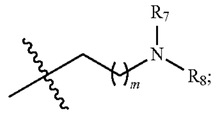

wherein $R^6$ is

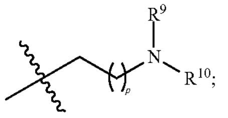

wherein m and p are each independently 0, 1, 2, 3, 4 or 5;
wherein $R^7$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_kR^A$ or $—(CH_2)_kCH(OR^{11})R^A$;
wherein $R^8$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_nR^B$ or $—(CH_2)_nCH(OR^{12})R^B$;
wherein $R^9$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_qR^C$ or $—(CH_2)_qCH(OR^{13})R^C$;
wherein $R^{10}$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_rR^D$ or $—(CH_2)_rCH(OR^{14})R^D$;
wherein k, n, q and r are each independently 1,2,3,4 or 5;
or wherein (i) $R^7$ and $R^8$ or (ii) $R^9$ and $R^{10}$ together form an optionally substituted 5- or 6-membered heterocycloalkyl or heteroaryl wherein the heterocycloalkyl or heteroaryl comprises 1 to 3 heteroatoms selected from N, O and S.

wherein $R^{11}$, $R^{12}$, $R^{13}$ and $R^{14}$ are each independently selected from H, methyl, ethyl or propyl wherein $R^A$, $R^B$, $R^C$ and $R^D$ are each independently selected from optionally substituted ($C_6$-$C_{20}$)alkyl, optionally substituted ($C_6$-$C_{20}$)alkenyl, optionally substituted ($C_6$-$C_{20}$)alkynyl, optionally substituted ($C_6$-$C_{20}$)acyl, optionally substituted —OC(O)alkyl, optionally substituted —OC(O)alkenyl, optionally substituted ($C_1$-$C_6$) monoalkylamino, optionally substituted ($C_1$-$C_6$) dialkylamino, optionally substituted ($C_1$-$C_6$)alkoxy, —OH, —$NH_2$;

wherein at least one of $R^7$, $R^8$, $R^9$, $R^{10}$ comprises a $R^A$, $R^B$, $R^C$ or $R^D$ moiety respectively wherein that $R^A$, $R^B$, $R^C$ or $R^D$ is independently selected from optionally substituted ($C_6$-$C_{20}$)alkyl, optionally substituted ($C_6$-$C_{20}$)alkenyl, optionally substituted ($C_6$-$C_{20}$)alkynyl, optionally substituted ($C_6$-$C_{20}$)acyl, optionally substituted —OC(O)($C_6$-$C_{20}$)alkyl or optionally substituted —OC(O)($C_6$-$C_{20}$)alkenyl; or a pharmaceutically acceptable salt thereof.

2. The cationic lipid or a pharmaceutically acceptable salt thereof of numbered embodiment 1 wherein any alkyl, alkenyl, alkynyl, acyl, alkoxy, monoalkylamino, dialkylamino heterocycloalkyl or heteroaryl are optionally substituted with one or more substituents selected from the groups consisting of ($C_1$-$C_6$)alkyl, ($C_2$-$C_6$)alkenyl, ($C_2$-$C_6$)alkynyl, ($C_1$-$C_6$)acyl, ($C_1$-$C_6$)alkoxy, halogen, —COR, —$CO_2H$, —$CO_2R$, —CN, —OH, —OR, —OCOR, —$OCO_2R$, —$NH_2$, —NHR, —$N(R)_2$, —SR or —$SO_2R$, or two geminal hydrogens on a carbon atom are replaced with the group =NH, wherein each instance of R independently is $C_1$-$C_{10}$ aliphatic alkyl.

3. The cationic lipid or a pharmaceutically acceptable salt thereof of any one of the preceding numbered embodiments wherein:

i) $R^A$ and $R^B$ are identical; and/or ii) $R^C$ and $R^D$ are identical

4. The cationic lipid or a pharmaceutically acceptable salt thereof of numbered embodiments 1 or 2 wherein:

i) $R^A$ and $R^B$ are different; and/or ii) $R^C$ and $R^D$ are different.

5. The cationic lipid or a pharmaceutically acceptable salt thereof of any one of numbered embodiments 1-3 wherein $R^A$, $R^B$, $R^C$ and $R^D$ are identical.

6. The cationic lipid or a pharmaceutically acceptable salt thereof of any one of numbered embodiments 1-4 wherein one or more of $R^A$, $R^B$, $R^C$ and $R^D$ are different.

7. The cationic lipid or a pharmaceutically acceptable salt thereof of any one of the preceding numbered embodiments wherein X is O.

8. The cationic lipid or a pharmaceutically acceptable salt thereof of any one of numbered embodiments 1-6 wherein X is S.

9. The cationic lipid or a pharmaceutically acceptable salt thereof of any one of the preceding numbered embodiments wherein only one of $R^1$, $R^2$, $R^3$, $R^4$ and $R^5$ is —OC(O)R'.

10. The cationic lipid or a pharmaceutically acceptable salt thereof of numbered embodiment 9 wherein none of $R^1$, $R^2$, $R^3$, $R^4$ or $R^5$ are OH.

11. The cationic lipid or a pharmaceutically acceptable salt thereof of any one of numbered embodiments 1-8 wherein two of $R^1$, $R^2$, $R^3$, $R^4$ and $R^5$ are —OC(O)R'.

12. The cationic lipid or a pharmaceutically acceptable salt thereof of numbered embodiment 11 wherein none of $R^1$, $R^2$, $R^3$, $R^4$ or $R^5$ are OH.

13. The cationic lipid or a pharmaceutically acceptable salt thereof of any one of numbered embodiments 1-8 wherein three of $R^1$, $R^2$, $R^3$, $R^4$ and $R^5$ are —OC(O)R'.

14. The cationic lipid or a pharmaceutically acceptable salt thereof of any one of the preceding numbered embodiments wherein $R^1$ and/or $R^5$ is —OC(O)R'.

15. The cationic lipid or a pharmaceutically acceptable salt thereof of any one of the preceding numbered embodiments wherein $R^2$ and/or $R^4$ is —OC(O)R'.

16. The cationic lipid or a pharmaceutically acceptable salt thereof of any one of the preceding numbered embodiments wherein $R^3$ is —OC(O)R'.

17. The cationic lipid or a pharmaceutically acceptable salt thereof of any one of the preceding numbered embodiments wherein:

i) p, q, and r are identical; or ii) one or more of p, q and r are different; or iii) q and r are identical and p is different.

18. The cationic lipid or a pharmaceutically acceptable salt thereof of any one of the preceding numbered embodiments wherein:

i) k, m, and n are identical; or ii) one or more of k, m and n are different; or iii) k and n are identical and m is different.

19. The cationic lipid or a pharmaceutically acceptable salt thereof of any one of the preceding numbered embodiments wherein m is 1, 2 or 3.

20. The cationic lipid or a pharmaceutically acceptable salt thereof of any one of the preceding numbered embodiments wherein p is 1, 2 or 3.

21. The cationic lipid or a pharmaceutically acceptable salt thereof of any one of the preceding numbered embodiments wherein R' is:

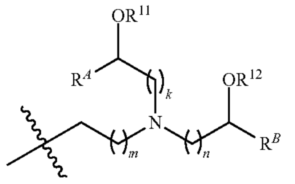

22. The cationic lipid or a pharmaceutically acceptable salt thereof of numbered embodiment 21 wherein:

i) k, m and n=1; or ii) k, m and n=1 and $R^{11}$ and $R^{12}$=H; or iii) k and n=1, and m=2; or iv) k and n=1, m=2 and $R^{11}$ and $R^{12}$=H; or v) k and n=1, and m=3; or vi) k and n=1, m=3 and $R^{11}$ and $R^{12}$=H.

23. The cationic lipid or a pharmaceutically acceptable salt thereof of any one of the preceding numbered embodiments wherein $R^6$ is:

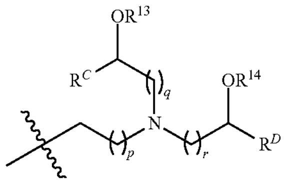

24. The cationic lipid or a pharmaceutically acceptable salt thereof of numbered embodiment 23 wherein:

i) p, q and r=1; or ii) p, q and r=1 and $R^{13}$ and $R^{14}$ are H; or iii) q and r=1, and p=2; or iv) q and r=1, p=2 and $R^{13}$ and $R^{14}$ are H.

25. The cationic lipid or a pharmaceutically acceptable salt thereof of any one of numbered embodiments 1-22 wherein $R^6$ is selected from the group consisting of:

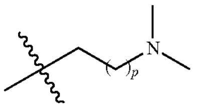
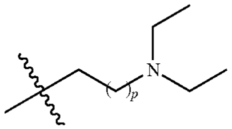
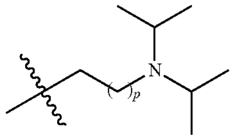
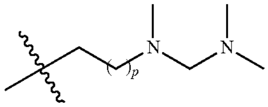
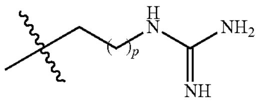
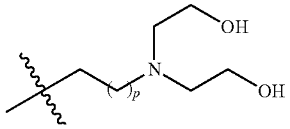
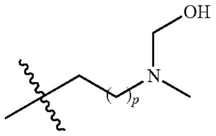
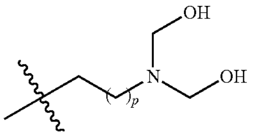
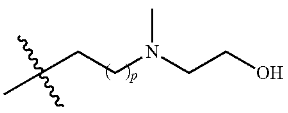
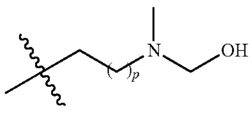
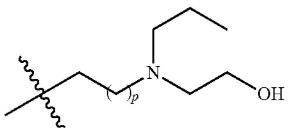
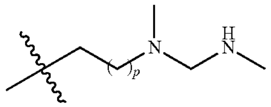
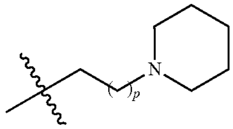
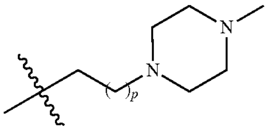

-continued

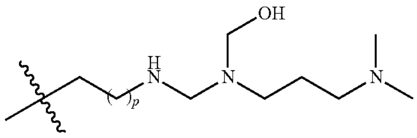
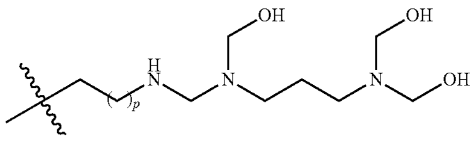
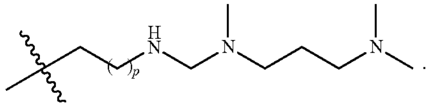

26. The cationic lipid or a pharmaceutically acceptable salt thereof of numbered embodiment 25 wherein $R^6$ is:

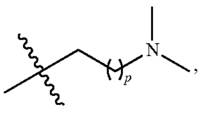

27. The cationic lipid of any one of the preceding numbered embodiments having a structure according to Formula (II):

(II)

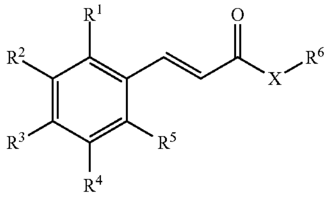

or a pharmaceutically acceptable salt thereof.

28. The cationic lipid of numbered embodiment 27 having a structure according to Formula (IIA):

(IIA)

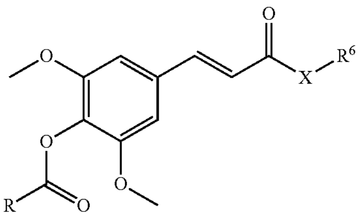

or a pharmaceutically acceptable salt thereof.

29. The cationic lipid of numbered embodiment 28 having a structure according to one of Formula (IIB), (IIC), (IID) or (IIE):

(IIB)
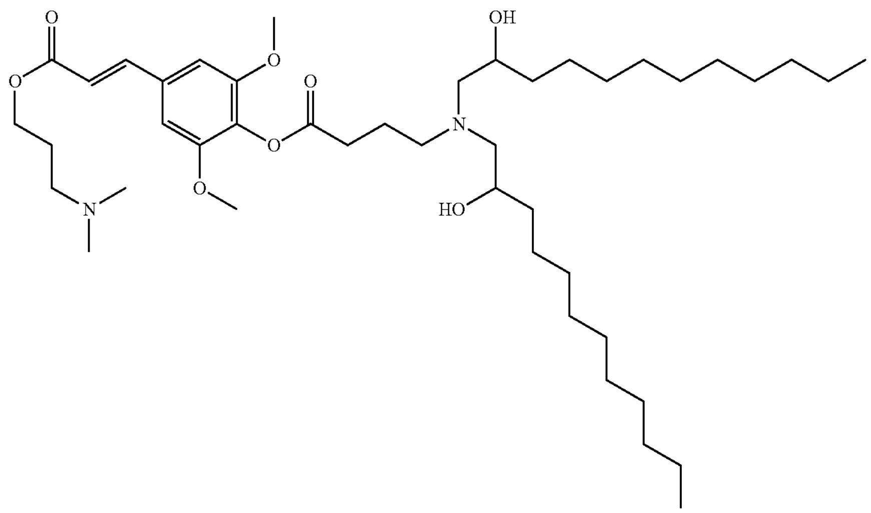
,
(IIC)
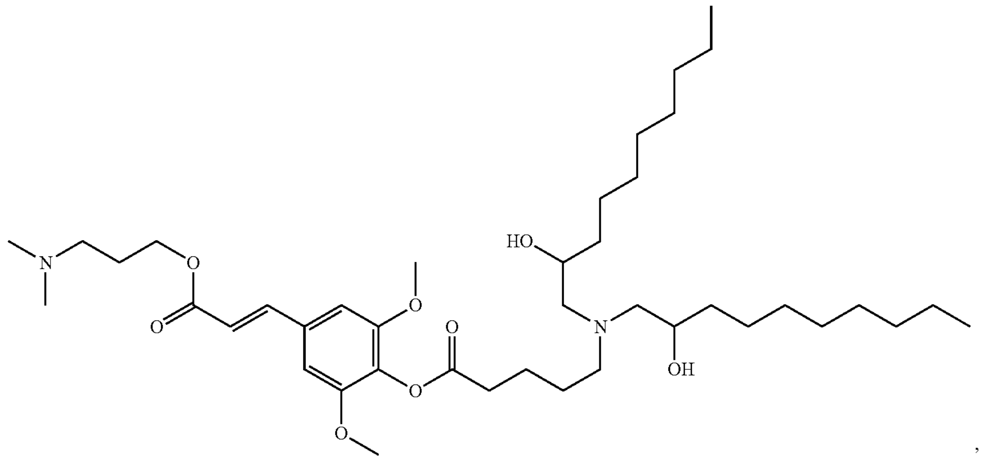
,

-continued
(IID)
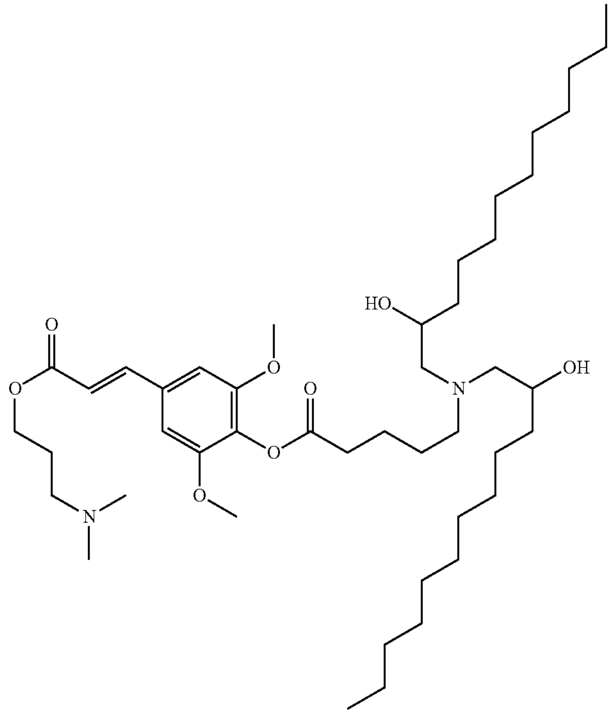
or
(IIE)
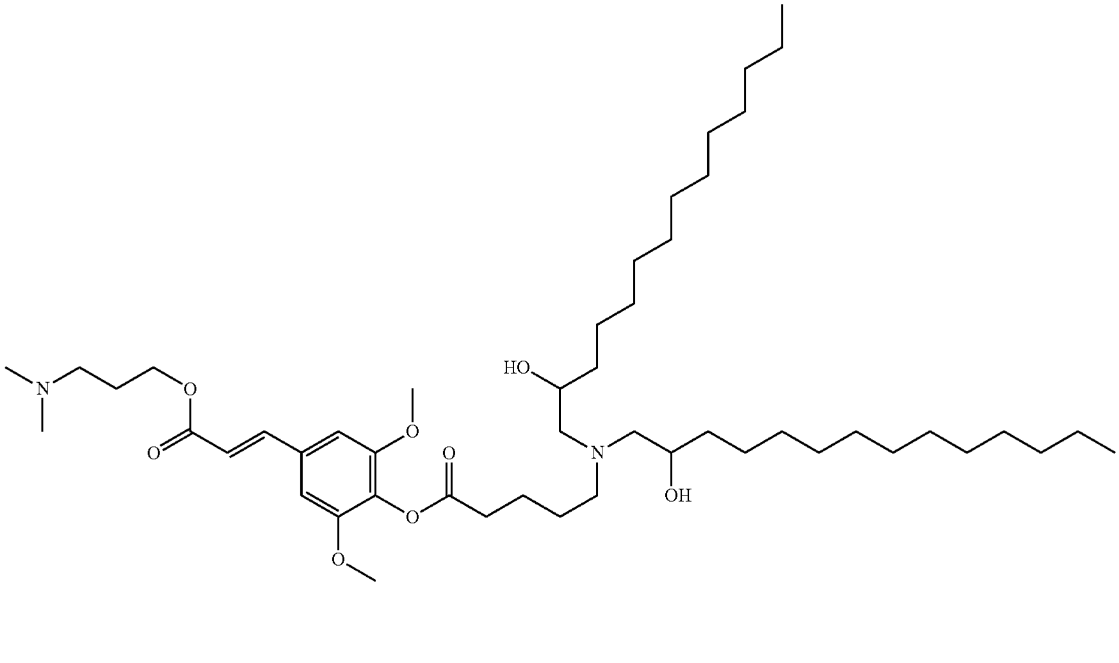
or a pharmaceutically acceptable salt thereof.

30. The cationic lipid of numbered embodiment 27 having a structure according to Formula (IIF):

(IIF)

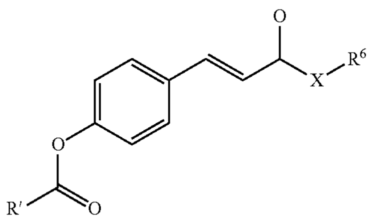

or a pharmaceutically acceptable salt thereof.

31. The cationic lipid of numbered embodiment 27 having a structure according to Formula (IIG):

(IIG)

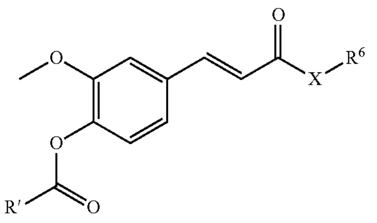

or a pharmaceutically acceptable salt thereof.

32. The cationic lipid of numbered embodiment 27 having a structure according to Formula (IIH):

(IIH)

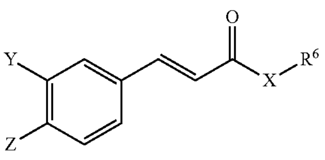

wherein one of Y and Z is OH and the other is —OC(O)R' or wherein both Y and Z are each independently —OC(O)R', or a pharmaceutically acceptable salt thereof.

33. The cationic lipid of any one of numbered embodiments 1-26 having a structure according to Formula (III):

(III)

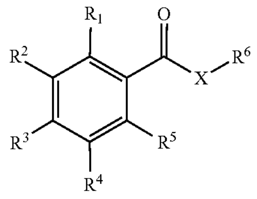

or a pharmaceutically acceptable salt thereof.

34. The cationic lipid of numbered embodiment 33 having a structure according to Formula (IIIA):

(IIIA)

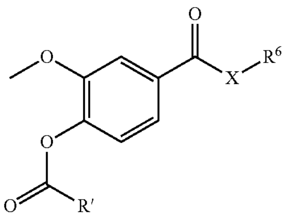

or a pharmaceutically acceptable salt thereof.

35. The cationic lipid of numbered embodiment 33 or numbered embodiment 34 having a structure according to Formula (IIIB):

(IIIB)

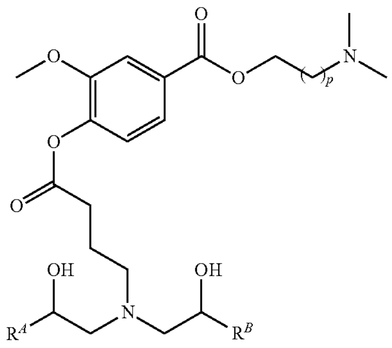

or a pharmaceutically acceptable salt thereof.

36. The cationic lipid of numbered embodiment 35 having a structure according to Formula (IIIC):

(IIIC)

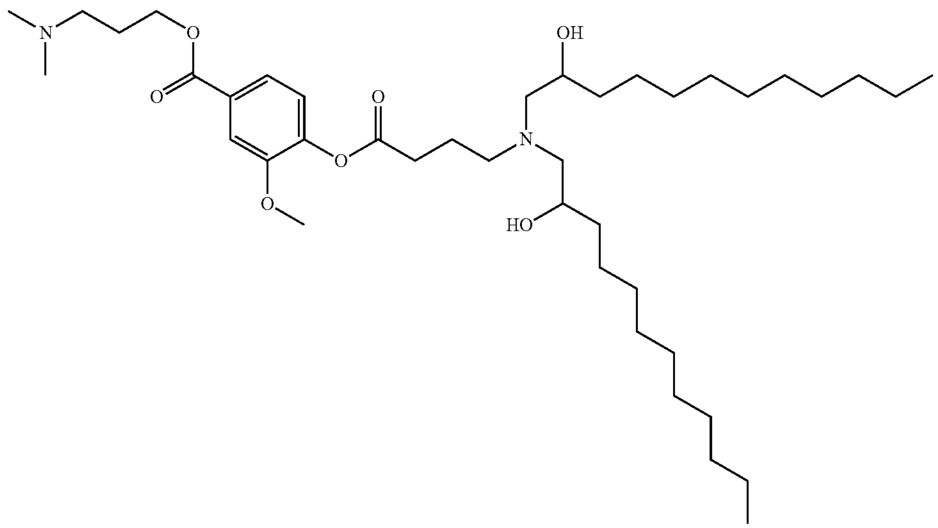

or a pharmaceutically acceptable salt thereof.

37. The cationic lipid of numbered embodiment 33 having a structure according to Formula (IIID):

(IIID)

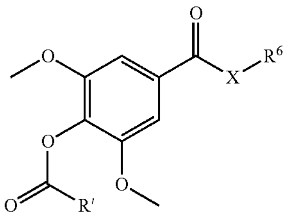

or a pharmaceutically acceptable salt thereof.

38. The cationic lipid of numbered embodiment 37 having a structure selected from Formula (IIIE), (IIIF), (IIIG), (IIIH), (IIII), (IIIJ) or (IIIK):

(IIIE)

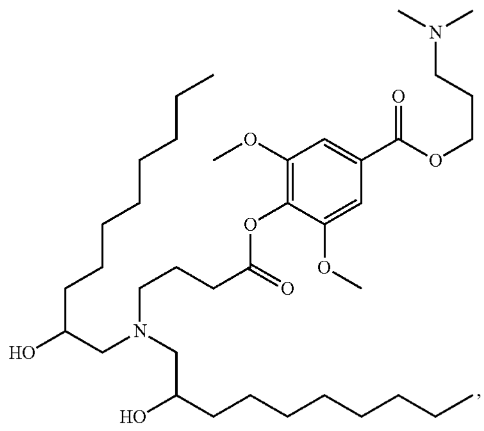
,

-continued
(IIIF)
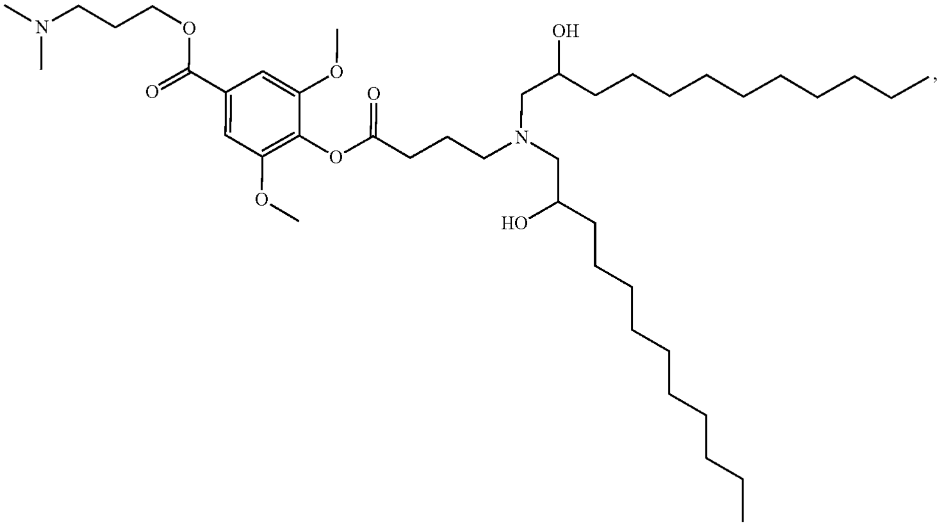
,
(IIIG)
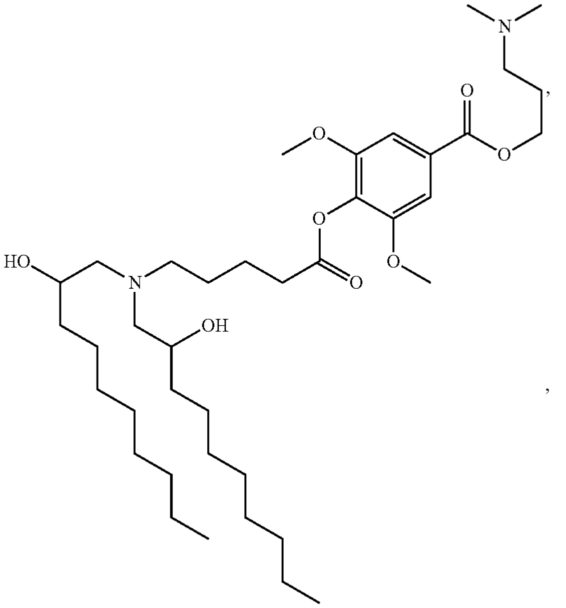
,
(IIIH)
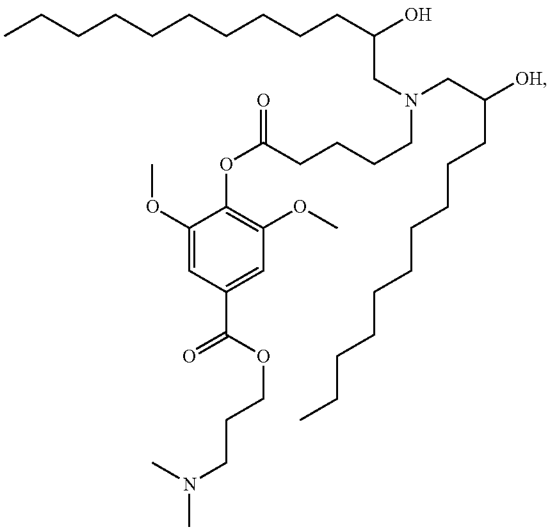
,

-continued
(IIII)
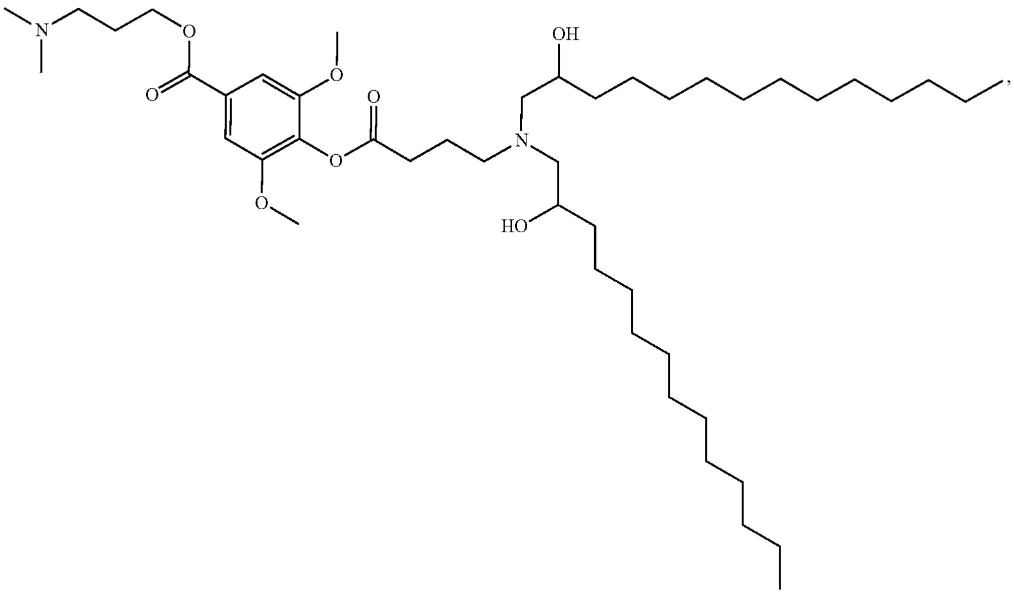
,
(IIIJ)
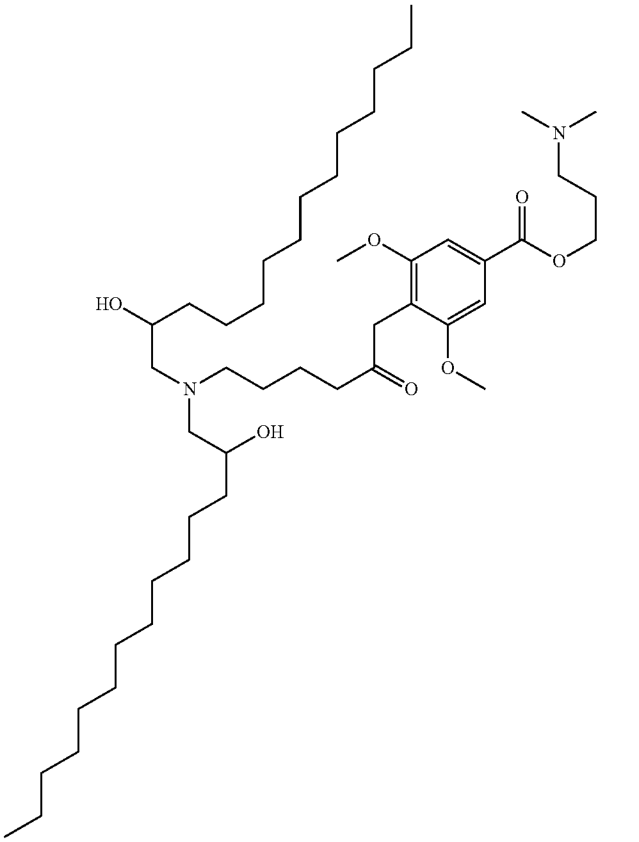
or

-continued (IIIK)

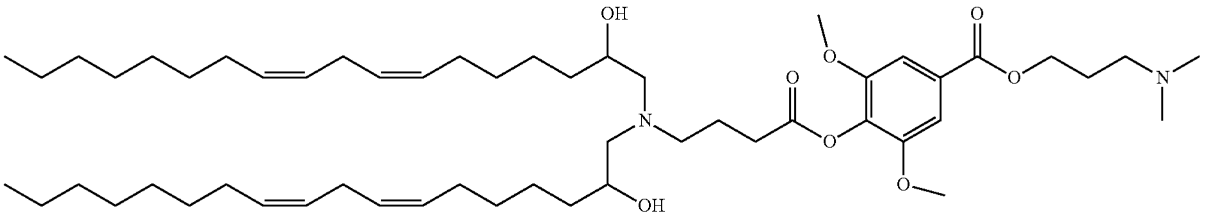

or a pharmaceutically acceptable salt thereof.

39. The cationic lipid of numbered embodiment 33 having a structure according to Formula (IIIL):

(IIIL)

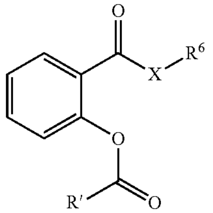

or a pharmaceutically acceptable salt thereof.

40. A cationic lipid of numbered embodiment 33 having a structure according to Formula (IV):

(IV)

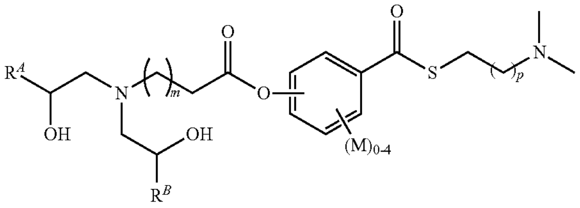

wherein M is selected from H, OH, OMe or Me, or a pharmaceutically acceptable salt thereof.

41. A cationic lipid of numbered embodiment 33 having a structure according to Formula (VI), (VII), (VIII), (IX) or (X):

(VI)

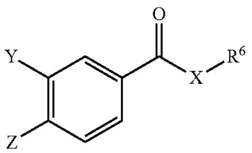

(VII)

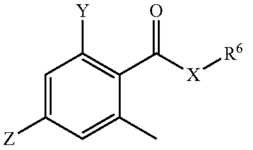

-continued (VIII)

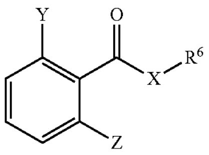

(IX)

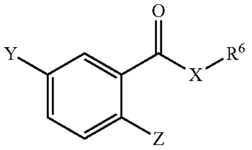

(X)

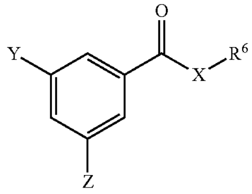

wherein one of Y and Z is OH and the other is —OC(O)R' or wherein both Y and Z are each independently —OC(O)R', or a pharmaceutically acceptable salt thereof.

42. The cationic lipid or a pharmaceutically acceptable salt thereof of numbered embodiment 41 wherein one of Y and Z is OH and the other is —OC(O)R'.

43. The cationic lipid or a pharmaceutically acceptable salt thereof of numbered embodiment 42 wherein Y is OH and Z is —OC(O)R'.

44. The cationic lipid or a pharmaceutically acceptable salt thereof of numbered embodiment 42 wherein Y is —OC(O)R' and Z is OH.

45. The cationic lipid or a pharmaceutically acceptable salt thereof of numbered embodiment 41 wherein both Y and Z are —OC(O)R'.

46. A compound selected from those listed in Tables 1-8 or a pharmaceutically acceptable salt thereof.

47. A composition comprising the cationic lipid of any one of the preceding numbered embodiments, one or more non-cationic lipids, one or more cholesterol-based lipids and one or more PEG-modified lipids.

48. The composition of numbered embodiment 47, wherein the composition is a lipid nanoparticle, optionally a liposome.

49. The composition of numbered embodiment 48, wherein the one or more cationic lipid(s) constitute(s) about 30 mol %-60 mol % of the lipid nanoparticle.

50. The composition of any one of numbered embodiments 48 or 49, wherein the one or more non-cationic lipid(s) constitute(s) 10 mol %-50 mol % of the lipid nanoparticle.

51. The composition of any one of numbered embodiments 48-50, wherein the one or more PEG-modified lipid (s) constitute(s) 1 mol %-10 mol % of the lipid nanoparticle.

52. The composition of any one of numbered embodiments 48-51, wherein the cholesterol-based lipid constitutes 10 mol %-50 mol % of the lipid nanoparticle.

53. The composition of any one of numbered embodiments 48-52, wherein the lipid nanoparticle encapsulates a nucleic acid, optionally an mRNA encoding a peptide or protein.

54. The composition of any one of numbered embodiments 48-52, wherein the lipid nanoparticle encapsulates an mRNA encoding a peptide or protein.

55. The composition of numbered embodiment 54, wherein the lipid nanoparticles have an encapsulation percentage for mRNA of at least 70%.

56. The composition of numbered embodiment 54, wherein the lipid nanoparticles have an encapsulation percentage for mRNA of at least 75%.

57. The composition of numbered embodiment 54, wherein the lipid nanoparticles have an encapsulation percentage for mRNA of at least 80%.

58. The composition of numbered embodiment 54, wherein the lipid nanoparticles have an encapsulation percentage for mRNA of at least 85%.

59. The composition of numbered embodiment 54, wherein the lipid nanoparticles have an encapsulation percentage for mRNA of at least 90%.

60. The composition of numbered embodiment 54, wherein the lipid nanoparticles have an encapsulation percentage for mRNA of at least 95%.

61. The composition of any one of numbered embodiments 54-60 for use in therapy.

62. The composition of any one of numbered embodiments 54-60 for use in a method of treating or preventing a disease amenable to treatment or prevention by the peptide or protein encoded by the mRNA, optionally wherein the disease is (a) a protein deficiency, optionally wherein the protein deficiency affects the liver, lung, brain or muscle, (b) an autoimmune disease, (c) an infectious disease, or (d) cancer.

63. The composition for use according to numbered embodiment 61 or 62, wherein the composition is administered intravenously, intrathecally or intramuscular, or by pulmonary delivery, optionally through nebulization.

64. A method for treating or preventing a disease wherein said method comprises administering to a subject in need thereof the composition of any one of numbered embodiments 54-60 and wherein the disease is amenable to treatment or prevention by the peptide or protein encoded by the mRNA, optionally wherein the disease is (a) a protein deficiency, optionally wherein the protein deficiency affects the liver, lung, brain or muscle, (b) an autoimmune disease, (c) an infectious disease, or (d) cancer.

65. The method of numbered embodiment 64, wherein the composition is administered intravenously, intrathecally or intramuscular, or by pulmonary delivery, optionally through nebulization.

What is claimed is:

1. A cationic lipid having a structure according to Formula (I):

(I)

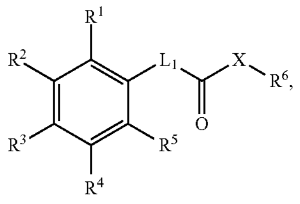

wherein $L_1$ is a bond, $(C_1\text{-}C_6)$alkyl or $(C_2\text{-}C_6)$alkenyl;

wherein X is O or S;

wherein $R^1$, $R^2$, $R^3$, $R^4$ and $R^5$ are each independently selected from H, OH, optionally substituted $(C_1\text{-}C_6)$ alkyl, optionally substituted $(C_2\text{-}C_6)$alkenyl, optionally substituted $(C_2\text{-}C_6)$alkynyl, optionally substituted $(C_1\text{-}C_6)$alkoxy and —OC(O)R';

wherein at least one of $R^1$, $R^2$, $R^3$, $R^4$ or $R^5$ is —OC(O)R';

wherein R' is

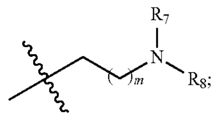

wherein $R^6$ is

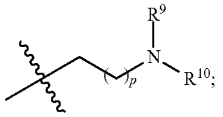

wherein m and p are each independently 0, 1, 2, 3, 4 or 5;

wherein $R^7$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_kR^A$ or $—(CH_2)_kCH(OR^{11})R^A$;

wherein $R^8$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_nR^B$ or $—(CH_2)_nCH(OR^{12})R^B$;

wherein $R^9$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_qR^C$ or $—(CH_2)_qCH(OR^{13})R^C$;

wherein $R^{10}$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_rR^D$ or $—(CH_2)_rCH(OR^{14})R^D$;

wherein k, n, q and r are each independently 1,2,3,4 or 5;

or wherein (i) $R^7$ and $R^8$ or (ii) $R^9$ and $R^{10}$ together form an optionally substituted 5- or 6-membered heterocycloalkyl or heteroaryl wherein the heterocycloalkyl or heteroaryl comprises 1 to 3 heteroatoms selected from N, O and S;

wherein $R^{11}$, $R^{12}$, $R^{13}$ and $R^{14}$ are each independently selected from H, methyl, ethyl or propyl;

wherein $R^A$, $R^B$, $R^C$ and $R^D$ are each independently selected from optionally substituted ($C_6$-$C_{20}$)alkyl, optionally substituted ($C_6$-$C_{20}$)alkenyl, optionally substituted ($C_6$-$C_{20}$)alkynyl, optionally substituted ($C_6$-$C_{20}$)acyl, optionally substituted —OC(O)alkyl, optionally substituted —OC(O)alkenyl, optionally substituted ($C_1$-$C_6$) monoalkylamino, optionally substituted ($C_1$-$C_6$) dialkylamino, optionally substituted ($C_1$-$C_6$) alkoxy, —OH, —$NH_2$;

wherein at least one of $R^7$, $R^8$, $R^9$, $R^{10}$ comprises a $R^A$, $R^B$, $R^C$ or $R^D$ moiety respectively wherein that $R^A$, $R^B$, $R^C$ or $R^D$ is independently selected from optionally substituted ($C_6$-$C_{20}$)alkyl, optionally substituted ($C_6$-$C_{20}$)alkenyl, optionally substituted ($C_6$-$C_{20}$)alkynyl, optionally substituted ($C_6$-$C_{20}$)acyl, optionally substituted —OC(O)($C_6$-$C_{20}$)alkyl or optionally substituted —OC(O)($C_6$-$C_{20}$)alkenyl;

or a pharmaceutically acceptable salt thereof.

2. The cationic lipid or a pharmaceutically acceptable salt thereof of claim 1 wherein X is O.

3. The cationic lipid or a pharmaceutically acceptable salt thereof of claim 1, wherein m is 1, 2 or 3.

4. The cationic lipid or a pharmaceutically acceptable salt thereof of claim 1, wherein p is 1, 2 or 3.

5. The cationic lipid or a pharmaceutically acceptable salt thereof of claim 1, wherein R' is:

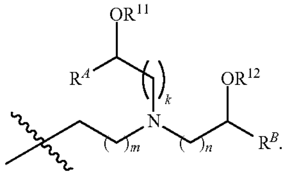

6. The cationic lipid or a pharmaceutically acceptable salt thereof of claim 5 wherein:

i) k, m and n=1;

ii) k and n=1, and m=2; or iii) k and n=1, and m=3.

7. The cationic lipid or a pharmaceutically acceptable salt thereof of claim 1, wherein R' is

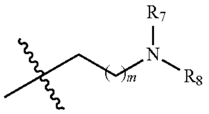

and $R^7$ and $R^8$ are each optionally substituted ($C_1$-$C_6$)alkyl substituted with —$CO_2R^{aa}$ wherein $R^{aa}$ is $C_1$-$C_{50}$ alkyl.

8. The cationic lipid or a pharmaceutically acceptable salt thereof of claim 1, wherein $R^6$ is:

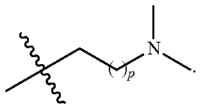 [SMILES: *CCN(C)C]

9. The cationic lipid of claim 1 having a structure according to Formula (II):

(II)

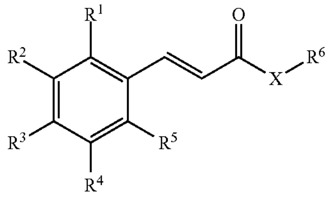

or a pharmaceutically acceptable salt thereof.

10. A cationic lipid of claim 1 having a structure according to Formula (VI), (VII), (VIII), (IX) or (X):

(VI)

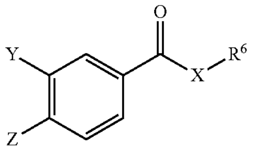

(VII)

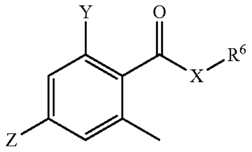

(VIII)

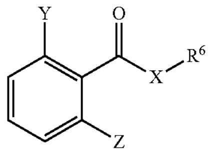

(XI)

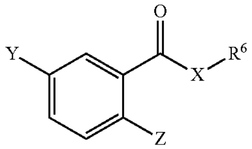

(X)

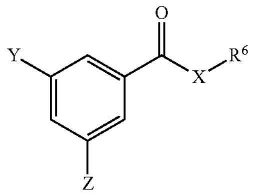

wherein one of Y and Z is OH and the other is —OC(O)R', or wherein both Y and Z are each independently —OC(O)R', or a pharmaceutically acceptable salt thereof.

11. The cationic lipid of claim 1, wherein the cationic lipid is selected from the group consisting of compound 1-564:
| No. | Structure |
|---|---|
| 1 | 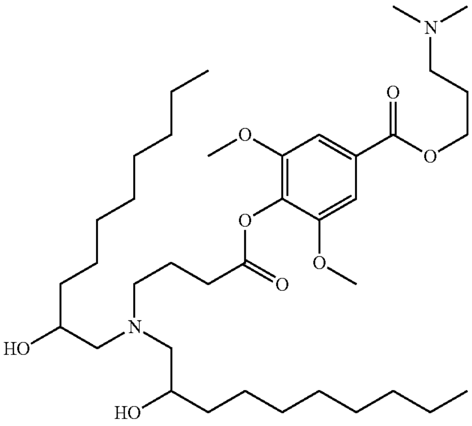 [SMILES: CCCCCCCCC(O)CN(CCCC(=O)Oc1c(OC)cc(C(=O)OCCCN(C)C)cc1OC)CC(O)CCCCCCCC] |
| 2 | 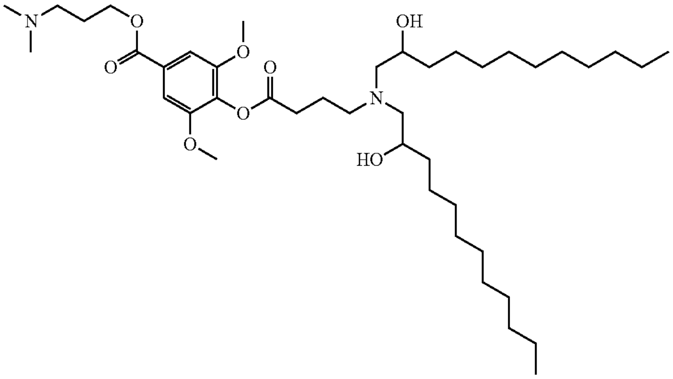 [SMILES: CCCCCCCCCCC(O)CN(CCCC(=O)Oc1c(OC)cc(C(=O)OCCCN(C)C)cc1OC)CC(O)CCCCCCCCCC] |
| 3 | 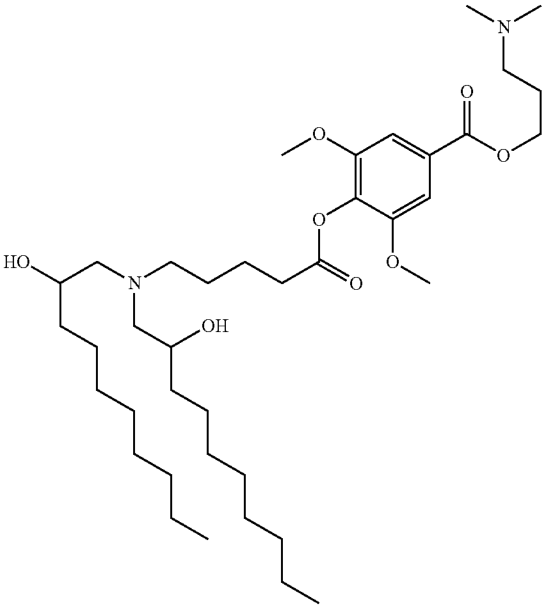 [SMILES: CCCCCCCCC(O)CN(CCCCC(=O)Oc1c(OC)cc(C(=O)OCCCN(C)C)cc1OC)CC(O)CCCCCCCC] |

-continued
| No. | Structure |
|---|---|
| 4 | 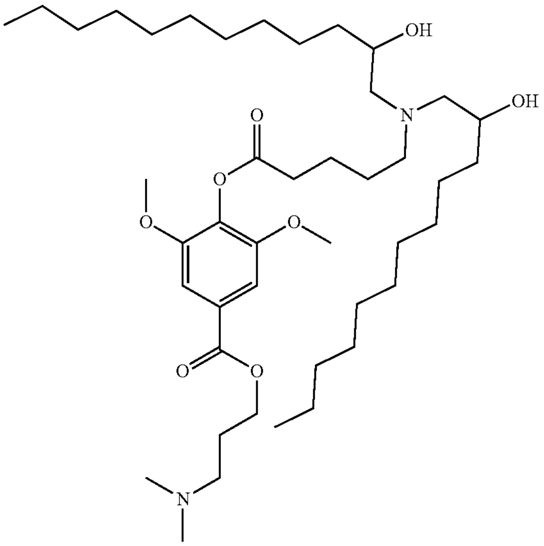 [SMILES: CCCCCCCCCCC(O)CN(CCCCC(=O)Oc1c(OC)cc(C(=O)OCCCN(C)C)cc1OC)CC(O)CCCCCCCCCC] |
| 5 | 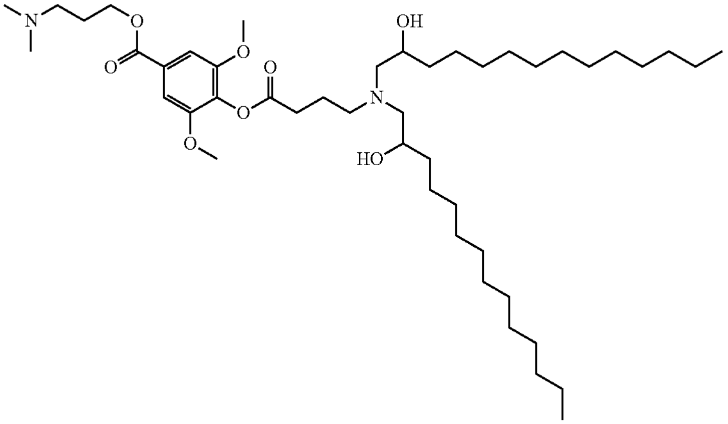 [SMILES: CCCCCCCCCCCCC(O)CN(CCCC(=O)Oc1c(OC)cc(C(=O)OCCCN(C)C)cc1OC)CC(O)CCCCCCCCCCCC] |
| 6 | 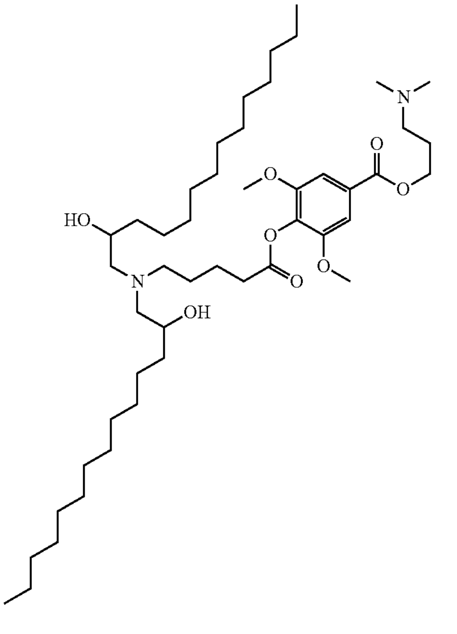 [SMILES: CCCCCCCCCCCCC(O)CN(CCCCC(=O)Oc1c(OC)cc(C(=O)OCCCN(C)C)cc1OC)CC(O)CCCCCCCCCCCC] |

-continued
| No. | Structure |
|---|---|
| 7 | 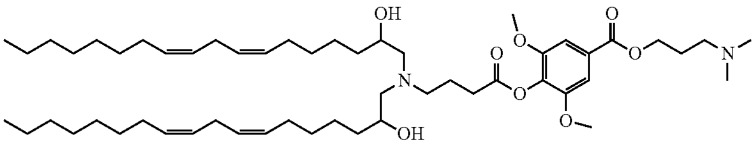 [SMILES: CCCCCCC/C=C\C/C=C\CCCCC(O)CN(CCCC(=O)Oc1c(OC)cc(C(=O)OCCCN(C)C)cc1OC)CC(O)CCCC/C=C\C/C=C\CCCCCCC] |
| 8 | 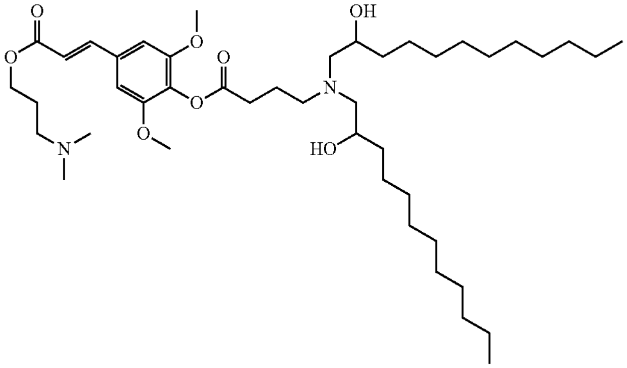 [SMILES: CCCCCCCCCCC(O)CN(CCCC(=O)Oc1c(OC)cc(/C=C/C(=O)OCCCN(C)C)cc1OC)CC(O)CCCCCCCCCC] |
| 9 | 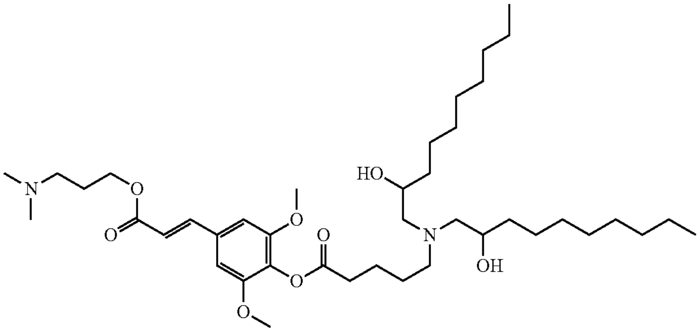 [SMILES: CCCCCCCCC(O)CN(CCCCC(=O)Oc1c(OC)cc(/C=C/C(=O)OCCCN(C)C)cc1OC)CC(O)CCCCCCCC] |
| 10 | 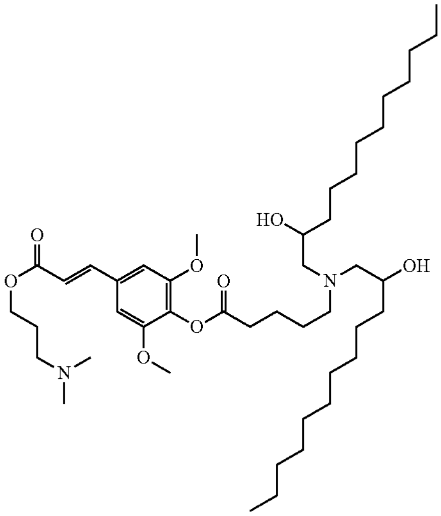 [SMILES: CCCCCCCCCCC(O)CN(CCCCC(=O)Oc1c(OC)cc(/C=C/C(=O)OCCCN(C)C)cc1OC)CC(O)CCCCCCCCCC] |

-continued
| No. Structure | |
|---|---|
| 11 | 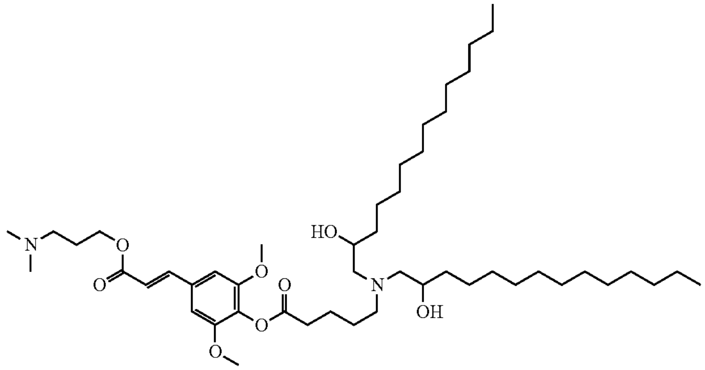 [SMILES: CCCCCCCCCCCCC(O)CN(CCCCC(=O)Oc1c(OC)cc(/C=C/C(=O)OCCCN(C)C)cc1OC)CC(O)CCCCCCCCCCCC] |
| 12 | 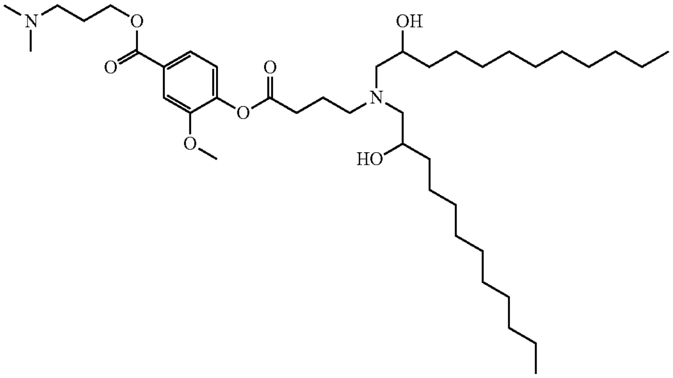 [SMILES: CCCCCCCCCCC(O)CN(CCCC(=O)Oc1ccc(C(=O)OCCCN(C)C)cc1OC)CC(O)CCCCCCCCCC] |
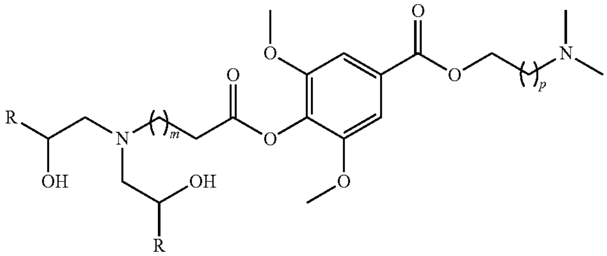
Syringic acid core
| No. | m | p | R |
|---|---|---|---|
| 13 | 1 | 1 | C8H17 |
| 1 | 2 | 2 | C8H17 |
| 14 | 3 | 3 | C8H17 |
| 15 | 4 | 4 | C8H17 |
| 16 | 1 | 2 | C8H17 |
| 17 | 1 | 3 | C8H17 |
| 18 | 1 | 4 | C8H17 |
| 19 | 2 | 1 | C8H17 |
| 20 | 2 | 3 | C8H17 |
| 21 | 2 | 4 | C8H17 |
| 22 | 3 | 1 | C8H17 |
| 3 | 3 | 2 | C8H17 |
| 23 | 3 | 4 | C8H17 |
| 24 | 4 | 1 | C8H17 |
| 25 | 4 | 2 | C8H17 |
| 26 | 4 | 3 | C8H17 |
| 27 | 1 | 1 | C10H21 |
| 2 | 2 | 2 | C10H21 |
| 28 | 2 | 3 | C10H21 |
| 29 | 3 | 3 | C10H21 |

-continued
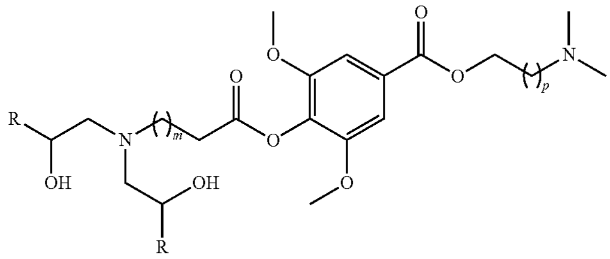
Syringic acid core
| No. | m | p | R |
|---|---|---|---|
| 30 | 4 | 4 | C10H21 |
| 31 | 1 | 2 | C10H21 |
| 32 | 1 | 3 | C10H21 |
| 33 | 1 | 4 | C10H21 |
| 34 | 2 | 1 | C10H21 |
| 36 | 2 | 4 | C10H21 |
| 37 | 3 | 1 | C10H21 |
| 4 | 3 | 2 | C10H21 |
| 38 | 3 | 4 | C10H21 |
| 39 | 4 | 1 | C10H21 |
| 40 | 4 | 2 | C10H21 |
| 41 | 4 | 3 | C10H21 |
| 42 | 1 | 1 | C12H25 |
| 5 | 2 | 2 | C12H25 |
| 43 | 3 | 3 | C12H25 |
| 44 | 4 | 4 | C12H25 |
| 45 | 1 | 2 | C12H25 |
| 46 | 1 | 3 | C12H25 |
| 47 | 1 | 4 | C12H25 |
| 48 | 2 | 1 | C12H25 |
| 49 | 2 | 3 | C12H25 |
| 50 | 2 | 4 | C12H25 |
| 51 | 3 | 1 | C12H25 |
| 6 | 3 | 2 | C12H25 |
| 52 | 3 | 4 | C12H25 |
| 53 | 4 | 1 | C12H25 |
| 54 | 4 | 2 | C12H25 |
| 55 | 4 | 3 | C12H25 |
| 56 | 1 | 1 | C14H29 |
| 57 | 2 | 2 | C14H29 |
| 58 | 3 | 3 | C14H29 |
| 59 | 4 | 4 | C14H29 |
| 60 | 1 | 2 | C14H29 |
| 61 | 1 | 3 | C14H29 |
| 62 | 1 | 4 | C14H29 |
| 63 | 2 | 1 | C14H29 |
| 64 | 2 | 3 | C14H29 |
| 65 | 2 | 4 | C14H29 |
| 66 | 3 | 1 | C14H29 |
| 67 | 3 | 2 | C14H29 |
| 68 | 3 | 4 | C14H29 |
| 69 | 4 | 1 | C14H29 |
| 70 | 4 | 2 | C14H29 |
| 71 | 4 | 3 | C14H29 |
| 72 | 1 | 1 | C16H33 |
| 73 | 2 | 2 | C16H33 |
| 74 | 3 | 3 | C16H33 |
| 75 | 4 | 4 | C16H33 |
| 76 | 1 | 2 | C16H33 |
| 77 | 1 | 3 | C16H33 |
| 78 | 1 | 4 | C16H33 |
| 79 | 2 | 1 | C16H33 |
| 80 | 2 | 3 | C16H33 |
| 81 | 2 | 4 | C16H33 |
| 82 | 3 | 1 | C16H33 |
| 83 | 3 | 2 | C16H33 |
| 84 | 3 | 4 | C16H33 |
| 85 | 4 | 1 | C16H33 |
| 86 | 4 | 2 | C16H33 |
| 87 | 4 | 3 | C16H33 |
| 88 | 1 | 1 | C16H31 |
| 89 | 2 | 2 | C16H31 |

-continued
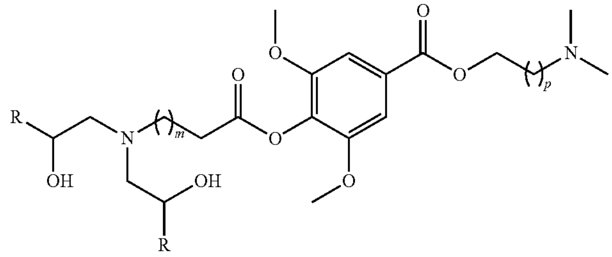
Syringic acid core
| No. | m | p | R |
|---|---|---|---|
| 90 | 3 | 3 | C16H31 |
| 91 | 4 | 4 | C16H31 |
| 92 | 1 | 2 | C16H31 |
| 93 | 1 | 3 | C16H31 |
| 94 | 1 | 4 | C16H31 |
| 95 | 2 | 1 | C16H31 |
| 96 | 2 | 3 | C16H31 |
| 97 | 2 | 4 | C16H31 |
| 98 | 3 | 1 | C16H31 |
| 99 | 3 | 2 | C16H31 |
| 100 | 3 | 4 | C16H31 |
| 101 | 4 | 1 | C16H31 |
| 102 | 4 | 2 | C16H31 |
| 103 | 4 | 3 | C16H31 |
| 104 | 1 | 1 | C16H29 |
| 7 | 2 | 2 | €16H29 |
| 105 | 3 | 3 | C16H29 |
| 106 | 4 | 4 | C16H29 |
| 107 | 1 | 2 | C16H29 |
| 108 | 1 | 3 | C16H29 |
| 109 | 1 | 4 | C16H29 |
| 110 | 2 | 1 | C16H29 |
| 111 | 2 | 3 | C16H29 |
| 112 | 2 | 4 | C16H29 |
| 113 | 3 | 1 | C16H29 |
| 114 | 3 | 2 | C16H29 |
| 115 | 3 | 4 | C16H29 |
| 116 | 4 | 1 | C16H29 |
| 117 | 4 | 2 | C16H29 |
| 118 | 4 | 3 | C16H29 |
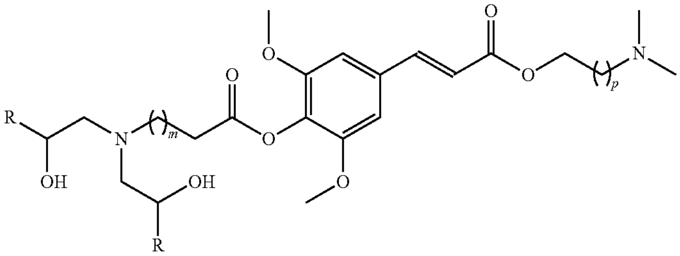
Sinapinic acid core
| No. | m | p | R |
|---|---|---|---|
| 119 | 1 | 1 | C8H17 |
| 120 | 2 | 2 | C8H17 |
| 121 | 3 | 3 | C8H17 |
| 122 | 4 | 4 | C8H17 |
| 123 | 1 | 2 | C8H17 |
| 124 | 1 | 3 | C8H17 |
| 125 | 1 | 4 | C8H17 |
| 126 | 2 | 1 | C8H17 |
| 127 | 2 | 3 | C8H17 |
| 128 | 2 | 4 | C8H17 |
| 129 | 3 | 1 | C8H17 |

-continued
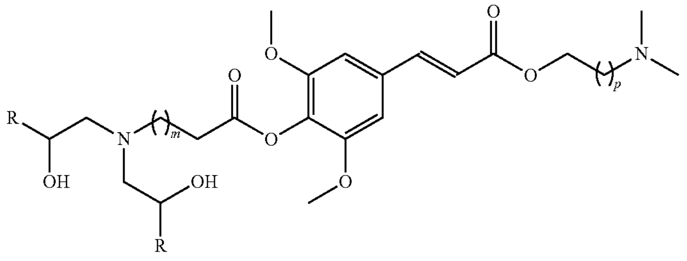
Sinapinic acid core
| No. | m | p | R |
|---|---|---|---|
| | 3 | 2 | C8H17 |
| 130 | 3 | 4 | C8H17 |
| 131 | 4 | 1 | C8H17 |
| 132 | 4 | 2 | C8H17 |
| 133 | 4 | 3 | C8H17 |
| 134 | 1 | 1 | C10H21 |
| 8 | 2 | 2 | C10H21 |
| 135 | 2 | 3 | C10H21 |
| 136 | 3 | 3 | C10H21 |
| 137 | 4 | 4 | C10H21 |
| 138 | 1 | 2 | C10H21 |
| 139 | 1 | 3 | C10H21 |
| 140 | 1 | 4 | C10H21 |
| 141 | 2 | 1 | C10H21 |
| 142 | 2 | 4 | C10H21 |
| 143 | 3 | 1 | C10H21 |
| 10 | 3 | 2 | C10H21 |
| 144 | 3 | 4 | C10H21 |
| 145 | 4 | 1 | C10H21 |
| 146 | 4 | 2 | C10H21 |
| 147 | 4 | 3 | C10H21 |
| 148 | 1 | 1 | C12H25 |
| 149 | 2 | 2 | C12H25 |
| 150 | 3 | 3 | C12H25 |
| 151 | 4 | 4 | C12H25 |
| 152 | 1 | 2 | C12H25 |
| 153 | 1 | 3 | C12H25 |
| 154 | 1 | 4 | C12H25 |
| 155 | 2 | 1 | C12H25 |
| 156 | 2 | 3 | C12H25 |
| 157 | 2 | 4 | C12H25 |
| 158 | 3 | 1 | C12H25 |
| 11 | 3 | 2 | €12H25 |
| 159 | 3 | 4 | C12H25 |
| 160 | 4 | 1 | C12H25 |
| 161 | 4 | 2 | C12H25 |
| 162 | 4 | 3 | C12H25 |
| 163 | 1 | 1 | C14H29 |
| 164 | 2 | 2 | C14H29 |
| 165 | 3 | 3 | C14H29 |
| 166 | 4 | 4 | C14H29 |
| 167 | 1 | 2 | C14H29 |
| 168 | 1 | 3 | C14H29 |
| 169 | 1 | 4 | C14H29 |
| 170 | 2 | 1 | C14H29 |
| 171 | 2 | 3 | C14H29 |
| 172 | 2 | 4 | C14H29 |
| 173 | 3 | 1 | C14H29 |
| 174 | 3 | 2 | C14H29 |
| 175 | 3 | 4 | C14H29 |
| 176 | 4 | 1 | C14H29 |
| 177 | 4 | 2 | C14H29 |
| 178 | 4 | 3 | C14H29 |
| 179 | 1 | 1 | C16H33 |
| 180 | 2 | 2 | C16H33 |
| 181 | 3 | 3 | C16H33 |
| 182 | 4 | 4 | C16H33 |
| 183 | 1 | 2 | C16H33 |
| 184 | 1 | 3 | C16H33 |
| 185 | 1 | 4 | C16H33 |
| 186 | 2 | 1 | C16H33 |
| 187 | 2 | 3 | C16H33 |

-continued
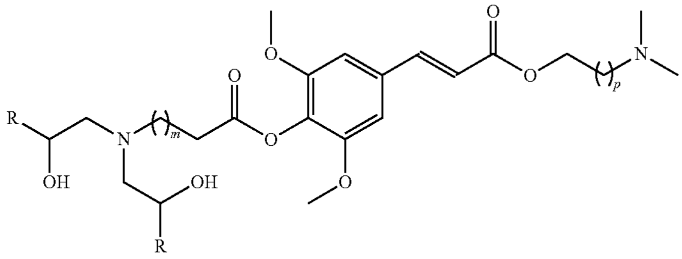
Sinapinic acid core
| No. | m | p | R |
|---|---|---|---|
| 188 | 2 | 4 | C16H33 |
| 189 | 3 | 1 | C16H33 |
| 190 | 3 | 2 | C16H33 |
| 191 | 3 | 4 | C16H33 |
| 192 | 4 | 1 | C16H33 |
| 193 | 4 | 2 | C16H33 |
| 194 | 4 | 3 | C16H33 |
| 195 | 1 | 1 | C16H31 |
| 196 | 2 | 2 | C16H31 |
| 197 | 3 | 3 | C16H31 |
| 198 | 4 | 4 | C16H31 |
| 199 | 1 | 2 | C16H31 |
| 200 | 1 | 3 | C16H31 |
| 201 | 1 | 4 | C16H31 |
| 202 | 2 | 1 | C16H31 |
| 203 | 2 | 3 | C16H31 |
| 204 | 2 | 4 | C16H31 |
| 205 | 3 | 1 | C16H31 |
| 206 | 3 | 2 | C16H31 |
| 207 | 3 | 4 | C16H31 |
| 208 | 4 | 1 | C16H31 |
| 209 | 4 | 2 | C16H31 |
| 210 | 4 | 3 | C16H31 |
| 21 | 1 | 1 | C16H29 |
| 212 | 2 | 2 | C16H29 |
| 213 | 3 | 3 | C16H29 |
| 214 | 4 | 4 | C16H29 |
| 215 | 1 | 2 | C16H29 |
| 216 | 1 | 3 | C16H29 |
| 217 | 1 | 4 | C16H29 |
| 218 | 2 | 1 | C16H29 |
| 219 | 2 | 3 | C16H29 |
| 220 | 2 | 4 | C16H29 |
| 221 | 3 | 1 | C16H29 |
| 222 | 3 | 2 | C16H29 |
| 223 | 3 | 4 | C16H29 |
| 224 | 4 | 1 | C16H29 |
| 225 | 4 | 2 | C16H29 |
| 226 | 4 | 3 | C16H29 |
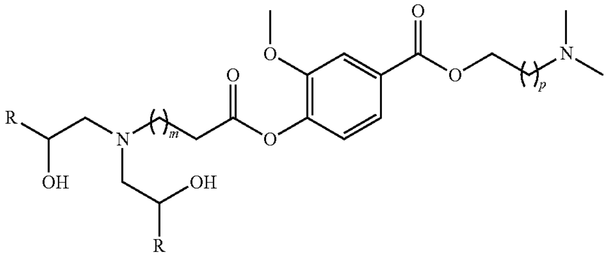
Vanillic acid core
| No. | m | p | R |
|---|---|---|---|
| 227 | 1 | 1 | C8H17 |
| 228 | 2 | 2 | C8H17 |

-continued
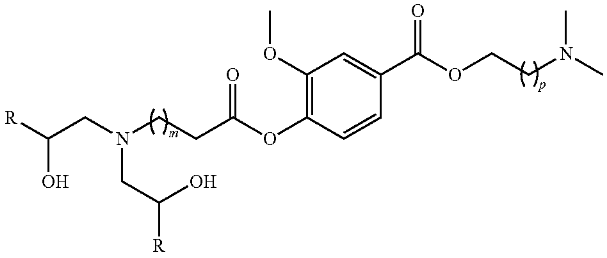
Vanillic acid core
| No. | m | p | R |
|---|---|---|---|
| 229 | 3 | 3 | C8H17 |
| 230 | 4 | 4 | C8H17 |
| 231 | 1 | 2 | C8H17 |
| 232 | 1 | 3 | C8H17 |
| 233 | 1 | 4 | C8H17 |
| 234 | 2 | 1 | C8H17 |
| 235 | 2 | 3 | C8H17 |
| 236 | 2 | 4 | C8H17 |
| 237 | 3 | 1 | C8H17 |
| 238 | 3 | 2 | C8H17 |
| 239 | 3 | 4 | C8H17 |
| 240 | 4 | 1 | C8H17 |
| 241 | 4 | 2 | C8H17 |
| 242 | 4 | 3 | C8H17 |
| 243 | 1 | 1 | C10H21 |
| 12 | 2 | 2 | C10H21 |
| 244 | 2 | 3 | C10H21 |
| 245 | 3 | 3 | C10H21 |
| 246 | 4 | 4 | C10H21 |
| 247 | 1 | 2 | C10H21 |
| 248 | 1 | 3 | C10H21 |
| 249 | 1 | 4 | C10H21 |
| 250 | 2 | 1 | C10H21 |
| 251 | 2 | 4 | C10H21 |
| 252 | 3 | 1 | C10H21 |
| 253 | 3 | 2 | C10H21 |
| 254 | 3 | 4 | C10H21 |
| 255 | 4 | 1 | C10H21 |
| 256 | 4 | 2 | C10H21 |
| 257 | 4 | 3 | C10H21 |
| 258 | 1 | 1 | C12H25 |
| 259 | 2 | 2 | C12H25 |
| 260 | 3 | 3 | C12H25 |
| 261 | 4 | 4 | C12H25 |
| 262 | 1 | 2 | C12H25 |
| 263 | 1 | 3 | C12H25 |
| 264 | 1 | 4 | C12H25 |
| 265 | 2 | 1 | C12H25 |
| 266 | 2 | 3 | C12H25 |
| 267 | 2 | 4 | C12H25 |
| 268 | 3 | 1 | C12H25 |
| 269 | 3 | 2 | C12H25 |
| 270 | 3 | 4 | C12H25 |
| 271 | 4 | 1 | C12H25 |
| 272 | 4 | 2 | C12H25 |
| 273 | 4 | 3 | C12H25 |
| 274 | 1 | 1 | C14H29 |
| 275 | 2 | 2 | C14H29 |
| 276 | 3 | 3 | C14H29 |
| 277 | 4 | 4 | C14H29 |
| 278 | 1 | 2 | C14H29 |
| 279 | 1 | 3 | C14H29 |
| 280 | 1 | 4 | C14H29 |
| 281 | 2 | 1 | C14H29 |
| 282 | 2 | 3 | C14H29 |
| 283 | 2 | 4 | C14H29 |
| 284 | 3 | 1 | C14H29 |
| 285 | 3 | 2 | C14H29 |
| 286 | 3 | 4 | C14H29 |
| 287 | 4 | 1 | C14H29 |
| 288 | 4 | 2 | C14H29 |
| 289 | 4 | 3 | C14H29 |

-continued
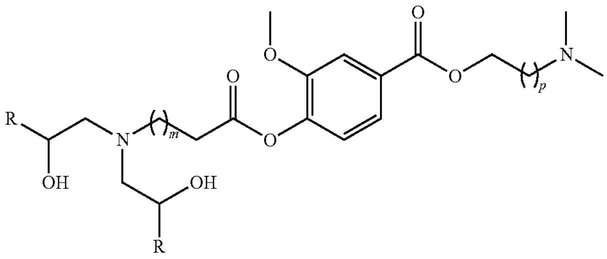
Vanillic acid core
| No. | m | p | R |
|---|---|---|---|
| 290 | 1 | 1 | C16H33 |
| 291 | 2 | 2 | C16H33 |
| 292 | 3 | 3 | C16H33 |
| 293 | 4 | 4 | C16H33 |
| 294 | 1 | 2 | C16H33 |
| 295 | 1 | 3 | C16H33 |
| 296 | 1 | 4 | C16H33 |
| 297 | 2 | 1 | C16H33 |
| 298 | 2 | 3 | C16H33 |
| 299 | 2 | 4 | C16H33 |
| 300 | 3 | 1 | C16H33 |
| 301 | 3 | 2 | C16H33 |
| 302 | 3 | 4 | C16H33 |
| 303 | 4 | 1 | C16H33 |
| 304 | 4 | 2 | C16H33 |
| 305 | 4 | 3 | C16H33 |
| 306 | 1 | 1 | C16H31 |
| 307 | 2 | 2 | C16H31 |
| 308 | 3 | 3 | C16H31 |
| 309 | 4 | 4 | C16H31 |
| 310 | 1 | 2 | C16H31 |
| 311 | 1 | 3 | C16H31 |
| 312 | 1 | 4 | C16H31 |
| 313 | 2 | 1 | C16H31 |
| 314 | 2 | 3 | C16H31 |
| 315 | 2 | 4 | C16H31 |
| 316 | 3 | 1 | C16H31 |
| 317 | 3 | 2 | C16H31 |
| 318 | 3 | 4 | C16H31 |
| 319 | 4 | 1 | C16H31 |
| 320 | 4 | 2 | C16H31 |
| 321 | 4 | 3 | C16H31 |
| 322 | 1 | 1 | C16H29 |
| 323 | 2 | 2 | C16H29 |
| 324 | 3 | 3 | C16H29 |
| 325 | 4 | 4 | C16H29 |
| 326 | 1 | 2 | C16H29 |
| 327 | 1 | 3 | C16H29 |
| 328 | 1 | 4 | C16H29 |
| 329 | 2 | 1 | C16H29 |
| 330 | 2 | 3 | C16H29 |
| 331 | 2 | 4 | C16H29 |
| 332 | 3 | 1 | C16H29 |
| 333 | 3 | 2 | C16H29 |
| 334 | 3 | 4 | C16H29 |
| 335 | 4 | 1 | C16H29 |
| 336 | 4 | 2 | C16H29 |
| 337 | 4 | 3 | C16H29 |

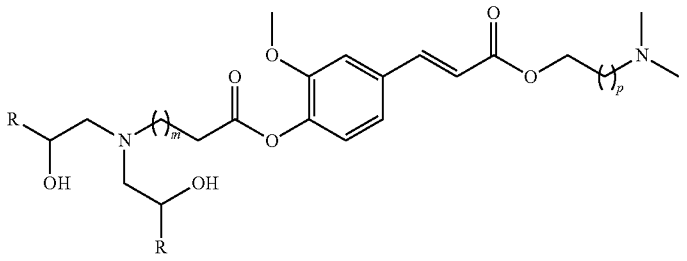
Ferulic Acid core
| No. | m | p | R |
|---|---|---|---|
| 338 | 1 | 1 | C8H17 |
| 339 | 2 | 2 | C8H17 |
| 340 | 3 | 3 | C8H17 |
| 341 | 4 | 4 | C8H17 |
| 342 | 1 | 2 | C8H17 |
| 343 | 1 | 3 | C8H17 |
| 344 | 1 | 4 | C8H17 |
| 345 | 2 | 1 | C8H17 |
| 346 | 2 | 3 | C8H17 |
| 347 | 2 | 4 | C8H17 |
| 348 | 3 | 1 | C8H17 |
| 349 | 3 | 2 | C8H17 |
| 350 | 3 | 4 | C8H17 |
| 351 | 4 | 1 | C8H17 |
| 352 | 4 | 2 | C8H17 |
| 353 | 4 | 3 | C8H17 |
| 354 | 1 | 1 | C10H21 |
| 355 | 2 | 2 | C10H21 |
| 356 | 2 | 3 | C10H21 |
| 357 | 3 | 3 | C10H21 |
| 358 | 4 | 4 | C10H21 |
| 359 | 1 | 2 | C10H21 |
| 360 | 1 | 3 | C10H21 |
| 361 | 1 | 4 | C10H21 |
| 362 | 2 | 1 | C10H21 |
| 363 | 2 | 4 | C10H21 |
| 364 | 3 | 1 | C10H21 |
| 365 | 3 | 2 | C10H21 |
| 366 | 3 | 4 | C10H21 |
| 367 | 4 | 1 | C10H21 |
| 368 | 4 | 2 | C10H21 |
| 369 | 4 | 3 | C10H21 |
| 370 | 1 | 1 | C12H25 |
| 371 | 2 | 2 | C12H25 |
| 372 | 3 | 3 | C12H25 |
| 373 | 4 | 4 | C12H25 |
| 374 | 1 | 2 | C12H25 |
| 375 | 1 | 3 | C12H25 |
| 376 | 1 | 4 | C12H25 |
| 377 | 2 | 1 | C12H25 |
| 378 | 2 | 3 | C12H25 |
| 379 | 2 | 4 | C12H25 |
| 380 | 3 | 1 | C12H25 |
| 381 | 3 | 2 | C12H25 |
| 382 | 3 | 4 | C12H25 |
| 383 | 4 | 1 | C12H25 |
| 384 | 4 | 2 | C12H25 |
| 385 | 4 | 3 | C12H25 |
| 386 | 1 | 1 | C14H29 |
| 387 | 2 | 2 | C14H29 |
| 388 | 3 | 3 | C14H29 |
| 389 | 4 | 4 | C14H29 |
| 390 | 1 | 2 | C14H29 |
| 391 | 1 | 3 | C14H29 |
| 392 | 1 | 4 | C14H29 |
| 393 | 2 | 1 | C14H29 |
| 394 | 2 | 3 | C14H29 |
| 395 | 2 | 4 | C14H29 |
| 396 | 3 | 1 | C14H29 |
| 397 | 3 | 2 | C14H29 |
| 398 | 3 | 4 | C14H29 |
| 399 | 4 | 1 | C14H29 |
| 400 | 4 | 2 | C14H29 |
| 401 | 4 | 3 | C14H29 |

-continued
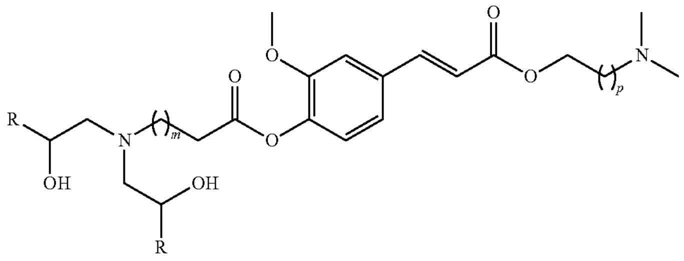
Ferulic Acid core
| No. | m | p | R |
|---|---|---|---|
| 402 | 1 | 1 | C16H33 |
| 403 | 2 | 2 | C16H33 |
| 404 | 3 | 3 | C16H33 |
| 405 | 4 | 4 | C16H33 |
| 406 | 1 | 2 | C16H33 |
| 407 | 1 | 3 | C16H33 |
| 408 | 1 | 4 | C16H33 |
| 409 | 2 | 1 | C16H33 |
| 410 | 2 | 3 | C16H33 |
| 411 | 2 | 4 | C16H33 |
| 412 | 3 | 1 | C16H33 |
| 413 | 3 | 2 | C16H33 |
| 414 | 3 | 4 | C16H33 |
| 415 | 4 | 1 | C16H33 |
| 416 | 4 | 2 | C16H33 |
| 417 | 4 | 3 | C16H33 |
| 418 | 1 | 1 | C16H31 |
| 419 | 2 | 2 | C16H31 |
| 420 | 3 | 3 | C16H31 |
| 421 | 4 | 4 | C16H31 |
| 422 | 1 | 2 | C16H31 |
| 423 | 1 | 3 | C16H31 |
| 424 | 1 | 4 | C16H31 |
| 425 | 2 | 1 | C16H31 |
| 426 | 2 | 3 | C16H31 |
| 427 | 2 | 4 | C16H31 |
| 428 | 3 | 1 | C16H31 |
| 429 | 3 | 2 | C16H31 |
| 430 | 3 | 4 | C16H31 |
| 431 | 4 | 1 | C16H31 |
| 432 | 4 | 2 | C16H31 |
| 433 | 4 | 3 | C16H31 |
| 434 | 1 | 1 | C16H29 |
| 435 | 2 | 2 | C16H29 |
| 436 | 3 | 3 | C16H29 |
| 437 | 4 | 4 | C16H29 |
| 438 | 1 | 2 | C16H29 |
| 439 | 1 | 3 | C16H29 |
| 440 | 1 | 4 | C16H29 |
| 441 | 2 | 1 | C16H29 |
| 442 | 2 | 3 | C16H29 |
| 443 | 2 | 4 | C16H29 |
| 444 | 3 | 1 | C16H29 |
| 445 | 3 | 2 | C16H29 |
| 446 | 3 | 4 | C16H29 |
| 447 | 4 | 1 | C16H29 |
| 448 | 4 | 2 | C16H29 |
| 449 | 4 | 3 | C16H29 |

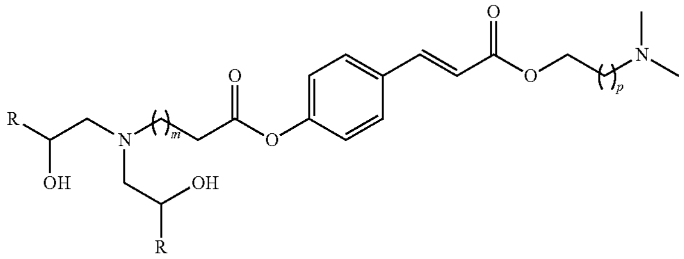
p-Coumaric Acid core
| No. | m | p | R |
|---|---|---|---|
| 450 | 1 | 1 | C8H17 |
| 451 | 2 | 2 | C8H17 |
| 452 | 3 | 3 | C8H17 |
| 453 | 4 | 4 | C8H17 |
| 454 | 1 | 2 | C8H17 |
| 455 | 1 | 3 | C8H17 |
| 456 | 1 | 4 | C8H17 |
| 457 | 2 | 1 | C8H17 |
| 458 | 2 | 3 | C8H17 |
| 459 | 2 | 4 | C8H17 |
| 460 | 3 | 1 | C8H17 |
| 461 | 3 | 2 | C8H17 |
| 462 | 3 | 4 | C8H17 |
| 463 | 4 | 1 | C8H17 |
| 464 | 4 | 2 | C8H17 |
| 465 | 4 | 3 | C8H17 |
| 466 | 1 | 1 | C10H21 |
| 467 | 2 | 2 | C10H21 |
| 468 | 2 | 3 | C10H21 |
| 469 | 3 | 3 | C10H21 |
| 470 | 4 | 4 | C10H21 |
| 471 | 1 | 2 | C10H21 |
| 472 | 1 | 3 | C10H21 |
| 473 | 1 | 4 | C10H21 |
| 474 | 2 | 1 | C10H21 |
| 475 | 2 | 4 | C10H21 |
| 476 | 3 | 1 | C10H21 |
| 477 | 3 | 2 | C10H21 |
| 478 | 3 | 4 | C10H21 |
| 479 | 4 | 1 | C10H21 |
| 480 | 4 | 2 | C10H21 |
| 481 | 4 | 3 | C10H21 |
| 482 | 1 | 1 | C12H25 |
| 483 | 2 | 2 | C12H25 |
| 484 | 3 | 3 | C12H25 |
| 485 | 4 | 4 | C12H25 |
| 486 | 1 | 2 | C12H25 |
| 487 | 1 | 3 | C12H25 |
| 488 | 1 | 4 | C12H25 |
| 489 | 2 | 1 | C12H25 |
| 490 | 2 | 3 | C12H25 |
| 491 | 2 | 4 | C12H25 |
| 492 | 3 | 1 | C12H25 |
| 493 | 3 | 2 | C12H25 |
| 494 | 3 | 4 | C12H25 |
| 495 | 4 | 1 | C12H25 |
| 496 | 4 | 2 | C12H25 |
| 497 | 4 | 3 | C12H25 |
| 498 | 1 | 1 | C14H29 |
| 499 | 2 | 2 | C14H29 |
| 500 | 3 | 3 | C14H29 |
| 501 | 4 | 4 | C14H29 |
| 502 | 1 | 2 | C14H29 |
| 503 | 1 | 3 | C14H29 |
| 504 | 1 | 4 | C14H29 |
| 505 | 2 | 1 | C14H29 |
| 506 | 2 | 3 | C14H29 |
| 507 | 2 | 4 | C14H29 |
| 508 | 3 | 1 | C14H29 |
| 509 | 3 | 2 | C14H29 |
| 510 | 3 | 4 | C14H29 |
| 511 | 4 | 1 | C14H29 |
| 512 | 4 | 2 | C14H29 |
| 513 | 4 | 3 | C14H29 |

-continued
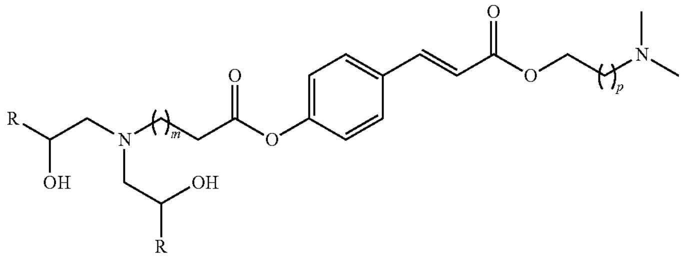
p-Coumaric Acid core
| No. | m | p | R |
|---|---|---|---|
| 514 | 1 | 1 | C16H33 |
| 515 | 2 | 2 | C16H33 |
| 516 | 3 | 3 | C16H33 |
| 517 | 4 | 4 | C16H33 |
| 518 | 1 | 2 | C16H33 |
| 519 | 1 | 3 | C16H33 |
| 520 | 1 | 4 | C16H33 |
| 521 | 2 | 1 | C16H33 |
| 522 | 2 | 3 | C16H33 |
| 523 | 2 | 4 | C16H33 |
| 524 | 3 | 1 | C16H33 |
| 525 | 3 | 2 | C16H33 |
| 526 | 3 | 4 | C16H33 |
| 527 | 4 | 1 | C16H33 |
| 528 | 4 | 2 | C16H33 |
| 529 | 4 | 3 | C16H33 |
| 530 | 1 | 1 | C16H31 |
| 531 | 2 | 2 | C16H31 |
| 532 | 3 | 3 | C16H31 |
| 533 | 4 | 4 | C16H31 |
| 534 | 1 | 2 | C16H31 |
| 535 | 1 | 3 | C16H31 |
| 536 | 1 | 4 | C16H31 |
| 537 | 2 | 1 | C16H31 |
| 538 | 2 | 3 | C16H31 |
| 539 | 2 | 4 | C16H31 |
| 540 | 3 | 1 | C16H31 |
| 541 | 3 | 2 | C16H31 |
| 542 | 3 | 4 | C16H31 |
| 543 | 4 | 1 | C16H31 |
| 544 | 4 | 2 | C16H31 |
| 545 | 4 | 3 | C16H31 |
| 546 | 1 | 1 | C16H29 |
| 547 | 2 | 2 | C16H29 |
| 548 | 3 | 3 | C16H29 |
| 549 | 4 | 4 | C16H29 |
| 550 | 1 | 2 | C16H29 |
| 551 | 1 | 3 | C16H29 |
| 552 | 1 | 4 | C16H29 |
| 553 | 2 | 1 | C16H29 |
| 554 | 2 | 3 | C16H29 |
| 555 | 2 | 4 | C16H29 |
| 556 | 3 | 1 | C16H29 |
| 557 | 3 | 2 | C16H29 |
| 558 | 3 | 4 | C16H29 |
| 559 | 4 | 1 | C16H29 |
| 560 | 4 | 2 | C16H29 |
| 561 | 4 | 3 | C16H29 |

| No. | Structure |
|---|---|
| 562 | 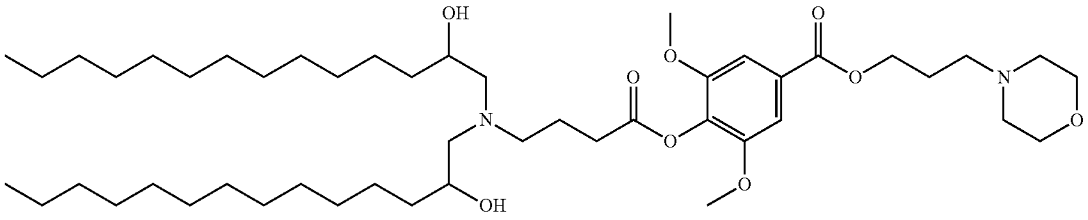 [SMILES: CCCCCCCCCCCCC(O)CN(CCCC(=O)Oc1c(OC)cc(C(=O)OCCCN2CCOCC2)cc1OC)CC(O)CCCCCCCCCCCC] |
| 563 | 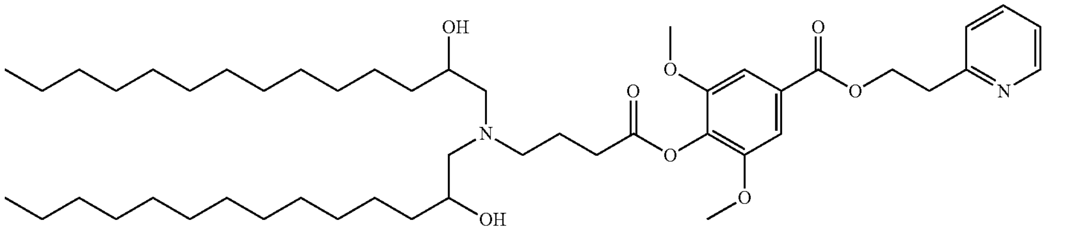 [SMILES: CCCCCCCCCCCCC(O)CN(CCCC(=O)Oc1c(OC)cc(C(=O)OCCc2ccccn2)cc1OC)CC(O)CCCCCCCCCCCC] |
| 564 | 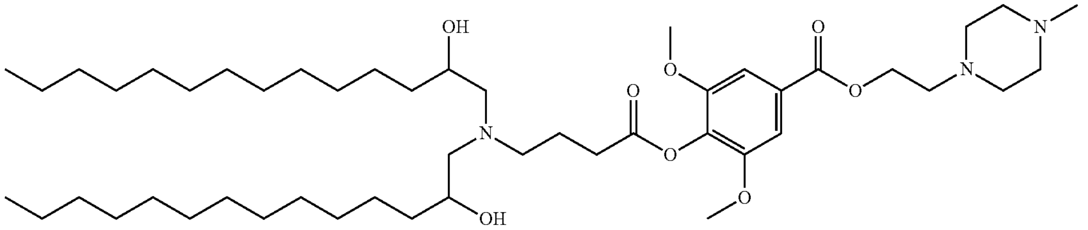 [SMILES: CCCCCCCCCCCCC(O)CN(CCCC(=O)Oc1c(OC)cc(C(=O)OCCN2CCN(C)CC2)cc1OC)CC(O)CCCCCCCCCCCC] |

or a pharmaceutically acceptable salt thereof.

12. The cationic lipid or a pharmaceutically acceptable salt thereof of claim 5 wherein:

i) k, m and n=1 and $R^{11}$ and $R^{12}$=H;

ii) k and n=1, m=2 and $R^{11}$ and $R^{12}$=H; or iii) k and n=1, m=3 and $R^{11}$ and $R^{12}$=H.

13. The cationic lipid of claim 9 having a structure according to (a) Formula (IIA):

(IIA)

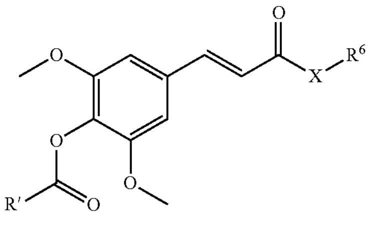

or a pharmaceutically acceptable salt thereof, (b) Formula (IIF):

(IIF)

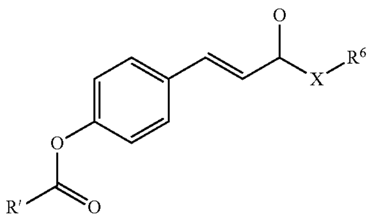

or a pharmaceutically acceptable salt thereof, (c) Formula (IIG):

(IIG)

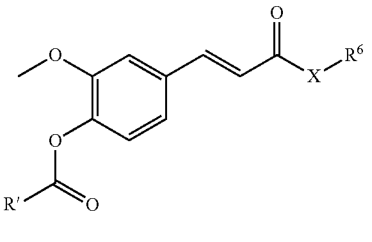

or a pharmaceutically acceptable salt thereof, or (d) Formula (IIH):

(IIH)

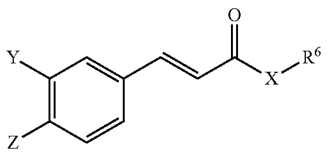

wherein one of Y and Z is OH and the other is —OC(O)R' or wherein both Y and Z are each independently —OC(O)R', or a pharmaceutically acceptable salt thereof.

14. The cationic lipid of claim 1 having a structure according to Formula (III):

(III)

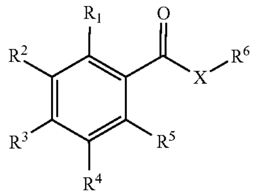

or a pharmaceutically acceptable salt thereof.

15. The cationic lipid of claim 14 having a structure according to:

(a) Formula (IIIA):

(IIIA)

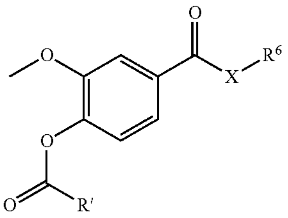

or a pharmaceutically acceptable salt thereof, (b) Formula (IIID):

(IIID)

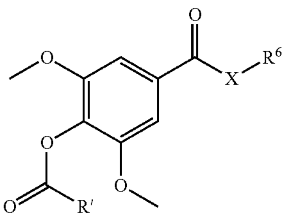

or a pharmaceutically acceptable salt thereof, or (c) Formula (IIIL):

(IIL)

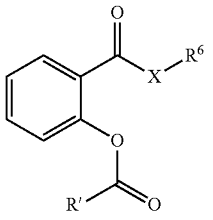

or a pharmaceutically acceptable salt thereof.

16. The cationic lipid of claim 14 having a structure according to Formula (IIID):

(IIID)

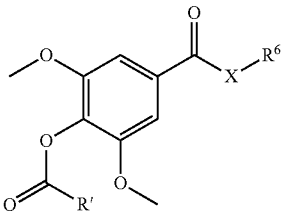

or a pharmaceutically acceptable salt thereof.

17. The cationic lipid of claim 1 having a structure according to Formula (IV):

(IV)

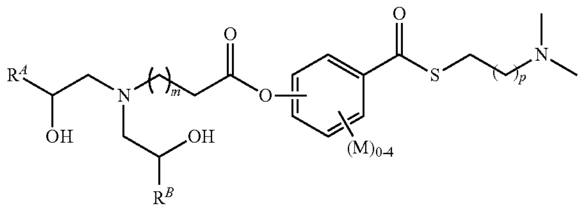

wherein M is selected from H, OH, OMe or Me, or a pharmaceutically acceptable salt thereof.

18. A cationic lipid that is:
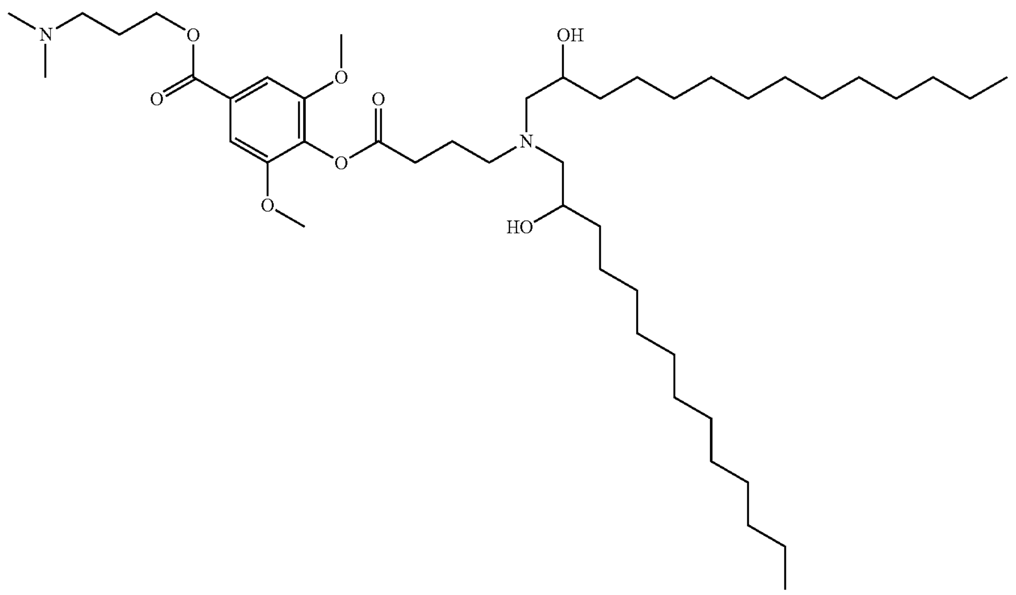 [SMILES: CCCCCCCCCCCCC(O)CN(CCCC(=O)Oc1c(OC)cc(C(=O)OCCCN(C)C)cc1OC)CC(O)CCCCCCCCCCCC]
or a pharmaceutically acceptable salt thereof.
19. A cationic lipid that is:
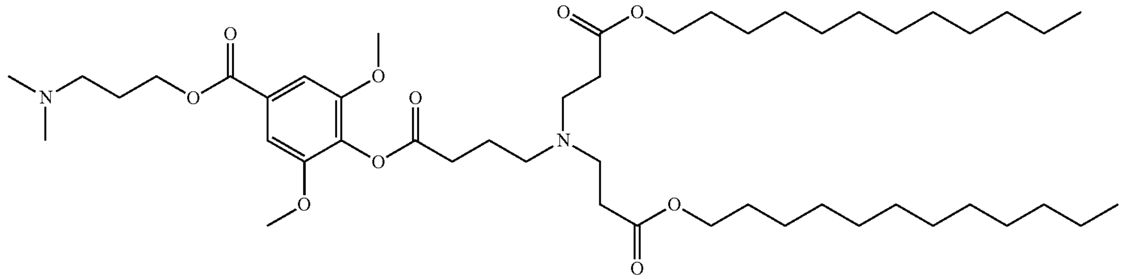
or
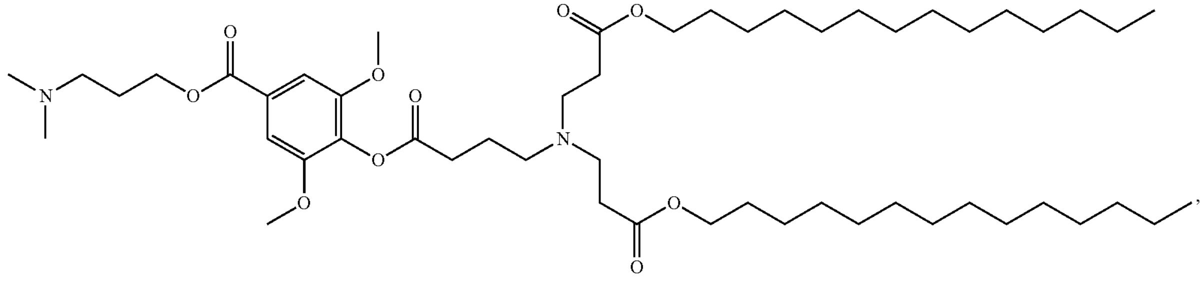
,
or a pharmaceutically acceptable salt thereof.
* * * * *